(12) United States Patent
Cao et al.

(10) Patent No.: US 10,556,879 B2
(45) Date of Patent: Feb. 11, 2020

(54) RETINOID COMPOUND, PREPARATION METHOD THEREFOR, INTERMEDIATES THEREOF AND APPLICATION THEREOF

(71) Applicants: SHANGHAI INSTITUTE OF ORGANIC CHEMISTRY, CHINESE ACADEMY OF SCIENCES, Shanghai (CN); HUAZHONG UNIVERSITY OF SCIENCE AND TECHNOLOGY, Wuhan, Hubei (CN)

(72) Inventors: Xin Cao, Shanghai (CN); Biao Yu, Shanghai (CN); Ning Wang, Shanghai (CN); Junwei Chen, Shanghai (CN)

(73) Assignees: SHANGHAI INSTITUTE OF ORGANIC CHEMISTRY, CHINESE ACADMENY OF SCIENCES, Shanghai (CN); HUAZHONG UNIVERSITY OF SCIENCE AND TECHNOLOGY, Wuhan, Hubei (CN)

( * ) Notice: Subject to any disclaimer, the term of this patent is extended or adjusted under 35 U.S.C. 154(b) by 0 days.

(21) Appl. No.: 16/083,879

(22) PCT Filed: Jan. 20, 2017

(86) PCT No.: PCT/CN2017/071922
§ 371 (c)(1),
(2) Date: Sep. 10, 2018

(87) PCT Pub. No.: WO2017/152725
PCT Pub. Date: Sep. 14, 2017

(65) Prior Publication Data
US 2019/0092744 A1  Mar. 28, 2019

(30) Foreign Application Priority Data

Mar. 11, 2016 (CN) .......................... 2016 1 0141143
May 11, 2016 (CN) .......................... 2016 1 0310944

(51) Int. Cl.

| | | |
|---|---|---|
| *A61K 31/385* | (2006.01) | |
| *C07D 335/06* | (2006.01) | |
| *C07C 69/84* | (2006.01) | |
| *C07D 239/28* | (2006.01) | |
| *A61P 35/00* | (2006.01) | |
| *C07D 213/85* | (2006.01) | |
| *A61P 35/02* | (2006.01) | |
| *C07D 409/06* | (2006.01) | |
| *C07C 69/76* | (2006.01) | |
| *C07D 241/24* | (2006.01) | |
| *C07C 233/54* | (2006.01) | |
| *C07C 67/343* | (2006.01) | |
| *A61P 35/04* | (2006.01) | |
| *C07C 63/70* | (2006.01) | |
| *C07C 69/78* | (2006.01) | |
| *C07C 229/56* | (2006.01) | |
| *C07D 213/79* | (2006.01) | |
| *C07D 213/84* | (2006.01) | |
| *C07D 409/10* | (2006.01) | |

(52) U.S. Cl.
CPC ............ *C07D 335/06* (2013.01); *A61P 35/00* (2018.01); *A61P 35/02* (2018.01); *A61P 35/04* (2018.01); *C07C 63/70* (2013.01); *C07C 67/343* (2013.01); *C07C 69/76* (2013.01); *C07C 69/78* (2013.01); *C07C 69/84* (2013.01); *C07C 229/56* (2013.01); *C07C 233/54* (2013.01); *C07D 213/79* (2013.01); *C07D 213/84* (2013.01); *C07D 213/85* (2013.01); *C07D 239/28* (2013.01); *C07D 241/24* (2013.01); *C07D 409/06* (2013.01); *C07D 409/10* (2013.01); *C07C 2602/10* (2017.05)

(58) Field of Classification Search
CPC ........................... A61K 31/385; C07D 335/06
USPC ................................... 549/23; 514/434, 432
See application file for complete search history.

(56) References Cited

U.S. PATENT DOCUMENTS

| | | | |
|---|---|---|---|
| 2,089,809 A | | 8/1937 | Penning |
| 4,810,804 A | * | 3/1989 | Chandraratna ...... C07D 215/12 514/311 |
| 5,023,341 A | | 6/1991 | Chandraratna |
| 5,089,509 A | | 2/1992 | Chandraratna |
| 5,256,694 A | | 10/1993 | Wuest et al. |
| 5,399,561 A | * | 3/1995 | Chandraratna .... C07D 215/227 514/252.01 |
| 5,776,699 A | | 7/1998 | Klein et al. |
| 5,877,207 A | * | 3/1999 | Klein ...................... C07C 57/50 514/456 |

(Continued)

FOREIGN PATENT DOCUMENTS

| | | |
|---|---|---|
| CN | 1050385 A | 4/1991 |
| CN | 1360890 A | 7/2002 |

(Continued)

OTHER PUBLICATIONS

Chandraratna, Roshantha A. S., "Tazarotene: the first receptor-selective topical retinoid for the treatment of psoriasis," Journal of American Academy of Dermatology 1997, 37, pp. S12-S17.

Chen, Xiaoli, "New Advance in Clinical Application of Tazarotene," Foreign Medical Sciences (Geriatrics), vol. 27. No. 5, pp. 193-196 (2006).

Fott et al, "Identification of Tazarotenic Acid as the First Xenobiotic Substrate of Human Retinoic Acid Hydroxylase CYP26A1 and CYP2661," Journal of Pharmacology and Experimental Therapeutics, vol. 357, No. 2, pp. 281-292 (March).

(Continued)

*Primary Examiner* — Niloofar Rahmani
(74) *Attorney, Agent, or Firm* — Foley & Lardner LLP

(57) ABSTRACT

Disclosed are a retinoid compound, a preparation method therefor, intermediates thereof and an application thereof. The retinoid compound I of the present invention has a good tumor growth inhibition rate.

9 Claims, 15 Drawing Sheets

(56) References Cited

U.S. PATENT DOCUMENTS

| | | | | |
|---|---|---|---|---|
| 5,958,954 | A | * | 9/1999 | Klein .................. C07D 213/55 |
| | | | | 514/333 |
| 6,001,885 | A | * | 12/1999 | Vega ..................... A61K 31/12 |
| | | | | 514/319 |
| 6,218,128 | B1 | * | 4/2001 | Klein .................. G01N 33/566 |
| | | | | 435/7.1 |
| 6,252,090 | B1 | * | 6/2001 | Vasudevan ........... A61K 31/192 |
| | | | | 534/778 |
| 6,291,677 | B1 | * | 9/2001 | Vasudevan ............. C07C 59/72 |
| | | | | 544/238 |
| 6,303,785 | B1 | * | 10/2001 | Vasudevan ............. C07C 59/62 |
| | | | | 544/236 |
| 6,387,892 | B1 | * | 5/2002 | Vasudevan ........... A61K 31/192 |
| | | | | 514/150 |
| 2005/0026950 | A1 | | 2/2005 | Olejnik et al. |
| 2007/0023888 | A1 | | 2/2007 | Fujii |
| 2007/0238881 | A1 | * | 10/2007 | Kumar ................. C07D 409/06 |
| | | | | 546/280.1 |

FOREIGN PATENT DOCUMENTS

| | | | |
|---|---|---|---|
| CN | 102595892 A | | 7/2012 |
| CN | 107176945 A | | 9/2017 |
| EP | 0 284 288 A1 | | 9/1988 |
| EP | 0 290 130 A1 | | 11/1988 |
| EP | 0 419 132 A | | 3/1991 |
| EP | 0441004 A1 | | 8/1991 |
| EP | 0785782 A1 | | 7/1997 |
| EP | 0 931 786 A | | 7/1999 |
| EP | 1212316 A2 | | 6/2002 |
| EP | 2130908 A2 | | 12/2009 |
| WO | 9206084 | * | 9/1991 |
| WO | WO-92/06084 A1 | | 4/1992 |
| WO | WO-92/06092 A1 | | 4/1992 |
| WO | WO-93/16068 A1 | | 8/1993 |
| WO | 2000019990 | * | 9/1999 |
| WO | WO-03/062369 A2 | | 7/2003 |
| WO | WO-2006/040644 A | | 4/2006 |
| WO | WO-2011/009023 A1 | | 1/2011 |
| WO | 2016055800 A2 | | 4/2016 |

OTHER PUBLICATIONS

International Search Report and Written Opinion (with English-language translation) issued in International Patent Application No. PCT/CN2017/071922 dated Apr. 21, 2017.

Johnson et al., "Synthesis and biological activity of high-affinity retinoic acid receptor antagonists", Bioorganic & Medicinal Chemistry, vol. 7, No. 7, pp. 1321-1338 (December).

Liu et al., "Soft fibrin gels promote selection and growth of tumorigenic cells," Nature Materials, vol. 11, pp. 734-741 (2012).

Partial European Search Report of European patent application No. 17762411.1 dated Dec. 7, 2018.

Shi-Yong Sun, "Recent developments of retinoids as therapeutic agents," Expert Opinion on Therapeutic Patents vol. 12, No. 4 (2002) pp. 529-542.

The Extended European Search Report issued in European patent application No. 17762411.1 dated Mar. 6, 2019.

GB Deacon et al., "Synthesis of perbromobenzoic acids and perbromobenzenes form aromatic carboxylic acids by permercuration and bromodemercuration", Australian Journal of Chemistry: An International Journal for Chemical Science, vol. 30, No. 2,1977, p. 293—Partial description.

Beard R L et al., "Synthesis and biological activity of 1,2,3,4-tetrahydroquinoline and 3,4-(1H)-dihyfroguinolin-2-one analogs of retinoic acid", Bioorganic & Medicinal Chemistry Letters, Pergamon, Amsterdam, NL, vol. 7,No. 18,1997, p. 2373-2378.

Pakala R et al., "Rar gamma agonists inhibit proliferation of vascular smooth muscle cells", Journal of Cardiovascular Pharmaco, Raven Press, NY, vol. 35, No. 2, 2000, p. 302-308.

Vakarov Sergey A et al., "Acylative kinetic resolution of racemic heterocyclic amines with (R)-2-phenoxypropionyl chloride", vol. 27, No. 24, 2016, p. 1231-1237.

\* cited by examiner

8a

8b

RETINOID COMPOUND, PREPARATION METHOD THEREFOR, INTERMEDIATES THEREOF AND APPLICATION THEREOF

The present application claims the benefit of the Chinese Patent Application No. CN201610141143.3 filed on Mar. 11, 2016 and the Chinese Patent Application No. CN201610310944.8 filed on May 11, 2016. The content of the above Chinese Patent Applications is incorporated herein by reference in its entirety.

FIELD OF INVENTION

The present invention relates to a retinoid compound, a preparation method, an intermediate and a use thereof.

PRIOR ARTS

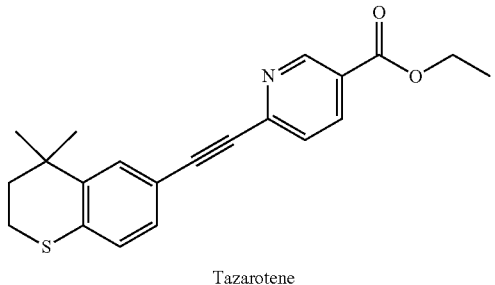 [SMILES: CCOC(=O)c1ccc(C#Cc2ccc3c(c2)C(C)(C)CCS3)nc1]

Tazarotene

Tazarotene is a retinoid drug with RAR subtype selectivity (*J Am Acad Dermatol.* 1997, 37, S12), mainly used for the treatment of topical epithelial hyperplasia skin (psoriasis, psoriasis, acne, etc.). Tazarotene is an ethyl ester prodrug, which is metabolized by enzyme to Tazarotenic acid as the carboxyl-type active metabolite in vivo. Tazarotenic acid can selectively interact with RARβ and RARγ receptors, and has a certain effect on RARβ, but has a weak effect on RXR.

CONTENT OF THE PRESENT INVENTION

The technical problem to be solved in the present invention is to overcome the poor inhibition rate of Tazarotene on tumor cells, thus the present invention provides a retinoid compound, a preparation method, an intermediate and a use thereof. The compound of the present invention exhibits a better inhibition rate on tumor cells.

The present invention provides a compound represented by formula I, an enantiomer, a diastereomer or a pharmaceutically acceptable salt thereof,

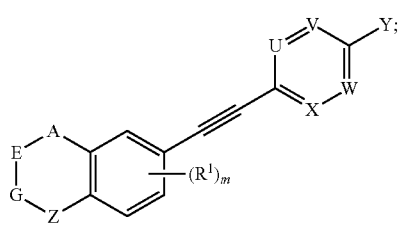

wherein, U is $CR^{9a}$ or N; V is $CR^{9b}$ or N; X is $CR^{9c}$ or N; W is $CR^{9d}$ or N;

in the definition of U, V, X and W, each of $R^{9a}$, $R^{9b}$, $R^{9c}$ and $R^{9d}$ is independently hydrogen, hydroxy, nitro, cyano, halogen (e.g. fluorine, chlorine, bromine or iodine), $C_1$-$C_6$ alkyl (e.g. methyl, ethyl, n-propyl, isopropyl, n-butyl, isobutyl, tert-butyl, pentyl or hexyl), $C_1$-$C_6$ alkyl substituted with halogen (the halogen can be fluorine, chlorine, bromine or iodine; the $C_1$-$C_6$ alkyl can be methyl, ethyl, n-propyl, isopropyl, n-butyl, isobutyl, tert-butyl, pentyl or hexyl; the "$C_1$-$C_6$ alkyl substituted with halogen" such as trifluoromethyl), $C_1$-$C_6$ alkoxy (e.g. methoxy, ethoxy, n-propoxy, isopropoxy, n-butoxy, isobutoxy, tert-butoxy, pentoxy or hexoxy), $-NR^{10}R^{11}$,

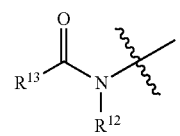

or $-COOR^{14}$;

each of $R^{10}$, $R^{11}$, $R^{12}$, $R^{13}$ and $R^{14}$ is independently hydrogen or $C_1$-$C_6$ alkyl (e.g. methyl, ethyl, n-propyl, isopropyl, n-butyl, isobutyl, tert-butyl, pentyl or hexyl);

the bond connecting AE, EG or GZ is independently a single bond or a double bond; when A, E, G or Z connects to two single bonds, the corresponding A, E, G and Z are independently $-(CR^2R^3)-$, $-C(=O)-$, $-(NR^4)-$, $-(N \to O)-$, $-O-$, $-S-$, $-S(=O)-$ or $-SO_2-$; when A, E, G or Z connects to a single bond and a double bond, the corresponding A, E, G and Z are independently $-(CR^5)=$ or $-N=$;

each of $R^2$, $R^3$, $R^4$ and $R^5$ is independently hydrogen, hydroxy, halogen (e.g. fluorine, chlorine, bromine or iodine), $C_1$-$C_6$ alkyl (e.g. methyl, ethyl, n-propyl, isopropyl, n-butyl, isobutyl, tert-butyl, pentyl or hexyl), $C_2$-$C_6$ alkenyl (e.g. vinyl or propenyl), $C_1$-$C_6$ alkyl substituted with halogen (the halogen can be fluorine, chlorine, bromine or iodine; the $C_1$-$C_6$ alkyl can be methyl, ethyl, n-propyl, isopropyl, n-butyl, isobutyl, tert-butyl, pentyl or hexyl; the "$C_1$-$C_6$ alkyl substituted with halogen" such as trifluoromethyl), $C_1$-$C_6$ alkoxy (e.g. methoxy, ethoxy, n-propoxy, isopropoxy, n-butoxy, isobutoxy, tert-butoxy, pentoxy or hexoxy), $C_1$-$C_6$ acyl (e.g. acetyl or formyl), $C_6$-$C_{10}$ aryl (e.g. phenyl) or "$C_3$-$C_6$ heteroaryl having 1 to 2 heteroatoms selected from the group consisting of oxygen, sulfur and nitrogen" (e.g. pyridinyl or pyrimidinyl);

m is 0, 1, 2 or 3;

when there are more than one substituents of $R^1$, the substituents are identical or different; $R^1$ is hydrogen, hydroxy, nitro, cyano, halogen (e.g. fluorine, chlorine, bromine or iodine), $C_1$-$C_6$ alkyl (e.g. methyl, ethyl, n-propyl, isopropyl, n-butyl, isobutyl, tert-butyl, pentyl or hexyl), $C_1$-$C_6$ alkyl substituted with halogen (the halogen can be fluorine, chlorine, bromine or iodine; the $C_1$-$C_6$ alkyl can be methyl, ethyl, n-propyl, isopropyl, n-butyl, isobutyl, tert-butyl, pentyl or hexyl; the "$C_1$-$C_6$ alkyl substituted with halogen" is for example trifluoromethyl), $C_1$-$C_6$ alkoxy (e.g. methoxy, ethoxy, n-propoxy, isopropoxy, n-butoxy, isobutoxy, tert-butoxy, pentoxy or hexoxy), $-NR^6R^7$ or $-COOR^8$;

each of $R^6$, $R^7$ and $R^8$ is independently hydrogen or $C_1$-$C_6$ alkyl (e.g. methyl, ethyl, n-propyl, isopropyl, n-butyl, isobutyl, tert-butyl, pentyl or hexyl);

Y is $-CN$, $-COOR^{15}$ or $-CO_2NHR^{16}$;

each of $R^{15}$ and $R^{16}$ is independently hydrogen, $C_1$-$C_6$ alkyl (e.g. methyl, ethyl, n-propyl, isopropyl, n-butyl, isobutyl, tert-butyl, pentyl or hexyl), $C_2$-$C_6$ alkenyl (e.g. vinyl or propenyl) or $C_1$-$C_6$ acyl (e.g. formyl or acetyl);

the compound represented by formula I is not

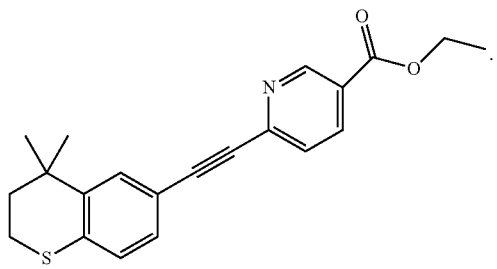 [SMILES: CCOC(=O)c1ccc(C#Cc2ccc3c(c2)C(C)(C)CCS3)nc1]

Preferably, A, E, G together with Z can form the ring selected from the group consisting of

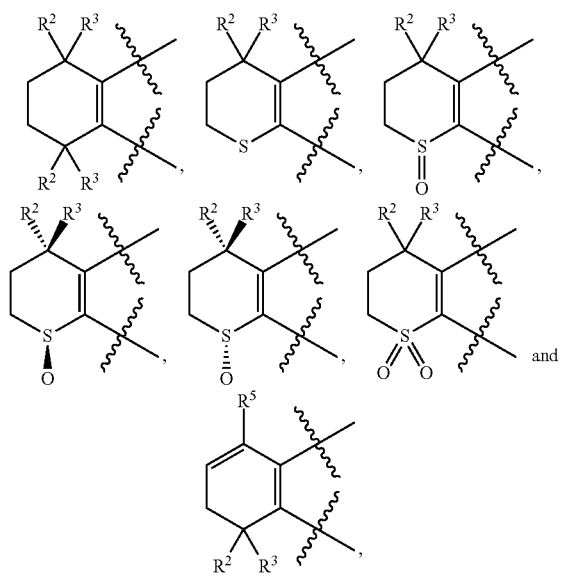

$R^2$, $R^3$ and $R^5$ are defined as above.

Preferably, in compound I, at least one (e.g. one, two, three or four) of U, V, X and W is N atom.

More preferably, in compound represented by formula I, when two of U, V, X and W are N atoms, the compound represented by formula I can be selected from the group consisting of

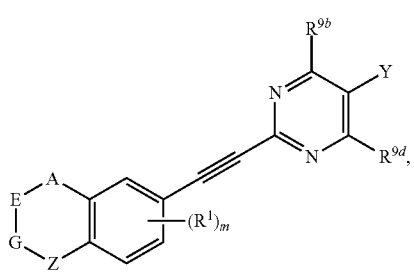

A

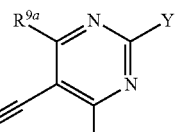

B

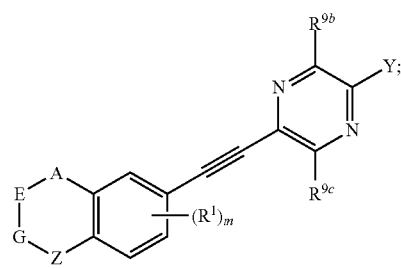

and

C wherein, A, E, G, Z, m, Y, $R^{9a}$, $R^{9b}$, $R^{9c}$ and $R^{9d}$ are defined as above.

Preferably, in compound A, when Y is —$COOR^{15}$, $R^{15}$ is hydrogen or ethyl.

Preferably, in compound A, Z is —$(CR^2R^3)$—, —S—, —S(=O)— or —$SO_2$—; more preferably, A, E, G together with Z form the ring selected from the group consisting of

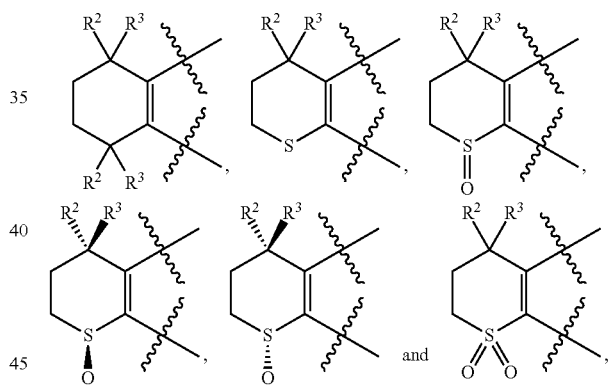

$R^2$ and $R^3$ are defined as above.

More preferably, in compound A, when Y is COOH, Z is —S—.

More preferably, in compound A, when Y is COOEt, Z is —$(CR^2R^3)$—, —S(=O)— or —$SO_2$—.

Preferably, in compound B, when Y is —$COOR^{15}$, $R^{15}$ is methyl or ethyl.

Preferably, in compound B, Z is —$(CR^2R^3)$—, —S— or —S(=O)—; more preferably, A, E, G together with Z form the ring selected from the group consisting of

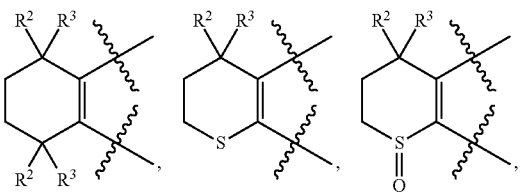

-continued

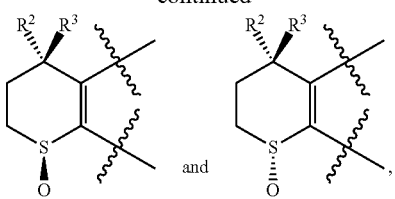

$R^2$ and $R^3$ are defined as above.

More preferably, in compound B, when Y is COOMe, Z is —$(CR^2R^3)$—, $R^2$ and $R^3$ are defined as above.

More preferably, in compound B, when Y is COOEt, Z is —$(CR^2R^3)$— or —S—, $R^2$ and $R^3$ are defined as above.

More preferably, in compound B, when Y is CN, Z is —$(CR^2R^3)$—, —S— or —S(=O)—, $R^2$ and $R^3$ are defined as above.

Preferably, in compound C, when Y is —$COOR^{15}$, $R^{15}$ is hydrogen or ethyl.

Preferably, in compound C, Z is —$(CR^2R^3)$—, —S— or —S(=O)—; more preferably, A, E, G together with Z form the ring selected from the group consisting of

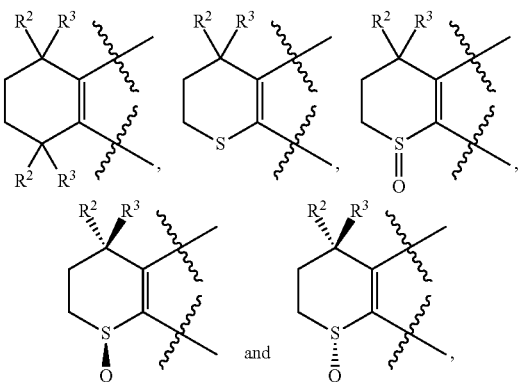

$R^2$ and $R^3$ are defined as above.

More preferably, in compound C, when Y is COOH, Z is —S—.

More preferably, in compound C, when Y is COOEt, Z is —$(CR^2R^3)$—, —S— or —S(=O)—, $R^2$ and $R^3$ are defined as above.

Preferably, in compound presented by formula I, when one of U, V, X and W is N atom, the compound represented by formula I can be selected from

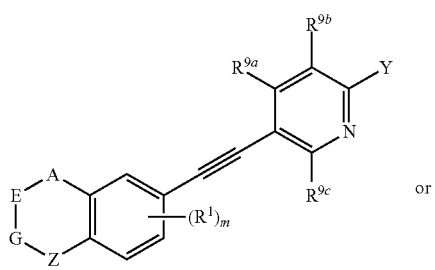

or

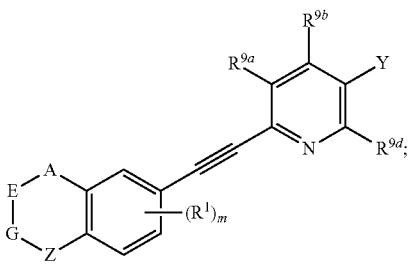

wherein, A, E, G, Z, m, Y, $R^{9a}$, $R^{9b}$, $R^{9c}$ and $R^{9d}$ are defined as above.

Preferably, in compound D, when Y is —$COOR^{15}$, $R^{15}$ is hydrogen or ethyl.

Preferably, in compound D, Z is —$(CR^2R^3)$—; more preferably, A, E, G together with Z form

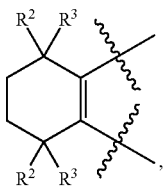

$R^2$ and $R^3$ are defined as above.

Preferably, in compound E, Y is CN.

Preferably, in compound E, Z is —$(CR^2R^3)$—; more preferably, A, E, G together with Z form

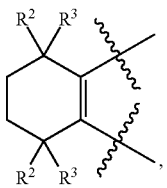

$R^2$ and $R^3$ are defined as above.

Preferably, in compound represented by formula I, when U is $CR^{9a}$, V is $CR^{9b}$, X is $CR^{9c}$, and W is $CR^{9d}$, the compound represented by formula I is as compound F:

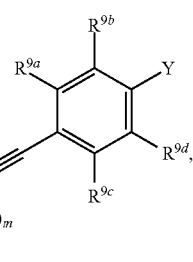

wherein, A, E, G, Z, m, Y, $R^{9a}$, $R^{9b}$, $R^{9c}$ and $R^{9d}$ are defined as above.

Preferably, in compound F, at least one (e.g. one, two, three or four) of $R^{9a}$, $R^{9b}$, $R^{9c}$ and $R^{9d}$ is not hydrogen.

Preferably, in compound F, when Y is —$COOR^{15}$, $R^{15}$ is hydrogen, methyl or ethyl.

Preferably, in compound F, Z is —(CR²R³)—, —S—, —S(=O)— or —SO₂—; more preferably, A, E, G together with Z form the ring selected from the group consisting of
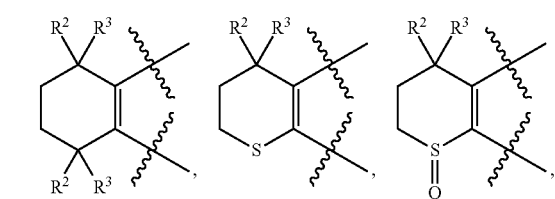
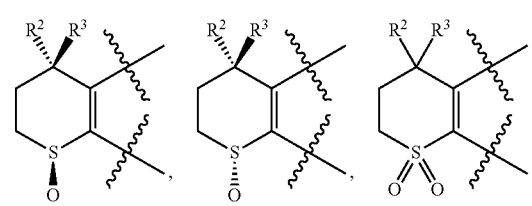
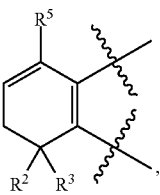
R², R³ and R⁵ are defined as above.
More preferably, the compound represented by formula I is selected from the group consisting of
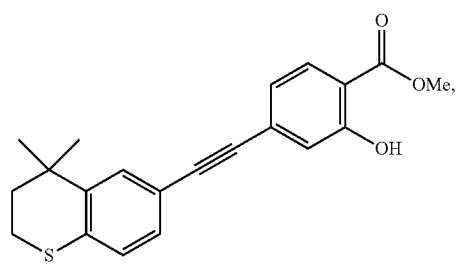
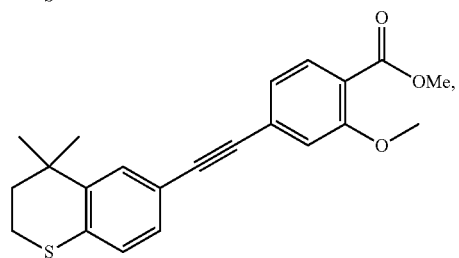
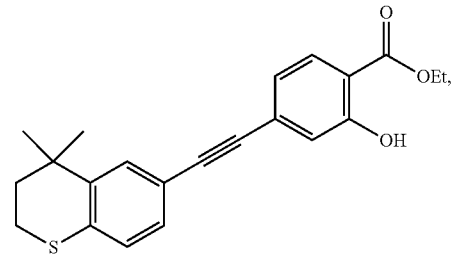
-continued
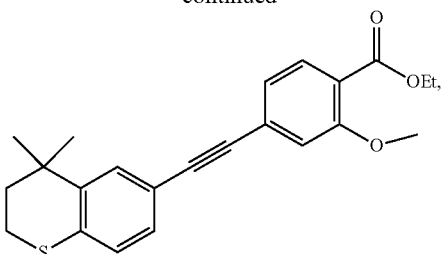
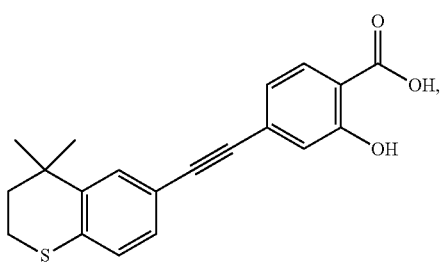
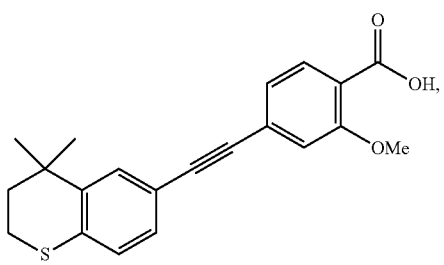
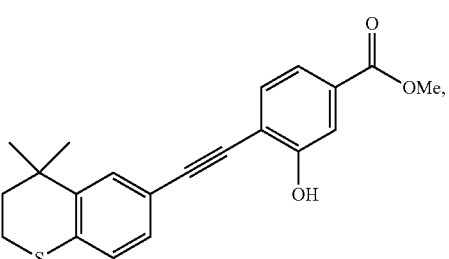
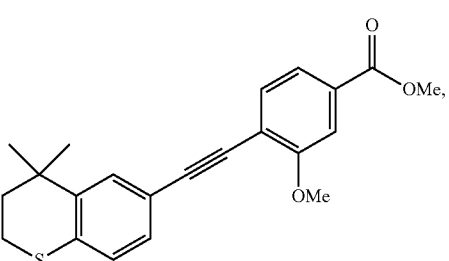
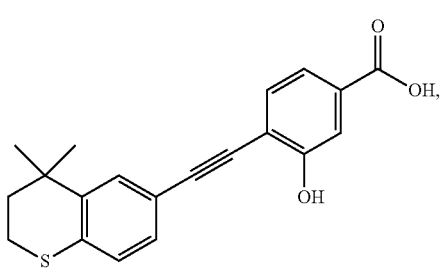

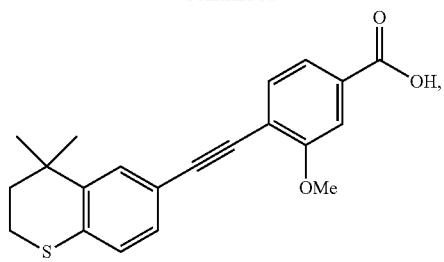
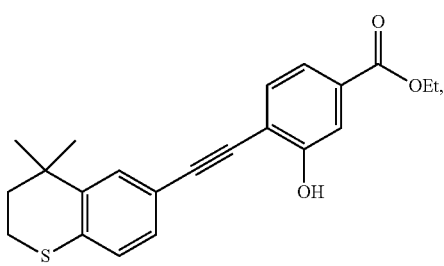
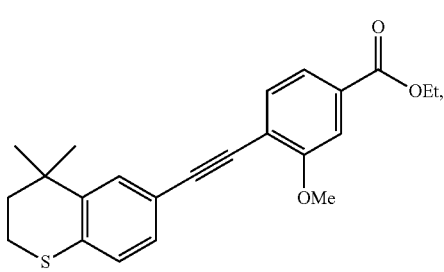
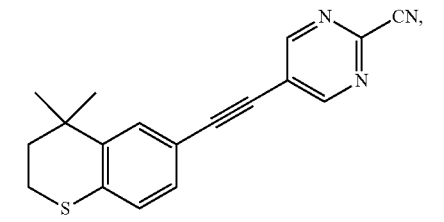
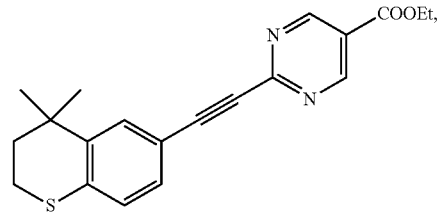
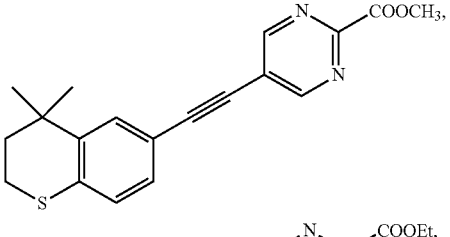
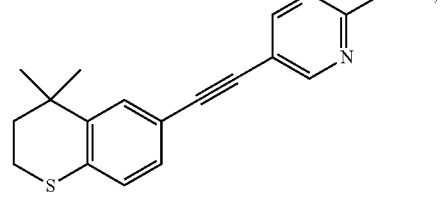
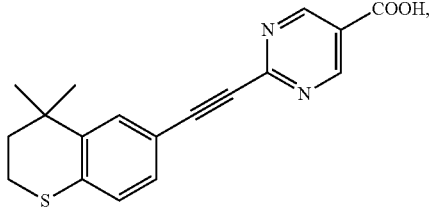
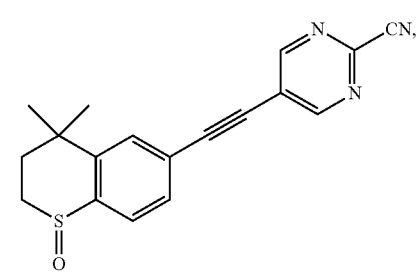
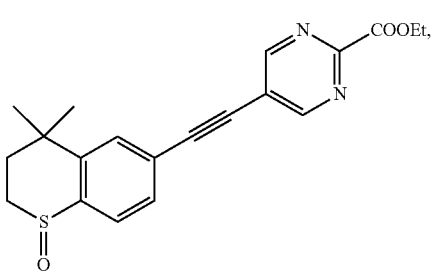
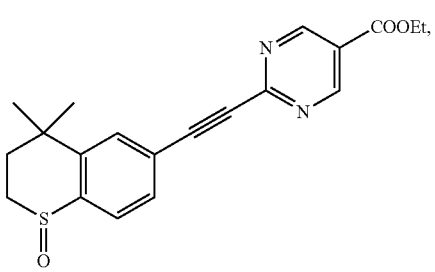
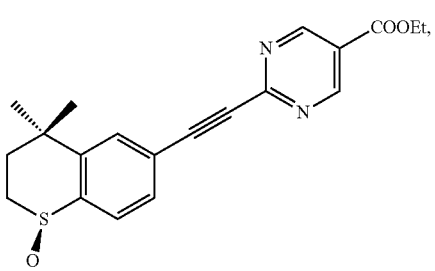
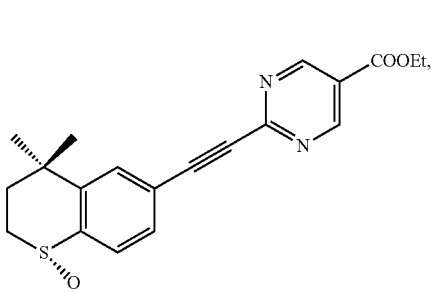

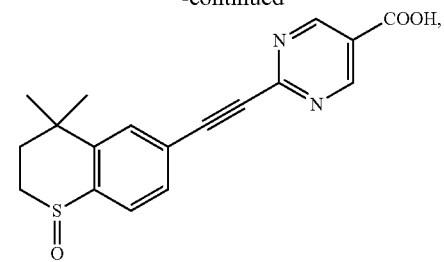
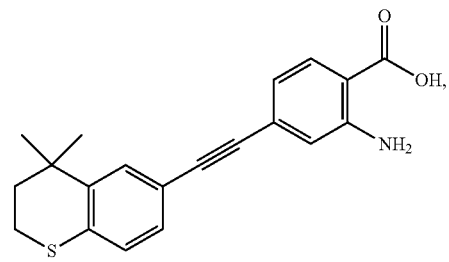
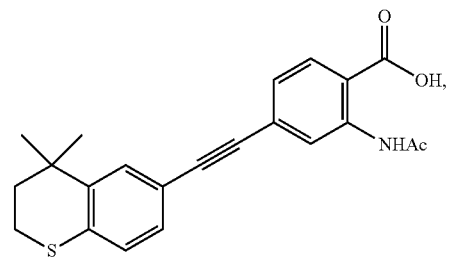
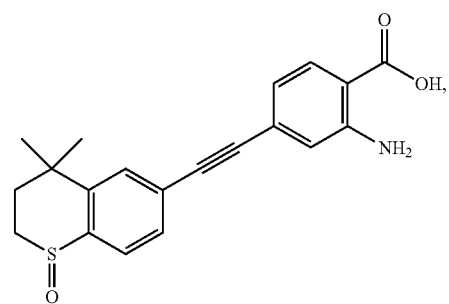
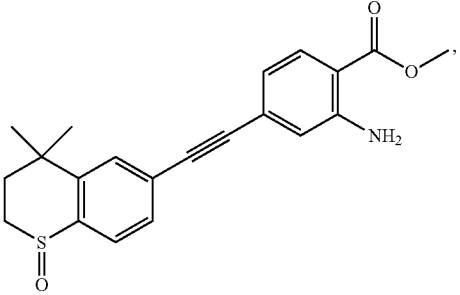
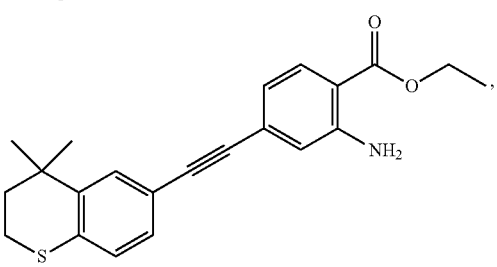
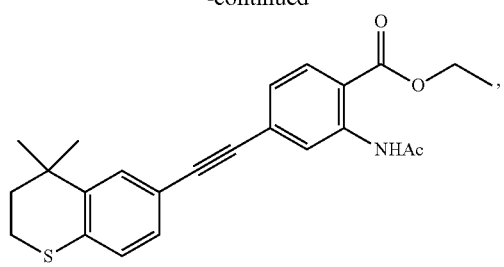
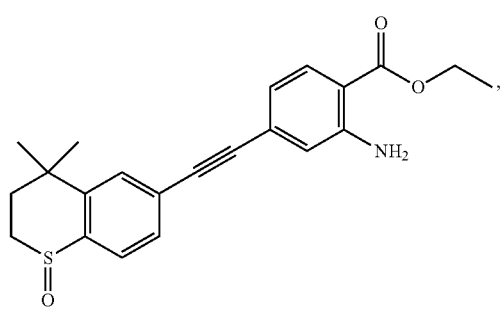
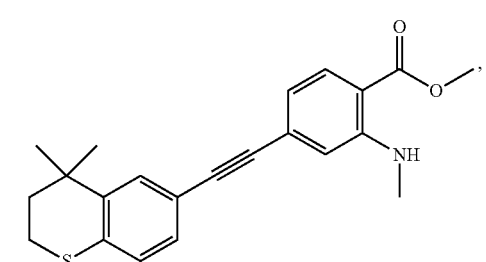
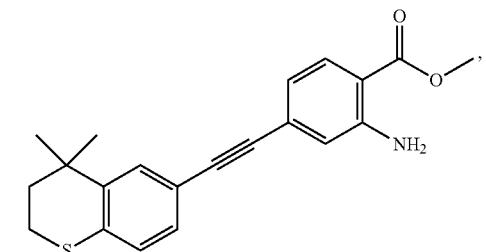
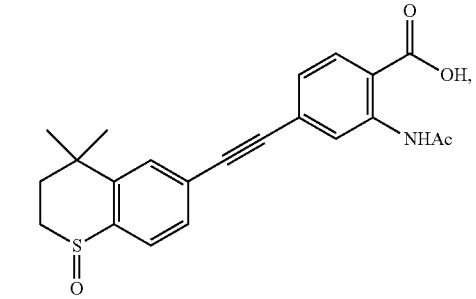
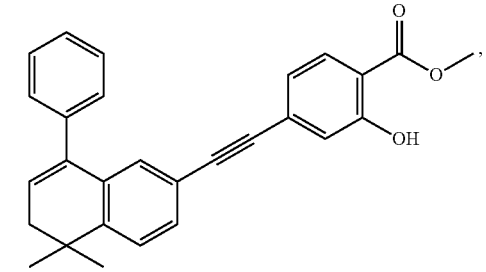

-continued
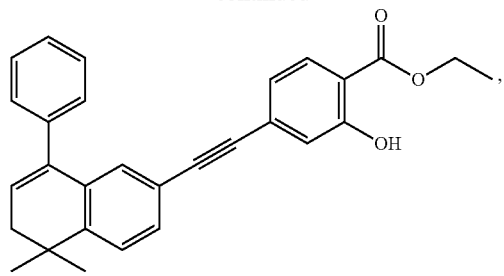
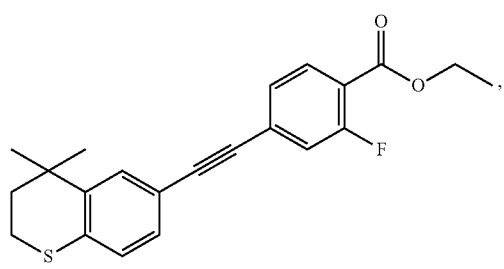
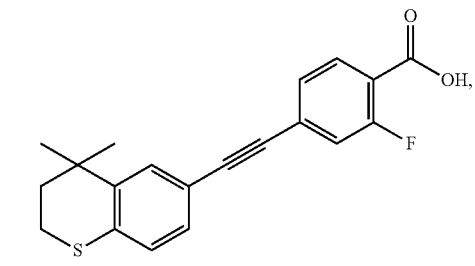
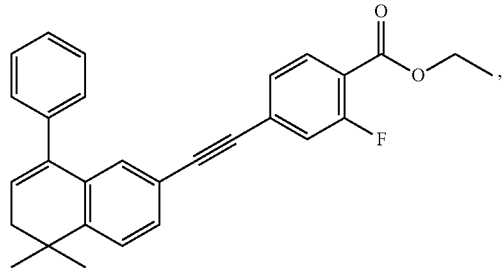
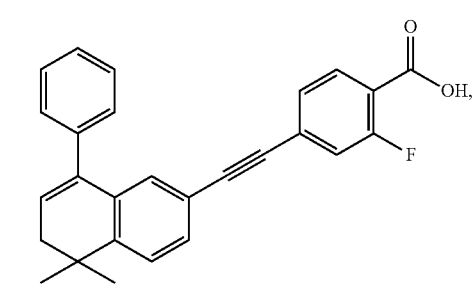
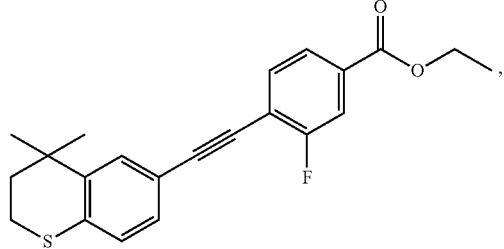
-continued
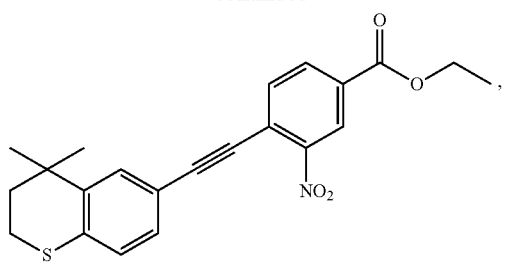
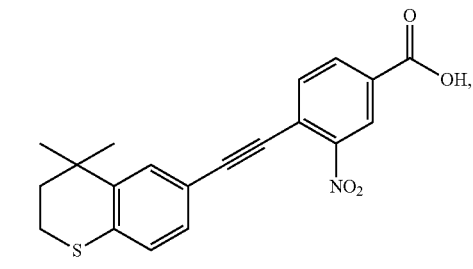
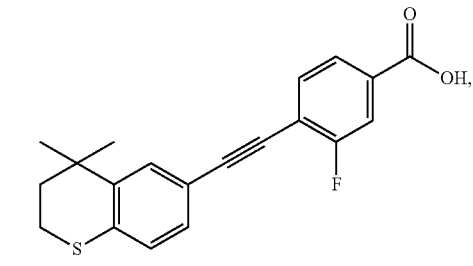
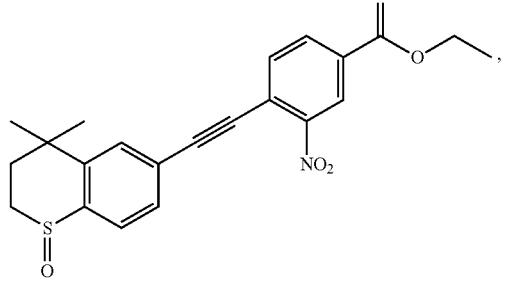
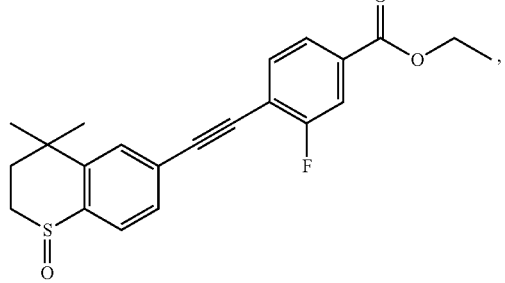
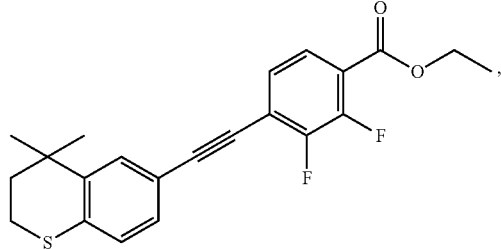

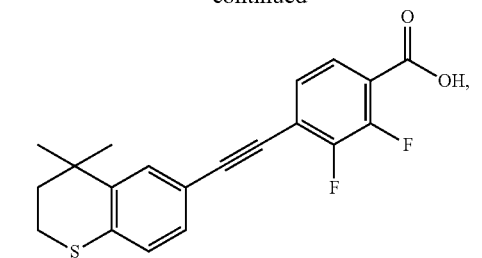
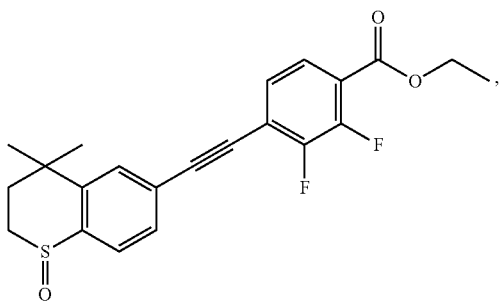
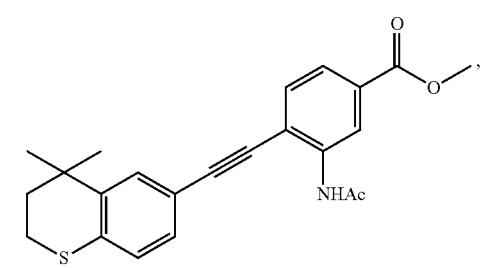
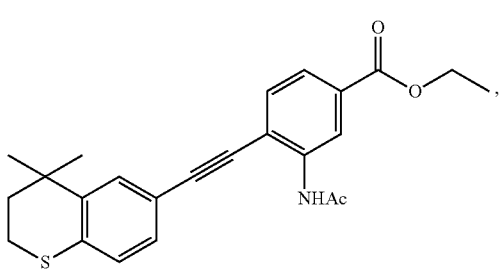
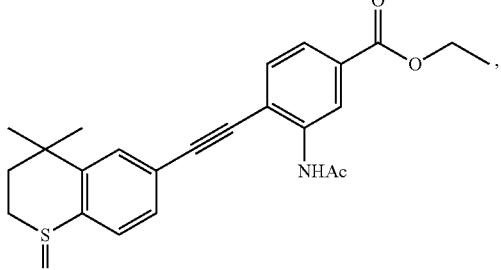
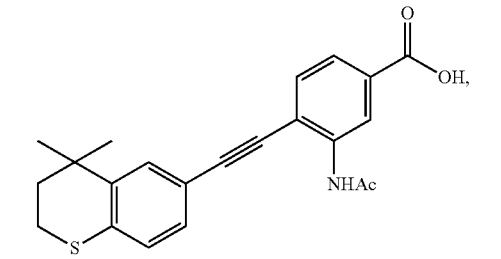
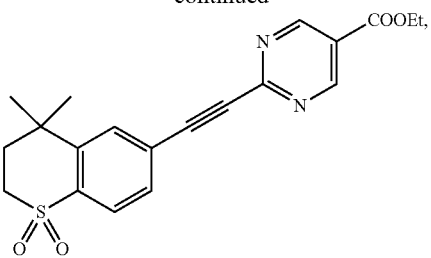
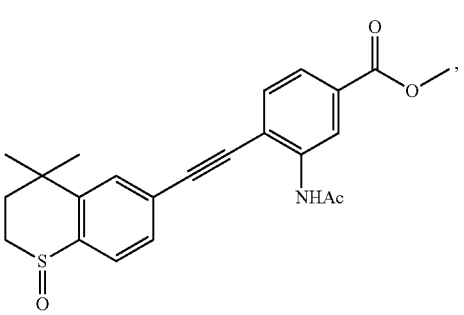
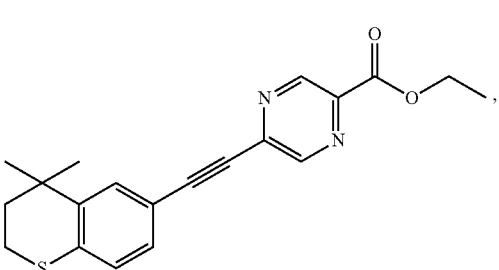
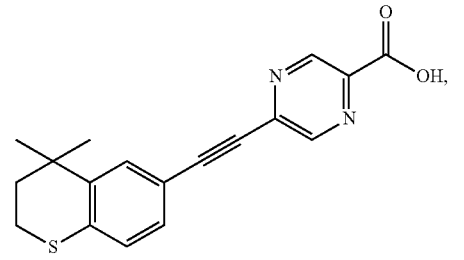
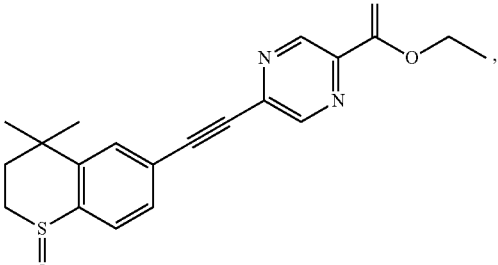
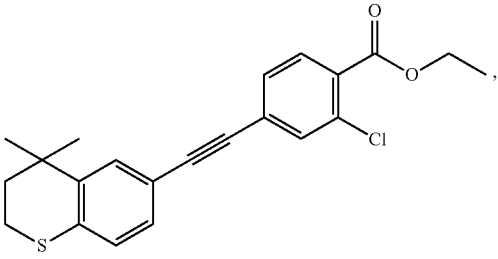

-continued
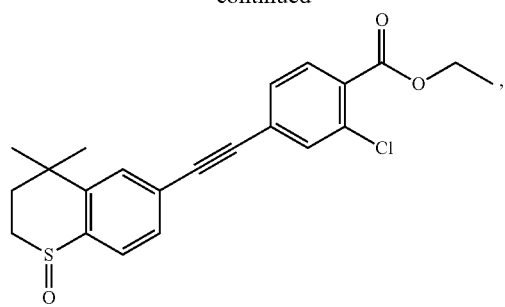
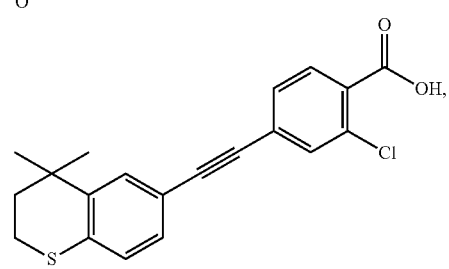
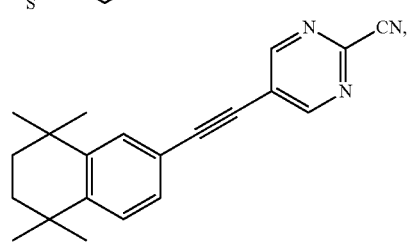
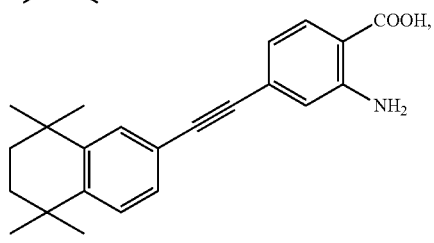
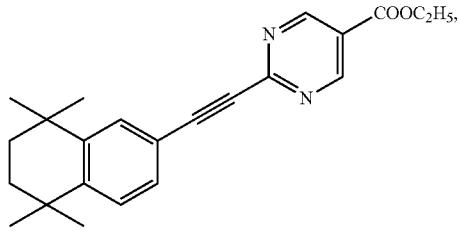
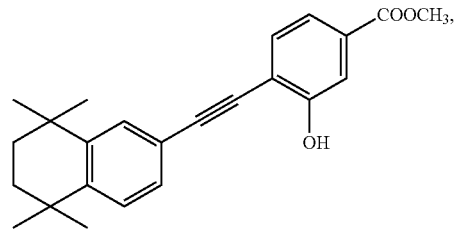
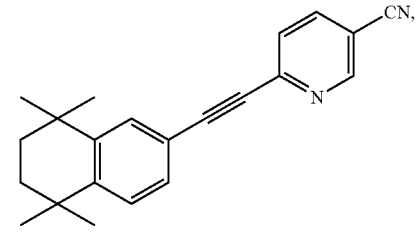
-continued
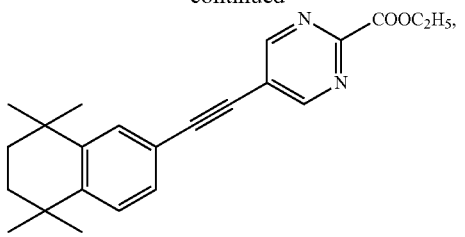
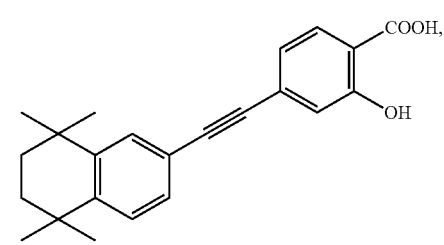
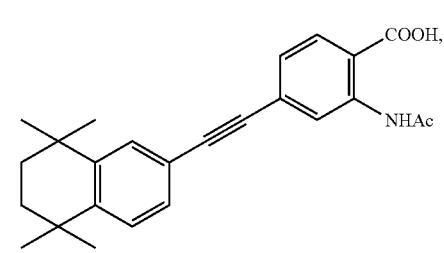
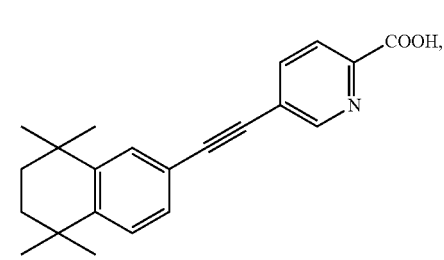
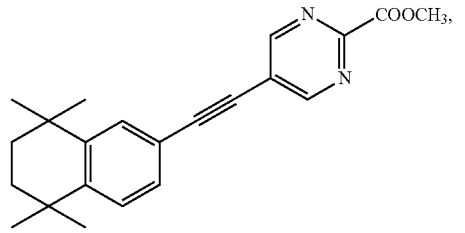
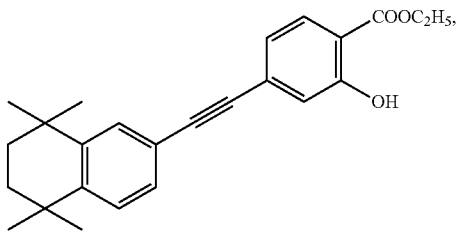
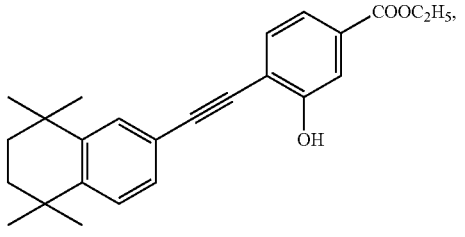

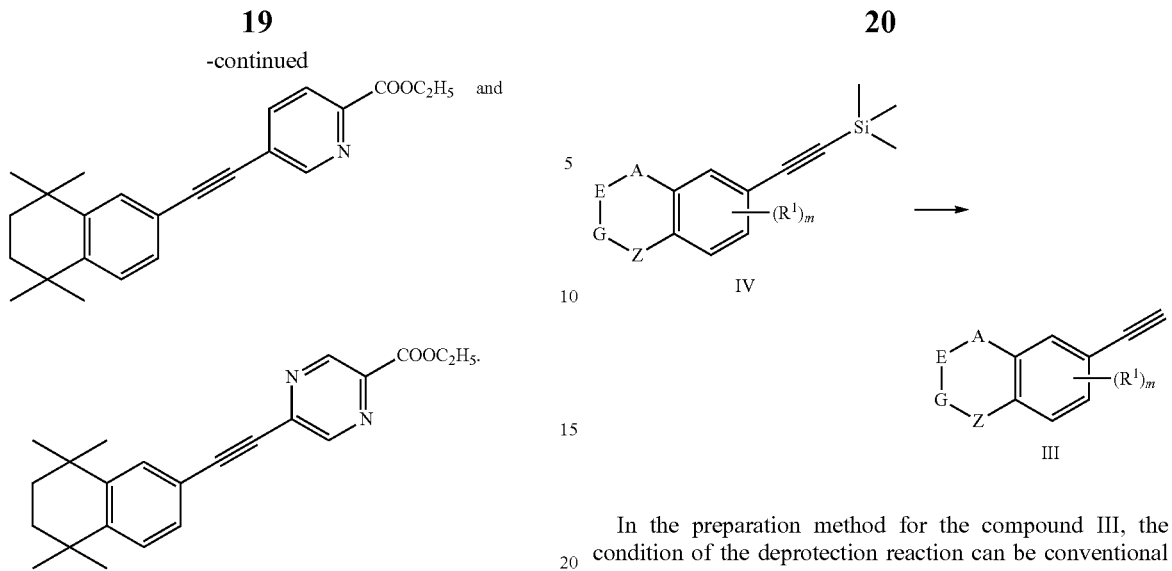

The present invention also provides a preparation method for the compound represented by formula I, which comprises conducting a coupling reaction with compound II and III to give compound I;

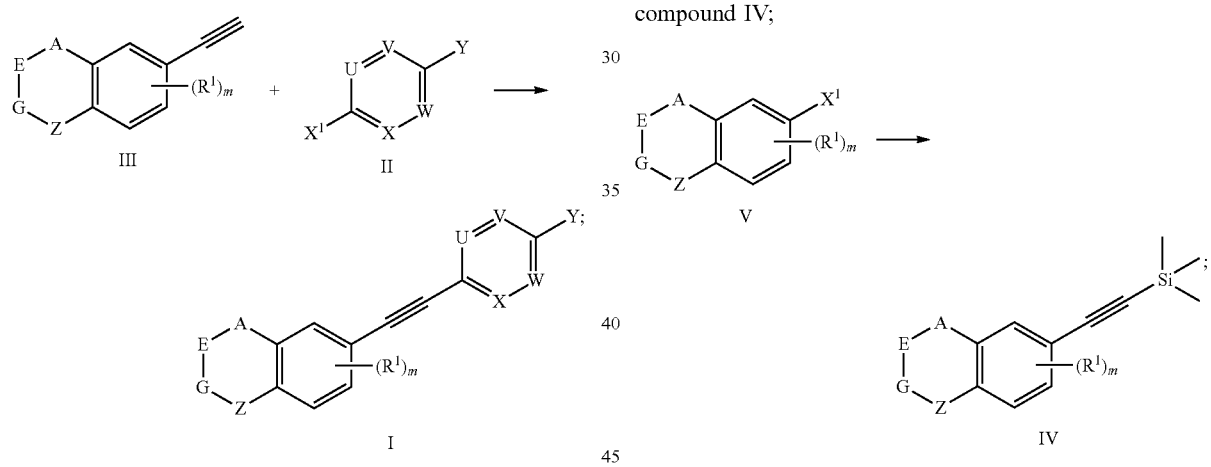

wherein, $X^1$ is halogen (e.g. fluorine, chlorine, bromine or iodine).

In the preparation method for the compound represented by formula I, the condition of the coupling reaction can be conventional conditions in the art, preferably that under an atmosphere of a protective gas (e.g. argon), in an organic solvent (e.g. DMF), in the presence of a catalyst (e.g. Pd/Cu catalyst; the "Pd/Cu catalyst" such as $Pd(PPh_3)_2Cl_2$ and CuI) and a base (e.g. diisopropylamine or triethylamine), conducting a coupling reaction with compound II and III to give compound I.

The compound represented by formula I can be converted to analogue with a different functional group by flexible functional group conversion and adjustment (including but not limited to esterification, ester hydrolysis, reduction, acylation, oxidation, etc.).

The preparation method for the compound represented by formula I can further comprise conducting a deprotection reaction of compound IV to give compound III;

In the preparation method for the compound III, the condition of the deprotection reaction can be conventional conditions in the art, preferably that in an organic solvent (e.g. tetrahydrofuran), in the presence of a base (e.g. tetra-n-butylammonium fluoride), conducting a deprotection reaction of compound IV to give compound III.

The preparation method for the compound represented by formula I can further comprise conducting a coupling reaction with compound V and trimethylethynyl silane to give compound IV;

wherein, $X^2$ is halogen (e.g. bromine or iodine).

In the preparation method for the compound represented by formula IV, the condition of the coupling reaction can be conventional conditions in the art, preferably that under an atmosphere of a protective gas (e.g. argon), in an organic solvent (e.g. DMF), in the presence of a catalyst (e.g. Pd/Cu catalyst; the "Pd/Cu catalyst" such as $Pd(PPh_3)_2Cl_2$ and CuI) and a base (e.g. diisopropylamine or triethylamine), conducting a coupling reaction of compound V with trimethylethynyl silane to give compound IV.

The present invention also provides a compound represented by formula II, III, IV or V,

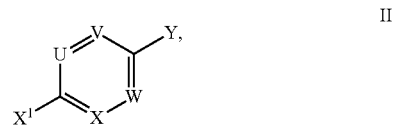

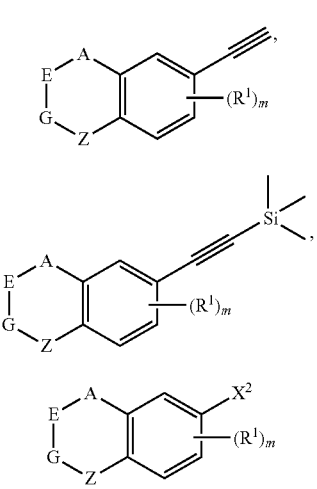

wherein, A, E, G, Z, R¹, m, X¹, Y, U, V, X and W are defined as above.

The present invention further provides a use of the compound represented by formula I, the enantiomer, the diastereomer or the pharmaceutically acceptable salt thereof in manufacturing a medicament for the treatment of a primary tumor. The tumor includes, but is not limited to, melanoma, esophageal cancer, gastric cancer, lung cancer, liver cancer, ovarian cancer, colon cancer, kidney cancer, cholangiocarcinoma, breast cancer or prostate cancer.

The present invention also provides a use of the compound represented by formula I, the enantiomer, the diastereomer or the pharmaceutically acceptable salt thereof in manufacturing a medicament for the prevention and/or the treatment of a metastatic tumor. The tumor includes, but is not limited to, melanoma, esophageal cancer, gastric cancer, lung cancer, liver cancer, ovarian cancer, colon cancer, kidney cancer, cholangiocarcinoma, breast cancer or prostate cancer.

The present invention also provides a use of the compound represented by formula I, the enantiomer, the diastereomer or the pharmaceutically acceptable salt thereof in manufacturing a medicament for the prevention and/or the treatment of leukemia and/or lymphoma.

The present invention also provides a use of the compound represented by formula I, the enantiomer, the diastereomer or the pharmaceutically acceptable salt thereof in manufacturing a medicament for the use selected from the group consisting of animal fetal growth, internal environment stability, vision, morphogenesis, skin aging and cell differentiation control.

The present invention also provides a use of the compound represented by formula I, the enantiomer, the diastereomer or the pharmaceutically acceptable salt thereof in manufacturing a medicament for the treatment of psoriasis.

The present invention also provides a use of the compound represented by formula I, the enantiomer, the diastereomer or the pharmaceutically acceptable salt thereof in manufacturing a medicament for the treatment of acne.

The present invention also provides a pharmaceutical composition, which comprises the compound represented by formula I, the enantiomer, the diastereomer or the pharmaceutically acceptable salt thereof, and a pharmaceutically acceptable carrier.

The route of administration of the pharmaceutical composition can be oral administration, injection and topical administration. When the pharmaceutical composition is administered by oral administration, the dosage form of the composition includes, but is not limited to, tablets, capsules, suspensions, solutions, emulsions, microspheres, nanosphere suspensions, controlled release niosomes or polymer niosomes. When the pharmaceutical composition is administered by injection, the dosage form of the composition solutions or suspensions for infusion or injection. Generally, the compounds of the present invention are daily administered at a dose of about 0.01 mg/kg to 100 mg/kg based on the body weight, the dose is divided into 1-3 part for administration. The concentration of the compounds of the present invention used systemically is generally 0.01% to 10% (weight), preferably 0.01% to 1% (weight) based on the weight of the composition. When the pharmaceutical composition is administered by topical administration, the pharmaceutical composition is especially used for the treatment of skin and mucosal diseases, can be used in the form of liquid, paste or solid, especially ointments, creams, solutions, gels, sprays, suspensions and adhesives. The form can also be microspheres, nanosphere suspensions, controlled release niosomes, polymer niosomes, gel patch or polymer patch. The concentration of the compounds which are administered by topical administration is usually 0.001% to 10% (weight), preferably 0.01% to 1% (weight) based on the total weight of the composition.

The pharmaceutical composition can also comprise inert additives, or a pharmaceutically active ingredient that is positively associated with the pharmaceutical composition, or a mixture of such ingredients. Of course, the person skilled in the art will be careful to select the above optional compound to be added into the above composition, ensuring that the advantage of the present invention is not or basically not affected by the predetermined additive.

In the present invention, the "$C_1$-$C_6$ acyl" refers to an alkyl acyl group having 1 to 6 carbon atoms, for example the acyl group having 1 carbon atom refers to HC(O)— (i.e. formyl), the acyl group having 2 carbon atoms refers to $CH_3C(O)$— (i.e. acetyl); propionyl, butyryl or valeryl.

In the present invention, unless otherwise specified, the following terms in the description and the claims of the invention have the following meanings:

The term "alkyl" refers to a saturated linier or branched monovalent hydrocarbon group having one to twenty carbon atoms. Examples of alkyl include, but are not limited to, methyl, ethyl, 1-propyl, 2-propyl, 1-butyl, 2-methyl-1-butyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-m ethyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl.

The term "alkenyl" refers to a linier, branched or cyclic non-aromatic hydrocarbon group having a specified number of carbon atoms and at least one carbon-carbon double bond. Alkenyl is preferably having one carbon-carbon double bond, and up to four non-aromatic carbon-carbon double bonds can be present. Thus, "$C_{2-12}$ alkenyl" refers to an alkenyl group having 2 to 12 carbon atoms. "$C_{2-6}$ alkenyl" refers to an alkenyl group having 2 to 6 carbon atoms, including vinyl, propenyl, butenyl, 2-methylbutenyl and cyclohexenyl.

The term "aryl" (used alone or included in other groups) refers to any stable monocyclic or bicyclic carbon ring which can have up to 7 atoms in each ring, wherein at least one ring is aromatic. Examples of the above aryl include phenyl, naphthyl, tetrahydronaphthyl, 2,3-dihydroindenyl, biphenyl, phenanthryl, anthryl or acenaphthyl. It is to be understood that when the aryl is a bicyclic substituent and one of the rings is non-aromatic, the linkage is through the aromatic ring.

The term "aromatic hetero group" or "heteroaryl" (used alone or included in other groups) refers to a stable monocyclic ring or bicyclic ring which can have up to 7 atoms in each ring, and at least one of the rings is an aromatic ring having 1 to 4 heteroatoms independently selected from O, N and S. The heteroaryl defined herein includes but not limited to acridinyl, carbazolyl, cinnolinyl, quinoxalinyl, pyrazolyl, indolyl, benzotriazolyl, furanyl, thienyl, benzothienyl, benzofuranyl, quinolinyl, isoquinolyl, oxazolyl, isoxazolyl, indolyl, pyrazinyl, pyridazinyl, pyridinyl, pyrimidyl, pyrryl, tetrahydroquinoline. As defined in the "heterocycloalkyl", "heteroaryl" can also be understood to include the N-oxide derivative of any nitrogenous heteroaryl. When the heteroaryl is a bicyclic substituent and one of the rings is non-aromatic or without any heteroatom, it can be understood, the linkage is through the aromatic ring or the heteroatom on the ring.

The term "halogen" includes F, Cl, Br, I.

The term "pharmaceutically acceptable salt" refers to a conventional acid addition or a base addition salt which retains the biological activity and the property of compound I and is formed from a suitable non-toxic organic acid, inorganic acid, organic base or inorganic base. Examples of the acid addition salt include the salt derived from an inorganic acid and an organic acid, the inorganic acid such as hydrochloric acid, hydrobromic acid, hydroiodic acid, sulfuric acid, sulfamic acid, phosphorous acid, phosphorothioic acid, phosphoric acid and nitric acid, the organic acid such as formic acid, acetic acid, propionic acid, p-toluenesulfonic acid, salicylic acid, methanesulfonic acid, oxalic acid, succinic acid, citric acid, maleic acid, lactic acid, tartaric acid, succinic acid, fumaric acid, mandelic acid, malic acid, camphorsulfonic acid, etc. Examples of the base addition salt include the salt derived from ammonium, potassium, sodium, calcium, and quaternary ammonium hydroxide (e.g. tetramethylammonium hydroxide). Modification of a pharmaceutical compound (i.e. drug) into a salt in order to obtain a compound with improved physical and chemical stability, hygroscopicity, flowability, and solubility is a conventional method well known to the pharmacists.

The "pharmaceutically acceptable" contained in the term "pharmaceutically acceptable carrier" refers to the compound is pharmaceutically acceptable and basically non-toxic when administered to a specific subject.

Without violating the common sense in the art, the above preferred conditions can be arbitrarily combined, then preferred embodiments of the present invention are obtained.

The reagents and raw materials used in the present invention are commercially available.

The positive and progressive effect of the present invention is that the compounds of the present invention exhibit a better inhibition rate on tumor cells.

BRIEF DESCRIPTION OF THE DRAWINGS

FIG. 3 shows the study of the inhibitory activity of WYC-209 on the tumor-repopulating cells of A549 lung cancer, wherein FIG. 3a shows the inhibitory activity of WYC-209 on A549 lung cancer when beginning administrating on the day 0; FIG. 3b shows the inhibitory activity of WYC-209 on A549 lung cancer when beginning administrating on the 3rd day.

FIG. 4 shows the study of the inhibitory activity of WYC-209 on the tumor-repopulating cells of MCF-7 breast cancer, wherein FIG. 4a shows the inhibitory activity of WYC-209 on MCF-7 breast cancer when beginning administrating on the day 0; FIG. 4b shows the inhibitory activity of WYC-209 on MCF-7 breast cancer when beginning administrating on the 3rd day.

FIG. 5 shows the study of the inhibitory activity of WYC-209 on the tumor-repopulating cells of MDA-MB-435S melanoma, wherein FIG. 5a shows the inhibitory activity of WYC-209 on MDA-MB-435S melanoma when beginning administrating on the day 0; FIG. 5b shows the inhibitory activity of WYC-209 on MDA-MB-435S melanoma when beginning administrating on the 3rd day.

FIG. 6 shows the study of the inhibitory activity of WYC-209 on the tumor-repopulating cells of A2780 ovarian cancer, wherein FIG. 6a shows the inhibitory activity of WYC-209 on A2780 ovarian cancer when beginning administrating on the day 0; FIG. 6b shows the inhibitory activity of WYC-209 on A2780 ovarian cancer when beginning administrating on the 3rd day.

FIG. 7 shows the study of the inhibitory activity of WYC-209 on the tumor-repopulating cells of Hs-746T gastric cancer, wherein FIG. 7a shows the inhibitory activity of WYC-209 on Hs-746T gastric cancer when beginning administrating on the day 0; FIG. 7b shows the inhibitory activity of WYC-209 on Hs-746T gastric cancer when beginning administrating on the 3rd day.

FIG. 8 shows the study of the inhibitory activity of WYC-209 on the tumor-repopulating cells of MDA-MB-231[※ 1] breast cancer, wherein FIG. 8a shows the inhibitory activity of WYC-209 on MDA-MB-231 breast cancer when beginning administrating on the day 0; FIG. 8b shows the inhibitory activity of WYC-209 on MDA-MB-231 breast cancer when beginning administrating on the 3rd day.

FIG. 9 shows the study of the inhibitory activity of WYC-331 on the tumor-repopulating cells of A2780 ovarian cancer and MDA-MB-231 breast cancer, wherein FIG. 9a shows the inhibitory activity of WYC-331 on A2780 ovarian cancer when beginning administrating on the 3rd day; FIG. 9b shows the inhibitory activity of WYC-331 on MDA-MB-231 breast cancer when beginning administrating on the 3rd day.

FIG. 10 shows the study of the toxicity of WYC-209 (WYC-209 inhibits the proliferation of B16 cells, but has no significant effect on 3T3 cells); wherein, FIG. 10a shows treating 3T3 cells with 10 μM WYC-209 for 18 hours; FIG. 10b shows treating B16 cells with no WYC-209 or 10 μM WYC-209 for 48 hours.

FIG. 11 shows the study of the toxicity of WYC-331; wherein, FIG. 11a shows treating 3T3 cells with 1 μM or 10 μM WYC-331 for 24 hours; FIG. 11b shows treating B16 cells with 1 μM or 10 μM WYC-331 for 24 hours.

FIG. 15 shows the study of the inhibitory activity of WYC-103 on metastatic melanoma in the lung; wherein, FIG. 15a shows the lung tissue on the 29th day of the experiment where injecting 3000 tumor-repopulating cells of melanoma and administrating WYC-103; FIG. 15*b* shows the lung tissue on the 29th day of the experiment where injecting 3000 tumor-repopulating cells of melanoma and administrating DMSO; FIG. 15*c* shows the lung tissue on the 35th day of the experiment where injecting 3000 tumor-repopulating cells of melanoma and administrating WYC-103; FIG. 15*d* shows the lung tissue on the 35th day of the experiment where injecting 3000 tumor-repopulating cells of melanoma and administrating DMSO; FIG. 15*e* shows the lung tissue on the 37th day of the experiment where administrating WYC-103; FIG. 15*f* shows the lung tissue on the 37th day of the experiment where administrating DMSO.

FIG. 16 shows the study of the inhibitory activity of WYC-209 on metastatic melanoma in the lung, wherein, FIG. 16*a* shows the lung tissue in the experiment where administrating DMSO; FIG. 16*b* shows the lung tissue in the experiment where administrating 1.0 μM WYC-209; FIG. 16*c* shows the lung tissue in the experiment where administrating 10 μM WYC-209.

DETAILED DESCRIPTION OF THE PREFERRED EMBODIMENT

Figure 1:
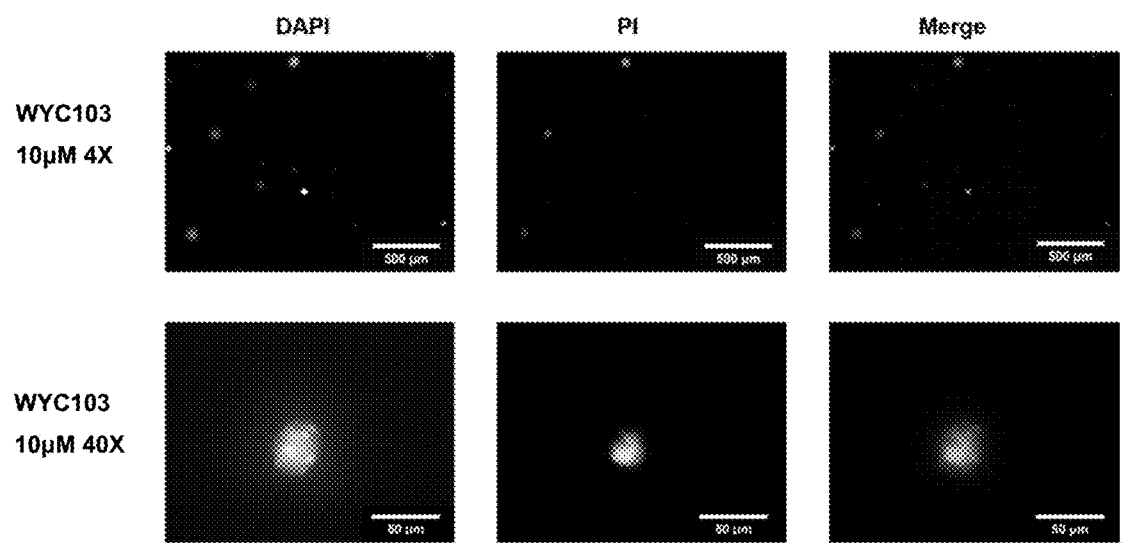
FIG. 1 shows the study of the effect of WYC-103 on the apoptosis of tumor-repopulating cells of B16-F1 melanoma.

The following embodiments further illustrate the present invention, but the present invention is not limited thereto. The experimental methods that do not specify the specific conditions in the following embodiments are selected according to conventional methods and conditions, or according to the description of the product.

Embodiment 1: methyl 4-((4,4-dimethylthiochroman-6-yl)ethynyl)-2-hydroxybenzoate

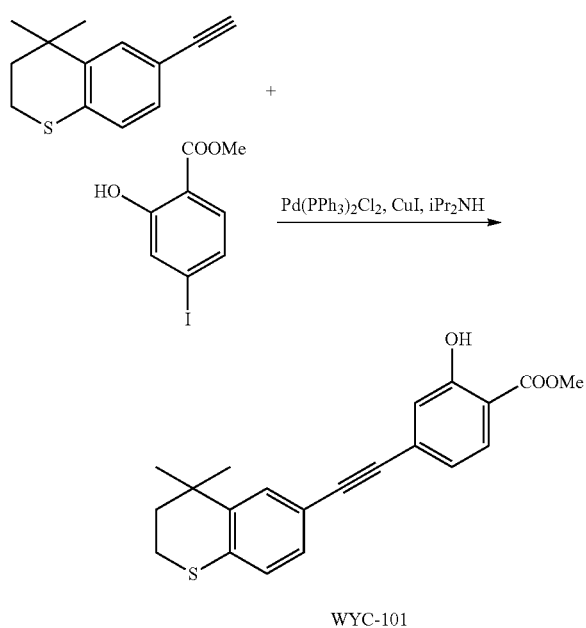

WYC-101

Commercially available 6-ethynyl-4,4-dimethylthiochroman (202.8 mg, 1 mmol) and methyl 2-hydroxy-4-iodobenzoate (292.1 mg, 1 mmol) used as raw material were added to a flask, followed by addition of Pd(PPh$_3$)$_2$Cl$_2$ (14 mg, 0.02 mmol) and CuI (7.6 mg, 0.04 mmol). After the flask was purged with argon for 3 times to remove oxygen, 2 mL dry DMF and 0.2 mL dry iPr$_2$NH were added via syringe. The reaction was continued at room temperature for 8 h and monitored by TLC. After completion of the reaction, the reaction was quenched with saturated ammonium chloride solution, and the mixture was diluted with ethyl acetate, washed with saturated ammonium chloride solution and saturated sodium chloride solution. The organic phase was dried over anhydrous sodium sulfate, filtered, concentrated and purified by flash column chromatography (PE: EtOAc=100:1 to 20:1) to give WYC-101 (296 mg, 81%). $^1$H NMR (400 MHz, CDCl$_3$) δ 7.79 (d, 1H), 7.53 (d, 1H), 7.18-7.20 (dd, 1H), 7.12 (d, 1H), 7.06-7.07 (d, 1H), 7.00-7.02 (dd, 1H), 3.95 (s, 3H), 3.03-3.06 (m, 2H), 1.94-1.97 (m, 1H), 1.34 (s, 6H); $^{13}$C NMR (101 MHz, CDCl$_3$) δ 170.09, 161.38, 161.12, 153.37, 142.25, 134.10, 130.91, 130.00, 129.85, 129.24, 126.73, 122.45, 120.25, 117.90, 111.95, 93.23, 88.03, 77.48, 77.16, 76.84, 52.52, 37.27, 32.54, 29.99, 23.43; ESI(+)–MS: 353.3 [M+1]$^+$.

Embodiment 2: methyl 4-((4,4-dimethylthiochroman-6-yl)ethynyl)-2-methoxybenzoate

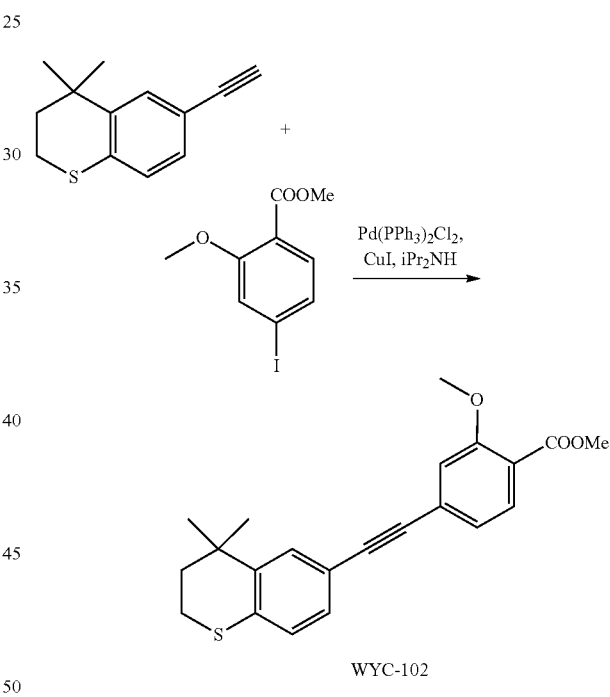

WYC-102

6-Ethynyl-4,4-dimethylthiochroman (202.8 mg, 1 mmol) and methyl 2-methoxy-4-iodobenzoate (292 mg, 1 mmol) were added to a flask, followed by addition of Pd(PPh$_3$)$_2$Cl$_2$ (14 mg, 0.02 mmol) and CuI (7.6 mg, 0.04 mmol). After the flask was purged with argon for 3 times to remove oxygen, 2 mL dry DMF and 0.2 mL dry iPr$_2$NH were added via syringe. The reaction was continued at room temperature for 8 h and monitored by TLC. After completion of the reaction, the reaction was quenched with saturated ammonium chloride solution, and the mixture was diluted with ethyl acetate, washed with saturated ammonium chloride solution and saturated sodium chloride solution. The organic phase was dried over anhydrous sodium sulfate, filtered, concentrated and purified by flash column chromatography (PE: EtOAc=100:1 to 50:1) to give WYC-102 (300 mg, 82%). $^1$H NMR (400 MHz, CDCl$_3$) δ 7.78 (d, 1H), 7.53 (d, 1H), 7.18-7.20 (dd, 1H), 7.11-7.13 (dd, 1H), 7.11 (d, 1H), 7.07 (d, 1H), 3.98 (s, 3H), 3.89 (s, 3H), 3.03-3.06 (m, 1H), 1.94-1.97 (m, 1H), 1.34 (s, 6H); $^{13}$C NMR (101 MHz, CDCl$_3$) δ 166.25, 159.05, 142.07, 133.98, 133.58, 131.89, 129.90, 129.13, 128.85, 126.70, 123.39, 119.42, 117.88, 114.84, 92.50, 88.07, 77.48, 77.16, 76.84, 56.18, 52.18, 37.23, 33.06, 30.06, 23.31; ESI(+)–MS: 367.4 [M+1]$^+$.

Embodiment 3: ethyl 4-((4,4-dimethylthiochroman-6-yl)ethynyl)-2-hydroxybenzoate

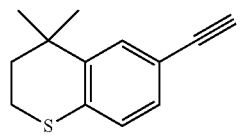

+

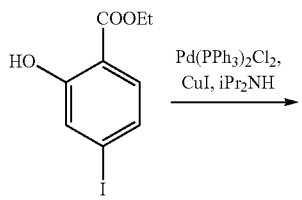

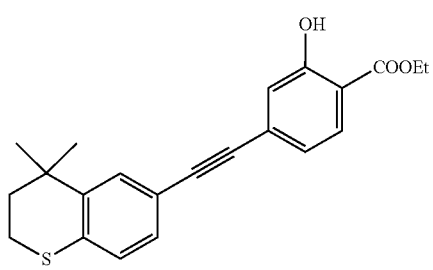

WYC-103

6-Ethynyl-4,4-dimethylthiochroman (202.8 mg, 1 mmol) and ethyl 2-hydroxy-4-iodobenzoate (292 mg, 1 mmol) were added to a flask, followed by addition of Pd(PPh$_3$)$_2$Cl$_2$ (14 mg, 0.02 mmol) and CuI (7.6 mg, 0.04 mmol). After the flask was purged with argon for 3 times to remove oxygen, 2 mL dry DMF and 0.2 mL dry iPr$_2$NH were added via syringe. The reaction was continued at room temperature for 8 h and monitored by TLC. After completion of the reaction, the reaction was quenched with saturated ammonium chloride solution, and the mixture was diluted with ethyl acetate, washed with saturated ammonium chloride solution and saturated sodium chloride solution. The organic phase was dried over anhydrous sodium sulfate, filtered, concentrated and purified by flash column chromatography (PE: EtOAc=100:1 to 50:1) to give WYC-103 (300 mg, 82%). $^1$H NMR (400 MHz, CDCl$_3$) δ 7.80 (d, 1H), 7.52 (s, 1H), 7.18-7.20 (d, 1H), 7.12 (s, 1H), 7.06-7.07 (s, 1H), 7.00-7.02 (s, 1H), 4.39-4.44 (q, 2H), 3.04-3.06 (t, 2H), 1.95-1.97 (t, 2H), 1.44 (t, 3H), 1.35 (s, 6H); $^{13}$C NMR (101 MHz, CDCl$_3$) δ 169.97, 161.45, 142.27, 134.07, 130.80, 130.02, 129.91, 129.26, 126.74, 122.37, 120.25, 117.94, 112.22, 93.19, 88.02, 77.48, 77.36, 77.16, 76.84, 61.71, 37.30, 33.12, 30.11, 29.85, 23.37, 14.34; ESI(+)–MS: 367.5 [M+1]$^+$.

Embodiment 4: ethyl 4-((4,4-dimethylthiochroman-6-yl)ethynyl)-2-methoxybenzoate

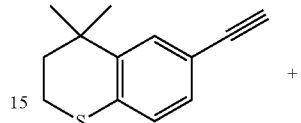

+

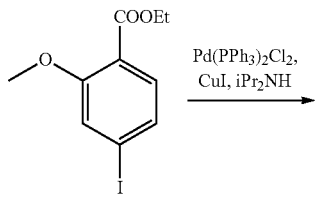

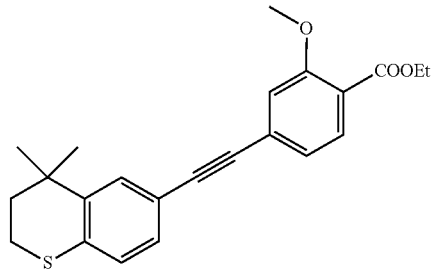

WYC-104

6-Ethynyl-4,4-dimethylthiochroman (202.8 mg, 1 mmol) and ethyl 2-methoxy-4-iodobenzoate (306 mg, 1 mmol) were added to a flask, followed by addition of Pd(PPh$_3$)$_2$Cl$_2$ (14 mg, 0.02 mmol) and CuI (7.6 mg, 0.04 mmol). After the flask was purged with argon for 3 times to remove oxygen, 2 mL dry DMF and 0.2 mL dry iPr$_2$NH were added via syringe. The reaction was continued at room temperature for 8 h and monitored by TLC. After completion of the reaction, the reaction was quenched with saturated ammonium chloride solution, and the mixture was diluted with ethyl acetate, washed with saturated ammonium chloride solution and saturated sodium chloride solution. The organic phase was dried over anhydrous sodium sulfate, filtered, concentrated and purified by flash column chromatography (PE: EtOAc=100:1 to 50:1) to give WYC-104 (293 mg, 77%). $^1$H NMR (400 MHz, CDCl$_3$) δ 7.77 (d, J=7.9 Hz, 1H), 7.53 (d, J=1.7 Hz, 1H), 7.20 (dd, J=8.2, 1.7 Hz, 1H), 7.14-7.11 (m, 1H), 7.11-7.05 (m, 2H), 4.36 (q, J=7.1 Hz, 2H), 3.93 (s, 3H), 3.07-3.04 (m, 2H), 1.95-1.98 (m, 2H), 1.39 (t, 3H), 1.35 (s, 6H); $^{13}$C NMR (101 MHz, CDCl$_3$) δ 165.81, 159.12, 142.28, 133.97, 131.77, 129.96, 129.19, 128.70, 126.76, 123.42, 119.93, 117.98, 114.94, 92.39, 77.48, 77.37, 77.16, 76.85, 61.07, 56.25, 37.31, 33.13, 30.14, 29.85, 23.37, 14.46; ESI(+)–MS: 381.4 [M+1]$^+$.

Embodiment 5: 4-((4,4-dimethylthiochroman-6-yl)ethynyl)-2-hydroxybenzoic Acid

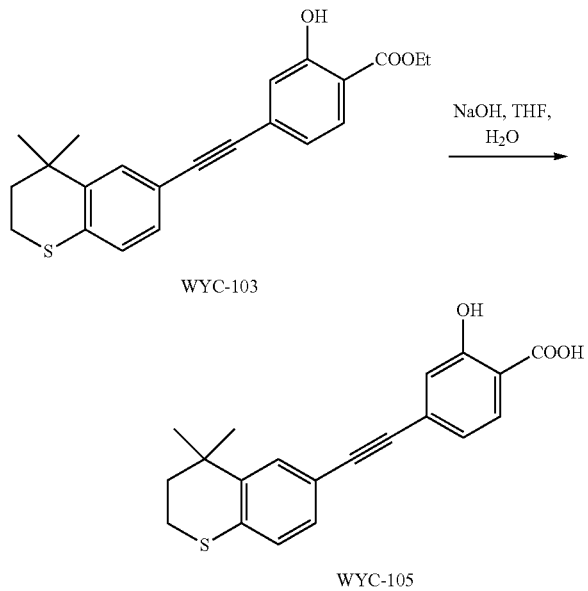

WYC-103 (183 mg, 0.5 mmol) was dissolved in 5 mL THF, then 1 mL 0.5M NaOH solution was added dropwise. The reaction was continued at room temperature for 8 hours and monitored by TLC. After completion of the reaction, the reaction solution was neutralized to pH 7 with 0.5M HCl solution, diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=10:1 to 1:1) to give WYC-105 (144 mg, 85%). $^1$H NMR (500 MHz, cdcl$_3$) δ 10.50 (s, 1H), 7.86-7.84 (d, 1H), 7.53 (d, 1H), 7.21-7.19 (dd, 1H), 7.14 (d, 1H), 7.08-7.06 (d, 1H), 7.05-7.04 (dd, 1H), 3.07-3.04 (m, 1H), 1.98-1.95 (m, 1H), 1.35 (s, 6H); $^{13}$C NMR (125 MHz, CDCl$_3$) δ 171.84, 161.46, 142.17, 131.83, 130.58, 129.91, 129.16, 126.63, 120.24, 117.56, 110.03, 89.85, 37.15, 32.99, 29.97, 29.70, 23.24; ESI(−)-MS: 337.1 [M−1]$^-$.

Embodiment 6: methyl 4-((4,4-dimethylthiochroman-6-yl)ethynyl)-2-methoxybenzoate

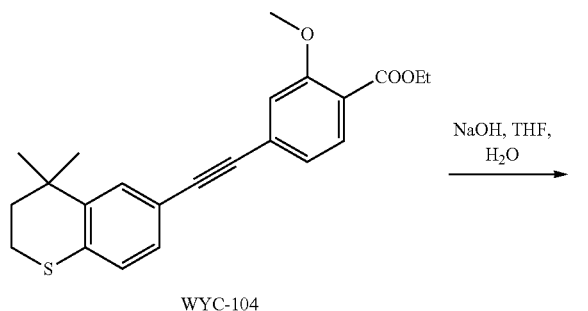

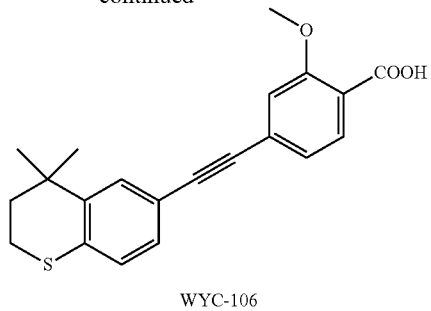

WYC-104 (190 mg, 0.5 mmol) was dissolved in 5 mL THF, then 1 mL 0.5M NaOH solution was added dropwise. The reaction was continued at room temperature for 8 hours and monitored by TLC. After completion of the reaction, the reaction solution was neutralized to pH 7 with 0.5M HCl solution, diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=10:1 to 4:1) to give WYC-106 (151 mg, 86%). $^1$H NMR (500 MHz, CDCl$_3$) δ 10.60 (s, 1H), 8.14 (d, J=7.9 Hz, 1H), 7.54 (s, 1H), 7.28 (m, 2H), 7.22 (m, 1H), 7.08 (d, J=7.9 Hz, 1H), 7.08 (s, 3H), 3.06 (m, 2H), 1.96 (m, 2H), 1.35 (s, 6H); $^{13}$C NMR (101 MHz, CDCl$_3$) δ 165.02, 157.85, 142.36, 134.56, 133.90, 130.59, 130.00, 129.21, 126.81, 125.42, 117.51, 116.99, 114.42, 94.06, 87.56, 77.48, 77.36, 77.16, 76.84, 56.98, 37.22, 33.12, 30.10, 29.83, 23.37; ESI(−)-MS: 351.2 [M−1]$^-$.

Embodiment 7: methyl 4-((4,4-dimethylthiochroman-6-yl)ethynyl)-3-hydroxybenzoate

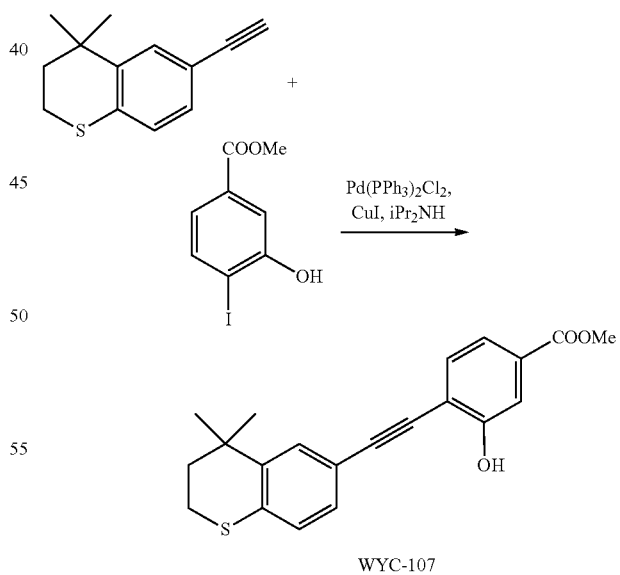

6-Ethynyl-4,4-dimethylthiochroman (202.8 mg, 1 mmol) and methyl 3-hydroxy-4-iodobenzoate (278.1 mg, 1 mmol) were added to a flask, followed by addition of Pd(PPh$_3$)$_2$Cl$_2$ (14 mg, 0.02 mmol) and CuI (7.6 mg, 0.04 mmol). After the flask was purged with argon for 3 times to remove oxygen, 2 mL dry DMF and 0.2 mL dry iPr$_2$NH were added via syringe. The reaction was continued at room temperature for 8 h and monitored by TLC. After completion of the reaction, the reaction was quenched with saturated ammonium chloride solution, and the mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=100:1 to 10:1) to give WYC-107 (245 mg, 71%). $^1$H NMR (500 MHz, CDCl$_3$) δ 7.64 (d, J=1.5 Hz, 1H), 7.58 (dd, J=8.0, 1.6 Hz, 1H), 7.52 (d, J=1.7 Hz, 1H), 7.46 (d, J=8.0 Hz, 1H), 7.19 (dd, J=8.2, 1.7 Hz, 1H), 7.08 (d, J=8.1 Hz, 1H), 6.02 (s, 1H), 3.91 (s, 3H), 3.06-3.04 (m, 2H), 1.94-1.97 (m, 2H), 1.34 (s, 6H); $^{13}$C NMR (101 MHz, CDCl$_3$) δ 166.45, 156.21, 142.31, 134.62, 131.53, 131.43, 129.70, 128.97, 126.73, 121.48, 117.03, 115.72, 114.61, 99.27, 81.86, 77.37, 77.05, 76.74, 52.33, 37.06, 32.99, 29.94, 23.24; ESI(+)–MS: 353.4 [M+1]$^+$.

Embodiment 8: methyl 4-((4,4-dimethylthiochroman-6-yl)ethynyl)-3-methoxybenzoate

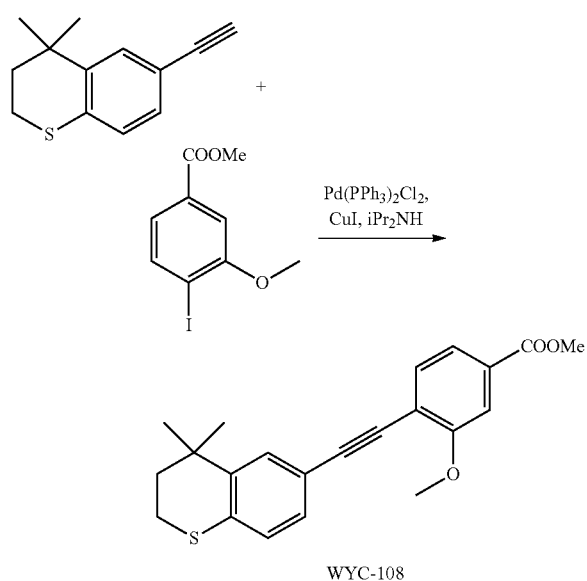

6-Ethynyl-4,4-dimethylthiochroman (202.8 mg, 1 mmol) and methyl 3-methoxy-4-iodobenzoate (292.1 mg, 1 mmol) were added to a flask, followed by addition of Pd(PPh$_3$)$_2$Cl$_2$ (14 mg, 0.02 mmol) and CuI (7.6 mg, 0.04 mmol). After the flask was purged with argon for 3 times to remove oxygen, 2 mL dry DMF and 0.2 mL dry iPr$_2$NH were added via syringe. The reaction was continued at room temperature for 8 h and monitored by TLC. After completion of the reaction, the reaction was quenched with saturated ammonium chloride solution, and the mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=100:1 to 10:1) to give WYC-108 (275 mg, 75%). $^1$H NMR (500 MHz, CDCl$_3$) δ 7.61-7.63 (d, 1H), 7.52-7.56 (m, 3H), 7.21-7.23 (dd, 1H), 7.05-7.07 (d, 1H), 3.97 (s, 3H), 3.93 (s, 3H), 3.03-3.06 (m, 1H), 1.94-1.97 (m, 1H), 1.34 (s, 6H); $^{13}$C NMR (126 MHz, cdcl$_3$) δ 166.59, 159.56, 141.99, 133.50, 133.19, 130.64, 129.80, 129.14, 126.49, 121.75, 118.27, 111.25, 96.82, 84.38, 77.26, 77.01, 76.76, 56.07, 52.29, 37.24, 32.97, 29.98, 23.22; ESI(+)–MS: 367.3 [M+1]$^+$.

Embodiment 9: 4-((4,4-dimethylthiochroman-6-yl)ethynyl)-3-methoxybenzoic Acid

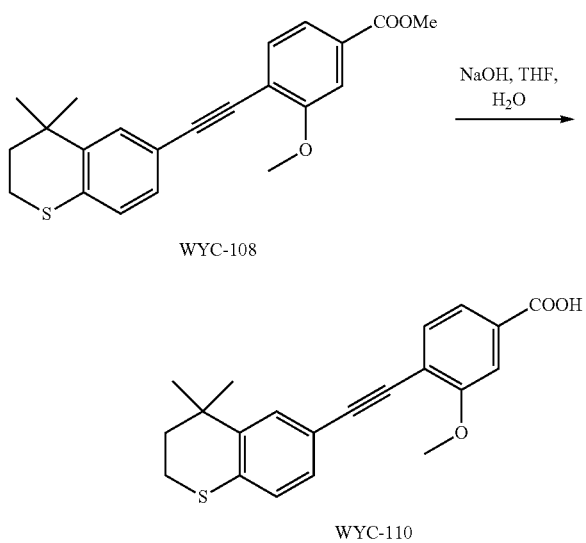

WYC-108 (190 mg, 0.5 mmol) was dissolved in 5 mL THF, and 1 mL 0.5M NaOH solution was added dropwise. The reaction was continued at room temperature for 8 hours and monitored by TLC. After completion of the reaction, the reaction solution was neutralized to pH 7 with 0.5M HCl solution, diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=10:1 to 2:1) to give WYC-110 (1541 mg, 80%). $^1$H NMR (500 MHz, CDCl$_3$) δ 7.69 (dd, 1H), 7.61 (s, 1H), 7.58-7.55 (m, 2H), 7.23 (dd, 1H), 7.07 (d, 1H), 3.99 (s, 3H), 3.06-3.04 (m, 2H), 1.97-1.95 (m, 2H), 1.34 (s, 6H); ESI(+)–MS: 339.3 [M+1]$^+$.

Embodiment 10: 2-cyano-5-((4,4-dimethylthiochroman-6-yl)ethynyl)pyrimidine

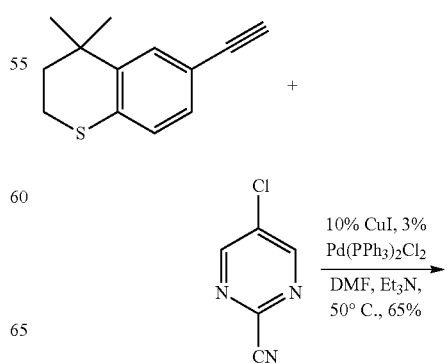

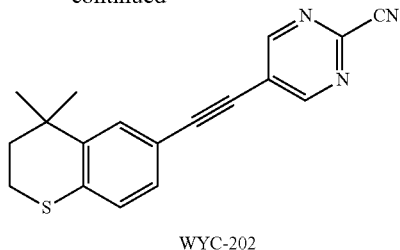

WYC-202

Commercially available 4,4-dimethyl-6-ethynylthiochroman (202.8 mg, 1.0 mmol) and 2-cyano-5-chloropyrimidine (93 mg, 0.67 mmol) used as raw material were added to a flask, followed by addition of Pd(PPh$_3$)$_2$Cl$_2$ (23 mg, 0.03 mmol) and CuI (19 mg, 0.1 mmol). After the flask was purged with argon for 3 times to remove oxygen, 2 mL dry DMF and 0.25 mL dry Et$_3$N were added via syringe. The reaction was continued at 50° C. for 22 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=30:1) to give WYC-202 (133 mg, 65%). $^1$H NMR (400 MHz, CDCl$_3$) δ 8.89 (s, 2H), 7.55 (d, J=1.6 Hz, 1H), 7.21 (dd, J=8.2, 1.7 Hz, 1H), 7.11 (d, J=8.2 Hz, 1H), 3.11-3.03 (m, 2H), 2.01-1.93 (m, 2H), 1.35 (s, 6H); $^{13}$C NMR (126 MHz, CDCl$_3$) δ 159.21, 142.59, 141.79, 136.33, 130.15, 129.31, 126.98, 122.88, 116.13, 115.70, 101.85, 81.24, 37.02, 33.15, 30.02, 23.42. ESI(+)–MS: 306.3 [M+1]$^+$.

Embodiment 11: ethyl 2-((4,4-dimethylthiochroman-6-yl)ethynyl)pyrimidin-5-carboxylate

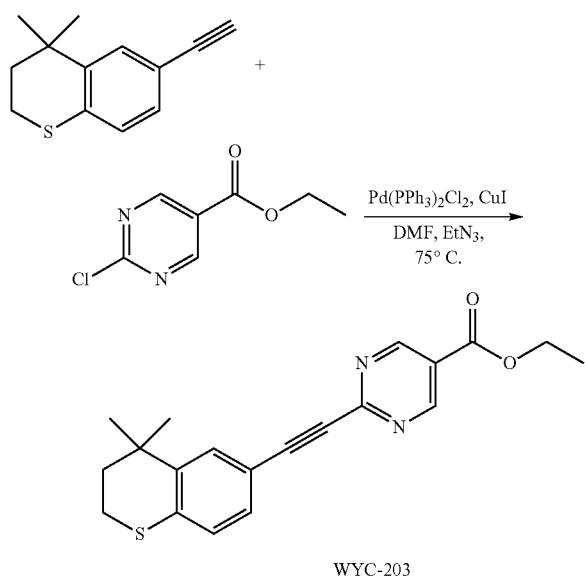

WYC-203

4,4-Dimethyl-6-ethynylthiochroman (202.8 mg, 1.0 mmol) and ethyl 2-chloropyrimidin-5-carboxylate (156 mg, 0.83 mmol) used as raw material were added to a flask, followed by addition of Pd(PPh$_3$)$_2$Cl$_2$ (42 mg, 0.06 mmol) and CuI (19 mg, 0.1 mmol). After the flask was purged with argon for 3 times to remove oxygen, 2 mL dry DMF and 0.3 mL dry Et$_3$N were added via syringe. The reaction was continued at 80° C. for 22 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=15:1) to give WYC-203 (257 mg, 73%). $^1$H NMR (500 MHz, CDCl$_3$) δ 9.24 (s, 2H), 7.69 (d, J=1.7 Hz, 1H), 7.33 (dd, J=8.2, 1.8 Hz, 1H), 7.09 (d, J=8.2 Hz, 1H), 4.45 (q, J=7.1 Hz, 1H), 3.11-2.99 (m, 2H), 1.99-1.92 (m, 2H), 1.43 (t, J=7.1 Hz, 3H), 1.33 (s, 6H); $^{13}$C NMR (126 MHz, CDCl$_3$) δ 163.52, 158.44, 155.85, 142.39, 136.48, 131.36, 130.15, 126.83, 121.88, 115.96, 92.65, 87.97, 62.14, 37.09, 33.14, 30.05, 23.43, 14.38. ESI(+)–MS: 353.2 [M+1]$^+$.

Embodiment 12: methyl 5-((4,4-dimethylthiochroman-6-yl)ethynyl)pyrimidin-2-carboxylate

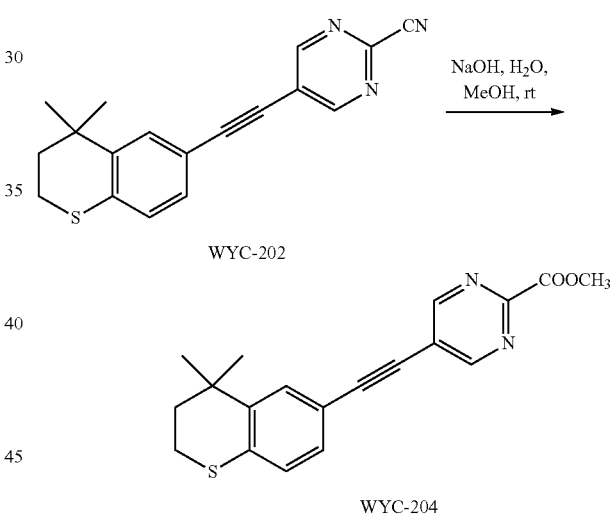

WYC-202 (50 mg, 0.164 mmol) was added to a flask, followed by addition of a solution of NaOH (20 mg, 0.491 mmol) in 0.5 mL water and 0.5 mL methanol. Then the reaction was continued at 60° C. for 5 h and monitored by TLC. After completion of the reaction, the reaction solution was neutralized to pH 7 with 1M HCl solution, diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=15:1) to give WYC-204 (39 mg, 74%). $^1$H NMR (500 MHz, CDCl$_3$) δ 8.63 (s, 2H), 7.51 (d, J=0.7 Hz, 1H), 7.17 (dd, J=8.1, 0.9 Hz, 1H), 7.07 (d, J=8.2 Hz, 1H), 4.04 (s, 3H), 3.11-2.91 (m, 2H), 2.04-1.90 (m, 2H), 1.34 (s, 6H); $^{13}$C NMR (126 MHz, CDCl$_3$) δ 164.02, 161.24, 142.32, 134.10, 129.72, 128.97, 126.77, 117.65, 113.33, 94.71, 81.81, 55.37, 37.28, 33.12, 30.11, 23.36. ESI(+)–MS: 339.2 [M+1]$^+$.

Embodiment 13: ethyl 5-((4,4-dimethylthiochroman-6-yl)ethynyl)pyrimidin-2-carboxylate

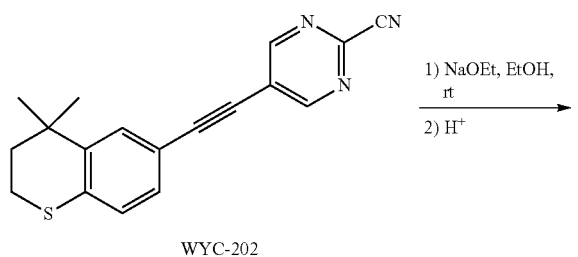

WYC-202 (50 mg, 0.164 mmol) was added to a flask, followed by addition of sodium ethoxide (34 mg, 0.492 mmol) and 5 mL ethanol. Then the reaction was continued at 45° C. overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=8:1) to give WYC-205 (36 mg, 62%). $^1$H NMR (500 MHz, CDCl$_3$) δ 8.62 (s, 2H), 7.51 (s, 1H), 7.17 (dd, J=8.1, 0.8 Hz, 1H), 7.07 (d, J=8.1 Hz, 1H), 4.45 (q, J=7.1 Hz, 2H), 3.09-3.00 (m, 2H), 2.00-1.92 (m, 2H), 1.45 (t, J=7.1 Hz, 3H), 1.34 (s, 6H); $^{13}$C NMR (126 MHz, CDCl$_3$) δ 163.61, 161.23, 142.32, 134.05, 129.72, 128.97, 126.77, 117.71, 113.13, 94.60, 81.91, 64.11, 37.30, 33.13, 30.11, 23.36, 14.55. ESI(+)–MS: 353.5 [M+1]$^+$.

Embodiment 14: 2-((4,4-dimethylthiochroman-6-yl)ethynyl)pyrimidin-5-carboxylic acid WYC-203 (50 mg, 0.142 mmol) was added to a flask, followed by addition of 2 mL 2.0 mol/L NaOH solution and 2 mL methanol. Then the reaction was continued at 45° C. for 5 h and monitored by TLC. After completion of the reaction, the reaction solution was neutralized to weak acidic with 1 mol/L HCl solution, diluted with ethyl acetate, extracted, washed with saturated sodium chloride solution. The organic phase was dried over anhydrous sodium sulfate, filtered, concentrated and purified by flash column chromatography (dichloromethane:methanol=15:1) to give WYC-206 (41 mg, 89%). $^1$H NMR (400 MHz, CD$_3$OD) δ 9.21 (s, 2H), 7.71 (d, J=1.6 Hz, 1H), 7.29 (dd, J=8.2, 1.8 Hz, 1H), 7.11 (d, J=8.2 Hz, 1H), 3.14-3.06 (m, 2H), 2.05-1.92 (m, 2H), 1.36 (s, 6H); $^{13}$C NMR (101 MHz, CD$_3$OD) δ 167.13, 159.54, 155.24, 143.92, 137.92, 131.86, 130.67, 127.84, 117.11, 111.42, 92.11, 88.26, 49.64, 49.43, 49.21, 49.00, 48.79, 48.57, 48.36, 38.12, 33.99, 30.18, 23.98. ESI(+)–MS: 325.3 [M+1]$^+$.

Embodiment 15: 2-cyano-5-((4,4-dimethyl-1-oxothiochroman-6-yl)ethynyl)pyrimidine WYC-202 (30 mg, 0.098 mmol) was added to a flask, followed by addition of 2 mL dry dichloromethane. After the mixture was cooled to 0° C. under an ice bath, mCPBA (24 mg, 0.098 mmol) was added. Then the reaction was continued for 1 hour under an ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:2) to give WYC-207 (27 mg, 86%). $^1$H NMR (500 MHz, CDCl$_3$) δ 8.95 (s, 2H), 7.82 (d, J=8.1 Hz, 1H), 7.64 (d, J=1.5 Hz, 1H), 7.55 (dd, J=8.0, 1.5 Hz, 1H), 3.30-3.08 (m, 2H), 2.44 (ddd, J=15.0, 10.1, 2.0 Hz, 1H), 1.93 (ddd, J=15.1, 9.2, 2.1 Hz, 1H), 1.49 (s, 3H), 1.36 (s, 3H); $^{13}$C NMR (126 MHz, CDCl$_3$) δ 159.64, 145.41, 142.59, 131.57, 130.38, 130.36, 124.24, 121.99, 115.52, 99.38, 83.14, 43.53, 34.76, 31.38, 31.31, 29.96. ESI(+)-MS: 322.3 [M+1]$^+$.

Embodiment 16: ethyl 5-((4,4-dimethyl-1-oxothiochroman-6-yl)ethynyl)pyrimidin-2-carboxylate

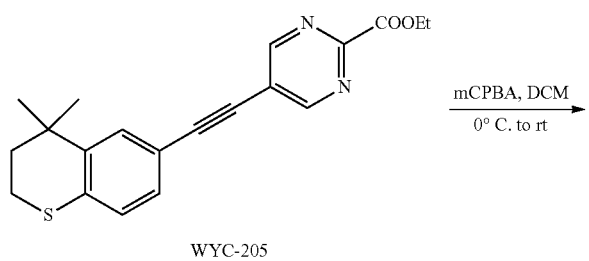

WYC-205

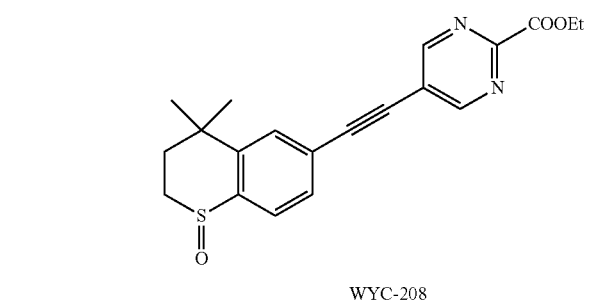

WYC-208

WYC-205 (70 mg, 0.2 mmol) was added to a flask, followed by addition of 3 mL dry dichloromethane. After the mixture was cooled to 0° C. under an ice bath, mCPBA (49 mg, 0.2 mmol) was added. Then the reaction was continued for 1 hour under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:2) to give WYC-208 (68 mg, 93%). $^1$H NMR (500 MHz, CDCl$_3$) δ 8.66 (s, 2H), 7.75 (d, J=8.0 Hz, 1H), 7.59 (s, 1H), 7.49 (d, J=7.7 Hz, 1H), 4.47 (q, J=7.1 Hz, 2H), 3.16 (dt, J=20.8, 11.7 Hz, 2H), 2.46 (dd, J=14.5, 10.3 Hz, 1H), 1.90 (dd, J=14.6, 8.0 Hz, 2H), 1.48 (s, 3H), 1.45 (t, J=7.1 Hz, 3H), 1.34 (s, 3H); $^{13}$C NMR (126 MHz, CDCl$_3$) δ 163.95, 161.56, 145.06, 131.11, 130.39, 129.99, 125.91, 112.28, 93.14, 84.74, 64.30, 43.37, 34.61, 31.36, 31.23, 29.76, 14.52. ESI(+)-MS: 369.4 [M+1]$^+$.

Embodiment 17: ethyl 2-((4,4-dimethyl-1-oxothiochroman-6-yl)ethynyl)pyrimidin-5-carboxylate

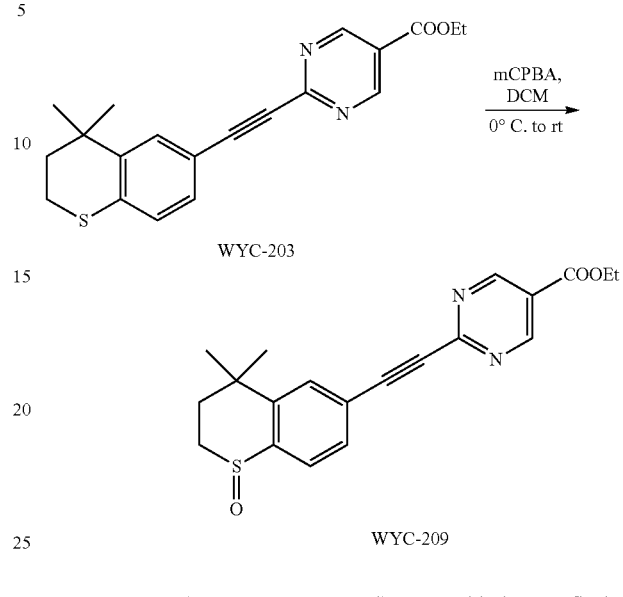

WYC-203 (48 mg, 0.14 mmol) was added to a flask, followed by addition of 3 mL dry dichloromethane. After the mixture was cooled to 0° C. under an ice bath, mCPBA (34 mg, 0.14 mmol) was added. Then the reaction was continued for 1 hour under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:2) to give WYC-209 (43 mg, 84%). $^1$H NMR (500 MHz, CDCl$_3$) δ 9.29 (s, 2H), 7.82-7.75 (m, 2H), 7.66 (d, J=7.9 Hz, 1H), 4.47 (q, J=7.1 Hz, 2H), 3.24 (t, J=11.1 Hz, 1H), 3.15 3.07 (m, 1H), 2.43 (dd, J=14.0, 10.4 Hz, 1H), 1.92 (dd, J=14.9, 8.8 Hz, 1H), 1.47 (s, 3H), 1.44 (t, J=7.2 Hz, 3H), 1.34 (s, 3H); $^{13}$C NMR (126 MHz, CDCl$_3$) δ 163.33, 158.54, 155.32, 145.19, 132.61, 131.06, 130.22, 124.22, 122.62, 89.60, 89.35, 62.32, 34.75, 31.36, 31.25, 29.93, 14.39. ESI(+)-MS: 369.4 [M+1]$^+$; HRMS-ESI (m/z) calculated C$_{20}$H$_{21}$N$_2$O$_3$S, 369.1273 [M+1]$^+$, found 369.1267.

WYC-209A: ethyl 2-((4,4-dimethyl-1S-oxothiochroman-6-yl)ethynyl)pyrimidin-5-carboxylate

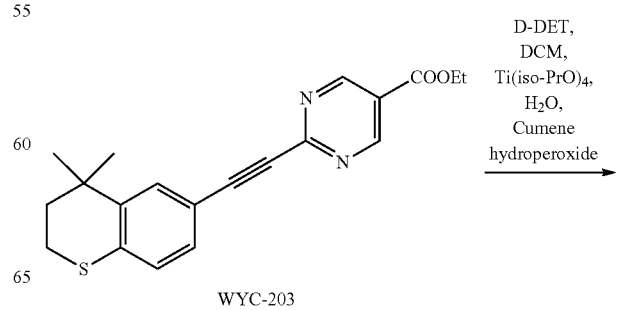

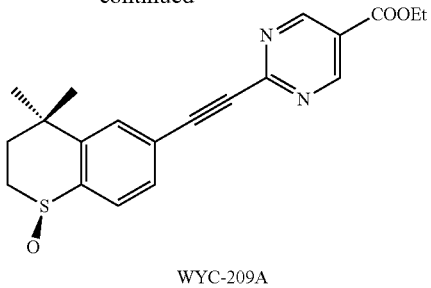

WYC-209A

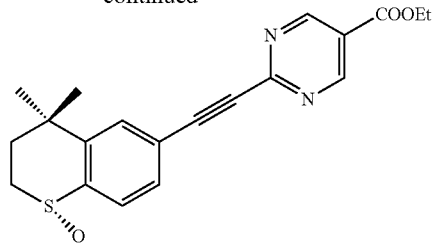

WYC-209B

Diethyl D-tartrate (82.7 mg, 0.4 mmol) was dissolved in anhydrous $CH_2Cl_2$ (1 mL), and Ti(iso-PrO)$_4$ (0.2 mmol, 58 μL) was quickly added at 16° C. After the mixture was stirred for 3 minutes, water (3.6 μL, 0.2 mmol) was slowly added dropwise, and the mixture was stirred for another 20 minutes. The mixture was cooled to −20° C., then WYC-203 (69 mg, 0.2 mmol) and cumene hydroperoxide (74 μL, 0.4 mmol) were quickly added, and the reaction was stopped after 3 hours. The reaction solution was poured into 10 mL mixed solution of ferrous sulfate (0.2 g) and citric acid (67 mg) in water, dioxane and diethyl ether (2:1:2), and the mixture was stirred for 15 minutes. The aqueous phase was extracted with diethyl ether, the organic layers were combined, washed with 0.5M $K_2CO_3$ and saturated sodium chloride solution, dried over anhydrous sodium sulfate, filtered, concentrated and purified by flash column chromatography (PE:EtOAc=1:2) to give WYC-209A (43 mg, 84%, ee %=90%). The product was recrystallized with diethyl ether to give WYC-209A (25 mg, ee %=99%). $^1$H NMR (500 MHz, CDCl$_3$) δ 9.29 (s, 2H), 7.82-7.75 (m, 2H), 7.66 (d, J=7.9 Hz, 1H), 4.47 (q, J=7.1 Hz, 2H), 3.24 (t, J=11.1 Hz, 1H), 3.15-3.07 (m, 1H), 2.43 (dd, J=14.0, 10.4 Hz, 1H), 1.92 (dd, J=14.9, 8.8 Hz, 1H), 1.47 (s, 3H), 1.44 (t, J=7.2 Hz, 3H), 1.34 (s, 3H); $^{13}$C NMR (126 MHz, CDCl$_3$) δ 163.33, 158.54, 155.32, 145.19, 132.61, 131.06, 130.22, 124.22, 122.62, 89.60, 89.35, 62.32, 34.75, 31.36, 31.25, 29.93, 14.39. ESI(+)–MS: 369.4 [M+1]$^+$. ee % was determined by chiral HPLC as follows: Agilent 1260 infinity liquid chromatograph, column Lux Cellulose-1 250*4.6 mm, mobile phase: acetonitrile/H$_2$O=80:20, 20° C., 0.7 mL/min; the retention time was 8.592 min.

WYC-209B: ethyl 2-((4,4-dimethyl-1R-oxothiochroman-6-yl)ethynyl)pyrimidin-5-carboxylate

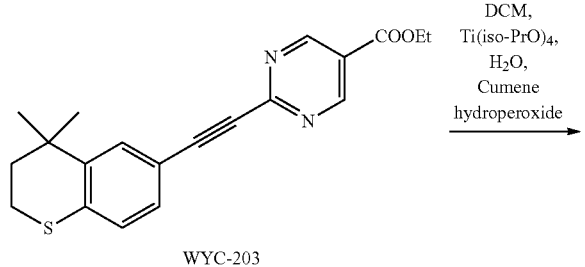

WYC-203

L-DET,
DCM,
Ti(iso-PrO)$_4$,
H$_2$O,
Cumene
hydroperoxide
→

Diethyl L-tartrate (82.7 mg, 0.4 mmol) was dissolved in anhydrous $CH_2Cl_2$ (1 mL), and Ti(iso-PrO)$_4$ (0.2 mmol, 58 μL) was quickly added at 16° C. After the mixture was stirred for 3 minutes, water (3.6 μL, 0.2 mmol) was slowly added dropwise and the mixture was stirred for another 20 minutes. The mixture was cooled to −20° C., then WYC-203 (69 mg, 0.2 mmol) and cumene hydroperoxide (74 μL, 0.4 mmol) were quickly added, and the reaction was stopped after 3 hours. The reaction solution was poured into 10 mL mixed solution of ferrous sulfate (0.2 g) and citric acid (67 mg) in water, dioxane and diethyl ether (2:1:2), and the mixture was stirred for 15 minutes. The aqueous phase was extracted with diethyl ether, the organic layers were combined, washed with 0.5M $K_2CO_3$ and saturated sodium chloride solution, dried over anhydrous sodium sulfate, filtered, concentrated and purified by flash column chromatography (PE:EtOAc=1:2) to give WYC-209B (43 mg, 84%, ee %=90%). The product was recrystallized with diethyl ether to give WYC-209B (25 mg, ee %=99%). $^1$H NMR (500 MHz, CDCl$_3$) δ 9.29 (s, 2H), 7.82-7.75 (m, 2H), 7.66 (d, J=7.9 Hz, 1H), 4.47 (q, J=7.1 Hz, 2H), 3.24 (t, J=11.1 Hz, 1H), 3.15-3.07 (m, 1H), 2.43 (dd, J=14.0, 10.4 Hz, 1H), 1.92 (dd, J=14.9, 8.8 Hz, 1H), 1.47 (s, 3H), 1.44 (t, J=7.2 Hz, 3H), 1.34 (s, 3H); $^{13}$C NMR (126 MHz, CDCl$_3$) δ 163.33, 158.54, 155.32, 145.19, 132.61, 131.06, 130.22, 124.22, 122.62, 89.60, 89.35, 62.32, 34.75, 31.36, 31.25, 29.93, 14.39. ESI(+)–MS: 369.4 [M+1]$^+$. ee % was determined by chiral HPLC as follows: Agilent 1260 infinity liquid chromatograph, column Lux Cellulose-1 250*4.6 mm, mobile phase: acetonitrile/H$_2$O=80:20, 20° C., 0.7 mL/min; the retention time was 9.147 min.

Figure 17:
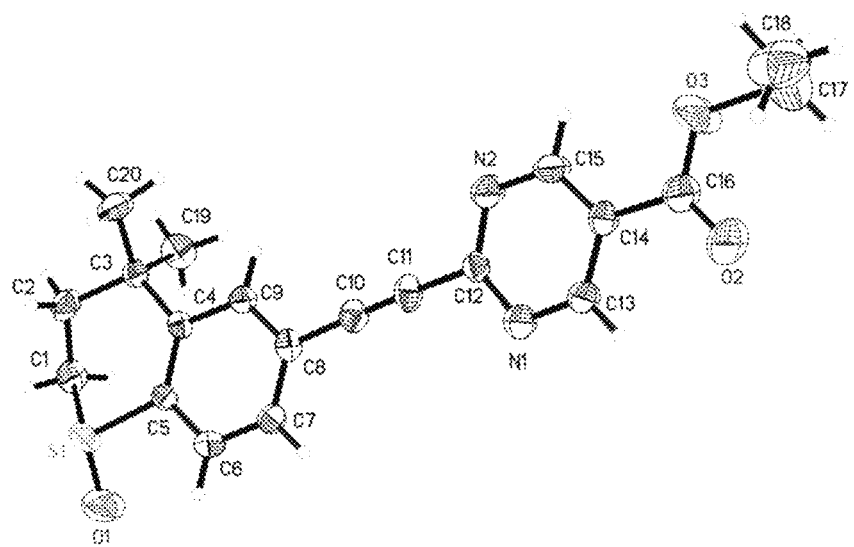
FIG. 17 shows the single crystal structure of WYC-209A.
Figure 18:
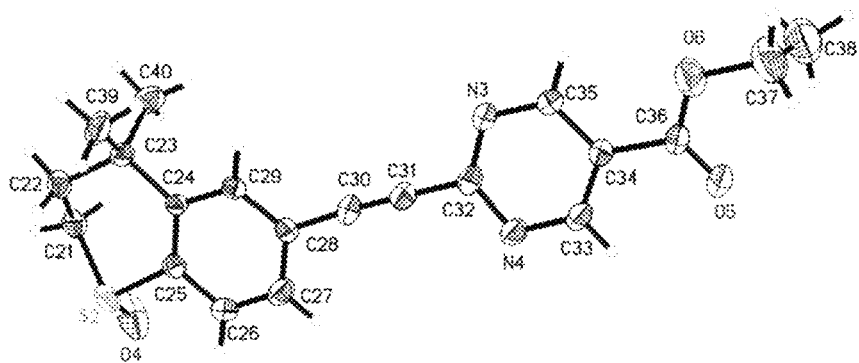
FIG. 18 shows the single crystal structure of WYC-209B.

The single crystal structure diagrams of WYC-209A and WYC-209B were shown in FIG. 17 and FIG. 18 respectively. The crystal belonged to monoclinic crystal system, the space group was P21, and the unit cell parameters were as follows: a=7.9718(11) Å, b=22.980(3) Å, c=10.4356(15 Å, α=90°, β=103.010(3)°, γ=90°, the unit cell volume was 1862.7(5) Å 3, the asymmetric unit number in unit cell Z=4, the density was 1.314 Mg/m3.

TABLE 1

Atomic coordinates (×10$^4$) and isotropic displacement parameters (Å$^2$ × 10$^3$)

| | x | y | z | U(eq) |
|---|---|---|---|---|
| S(1) | −4896(2) | 5378(1) | 9438(2) | 64(1) |
| S(2) | 9768(2) | 9738(1) | 5287(2) | 60(1) |
| N(1) | 1166(9) | 7867(3) | 5358(7) | 68(2) |
| N(2) | 3322(10) | 7134(3) | 5625(7) | 70(2) |
| N(3) | 1503(9) | 8087(3) | 9298(6) | 60(2) |
| N(4) | 3711(8) | 7376(3) | 9624(7) | 63(2) |
| O(1) | −5859(9) | 5779(3) | 10024(8) | 114(3) |
| O(2) | 3797(11) | 8790(3) | 3055(8) | 115(3) |
| O(3) | 5939(11) | 8134(4) | 3481(9) | 131(3) |

TABLE 1-continued

Atomic coordinates (×10⁴) and isotropic displacement parameters ($Å^2 \times 10^3$)

|  | x | y | z | U(eq) |
|---|---|---|---|---|
| O(4) | 11314(7) | 9798(4) | 6315(6) | 115(3) |
| O(5) | 1038(10) | 6474(3) | 11962(9) | 121(3) |
| O(6) | −1155(8) | 7052(3) | 11353(7) | 97(2) |
| C(1) | −3530(11) | 4926(3) | 10594(7) | 65(2) |
| C(2) | −2367(10) | 4602(3) | 9909(7) | 64(2) |
| C(3) | −944(9) | 4969(3) | 9545(6) | 48(2) |
| C(4) | −1618(8) | 5549(3) | 8933(5) | 39(1) |
| C(5) | −3243(8) | 5771(3) | 8896(6) | 40(1) |
| C(6) | −3757(9) | 6307(3) | 8344(6) | 50(2) |
| C(7) | −2673(9) | 6630(3) | 7800(6) | 50(2) |
| C(8) | −1059(9) | 6425(3) | 7787(6) | 46(2) |
| C(9) | −526(9) | 5892(3) | 8371(6) | 46(2) |
| C(10) | 60(10) | 6751(3) | 7154(7) | 53(2) |
| C(11) | 913(11) | 7023(3) | 6582(7) | 59(2) |
| C(12) | 1867(9) | 7364(3) | 5806(6) | 48(2) |
| C(13) | 2019(10) | 8163(3) | 4650(8) | 62(2) |
| C(14) | 3524(10) | 7974(3) | 4364(7) | 56(2) |
| C(15) | 4120(12) | 7454(3) | 4910(7) | 70(2) |
| C(16) | 4393(13) | 8342(4) | 3535(9) | 74(2) |
| C(17) | 7143(16) | 8549(6) | 2894(10) | 109(4) |
| C(18) | 6503(17) | 8410(6) | 1579(12) | 131(5) |
| C(19) | 510(11) | 5085(4) | 10778(7) | 74(2) |
| C(20) | −240(12) | 4602(4) | 8538(9) | 74(2) |
| C(21) | 8964(12) | 10485(4) | 5260(10) | 55(2) |
| C(22) | 7109(12) | 10483(5) | 4503(10) | 52(2) |
| C(23) | 5908(9) | 10236(3) | 5340(7) | 50(2) |
| C(24) | 6529(7) | 9648(3) | 5968(5) | 37(1) |
| C(25) | 8142(8) | 9413(3) | 6009(6) | 42(2) |
| C(26) | 8650(9) | 8878(3) | 6594(7) | 55(2) |
| C(27) | 7552(10) | 8576(3) | 7197(7) | 57(2) |
| C(28) | 5936(8) | 8802(3) | 7184(6) | 41(1) |
| C(29) | 5458(8) | 9327(3) | 6566(6) | 41(1) |
| C(30) | 4800(10) | 8488(3) | 7839(6) | 51(2) |
| C(31) | 3955(10) | 8211(3) | 8418(7) | 52(2) |
| C(32) | 2989(9) | 7879(3) | 9141(6) | 48(2) |
| C(33) | 2812(10) | 7071(3) | 10342(8) | 63(2) |
| C(34) | 1310(9) | 7251(3) | 10593(7) | 49(2) |
| C(35) | 662(11) | 7776(3) | 10023(8) | 62(2) |
| C(36) | 405(11) | 6883(4) | 11401(8) | 66(2) |
| C(37) | −2274(14) | 6657(6) | 12000(11) | 107(4) |
| C(38) | −1890(19) | 6799(6) | 13361(13) | 130(5) |
| C(39) | 4275(12) | 10156(4) | 4320(7) | 72(2) |
| C(40) | 5551(13) | 10640(4) | 6396(8) | 74(2) |

Embodiment 18: 2-((4,4-dimethyl-1-oxothiochroman-6-yl)ethynyl)pyrimidin-5-carboxylic Acid

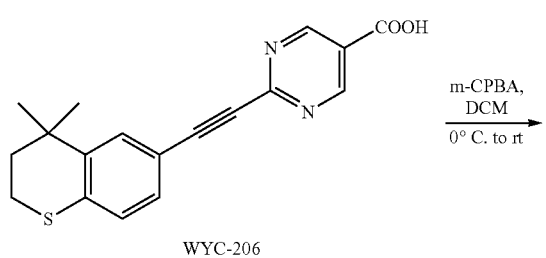

WYC-206

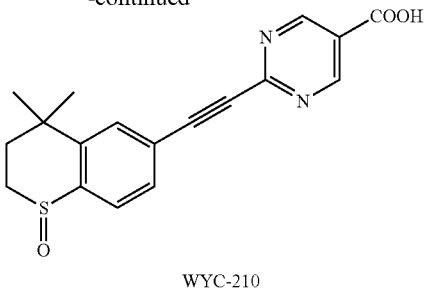

WYC-210

WYC-206 (34 mg, 0.105 mmol) was added to a flask, followed by addition of 1.5 mL dry dichloromethane. After the mixture was cooled to 0° C. under an ice bath, mCPBA (26 mg, 0.105 mmol) was added. Then the reaction was continued for 1 hour under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (DCM:MeOH=12:1) to give WYC-210 (23 mg, 68%). ¹H NMR (500 MHz, pyridine) δ 9.66 (s, 2H), 7.99-7.85 (m, 2H), 7.65 (d, J=7.8 Hz, 1H), 3.20 (t, J=10.7 Hz, 1H), 3.14-3.02 (m, 1H), 2.32 (dd, J=12.9, 10.4 Hz, 1H), 1.72 (dd, J=13.2, 9.4 Hz, 1H), 1.25 (s, 3H), 1.18 (s, 3H). ¹³C NMR (126 MHz, pyridine) δ 166.30, 159.03, 155.15, 145.73, 142.20, 132.56, 130.90, 130.31, 125.00, 124.29, 90.65, 88.52, 43.70, 34.73, 30.89, 30.62, 29.97. ESI(+)-MS: 341.1 [M+1]⁺.

Embodiment 19: 2-amino-4-((4,4-dimethylthiochroman-6-yl)ethynyl)benzoic Acid

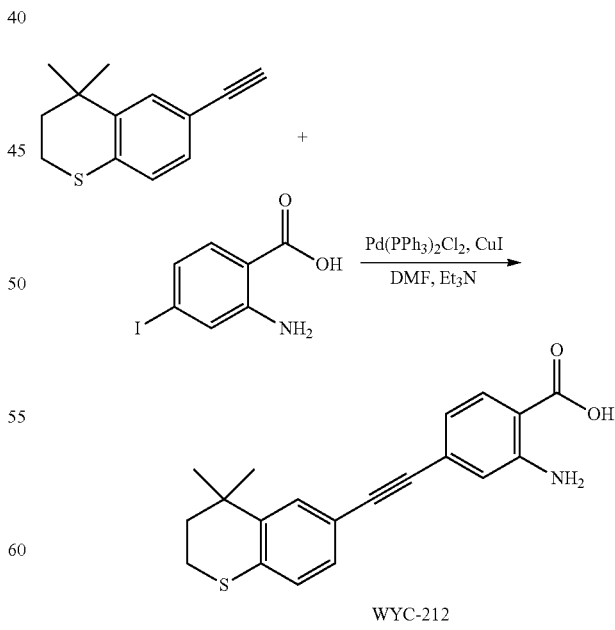

WYC-212

6-Ethynyl-4,4-dimethylthiochroman (405.6 mg, 2 mmol) and 2-amino-4-iodobenzoic acid (263 mg, 1 mmol) were added to a flask, followed by addition of Pd(PPh₃)₂Cl₂ (42 mg, 0.06 mmol) and CuI (23 mg, 0.12 mmol). After the flask was purged with argon for 3 times to remove oxygen, 10 mL dry DMF and 0.2 mL dry Et₃N were added via syringe. Then the reaction was continued at 75° C. for 12 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=5:1) to give WYC-212 (286 mg, 85%). $^1$H NMR (500 MHz, CDCl₃) δ 7.88 (d, J=8.3 Hz, 1H), 7.52 (d, J=1.7 Hz, 1H), 7.18 (dd, J=8.1, 1.8 Hz, 1H), 7.06 (d, J=8.1 Hz, 1H), 6.84 (d, J=1.3 Hz, 1H), 6.81 (dd, J=8.3, 1.5 Hz, 1H), 3.08-3.02 (m, 3H), 1.99-1.94 (m, 2H), 1.35 (s, 6H); $^{13}$C NMR (126 MHz, CDCl₃) δ 165.25, 165.23, 163.21, 161.20, 142.29, 134.42, 133.26, 133.25, 131.70, 131.64, 129.97, 129.27, 126.75, 125.15, 125.12, 117.73, 117.05, 116.92, 116.66, 116.47, 98.04, 98.02, 81.71, 61.62, 37.29, 33.13, 30.09, 23.38, 14.42. ESI(+)-MS: 338.3 [M+1]⁺.

Embodiment 20: 2-acetamido-4-((4,4-dimethylthiochroman-6-yl)ethynyl)benzoic Acid

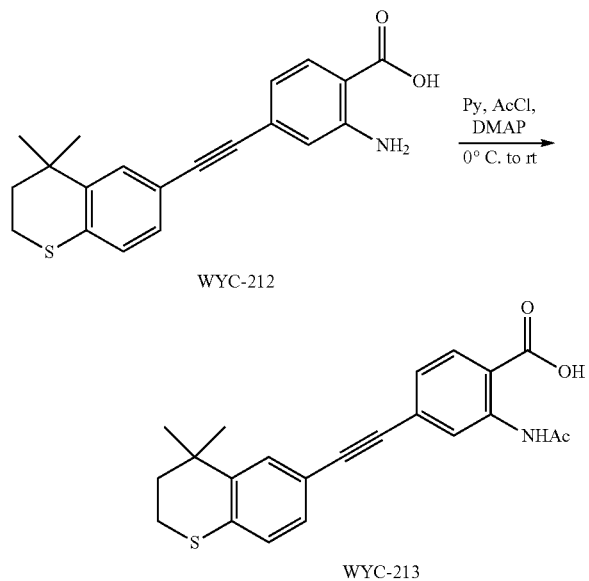

WYC-212 (200 mg, 0.3 mmol) was added to a flask, followed by addition of 10 mg DMAP, then 5 mL dry pyridine was added under argon atmosphere. The mixture was cooled to 0° C. under an ice bath, and 43 μL acetyl chloride was added dropwise. The reaction was continued for 10 min under the ice bath and another 5 h at room temperature, meanwhile TLC was used to monitor the reaction. After completion of the reaction, the reaction was quenched with methanol. The mixture was diluted with ethyl acetate, washed with 1 mol/L hydrochloric acid to remove pyridine, then washed with saturated sodium chloride solution. The organic phase was dried over anhydrous sodium sulfate, filtered, concentrated and purified by flash column chromatography (PE:EtOAc=20:1) to give WYC-213 (195 mg, 87%). $^1$H NMR (500 MHz, CDCl₃) δ 8.13 (d, J=8.1 Hz, 1H), 7.64 (d, J=1.3 Hz, 1H), 7.58 (dd, J=8.1, 1.5 Hz, 1H), 7.55 (d, J=1.7 Hz, 1H), 7.21 (dd, J=8.1, 1.8 Hz, 1H), 7.09 (d, J=8.1 Hz, 1H), 3.09-3.03 (m, 2H), 2.47 (s, 3H), 1.99-1.92 (m, 2H), 1.35 (s, 6H). $^{13}$C NMR (126 MHz, CDCl₃) δ 160.95, 159.37, 146.56, 142.37, 134.76, 132.31, 131.05, 130.06, 129.32, 128.95, 128.49, 126.82, 117.47, 115.64, 95.32, 87.52, 37.23, 33.13, 30.09, 23.39, 21.54. ESI(+)-MS: 380.4 [M+1]⁺.

Embodiment 21: 6-ethynyl-4,4-dimethyl-1-oxothiochroman

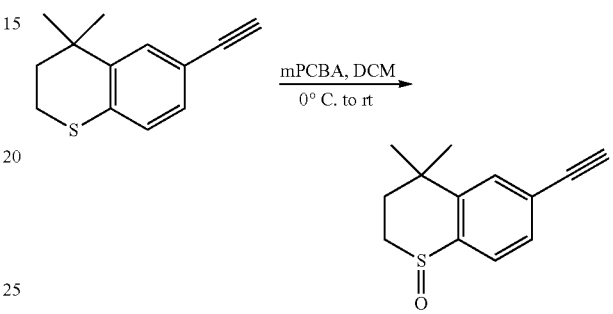

6-Ethynyl-4,4-dimethylthiochroman (2.03 g, 10 mmol) was added to a flask, followed by addition of 27 mL dry dichloromethane. After the mixture was cooled to 0° C. under an ice bath, mCPBA (1.73 g, 10 mmol) was added. Then the reaction was continued for 1 h under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=3:1) to give 1-oxo-6-ethynyl-4,4-dimethylthiochroman (1.43 g, 72%). $^1$H NMR (500 MHz, CDCl₃) δ 7.41 (d, J=8.0 Hz, 1H), 7.26 (s, 1H), 7.15 (d, J=8.0 Hz, 1H), 2.93-2.74 (m, 3H), 2.14 (ddd, J=14.6, 10.5, 1.7 Hz, 1H), 1.58 (ddd, J=15.0, 8.7, 1.8 Hz, 1H), 1.14 (s, 3H), 1.01 (s, 3H); $^{13}$C NMR (126 MHz, CDCl₃) δ 144.82, 138.91, 131.70, 130.53, 130.17, 125.60, 82.69, 79.39, 43.23, 34.47, 31.27, 31.13, 29.67. ESI(+)-MS: 219.3 [M+1]⁺.

Embodiment 22: 2-amino-4-((4,4-dimethyl-1-oxothiochroman-6-yl)ethynyl)benzoic Acid

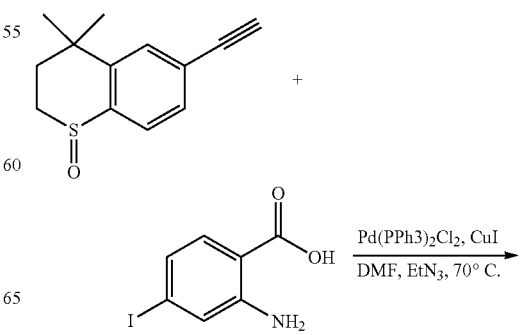

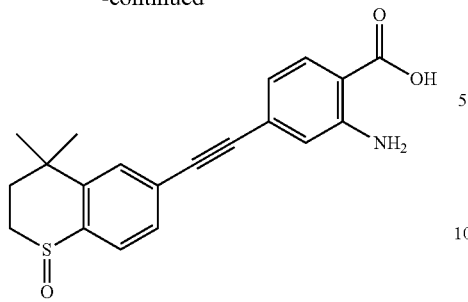

WYC-214

1-Oxo-6-ethynyl-4,4-dimethylthiochroman (263 mg, 1.0 mmol) and 2-amino-4-iodobenzoic acid (262 mg, 1.2 mmol) were added to a flask, followed by addition of Pd(PPh₃)₂Cl₂ (42 mg, 0.06 mmol) and CuI (23 mg, 0.12 mmol). After the flask was purged with argon for 3 times to remove oxygen, 4 mL dry DMF and 0.2 mL dry Et₃N were added via syringe. Then the reaction was continued at 70° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=50:1) to give the product (275 mg, 78%). ¹H NMR (500 MHz, pyridine) δ 8.37 (d, J=8.1 Hz, 1H), 7.92 (d, J=8.0 Hz, 1H), 7.86 (s, 1H), 7.59 (s, 1H), 7.36 (s, 1H), 7.03 (d, J=8.1 Hz, 1H), 5.67 (s, 1H), 3.20-3.14 (m, 1H), 3.11-3.05 (m, 1H), 2.38 (ddd, J=14.2, 10.3, 1.7 Hz, 1H), 1.74-1.68 (m, 1H), 1.26 (s, 3H), 1.17 (s, 3H); ¹³C NMR (126 MHz, pyridine) δ 171.06, 152.34, 145.52, 140.46, 132.80, 131.65, 130.43, 130.20, 127.92, 126.32, 119.79, 118.58, 112.43, 91.82, 90.33, 55.01, 43.59, 34.63, 30.93, 30.63, 29.80. ESI(+)−MS: 354.3 [M+1]⁺.

Embodiment 23: methyl 2-amino-4-((4,4-dimethyl-1-oxothiochroman-6-yl)ethynyl)benzoate

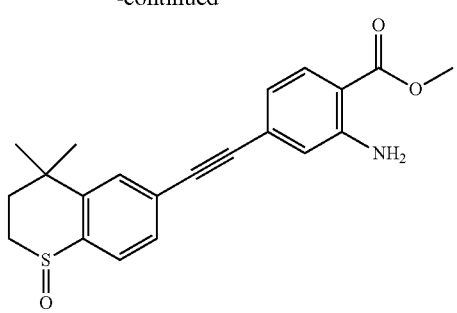

WYC-215

WYC-214 (150 mg, 0.425 mmol) was added to a flask, followed by addition of sodium carbonate (176 mg, 1.275 mmol), then 3 mL dry DMF and iodomethane (40 μL, 0.637 mmol) were added under argon atmosphere. The mixture was slowly heated to 100° C., then the reaction was continued for 6 h and monitored by TLC. After completion of the reaction, the reaction solution was cooled to room temperature, diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=20:1) to give WYC-215 (143 mg, 92%). ¹H NMR (500 MHz, CDCl₃) δ 7.84 (d, J=8.3 Hz, 1H), 7.73 (d, J=8.1 Hz, 1H), 7.58 (d, J=1.5 Hz, 1H), 7.48 (dd, J=8.0, 1.6 Hz, 1H), 6.87 (d, J=1.3 Hz, 1H), 6.81 (dd, J=8.3, 1.5 Hz, 1H), 3.88 (s, 3H), 3.20 (ddd, J=12.9, 10.6, 2.2 Hz, 1H), 3.10 (ddd, J=13.1, 8.7, 2.3 Hz, 1H), 2.46 (ddd, J=14.9, 10.5, 2.2 Hz, 1H), 1.89 (ddd, J=15.1, 8.7, 2.2 Hz, 3H), 1.47 (s, 3H), 1.33 (s, 3H); ¹³C NMR (126 MHz, CDCl₃) δ 168.19, 150.04, 144.92, 138.59, 131.48, 131.30, 130.34, 130.18, 128.13, 126.44, 119.72, 119.64, 111.06, 90.93, 90.26, 51.84, 43.28, 34.57, 31.36, 31.21, 29.73. ESI(+)−MS: 368.4 [M+1]⁺.

Embodiment 24: ethyl 2-amino-4-((4,4-dimethylthiochroman-6-yl)ethynyl)benzoate

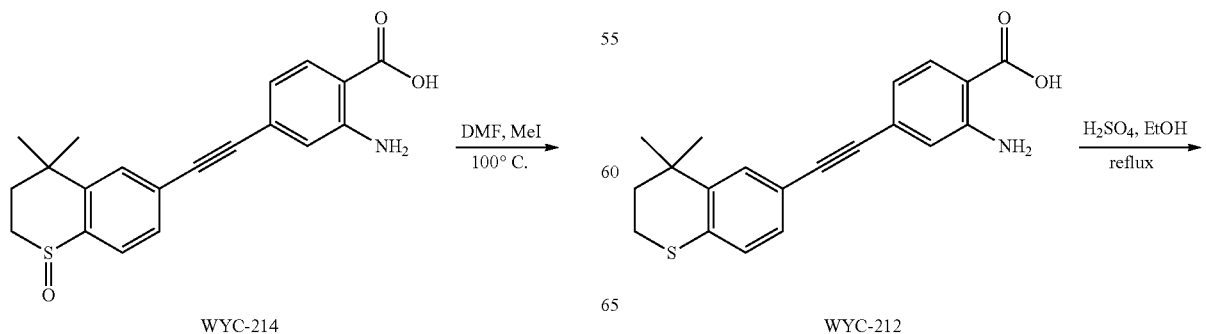

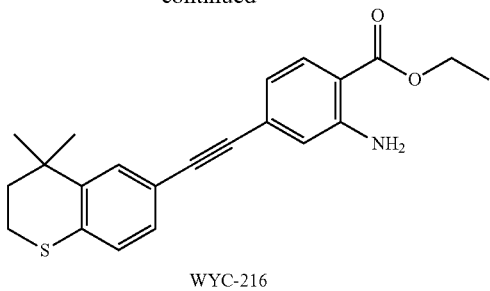

WYC-216

WYC-212 (50 mg, 0.15 mmol) was added to a flask, followed by addition of 2 mL anhydrous ethanol under argon atmosphere. The mixture was cooled to 0° C. under an ice bath, then 0.15 mL concentrated sulfuric acid was added dropwise. After completion of the dropwise addition, the reaction solution was heated to reflux and stirred for 4 h, meanwhile TLC was used to monitor the reaction. After completion of the reaction, the reaction solution was cooled to room temperature, treated with 2 mol/L sodium hydroxide to neutralize sulfuric acid to make a neutral solution, then washed with saturated sodium chloride solution. The organic phase was dried over anhydrous sodium sulfate, filtered, dried, and purified by flash column chromatography (PE:EtOAc=10:1) to give WYC-216 (14 mg, 25%). $^1$H NMR (500 MHz, CDCl$_3$) δ 7.84 (d, J=8.3 Hz, 1H), 7.51 (d, J=1.6 Hz, 1H), 7.17 (dd, J=8.1, 1.7 Hz, 1H), 7.06 (d, J=8.1 Hz, 1H), 6.83 (d, J=1.3 Hz, 1H), 6.79 (dd, J=8.3, 1.4 Hz, 1H), 4.33 (q, J=7.1 Hz, 2H), 3.06-3.03 (m, 2H), 1.97-1.94 (m, 2H), 1.39 (t, J=7.1 Hz, 3H), 1.34 (s, 6H). $^{13}$C NMR (126 MHz, CDCl$_3$) δ 167.92, 150.10, 142.22, 133.72, 131.35, 129.95, 129.19, 129.02, 126.70, 119.55, 119.39, 118.23, 110.80, 91.99, 88.37, 60.61, 37.36, 33.12, 30.13, 23.37, 14.50. ESI(+)–MS: 366.4 [M+1]$^+$.

Embodiment 25: ethyl 2-acetamido-4-((4,4-dimethylthiochroman-6-yl)ethynyl)benzoate

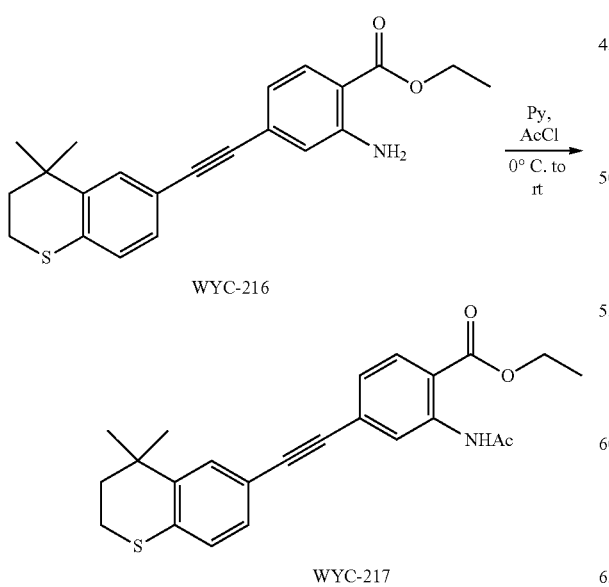

WYC-216

WYC-217

WYC-216 (80 mg, 0.22 mmol) was added to a flask, and 6 mg DMAP was added. The flask was purged with argon, then 2 mL dry pyridine was added. Then the mixture was cooled to 0° C. under an ice bath, and acetyl chloride (31 μL, 0.44 mmol) was added dropwise. The reaction was continued for 10 min under the ice bath and another 9 h at room temperature, meanwhile TLC was used to monitor the reaction. After completion of the reaction, the reaction was quenched with methanol. The mixture was diluted with ethyl acetate, washed with 1 mol/L hydrochloric acid to remove pyridine, then washed with saturated sodium bicarbonate solution and saturated sodium chloride solution. The organic phase was dried over anhydrous sodium sulfate, filtered, concentrated and purified by flash column chromatography (PE:EtOAc=10:1) to give WYC-217 (71 mg, 79%). $^1$H NMR (500 MHz, CDCl$_3$) δ 11.12 (s, 1H), 8.88 (d, J=1.4 Hz, 1H), 7.99 (d, J=8.3 Hz, 1H), 7.55 (d, J=1.7 Hz, 1H), 7.20 (dd, J=3.6, 1.7 Hz, 1H), 7.18 (dd, J=3.8, 1.7 Hz, 1H), 7.06 (d, J=8.1 Hz, 1H), 4.38 (q, J=7.1 Hz, 2H), 3.06-3.03 (m, 2H), 2.24 (s, 3H), 1.97-1.94 (m, 2H), 1.42 (t, J=7.1 Hz, 3H), 1.35 (s, 6H). $^{13}$C NMR (126 MHz, CDCl$_3$) δ 169.17, 168.11, 142.25, 141.59, 133.98, 130.81, 130.17, 130.04, 129.24, 126.70, 125.26, 122.97, 118.06, 114.16, 93.43, 88.37, 61.65, 37.36, 33.13, 30.13, 25.68, 23.38, 14.34. ESI(+)–MS: 408.4 [M+1]$^+$.

Embodiment 26: ethyl 2-amino-4-((4,4-dimethyl-1-oxothiochroman-6-yl)ethynyl)benzoate

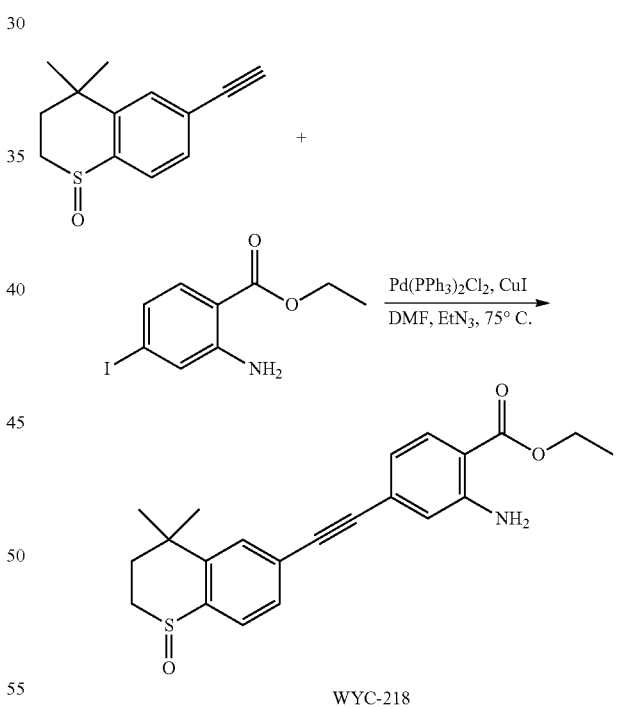

WYC-218

Ethyl 2-amino-4-iodobenzoate (262.0 mg, 1.2 mmol) and 1-oxo-6-ethynyl-4,4-dimethylthiochroman (263.0 mg, 1 mmol) were added to a flask, followed by addition of Pd(PPh$_3$)$_2$Cl$_2$ (42 mg, 0.06 mmol) and CuI (23 mg, 0.12 mmol). After the flask was purged with argon for 3 times to remove oxygen, 15 mL dry DMF and 0.2 mL dry Et$_3$N were added via syringe. The reaction was continued at 75° C. for 12 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (DCM: MeOH=40:1) to give WYC-218 (275 mg, 78%). $^1$H NMR (500 MHz, pyridine) δ 8.39 (d, J=8.1 Hz, 1H), 7.97-7.82 (m, 2H), 7.61 (s, 1H), 7.38 (s, 1H), 7.05 (d, J=8.1 Hz, 1H), 3.25-3.01 (m, 2H), 2.40 (ddd, J=14.2, 10.3, 1.7 Hz, 1H), 1.73 (ddd, J=14.8, 8.8, 1.5 Hz, 1H), 1.28 (s, 3H), 1.19 (s, 3H). $^{13}$C NMR (126 MHz, pyridine) δ171.75, 153.03, 150.76, 150.74, 150.55, 150.53, 150.33, 150.31, 146.21, 141.15, 133.49, 132.34, 131.12, 130.89, 128.61, 127.01, 120.48, 119.27, 113.12, 92.51, 91.02, 44.28, 35.32, 31.62, 31.32, 30.49. ESI(+)–MS: 382.4 [M+1]$^+$.

Embodiment 27: methyl 2-methylamino-4-((4,4-dimethylthiochroman-6-yl)ethynyl)benzoate

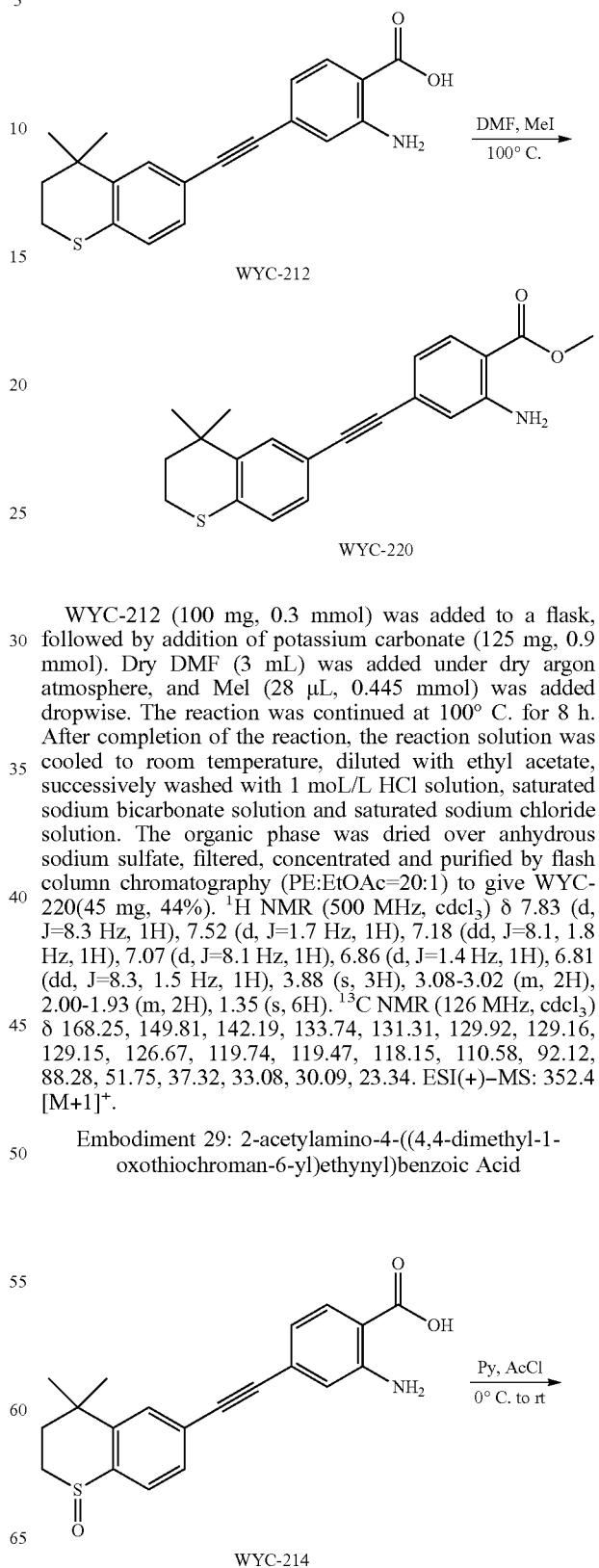

WYC-212 (100 mg, 0.3 mmol) was added to a flask, followed by addition of sodium carbonate (125 mg, 0.9 mmol). Then 3 mL dry DMF and iodomethane (28 μL, 0.445 mmol) were added under argon atmosphere, the reaction solution was slowly heated to 100° C. and stirred for 4 h, meanwhile TLC was used to monitor the reaction. After completion of the reaction, the reaction solution was cooled to room temperature, diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=20:1) to give WYC-219 (43 mg, 39%) and 3-69-2-2 (45 mg, 43%). $^1$H NMR (500 MHz, CDCl$_3$) δ 7.87 (d, J=8.2 Hz, 1H), 7.54 (s, 1H), 7.20 (d, J=8.1 Hz, 1H), 7.06 (d, J=8.1 Hz, 1H), 6.88 (s, 1H), 6.78 (d, J=8.2 Hz, 1H), 3.86 (s, 3H), 3.08-3.02 (m, 2H), 2.95 (s, 3H), 1.99-1.94 (m, 2H), 1.35 (s, 6H). $^{13}$C NMR (126 MHz, CDCl$_3$) δ 168.77, 151.15, 142.24, 133.75, 131.64, 130.02, 129.68, 129.24, 126.71, 118.37, 118.24, 114.31, 110.05, 92.11, 88.89, 51.79, 37.38, 33.14, 30.15, 23.39. ESI(+)–MS: 366.2 [M+1]$^+$.

Embodiment 28: methyl 2-amino-4-((4,4-dimethyl-thiochroman-6-yl)ethynyl)benzoate

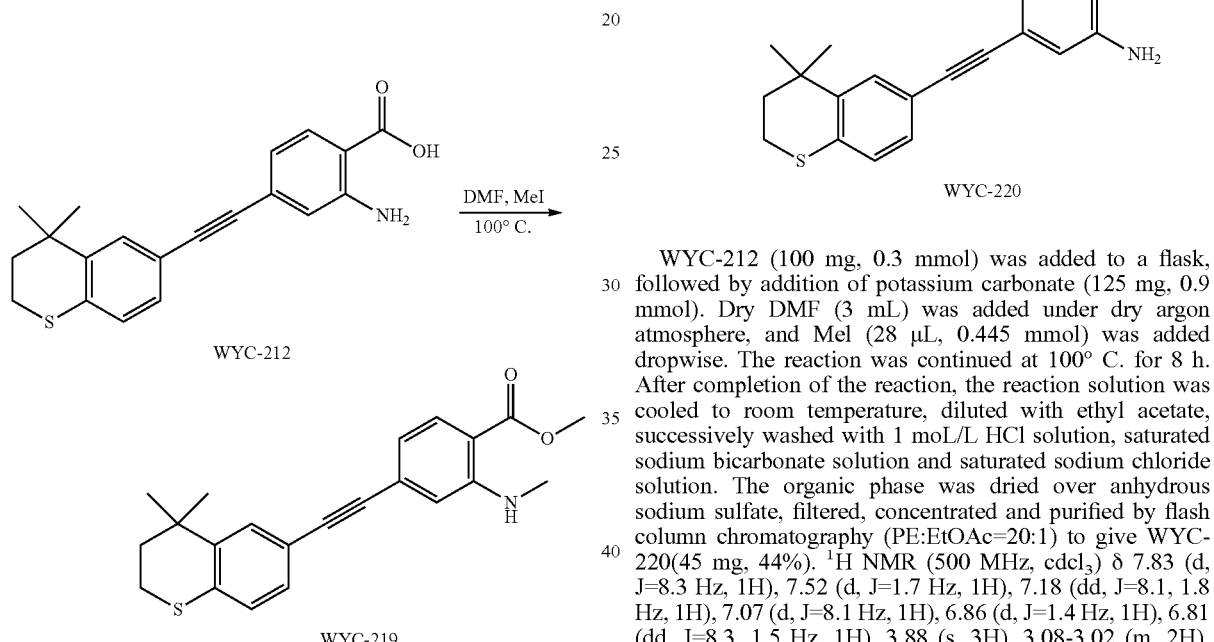

WYC-212 (100 mg, 0.3 mmol) was added to a flask, followed by addition of potassium carbonate (125 mg, 0.9 mmol). Dry DMF (3 mL) was added under dry argon atmosphere, and MeI (28 μL, 0.445 mmol) was added dropwise. The reaction was continued at 100° C. for 8 h. After completion of the reaction, the reaction solution was cooled to room temperature, diluted with ethyl acetate, successively washed with 1 moL/L HCl solution, saturated sodium bicarbonate solution and saturated sodium chloride solution. The organic phase was dried over anhydrous sodium sulfate, filtered, concentrated and purified by flash column chromatography (PE:EtOAc=20:1) to give WYC-220 (45 mg, 44%). $^1$H NMR (500 MHz, cdcl$_3$) δ 7.83 (d, J=8.3 Hz, 1H), 7.52 (d, J=1.7 Hz, 1H), 7.18 (dd, J=8.1, 1.8 Hz, 1H), 7.07 (d, J=8.1 Hz, 1H), 6.86 (d, J=1.4 Hz, 1H), 6.81 (dd, J=8.3, 1.5 Hz, 1H), 3.88 (s, 3H), 3.08-3.02 (m, 2H), 2.00-1.93 (m, 2H), 1.35 (s, 6H). $^{13}$C NMR (126 MHz, cdcl$_3$) δ 168.25, 149.81, 142.19, 133.74, 131.31, 129.92, 129.16, 129.15, 126.67, 119.74, 119.47, 118.15, 110.58, 92.12, 88.28, 51.75, 37.32, 33.08, 30.09, 23.34. ESI(+)–MS: 352.4 [M+1]$^+$.

Embodiment 29: 2-acetylamino-4-((4,4-dimethyl-1-oxothiochroman-6-yl)ethynyl)benzoic Acid -continued

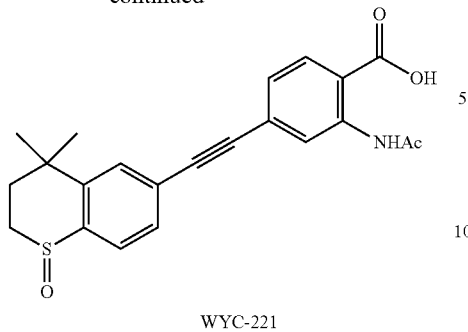

WYC-221

WYC-214 (152 mg, 0.42 mmol) was added to a flask, followed by addition of 10 mg DMAP. 5 mL dry dichloromethane and 0.212 mL pyridine were added under argon atmosphere. After the reaction solution was cooled to 0° C. under an ice bath, acetyl chloride (67 μL, 0.84 mmol) was added dropwise, and the reaction was continued for 10 min under the ice bath and another 12 h at room temperature, meanwhile TLC was used to monitor the reaction. After completion of the reaction, the reaction was quenched with methanol. The mixture was diluted with ethyl acetate, washed with 1 mol/L hydrochloric acid to remove pyridine, then washed with saturated sodium bicarbonate solution and saturated sodium chloride solution. The organic phase was dried over anhydrous sodium sulfate, filtered, concentrated and purified by flash column chromatography (PE: EtOAc=1:3) to give WYC-221(147 mg, 89%). $^1$H NMR (500 MHz, CDCl$_3$) δ 8.12 (d, J=8.3 Hz, 1H), 7.63 (d, J=1.3 Hz, 1H), 7.57 (dd, J=8.1, 1.5 Hz, 1H), 7.54 (d, J=1.7 Hz, 1H), 7.21 (dd, J=8.1, 1.8 Hz, 1H), 7.08 (d, J=8.1 Hz, 1H), 3.07-3.03 (m, 2H), 2.46 (s, 3H), 1.99-1.94 (m, 2H), 1.35 (s, 6H). $^{13}$C NMR (126 MHz, CDCl$_3$) δ 160.87, 159.36, 146.58, 142.34, 134.73, 132.26, 131.01, 130.04, 129.30, 128.95, 128.45, 126.80, 117.45, 115.64, 95.28, 87.51, 37.21, 33.11, 30.07, 23.38, 21.54. ESI(+)-MS: 396.2 [M+1]$^+$.

Embodiment 30: 2-(3-bromophenyl)acetaldehyde

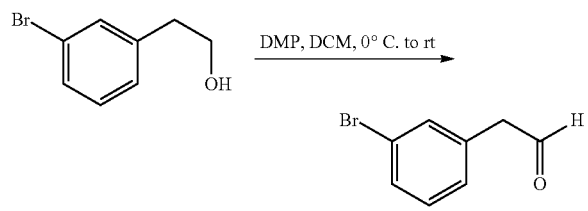

2-(3-Bromophenyl)ethanol (676 μL, 5 mmol) was added to a flask, followed by addition of 10 mL dry dichloromethane, then DMP (2.5 g, 6 mmol) was added under an ice bath. The reaction was continued for 2 h under the ice bath and another 0.5 h at room temperature, meanwhile TLC was used to monitor the reaction. After completion of the reaction, the reaction solution was cooled to 0° C. and the reaction was quenched with sodium thiosulfate solution. The mixture was diluted with ethyl acetate and washed with saturated sodium chloride solution. The organic phase was dried over anhydrous sodium sulfate, filtered, concentrated and purified by flash column chromatography (PE: EtOAc=15:1) to give 2-(3-bromophenyl)acetaldehyde (0.86 g, 87%). $^1$H NMR (300 MHz, CDCl$_3$) δ 9.74 (1H, t, J=2.0), 7.46-7.37 (2H, m), 7.30-7.14 (2H, m), 3.67 (2H, d, J=2.0). $^{13}$C NMR (75 MHz, CDCl$_3$) δ 198.9, 134.5, 133.0, 131.0, 130.9, 128.7, 123.3, 60.8. ESI(+)-MS: 199.1 [M+1]$^+$.

Embodiment 31: ethyl 4-(3-bromophenyl)-2-butenoate

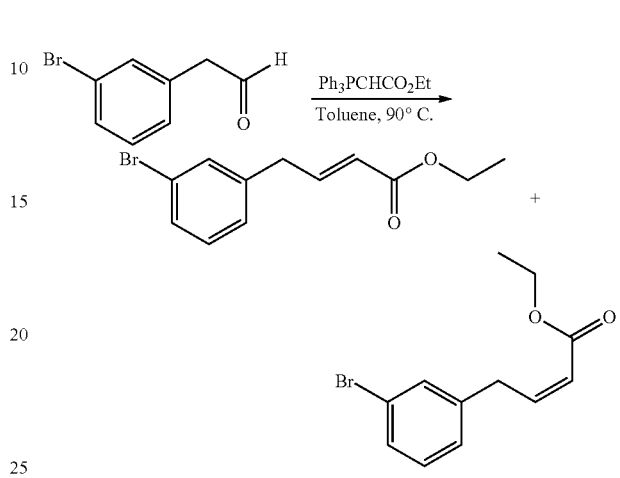

2-(3-bromophenyl)acetaldehyde (400 mg, 2.02 mmol) and Ph$_3$PCH=CO$_2$Et (703 mg, 2.02 mmol) were added to a flask, followed by addition of 10 mL dry toluene under argon atmosphere. The reaction was continued at 90° for 8 h and monitored by TLC. After completion of the reaction, the reaction solution was cooled to 0° C., diluted with ethyl acetate, washed with saturated sodium chloride solution. The organic phase was dried over anhydrous sodium sulfate, filtered, concentrated and purified by flash column chromatography (PE:EtOAc=250:1) to give ethyl 4-(3-bromophenyl)-2-butenoate (514 mg, 96%). E-configuration: $^1$H NMR (500 MHz, CDCl$_3$) δ 7.36 (d, J=8.0 Hz, 1H), 7.31 (s, 1H), 7.17 (t, J=7.8 Hz, 1H), 7.11-6.99 (m, 2H), 5.80 (dt, J=15.6, 1.6 Hz, 1H), 4.17 (q, J=7.1 Hz, 2H), 3.47 (dd, J=6.8, 1.0 Hz, 2H), 1.27 (t, J=7.1 Hz, 3H). $^{13}$C NMR (126 MHz, CDCl$_3$) δ 166.29, 146.15, 140.06, 131.88, 130.29, 129.90, 127.53, 123.02, 122.77, 77.41, 77.16, 76.91, 60.44, 38.00, 14.32. Z-configuration: $^1$H NMR (500 MHz, CDCl$_3$) δ 7.38 (s, 1H), 7.36-7.33 (m, 1H), 7.16 (dd, J=4.1, 1.4 Hz, 2H), 6.30 (dt, J=11.4, 7.6 Hz, 1H), 5.88 (dt, J=11.4, 1.7 Hz, 1H), 4.22 (q, J=7.1 Hz, 2H), 4.00 (dd, J=7.6, 1.4 Hz, 2H), 1.31 (t, J=7.1 Hz, 3H). $^{13}$C NMR (126 MHz, CDCl$_3$) δ 166.33, 146.76, 141.84, 131.76, 130.25, 129.60, 127.41, 122.74, 120.73, 60.23, 34.73, 14.39.

Embodiment 32: ethyl 4-(3-bromophenyl)butanoate

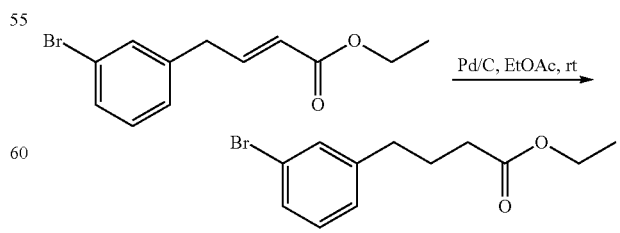

Ethyl 4-(3-bromophenyl)-2-butenoate (1.05 g, 3.92 mmol) was added to a flask, followed by addition of (10% wt) dry Pd/C (220 mg, 0.194 mmol), then 20 mL ethyl acetate was added under argon atmosphere. After the flask was purged with hydrogen for 3 times, the reaction was continued at room temperature under normal pressure for 24 h and monitored by TLC. After completion of the reaction, the reaction solution was filtered, concentrated and purified by flash column chromatography (PE:EtOAc=15:1) to give ethyl 4-(3-bromophenyl)butanoate (1.04 g, 98%). $^1$H NMR (500 MHz, CDCl$_3$) δ 7.32 (dd, J=9.5, 1.3 Hz, 2H), 7.16-7.08 (m, 2H), 4.12 (q, J=7.1 Hz, 2H), 2.64-2.59 (m, 2H), 2.30 (t, J=7.4 Hz, 2H), 1.96-1.90 (m, 2H), 1.25 (t, J=7.1 Hz, 3H). $^{13}$C NMR (126 MHz, CDCl$_3$) δ 173.27, 143.87, 131.59, 130.01, 129.18, 127.22, 122.51, 60.40, 34.82, 33.57, 26.36, 14.33. ESI(+)–MS: 271.2 [M+1]$^+$.

Embodiment 33:
5-(3-bromophenyl)-2-methyl-2-pentanol

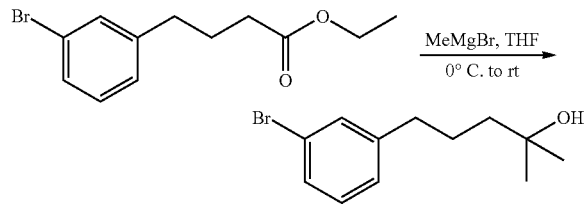

Ethyl 4-(3-bromophenyl)butanoate (0.53 g, 1.96 mmol) was added to a flask, followed by addition of 15 mL tetrahydrofuran under argon atmosphere. After the mixture was cooled to 0° C. under an ice bath, methylmagnesium bromide (2 mL, 5.89 mmol) was added dropwise. The reaction was continued for 3 h at 0° C. and another 1 h at room temperature, meanwhile TLC was used to monitor the reaction. After completion of the reaction, the reaction solution was cooled to 0° C. and the reaction was quenched with ice water. The mixture was diluted with ethyl acetate, neutralized with 1 mol/L hydrochloric acid, washed with saturated sodium carbonate solution and saturated sodium chloride solution. The organic phase was dried over anhydrous sodium sulfate, filtered, concentrated and purified by flash column chromatography (PE:EtOAc=15:1) to give 5-(3-bromophenyl)-2-methyl-2-pentanol (466 mg, 93%). $^1$H NMR (400 MHz, CDCl$_3$) δ 7.37-7.26 (m, 2H), 7.22-7.10 (m, 2H), 2.62 (dt, J=15.0, 7.7 Hz, 2H), 1.76-1.64 (m, 2H), 1.56-1.47 (m, 2H), 1.22 (s, 6H). $^{13}$C NMR (126 MHz, CDCl$_3$) δ 144.81, 131.40, 129.84, 128.81, 127.05, 122.33, 70.73, 43.29, 35.95, 29.22, 26.00. ESI(+)–MS: 257.1 [M+1]$^+$.

Embodiment 34:
7-bromo-4,4-dimethyl-3,4-dihydronaphth-1-(2H)-one

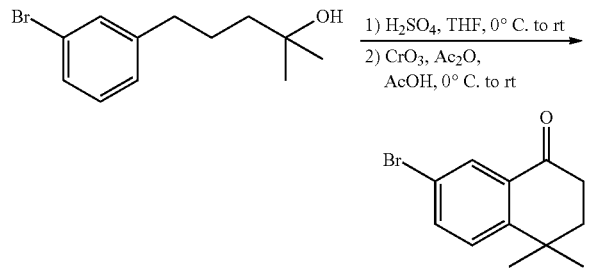

5-(3-Bromophenyl)-2-methyl-2-pentanol (340 mg, 1.33 mmol) was added to a flask, followed by addition of 2 mL dry dichloromethane under argon atmosphere. After the mixture was cooled to 0° C. under an ice bath, 0.2 mL concentrated sulfuric acid was added dropwise, and the reaction was continued at room temperature for 4 h and monitored by TLC. After completion of the reaction, the reaction solution was diluted with water, neutralized with 1 mol/L sodium hydroxide to neutralize sulfuric acid, diluted with ethyl acetate, washed with saturated sodium carbonate solution and saturated sodium chloride solution. The organic phase was dried over anhydrous sodium sulfate, filtered and evaporated to give 320 mg white solid, which was added to a flask, followed by addition of 4.3 mL. 71 mg chromium trioxide was dissolved in a mixed solution of 0.648 mL acetic acid and 0.342 mL acetic anhydride, which was added to the flask under an ice bath. The reaction was continued for 2 h and monitored by TLC. After completion of the reaction, the reaction solution was diluted with EtOAc, washed three times with water, then washed with saturated sodium carbonate solution and saturated sodium chloride solution. The organic phase was dried over anhydrous sodium sulfate, filtered, concentrated and purified by flash column chromatography (PE:EtOAc=10:1) to give 7-bromo-4,4-dimethyl-3,4-dihydronaphth-1-(2H)-one (268 mg, 80%). $^1$H NMR (400 MHz, CDCl$_3$) δ 7.37 (dd, J=8.5, 1.6 Hz, 1H), 7.33-7.21 (m, 2H), 2.24-2.05 (m, 2H), 1.87-1.77 (m, 1H), 1.58-1.49 (m, 1H), 1.35 (s, 3H), 1.30 (s, 3H). $^{13}$C NMR (126 MHz, CDCl$_3$) δ 197.03, 151.09, 136.63, 132.77, 130.15, 128.04, 120.57, 36.86, 35.04, 33.89, 29.65. ESI(+)–MS: 253.1 [M+1]$^+$.

Embodiment 35: 7-bromo-4,4-dimethyl-1-phenyl-1,2,3,4-tetrahydronaphth-1-ol

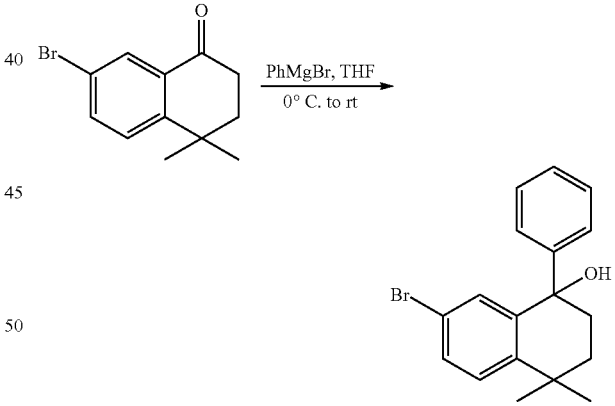

7-Bromo-4,4-dimethyl-3,4-dihydronaphth-1-(2H)-one (340 mg, 1.35 mmol) was added to a flask, followed by addition of 3 mL tetrahydrofuran under argon atmosphere. After the mixture was cooled to 0° C. under an ice bath, phenylmagnesium bromide (2.7 mL, 2.7 mmol) was added dropwise. The reaction was continued for 0.5 h at 0° C. and another 18 h at room temperature, meanwhile TLC was used to monitor the reaction. After completion of the reaction, the reaction solution was cooled to 0° C. and the reaction was quenched with ice water. The mixture was diluted with ethyl acetate, neutralized with 1 mol/L hydrochloric acid, washed with saturated sodium carbonate solution and saturated sodium chloride solution. The organic phase was dried over anhydrous sodium sulfate, filtered, concentrated and purified by flash column chromatography (PE:EtOAc=100:1) to give 7-bromo-4,4-dimethyl-1-phenyl-1,2,3,4-tetrahydronaphth-1-ol (280 mg, 63%). $^1$H NMR (400 MHz, CDCl$_3$) δ 7.39-7.08 (m, 8H), 2.24-2.05 (m, 2H), 1.87-1.77 (m, 1H), 1.58-1.49 (m, 1H), 1.35 (s, 3H), 1.30 (s, 3H). $^{13}$C NMR (126 MHz, CDCl$_3$) δ 148.11, 145.41, 143.32, 131.50, 131.18, 128.46, 128.08, 127.15, 126.59, 119.96, 75.87, 37.69, 34.77, 34.09, 31.56, 31.45. ESI(+)-MS: 331.1 [M+1]$^+$.

Embodiment 36: 6-bromo-1,1-dimethyl-4-phenyl-1,2-dihydronaphthalene

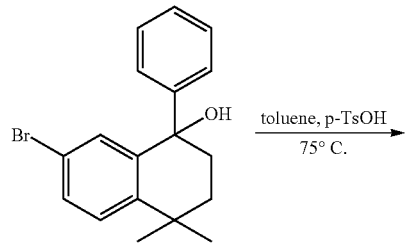

7-Bromo-4,4-dimethyl-1-phenyl-1,2,3,4-tetrahydronaphthalen-1-ol (260 mg, 0.79 mmol) was added to a flask, followed by addition of p-toluenesulfonic acid (27 mg, 0.16 mmol), then 2 mL dry toluene was added under argon atmosphere. The reaction was continued at 75° C. for 0.5 h and monitored by TLC. After completion of the reaction, the reaction solution was cooled to room temperature and the reaction was quenched with ice water. The mixture was diluted with ethyl acetate, washed with saturated sodium carbonate solution and saturated sodium chloride solution. The organic phase was dried over anhydrous sodium sulfate, filtered, concentrated and purified by flash column chromatography (PE:EtOAc=250:1) to give 6-bromo-1,1-dimethyl-4-phenyl-1,2-dihydronaphthalene (224 mg, 91%). $^1$H NMR (500 MHz, CDCl$_3$) δ 7.44-7.40 (m, 2H), 7.39-7.33 (m, 4H), 7.24 (d, J=8.3 Hz, 1H), 7.17 (d, J=2.1 Hz, 1H), 6.03 (t, J=4.7 Hz, 1H), 2.36 (d, J=4.7 Hz, 2H), 1.34 (s, 6H). $^{13}$C NMR (126 MHz, CDCl$_3$) δ 145.59, 144.16, 140.35, 138.75, 136.15, 133.57, 131.80, 130.41, 128.72, 128.56, 127.87, 127.46, 127.02, 125.79, 119.96, 63.05, 38.87, 33.65, 28.18. ESI(+)-MS: 312.1 [M+1]$^+$.

Embodiment 37: ((5,5-dimethyl-8-phenyl-5,6-dihydronaphth-2-yl)ethynyl)trimethylsilane

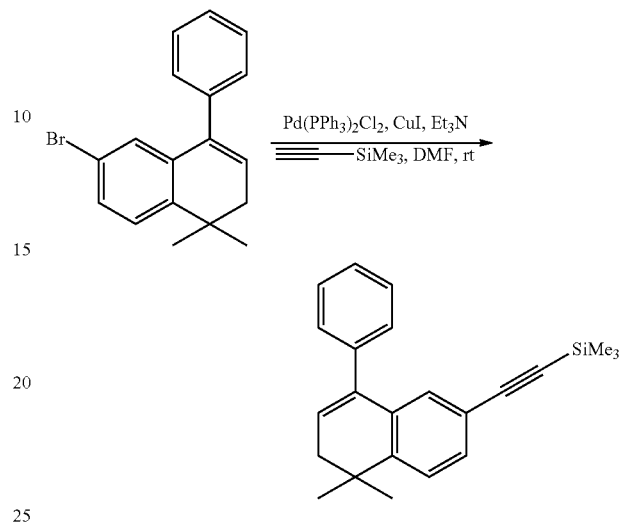

6-Bromo-1,1-dimethyl-4-phenyl-1,2-dihydronaphthalene (310 mg, 1.0 mmol) and trimethylethynylsilane (0.28 μL, 2 mmol) was added to a flask, followed by addition of Pd(PPh$_3$)$_2$Cl$_2$ (21 mg, 0.03 mmol) and CuI (11 mg, 0.06 mmol). After the flask was purged with argon for 3 times to remove oxygen, 5 mL dry DMF and 0.2 mL dry Et$_3$N were added via syringe. The reaction was continued at room temperature over night and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (petroleum ether) to give ((5,5-dimethyl-8-phenyl-5,6-dihydronaphth-2-yl)ethynyl)trimethylsilane (275 mg, 83%). $^1$H NMR (500 MHz, CDCl$_3$) δ 7.44-7.38 (m, 2H), 7.36-7.32 (m, 4H), 7.28 (d, J=7.9 Hz, 10H), 7.11 (d, J=1.6 Hz, 1H), 5.97 (t, J=4.7 Hz, 1H), 2.33 (d, J=4.7 Hz, 2H), 1.31 (s, 6H), 0.19 (s, 9H). $^{13}$C NMR (126 MHz, CDCl$_3$) δ 146.01, 140.79, 139.09, 133.98, 131.51, 129.25, 128.83, 128.49, 127.29, 127.27, 123.92, 120.66, 105.45, 93.41, 38.88, 33.90, 28.19, 0.16. ESI(+)-MS: 331.2 [M+1]$^+$.

Embodiment 38: 6-ethynyl-1,1-dimethyl-4-phenyl-1,2-dihydronaphthalene

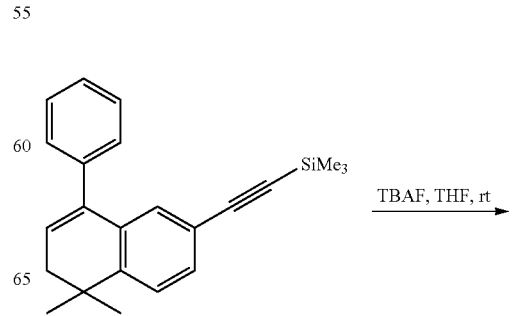

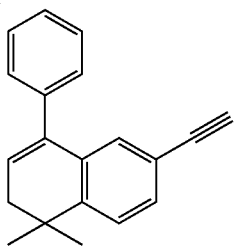

((5,5-dimethyl-8-phenyl-5,6-dihydronaphth-2-yl)ethynyl)trimethylsilane (300 mg, 0.91 mmol) was added to a flask, followed by addition of TBAF (30 Mg, 0.115 mmol) and 2 mL dry tetrahydrofuran. The reaction was continued for 4 h and monitored by TLC. After completion of the reaction, the reaction solution was diluted with ethyl acetate, washed with saturated ammonium chloride solution and saturated sodium chloride solution. The organic phase was dried over anhydrous sodium sulfate, filtered, concentrated and purified by flash column chromatography (PE:EA=1000:1) to give 6-ethynyl-1,1-dimethyl-4-phenyl-1,2-dihydronaphthalene (225 mg, 96.6%). $^1$H NMR (500 MHz, CDCl$_3$) δ 77.47-77.34 (m, 7H), 77.22 (d, J=1.6 Hz, 1H), 76.04 (t, J=4.7 Hz, 1H), 72.98 (s, 1H), 72.39 (d, J=4.7 Hz, 2H), 71.38 (s, 6H). $^{13}$C NMR (126 MHz, CDCl$_3$) δ 146.23, 140.58, 138.97, 134.13, 131.41, 129.62, 128.77, 128.49, 127.34, 127.27, 124.04, 119.59, 83.98, 76.59, 38.83, 33.85, 28.18. ESI(+)–MS: 259.2 [M+1]$^+$.

Embodiment 39: methyl 4-((5,5-dimethyl-8-phenyl-5,6-dihydronaphth-2-yl)ethynyl)-2-hydroxybenzoate

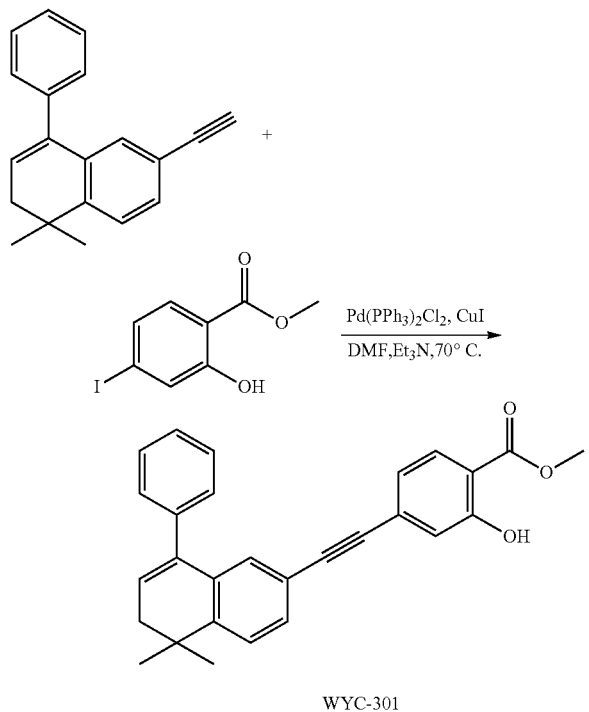

6-Ethynyl-1,1-dimethyl-4-phenyl-1,2-dihydronaphthalene (116 mg, 0.45 mmol) and methyl 2-hydroxy-4-iodobenzoate (μL, 0.9 mmol) was added to a flask, followed by addition of Pd(PPh$_3$)$_2$Cl$_2$ (9.5 mg, 0.0135 mmol) and CuI (5.1 mg, 0.027 mmol). After the flask was purged with argon for 3 times to remove oxygen, 3 mL dry DMF and 0.2 mL dry Et$_3$N were added via syringe. The reaction was continued at room temperature for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EA=500:1) to give WYC-301 (155 mg, 79%). $^1$H NMR (500 MHz, CDCl$_3$) δ 10.75 (s, 1H), 7.76 (d, J=8.2 Hz, 1H), 7.43 (dd, J=7.7, 7.1 Hz, 7H), 7.37 (dd, J=9.3, 3.7 Hz, 4H), 7.21 (d, J=1.3 Hz, 1H), 7.09 (d, J=1.2 Hz, 1H), 6.97 (dd, J=8.2, 1.2 Hz, 1H), 6.02 (t, J=4.6 Hz, 1H), 3.94 (s, 3H), 2.37 (d, J=4.7 Hz, 2H), 1.36 (s, 6H). $^{13}$C NMR (126 MHz, CDCl$_3$) δ 170.27, 161.31, 146.42, 140.63, 138.99, 134.24, 131.17, 130.83, 129.82, 129.20, 128.80, 128.54, 127.41, 127.38, 124.18, 122.47, 120.36, 120.07, 111.98, 92.99, 87.93, 52.47, 38.85, 33.94, 28.19. ESI(+)–MS: 409.3 [M+1]$^+$.

Embodiment 40: ethyl 4-((5,5-dimethyl-8-phenyl-5,6-dihydronaphth-2-yl)ethynyl)-2-hydroxybenzoate

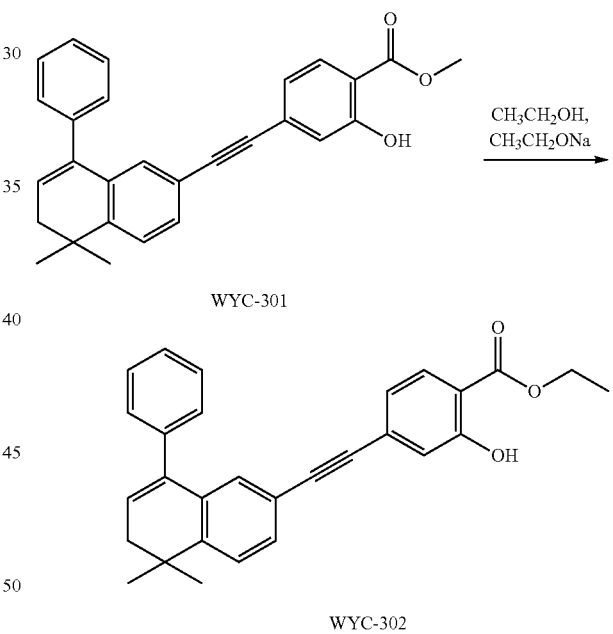

WYC-301 (250 mg, 0.613 mmol) was added to a flask, followed by addition of sodium ethoxide (125 mg, 1.83 mmol) and 5 mL ethanol. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=100:1) to give WYC-302 (230 mg, 92%). $^1$H NMR (500 MHz, CDCl$_3$) δ 10.82 (s, 1H), 7.77 (d, J=8.2 Hz, 1H), 7.45-7.39 (m, 3H), 7.38-7.34 (m, 4H), 7.19 (d, J=1.5 Hz, 1H), 7.07 (d, J=1.4 Hz, 1H), 6.95 (dd, J=8.2, 1.5 Hz, 1H), 6.01 (t, J=4.7 Hz, 1H), 4.40 (q, J=7.1 Hz, 2H), 2.37 (d, J=4.7 Hz, 2H), 1.41 (t, J=7.1 Hz, 3H), 1.35 (s, 6H). $^{13}$C NMR (126 MHz, CDCl$_3$) δ 169.92, 161.39, 146.40, 140.65, 139.01, 134.25, 131.18, 130.70, 129.83, 129.20, 128.82, 128.55, 127.42, 127.39, 124.19, 122.39, 120.37, 120.11, 112.25, 92.89, 87.99, 61.68, 38.86, 33.96, 28.21, 14.32. ESI(+)−MS: 423.4 [M+1]$^+$.

Embodiment 41: ethyl 2-fluoro-4-iodobenzoate

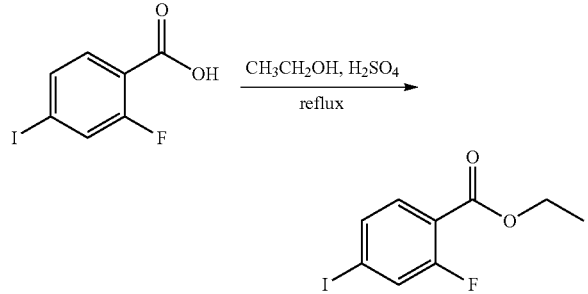

2-Fluoro-4-iodobenzoic acid (1.0 g, 3.76 mmol) was added to a flask, followed by addition of 10 mL anhydrous ethanol under argon atmosphere. The mixture was cooled to 0° C. under an ice bath, then 0.5 mL concentrated sulfuric acid was added dropwise. After completion of the dropwise addition, the reaction solution was heated to reflux and stirred for 4 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=15:1) to give ethyl 2-fluoro-4-iodobenzoate (990 mg, 90%). $^1$H NMR (500 MHz, CDCl$_3$) δ 7.62-7.57 (m, 1H), 7.52 (dd, J=8.3, 1.6 Hz, 1H), 7.49 (dd, J=9.9, 1.5 Hz, 1H), 4.36 (q, J=7.1 Hz, 2H), 1.36 (t, J=7.1 Hz, 3H). $^{13}$C NMR (126 MHz, CDCl$_3$) δ 163.87, 163.84, 162.18, 160.06, 133.48, 133.45, 133.05, 133.04, 126.54, 126.34, 118.76, 118.68, 99.59, 99.52, 61.59, 14.29. ESI(+)−MS: 294.1 [M+1]$^+$.

Embodiment 42: ethyl 2-fluoro-4-((4,4-dimethylthiochroman-6-yl)ethynyl)benzoate

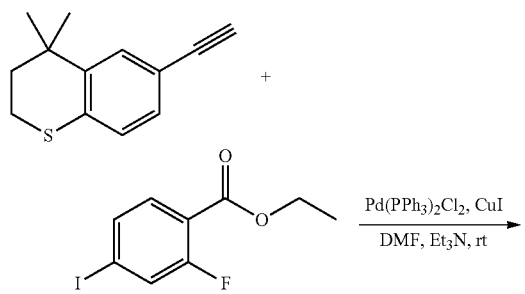

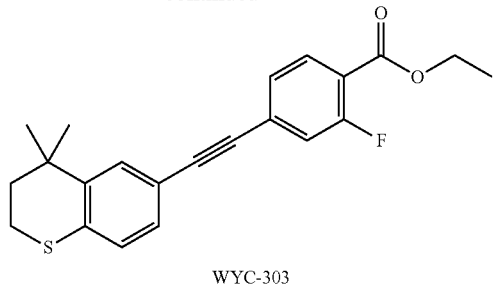

WYC-303

6-Ethynyl-4,4-dimethylthiochroman (275 mg, 1.36 mmol) and ethyl 2-fluoro-4-iodobenzoate (200 mg, 0.68 mmol) were added to a flask, followed by addition of Pd(PPh$_3$)$_2$Cl$_2$ (28.6 mg, 0.0408 mmol) and CuI (15.5 mg, 0.0816 mmol). After the flask was purged with argon for 3 times to remove oxygen, 3 mL dry DMF and 0.3 mL dry Et$_3$N were added via syringe. The reaction was continued at 80° C. for 6 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EA=200:1) to give WYC-303 (215 mg, 86%). $^1$H NMR (500 MHz, CDCl$_3$) δ 7.90 (t, J=7.8 Hz, 1H), 7.52 (d, J=1.7 Hz, 1H), 7.32 (dd, J=8.1, 1.4 Hz, 1H), 7.28 (d, J=1.4 Hz, 1H), 7.25 (d, J=1.4 Hz, 1H), 7.19 (dd, J=8.2, 1.7 Hz, 1H), 7.07 (d, J=8.1 Hz, 1H), 4.40 (q, J=7.1 Hz, 2H), 3.07-3.03 (m, 2H), 1.98-1.94 (m, 2H), 1.40 (t, J=7.1 Hz, 3H), 1.35 (s, 6H). $^{13}$C NMR (126 MHz, CDCl$_3$) δ 164.12, 164.09, 162.75, 160.68, 142.32, 134.45, 132.15, 132.14, 129.98, 129.20, 127.08, 127.05, 126.78, 119.79, 119.60, 117.57, 93.98, 87.00, 86.98, 61.55, 37.25, 33.12, 30.09, 23.37, 14.40. ESI(+)−MS: 369.4 [M+1]$^+$.

Embodiment 43: 2-fluoro-4-((4,4-dimethylthiochroman-6-yl)ethynyl)benzoic Acid

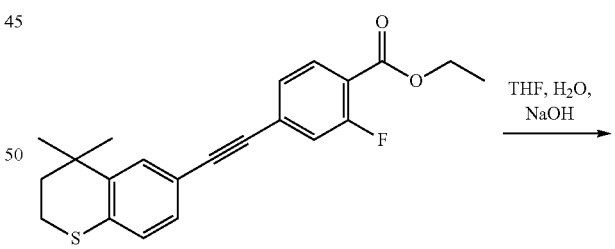

WYC-303

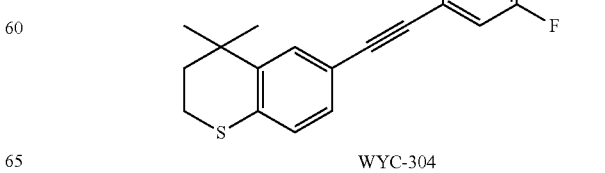

WYC-304

WYC-303 (15 mg, 0.04 mmol) was added to a flask, followed by addition of sodium ethoxide (8.3 mg, 0.12 mmol) and 1 mL tetrahydrofuran. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:1) to give WYC-304 (11 mg, 80%). $^1$H NMR (500 MHz, CDCl$_3$) δ 7.99 (t, J=7.9 Hz, 1H), 7.53 (d, J=1.7 Hz, 1H), 7.35 (dd, J=8.1, 1.5 Hz, 1H), 7.30 (dd, J=11.3, 1.4 Hz, 1H), 7.19 (dd, J=8.1, 1.8 Hz, 1H), 7.08 (d, J=8.1 Hz, 1H), 3.07-3.04 (m, 3H), 1.98-1.95 (m, 2H), 1.35 (s, 6H). $^{13}$C NMR (126 MHz, CDCl$_3$) δ 167.53, 163.34, 161.26, 142.36, 134.65, 132.80, 131.19, 131.11, 130.04, 129.25, 127.25, 127.22, 126.81, 119.89, 119.70, 117.45, 116.98, 94.69, 86.92, 37.24, 33.14, 30.09, 23.39. ESI(+)–MS: 339.3 [M+1]$^+$.

Embodiment 44: ethyl 4-((5,5-dimethyl-8-phenyl-5,6-dihydronaphth-2-yl)ethynyl)-2-fluorobenzoate

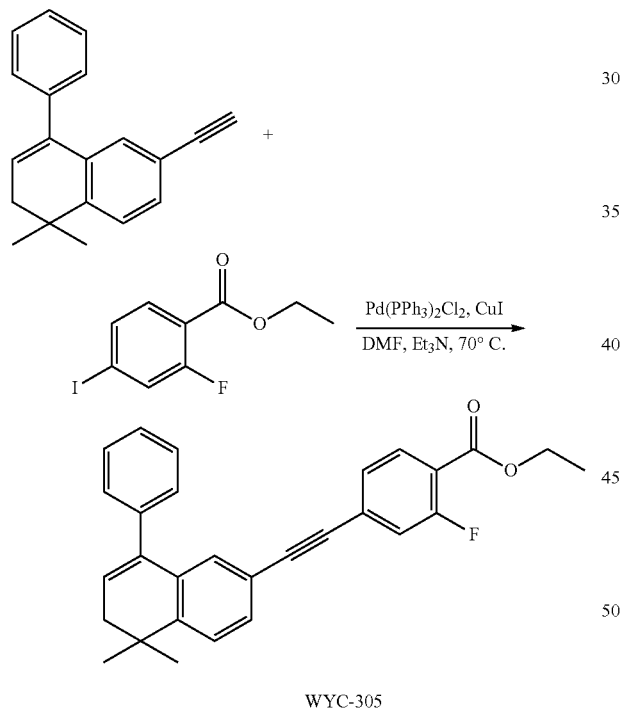

6-Ethynyl-1,1-dimethyl-4-phenyl-1,2-dihydronaphthalene (180 mg, 0.7 mmol) and ethyl 2-fluoro-4-iodo-benzoate (410 mg, 1.4 mmol) were added to a flask, followed by addition of Pd(PPh$_3$)$_2$Cl$_2$ (30 mg, 0.042 mmol) and CuI (16.0 mg, 0.084 mmol). After the flask was purged with argon for 3 times to remove oxygen, 5 mL dry DMF and 0.5 mL dry Et$_3$N were added via syringe. The reaction was continued at 70° C. for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EA=200:1) to give WYC-305 (215 mg, 72%). $^1$H NMR (500 MHz, CDCl$_3$) δ 7.87 (t, J=7.8 Hz, 1H), 7.44-7.39 (m, 7H), 7.37 (ddd, J=6.3, 3.4, 1.5 Hz, 4H), 7.29-7.26 (m, 1H), 7.24-7.18 (m, 2H), 6.02 (t, J=4.7 Hz, 1H), 4.39 (q, J=7.1 Hz, 2H), 2.37 (d, J=4.7 Hz, 2H), 1.39 (t, J=7.1 Hz, 3H), 1.35 (s, 6H). $^{13}$C NMR (126 MHz, CDCl$_3$) δ 164.12, 164.09, 162.70, 160.63, 146.67, 140.62, 138.95, 134.33, 132.08, 132.07, 131.17, 129.92, 129.84, 129.20, 128.82, 128.57, 127.53, 127.41, 127.17, 127.14, 124.25, 119.91, 119.77, 119.72, 118.51, 118.43, 93.66, 86.96, 86.94, 61.55, 38.84, 33.98, 28.20, 14.39. ESI(+)–MS: 425.5 [M+1]$^+$.

Embodiment 45: 4-((5,5-dimethyl-8-phenyl-5,6-dihydronaphth-2-yl)ethynyl)-2-fluorobenzic Acid

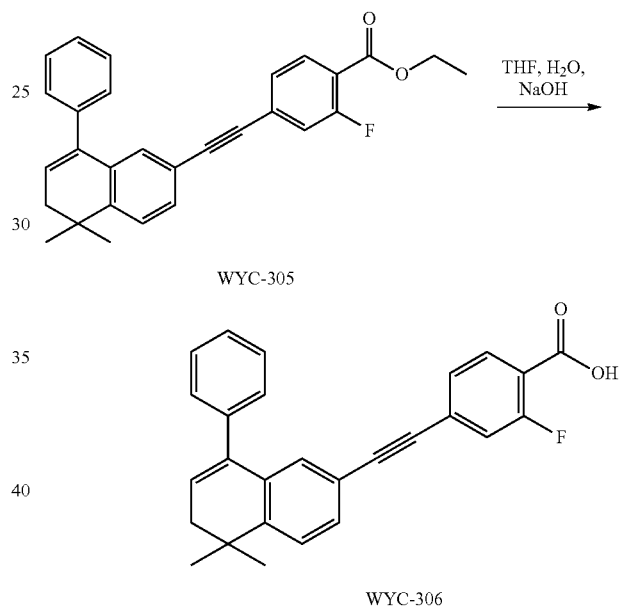

WYC-305 (70 mg, 0.19 mmol) was added to a flask, followed by addition of sodium ethoxide (26 mg, 0.38 mmol) and 2 mL tetrahydrofuran. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=2:1) to give WYC-306 (53 mg, 75%). $^1$H NMR (500 MHz, CDCl$_3$) δ 7.95 (t, J=7.9 Hz, 1H), 7.44-7.39 (m, 7H), 7.39-7.35 (m, 4H), 7.30 (dd, J=8.2, 1.4 Hz, 1H), 7.24 (d, J=1.3 Hz, 1H), 7.19 (d, J=1.5 Hz, 1H), 6.02 (t, J=4.7 Hz, 1H), 2.37 (d, J=4.7 Hz, 2H), 1.35 (s, 6H). $^{13}$C NMR (126 MHz, CDCl$_3$) δ 167.97, 163.32, 161.23, 146.83, 140.60, 138.92, 134.36, 132.74, 131.22, 129.24, 128.83, 128.58, 127.57, 127.43, 127.36, 127.33, 124.29, 120.02, 119.83, 119.64, 116.90, 94.43, 86.86, 38.84, 34.00, 28.20. ESI(+)–MS: 395.4 [M+1]$^+$.

Embodiment 46: ethyl 3-fluoro-4-iodobenzoate

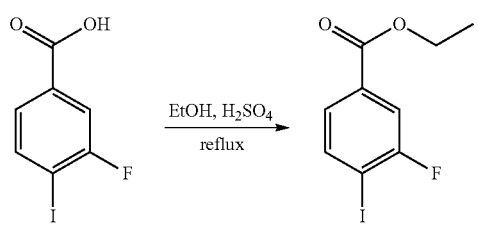

3-Fluoro-4-iodobenzoic acid (0.95 g, 3.57 mmol) was added to a flask, followed by addition of 5 mL anhydrous ethanol under argon atmosphere. The mixture was cooled to 0° C. under an ice bath, then 0.3 mL concentrated sulfuric acid was added dropwise. After completion of the dropwise addition, the reaction solution was heated to reflux and stirred for 4 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=15:1) to give ethyl 3-fluoro-4-iodobenzoate (920 mg, 88%). $^1$H NMR (500 MHz, CDCl$_3$) δ 7.80 (dd, J=8.2, 6.2 Hz, 1H), 7.65 (dd, J=8.4, 1.8 Hz, 1H), 7.53 (dd, J=8.2, 1.8 Hz, 1H), 4.36 (q, J=7.1 Hz, 2H), 1.37 (t, J=7.2 Hz, 3H). $^{13}$C NMR (126 MHz, CDCl$_3$) δ 164.99, 164.97, 162.64, 160.67, 139.61, 139.59, 132.94, 132.89, 126.51, 126.48, 116.46, 116.26, 87.88, 87.67, 61.65, 14.33. ESI(+)-MS: 295.1 [M+1]$^+$.

Embodiment 47: ethyl 4-iodo-3-nitrobenzoate

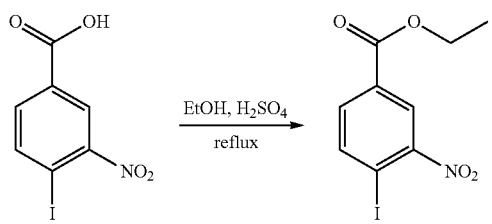

4-Iodo-3-nitrobenzoic acid (1.9 g, 6.48 mmol) was added to a flask, followed by addition of 10 mL anhydrous ethanol under argon atmosphere. The mixture was cooled to 0° C. under an ice bath, then 0.6 mL concentrated sulfuric acid was added dropwise. After completion of the dropwise addition, the reaction solution was heated to reflux and stirred for 6 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=10:1) to give ethyl 4-iodo-3-nitrobenzoate (1.88 g, 90.5%). $^1$H NMR (500 MHz, CDCl$_3$) δ 8.39 (d, J=2.0 Hz, 1H), 8.10 (d, J=8.2 Hz, 1H), 7.85 (dd, J=8.2, 2.0 Hz, 1H), 4.39 (q, J=7.1 Hz, 2H), 1.39 (t, J=7.1 Hz, 3H). $^{13}$C NMR (126 MHz, CDCl$_3$) δ 164.03, 153.15, 142.33, 133.47, 131.96, 125.98, 92.02, 62.16, 14.29. ESI(+)-MS: 322.1 [M+1]$^+$.

Embodiment 48: ethyl 3-fluoro-4-((4,4-dimethylthiochroman-6-yl)ethynyl)benzoate

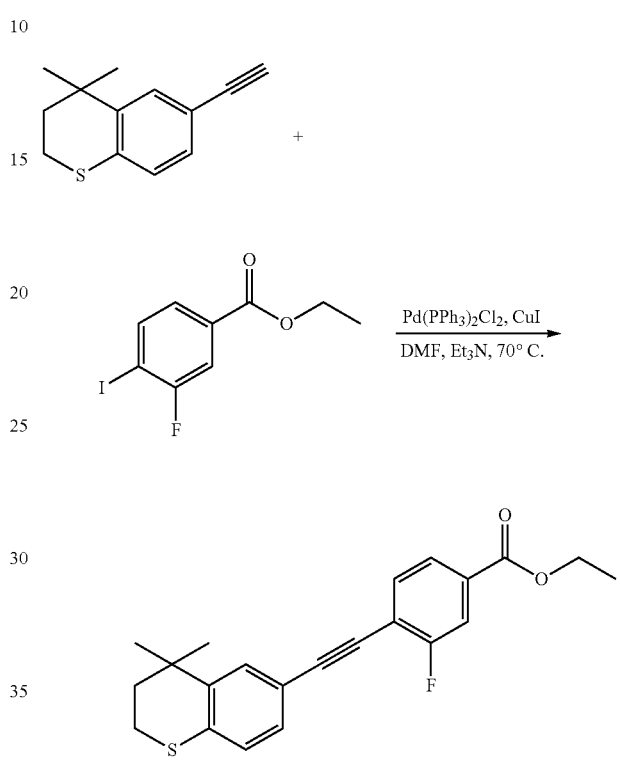

WYC-307

6-Ethynyl-4,4-dimethylthiochroman (405.6 mg, 2 mmol) and ethyl 3-fluoro-4-iodobenzoate (294 mg, 1.0 mmol) were added to a flask, followed by addition of Pd(PPh$_3$)$_2$Cl$_2$ (84 mg, 0.12 mmol) and CuI (46.0 mg, 0.24 mmol). After the flask was purged with argon for 3 times to remove oxygen, 5 mL dry DMF and 0.5 mL dry Et$_3$N were added via syringe. The reaction was continued at 70° C. for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EA=500:3) to give WYC-307(250 mg, 68%). $^1$H NMR (500 MHz, CDCl$_3$) δ 7.81 (dd, J=8.0, 1.3 Hz, 1H), 7.76 (dd, J=9.8, 1.3 Hz, 1H), 7.56 (dd, J=11.1, 4.2 Hz, 2H), 7.22 (dd, J=8.1, 1.6 Hz, 1H), 7.08 (d, J=8.1 Hz, 1H), 4.39 (q, J=7.1 Hz, 2H), 3.05 (dd, J=7.1, 5.1 Hz, 2H), 1.98-1.94 (m, 2H), 1.40 (t, J=7.1 Hz, 3H), 1.35 (s, 6H). $^{13}$C NMR (126 MHz, CDCl$_3$) δ 165.25, 165.23, 163.21, 161.20, 142.29, 134.42, 133.26, 133.25, 131.70, 131.64, 129.97, 129.27, 126.75, 125.15, 125.12, 117.73, 117.05, 116.92, 116.66, 116.47, 98.04, 98.02, 81.71, 61.62, 37.29, 33.13, 30.09, 23.38, 14.42. ESI(+)-MS: 369.3 [M+1]$^+$.

Embodiment 49: ethyl 3-nitro-4-((4,4-dimethylthio-chroman-6-yl)ethynyl)benzoate

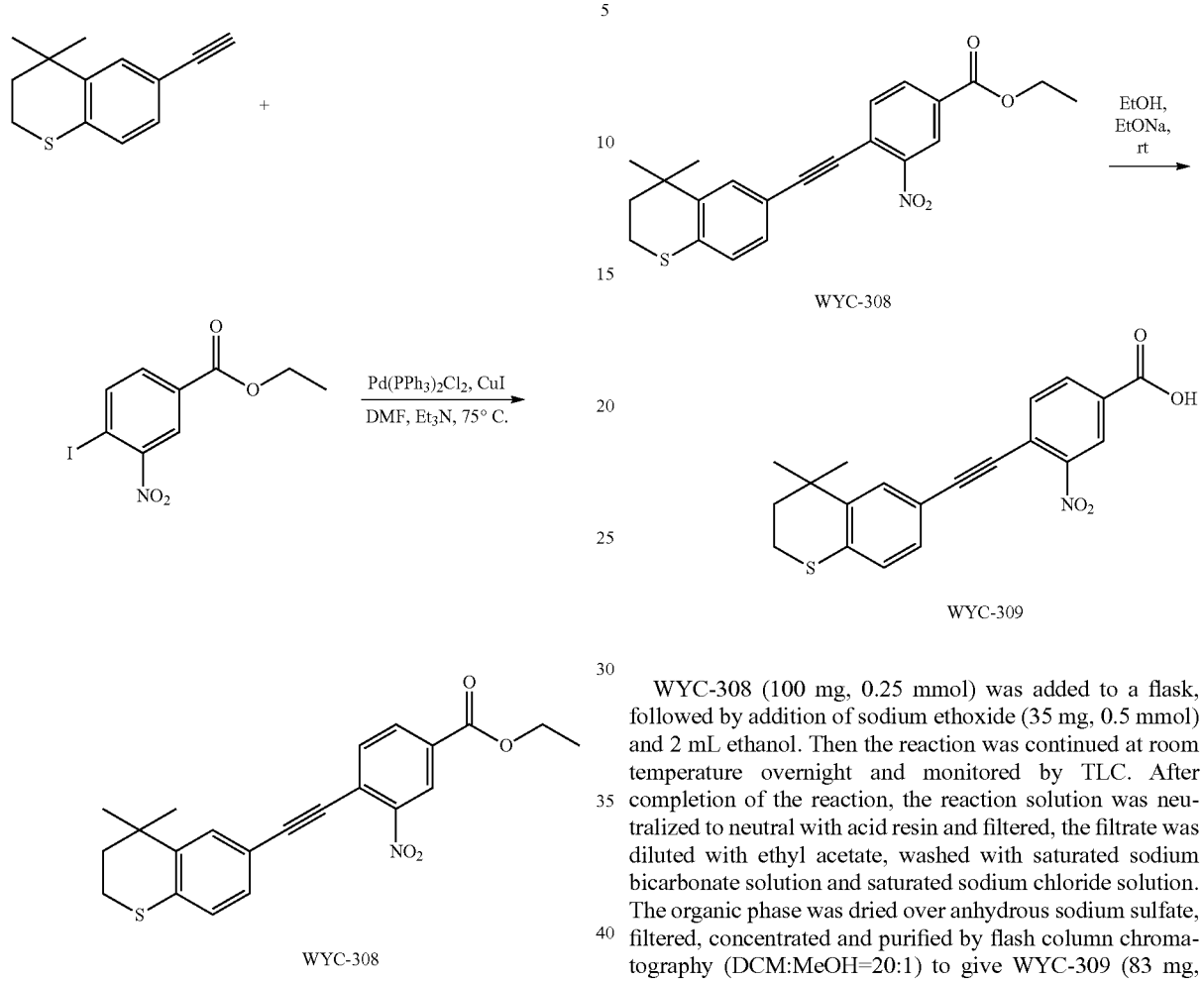

WYC-308

6-Ethynyl-4,4-dimethylthiochroman (405.6 mg, 2 mmol) and ethyl 3-nitro-4-iodobenzoate (303 mg, 1.0 mmol) were added to a flask, followed by addition of Pd(PPh$_3$)$_2$Cl$_2$ (84 mg, 0.12 mmol) and CuI (46.0 mg, 0.24 mmol). After the flask was purged with argon for 3 times to remove oxygen, 5 mL dry DMF and 0.5 mL dry Et$_3$N were added via syringe. The reaction was continued at 70° C. for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EA=50:1) to give WYC-308 (384 mg, 97%). $^1$H NMR (400 MHz, CDCl$_3$) δ 8.69 (d, J=1.2 Hz, 1H), 8.20 (dd, J=8.1, 1.6 Hz, 1H), 7.74 (d, J=8.1 Hz, 1H), 7.57 (s, 1H), 7.23-7.25 (m, 1H), 7.08 (d, J=8.2 Hz, 1H), 4.42 (q, J=7.1 Hz, 2H), 3.04 (dd, J=7.2, 4.9 Hz, 2H), 1.98-1.85 (m, 2H), 1.41 (t, J=7.1 Hz, 3H), 1.34 (s, 6H). $^{13}$C NMR (126 MHz, CDCl$_3$) δ 164.34, 149.33, 142.43, 135.66, 134.63, 133.24, 130.35, 130.30, 129.65, 126.86, 126.01, 123.20, 117.23, 101.65, 84.50, 62.11, 37.16, 33.12, 30.04, 23.43, 14.43. ESI(+)–MS: 396.2 [M+1]$^+$.

Embodiment 50: 3-nitro-4-((4,4-dimethylthiochroman-6-yl)ethynyl)benzoic Acid

WYC-308 (100 mg, 0.25 mmol) was added to a flask, followed by addition of sodium ethoxide (35 mg, 0.5 mmol) and 2 mL ethanol. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (DCM:MeOH=20:1) to give WYC-309 (83 mg, 90.4%). $^1$H NMR (400 MHz, CDCl$_3$) δ 8.78 (s, 1H), 8.26 (d, J=8.1 Hz, 1H), 7.78 (d, J=8.0 Hz, 1H), 7.58 (s, 1H), 7.24 (s, 1H), 7.09 (d, J=8.1 Hz, 1H), 3.10-3.04 (m, 2H), 2.00-1.93 (m, 2H), 1.36 (s, 6H). $^{13}$C NMR (101 MHz, CDCl$_3$) δ 168.58, 149.36, 142.46, 135.91, 134.83, 133.69, 130.42, 129.73, 126.89, 126.73, 124.17, 117.12, 102.51, 84.56, 37.14, 33.13, 30.11, 30.04, 23.45. ESI(+)–MS: 3 [M+1]$^+$.

Embodiment 51: 3-fluoro-4((4,4-dimethylthiochroman-6-yl)ethynyl)benzoic Acid

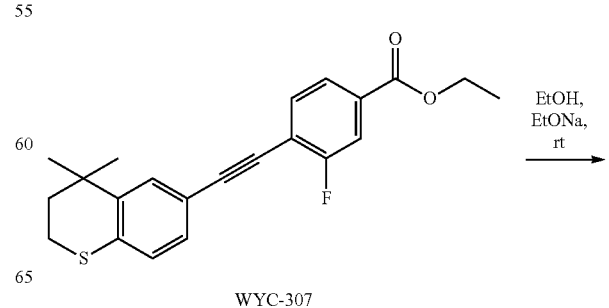

WYC-307

-continued

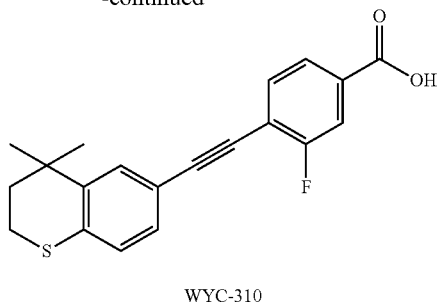

WYC-310

WYC-307 (332 mg, 0.9 mmol) was added to a flask, followed by addition of sodium ethoxide (83 mg, 1.2 mmol) and 7 mL ethanol. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EA=1:1) to give WYC-310 (303 mg, 99%). $^1$H NMR (400 MHz, CDCl$_3$) δ 7.85 (dd, J=8.1, 1.2 Hz, 1H), 7.80 (dd, J=9.7, 1.1 Hz, 1H), 7.61-7.56 (m, 1H), 7.54 (d, J=1.5 Hz, 1H), 7.21 (d, J=8.2 Hz, 1H), 7.07 (d, J=8.2 Hz, 1H), 3.11-2.99 (m, 2H), 1.99-1.90 (m, 2H), 1.34 (s, 6H). $^{13}$C NMR (101 MHz, CDCl$_3$) δ 169.23, 163.46, 160.95, 142.34, 134.64, 133.45, 130.03, 129.32, 126.79, 125.79, 117.62, 117.27, 117.04, 110.16, 98.73, 81.63, 37.28, 33.15, 30.10, 23.40. ESI(+)–MS: 341.2 [M+1]$^+$.

Embodiment 52: ethyl 3-nitro-4-((4,4-dimethyl-1-oxothiochroman-6-yl)ethynyl)benzoate

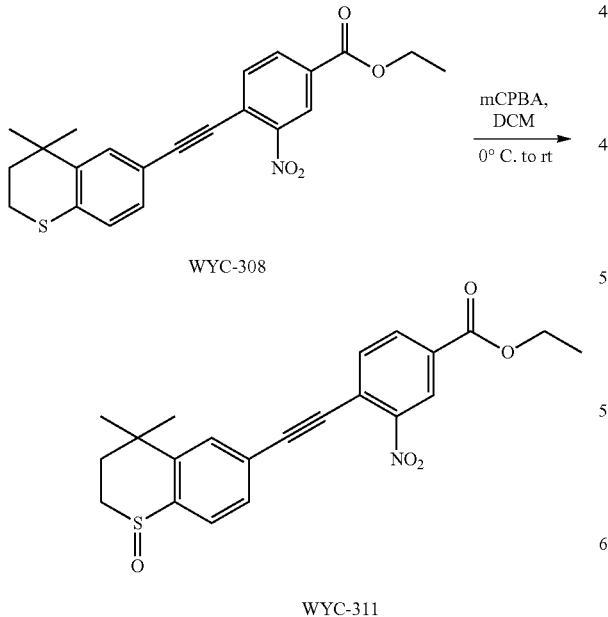

WYC-308

WYC-311

WYC-308 (100 mg, 0.25 mmol) was added to a flask, followed by addition of 5 mL dry dichloromethane. After the mixture was cooled to 0° C. under an ice bath, mCPBA (60 mg, 0.25 mmol) was added. Then the reaction was continued for 1 h under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=3:1) to give WYC-311 (92 mg, 88%). $^1$H NMR (500 MHz, CDCl$_3$) δ 8.73 (d, J=1.6 Hz, 1H), 8.26 (dd, J=8.1, 1.7 Hz, 1H), 7.80 (dd, J=13.0, 8.1 Hz, 2H), 7.66 (d, J=1.5 Hz, 1H), 7.57 (dd, J=8.0, 1.6 Hz, 1H), 4.44 (q, J=7.1 Hz, 2H), 3.23 (ddd, J=12.8, 10.3, 2.3 Hz, 1H), 3.12 (ddd, J=13.1, 9.1, 2.3 Hz, 1H), 2.44 (ddd, J=15.1, 10.3, 2.3 Hz, 1H), 1.91 (ddd, J=15.1, 9.0, 2.3 Hz, 1H), 1.48 (s, 3H), 1.43 (t, J=7.1 Hz, 3H), 1.35 (s, 3H). $^{13}$C NMR (126 MHz, CDCl$_3$) δ 164.10, 149.65, 145.16, 139.98, 134.95, 133.42, 131.67, 131.30, 130.53, 130.26, 126.01, 125.35, 122.13, 98.90, 86.27, 62.24, 43.39, 34.67, 31.36, 31.24, 29.89, 14.40. ESI(+)–MS: 412.2 [M+1]$^+$.

Embodiment 53: ethyl 3-fluoro-4-((4,4-dimethyl-1-oxothiochroman-6-yl)ethynyl)benzoate

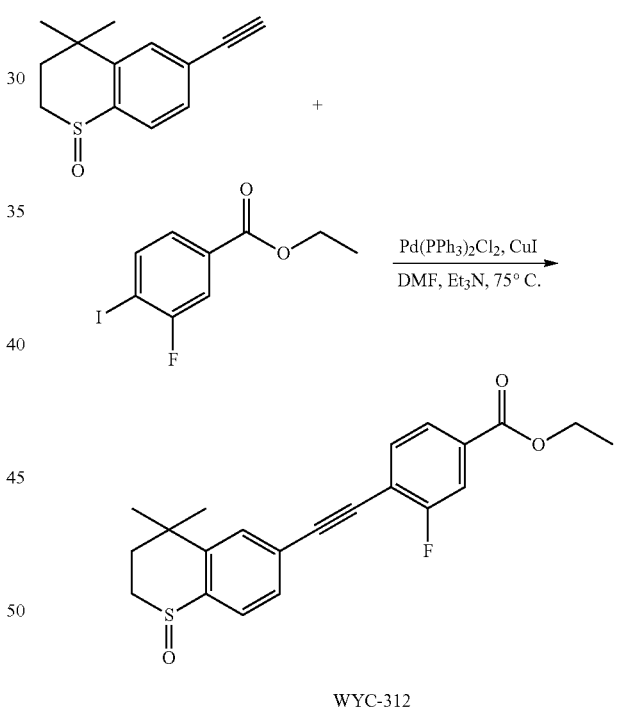

WYC-312

1-Oxo-6-ethynyl-4,4-dimethylthiochroman (223 mg, 1.2 mmol) and ethyl 3-fluoro-4-iodobenzoate (200 mg, 0.8 mmol) were added to a flask, followed by addition of Pd(PPh$_3$)$_2$Cl$_2$ (32 mg, 0.0459 mmol) and CuI (17.5 mg, 0.0918 mmol). After the flask was purged with argon for 3 times to remove oxygen, 3 mL dry DMF and 0.3 mL dry Et$_3$N were added via syringe. Then the reaction was continued at 75° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=3:2) to give WYC-312 (254 mg, 82.5%). ¹H NMR (500 MHz, CDCl₃) δ 7.84 (dd, J=8.0, 1.5 Hz, 1H), 7.81-7.75 (m, 2H), 7.63-7.58 (m, 2H), 7.54 (dd, J=8.0, 1.6 Hz, 1H), 4.40 (q, J=7.1 Hz, 2H), 3.22 (ddd, J=12.9, 10.4, 2.3 Hz, 1H), 3.11 (ddd, J=13.1, 8.9, 2.4 Hz, 1H), 2.46 (ddd, J=15.1, 10.4, 2.3 Hz, 1H), 1.91 (ddd, J=15.1, 8.9, 2.3 Hz, 1H), 1.49 (s, 3H), 1.41 (t, J=7.1 Hz, 4H), 1.35 (s, 4H). ¹³C NMR (126 MHz, CDCl₃₃) δ 165.04, 163.42, 161.41, 145.01, 139.21, 133.49, 132.58, 132.52, 132.26, 132.18, 131.33, 130.29, 130.27, 128.67, 128.57, 125.87, 125.22, 125.19, 116.78, 116.60, 116.06, 115.93, 96.03, 96.00, 84.16, 61.73, 43.34, 34.62, 31.36, 31.22, 29.81, 14.40. ESI(+)−MS: 385.2 [M+1]⁺.

Embodiment 54: ethyl 2,3-difluoro-4-iodobenzoate

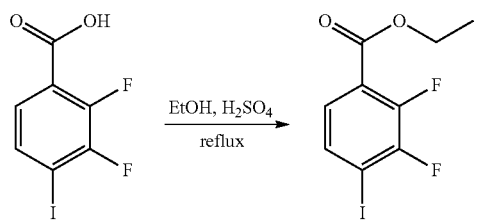

2,3-Difluoro-4-iodobenzoic acid (0.5 g, 1.76 mmol) was added to a flask, followed by addition of 4 mL anhydrous ethanol under argon atmosphere. The mixture was cooled to 0° C. under an ice bath, then 0.3 mL concentrated sulfuric acid was added dropwise. After completion of the dropwise addition, the reaction solution was heated to reflux and stirred for 6 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=10:1) to give ethyl 2,3-difluoro-4-iodobenzoate (0.48 g, 87%). ¹H NMR (500 MHz, CDCl₃) δ 7.55 (ddd, J=8.4, 5.2, 1.8 Hz, 1H), 7.44 (ddd, J=8.4, 6.3, 1.8 Hz, 1H), 4.38 (q, J=7.1 Hz, 2H), 1.38 (t, J=7.1 Hz, 3H). ¹³C NMR (126 MHz, CDCl₃) δ 163.13, 163.10, 163.08, 152.43, 152.31, 150.69, 150.56, 150.46, 150.35, 148.56, 148.44, 133.21, 133.17, 127.48, 127.44, 121.24, 121.18, 88.19, 88.01, 61.98, 14.27. ESI(+)−MS: 313.1 [M+1]⁺.

Embodiment 55: ethyl 2,3-difluoro-4((4,4-dimethylthiochroman-6-yl)ethynyl)benzoate

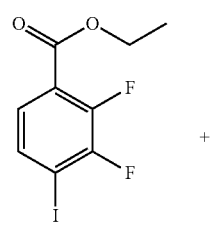

+

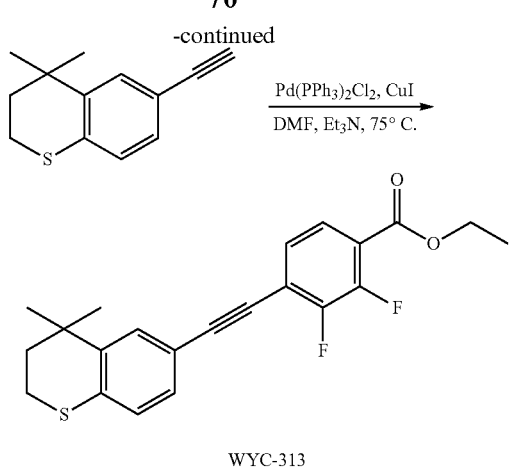

Ethyl 2,3-difluoro-4-iodobenzoate (200 mg, 0.64 mmol) and 6-ethynyl-4,4-dimethylthiochroman (195 mg, 0.96 mmol) were added to a flask, followed by addition of Pd(PPh₃)₂Cl₂ (20 mg, 0.0288 mmol) and CuI (11 mg, 0.0576 mmol). After the flask was purged with argon for 3 times to remove oxygen, 2 mL dry DMF and 0.2 mL dry Et₃N were added via syringe. Then the reaction was continued at 75° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=100:1) to give WYC-313 (215 mg, 82%). ¹H NMR (500 MHz, CDCl₃) δ 7.65 (ddd, J=8.3, 6.5, 1.8 Hz, 1H), 7.54 (d, J=1.7 Hz, 1H), 7.28 (ddd, J=8.0, 4.9, 1.9 Hz, 1H), 7.21 (dd, J=8.2, 1.8 Hz, 1H), 7.08 (d, J=8.2 Hz, 1H), 4.41 (q, J=7.1 Hz, 2H), 3.07-3.03 (m, 2H), 1.97-1.93 (m, 2H), 1.40 (t, J=7.1 Hz, 3H), 1.34 (s, 6H). ¹³C NMR (126 MHz, CDCl₃) δ 163.34, 152.40, 152.29, 151.69, 151.58, 150.38, 150.27, 149.60, 149.49, 142.32, 134.92, 129.98, 129.27, 127.01, 126.98, 126.76, 126.01, 125.97, 120.13, 120.07, 118.59, 118.51, 117.25, 99.26, 99.23, 80.63, 80.60, 61.87, 37.18, 33.09, 30.02, 23.35, 14.33. ESI(+)−MS: 387.2 [M+1]⁺.

Embodiment 56: 2,3-difluoro-4((4,4-dimethylthiochroman-6-yl)ethynyl)benzoic Acid

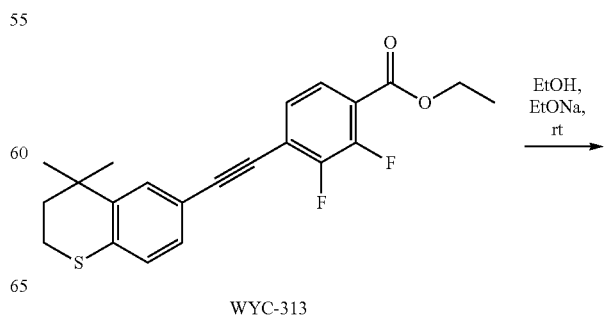

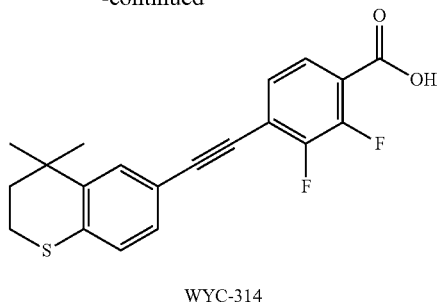

WYC-314

WYC-313 (84 mg, 0.218 mmol) was added to a flask, followed by addition of sodium ethoxide (44.4 mg, 0.653 mmol) and 2 mL ethanol. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EA=1:1) to give WYC-314 (68 mg, 87.5%). $^1$H NMR (500 MHz, pyridine) δ 8.01 (t, J=7.4 Hz, 1H), 7.82 (s, 1H), 7.45 (t, J=7.2 Hz, 1H), 7.40 (d, J=8.1 Hz, 1H), 7.24 (d, J=8.1 Hz, 1H), 2.95-2.89 (m, 2H), 1.78-1.71 (m, 2H), 1.19 (s, 6H). ESI(−)-MS: 357.2 [M−1]$^−$.

Embodiment 57: ethyl 2,3-difluoro-4-((4,4-dimethyl-1-oxothiochroman-6-yl)ethynyl)benzoate

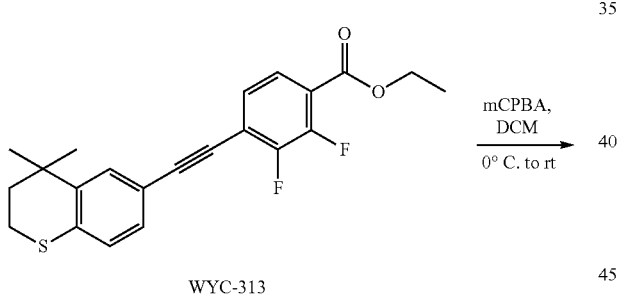

WYC-313

WYC-315

WYC-313 (90 mg, 0.233 mmol) was added to a flask, followed by addition of 5 mL dry dichloromethane. After the mixture was cooled to 0° C. under an ice bath, mCPBA (58 mg, 0.233 mmol) was added. Then the reaction was continued for 1 h under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=3:1) to give WYC-315 (76 mg, 78%). $^1$H NMR (500 MHz, CDCl$_3$) δ 7.76 (d, J=8.0 Hz, 1H), 7.71-7.65 (m, 1H), 7.62 (s, 1H), 7.53 (dd, J=8.0, 0.8 Hz, 1H), 7.32 (dd, J=10.4, 3.9 Hz, 1H), 4.41 (q, J=7.1 Hz, 2H), 3.26-3.18 (m, 1H), 3.15-3.07 (m, 1H), 2.44 (ddd, J=14.8, 10.3, 2.0 Hz, 1H), 1.90 (ddd, J=15.1, 8.9, 2.0 Hz, 1H), 1.47 (s, 3H), 1.40 (t, J=7.1 Hz, 3H), 1.34 (s, 3H). $^{13}$C NMR (126 MHz, CDCl$_3$) δ 163.22, 163.20, 163.17, 152.69, 152.58, 151.65, 151.54, 150.66, 150.55, 149.55, 145.10, 139.57, 131.40, 130.30, 130.27, 127.25, 127.22, 126.15, 126.12, 125.41, 121.05, 120.99, 117.60, 117.59, 117.50, 117.48, 97.09, 97.05, 82.93, 82.90, 62.02, 43.34, 34.63, 31.34, 31.21, 29.82, 14.32. ESI(+)-MS: 403.1 [M+1]$^+$.

Embodiment 58: methyl 3-acetamido-4-iodobenzoate

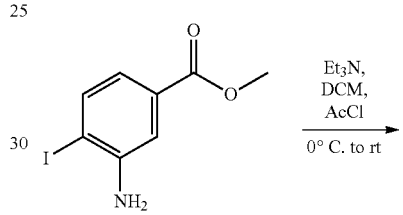

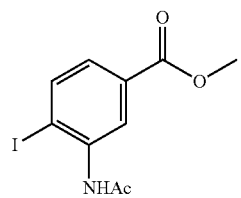

Methyl 3-amino-4-iodobenzoate (1.5 g, 5.43 mmol) was added to a flask, followed by addition of 20 mL dry dichloromethane and 4.5 mL dry triethylamine, then 0.77 mL acetyl chloride was added dropwise under an ice bath. The reaction was continued at room temperature overnight and monitored by TLC. After completion of the reaction, the reaction was quenched with methanol. The mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=10:1) to give methyl 3-acetamido-4-iodobenzoate (1.34 g, 77.5%). $^1$H NMR (500 MHz, CDCl$_3$) δ 8.75 (s, 1H), 7.86 (d, J=8.3 Hz, 1H), 7.54-7.39 (m, 2H), 3.90 (s, 3H), 2.25 (s, 3H). $^{13}$C NMR (126 MHz, CDCl$_3$) δ 168.29, 166.28, 138.97, 138.54, 131.46, 126.74, 122.89, 96.10, 52.44, 24.78. ESI(+)-MS: 320.1 [M+1]$^+$.

Embodiment 59: methyl 3-acetamido-4-((4,4-dimethylthiochroman-6-yl)ethynyl)benzoate

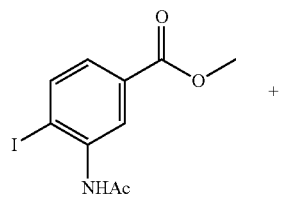

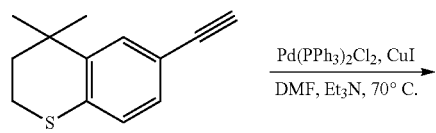

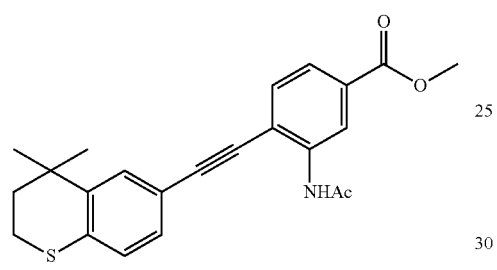

WYC-316

Methyl 3-acetamido-4-iodobenzoate (319 mg, 1 mmol) and 6-ethynyl-4,4-dimethylthiochroman (304 mg, 1.5 mmol) were added to a flask, followed by addition of Pd(PPh$_3$)$_2$Cl$_2$ (47 mg, 0.0675 mmol) and CuI (26 mg, 0.135 mmol). After the flask was purged with argon for 3 times to remove oxygen, 5 mL dry DMF and 0.3 mL dry Et$_3$N were added via syringe. Then the reaction was continued at 70° C. for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=10:1) to give WYC-316 (298 mg, 76%). $^1$H NMR (500 MHz, CDCl$_3$) δ 9.00 (s, 1H), 7.97 (s, 1H), 7.74 (dd, J=8.1, 1.2 Hz, 1H), 7.57-7.50 (m, 2H), 7.18 (dd, J=8.1, 1.7 Hz, 1H), 7.10 (d, J=8.1 Hz, 1H), 3.91 (s, 3H), 3.10-3.02 (m, 2H), 2.26 (s, 3H), 1.98-1.93 (m, 2H), 1.35 (s, 6H). $^{13}$C NMR (126 MHz, CDCl$_3$) δ 168.23, 166.55, 142.53, 138.77, 135.02, 131.51, 130.80, 129.71, 128.90, 126.92, 124.65, 120.35, 117.03, 110.11, 99.62, 83.25, 52.42, 37.09, 33.11, 30.02, 25.03, 23.36. ESI(+)-MS: 394.2 [M+1]$^+$.

Embodiment 60: ethyl 3-acetamido-4-((4,4-dimethylthiochroman-6-yl)ethynyl)benzoate

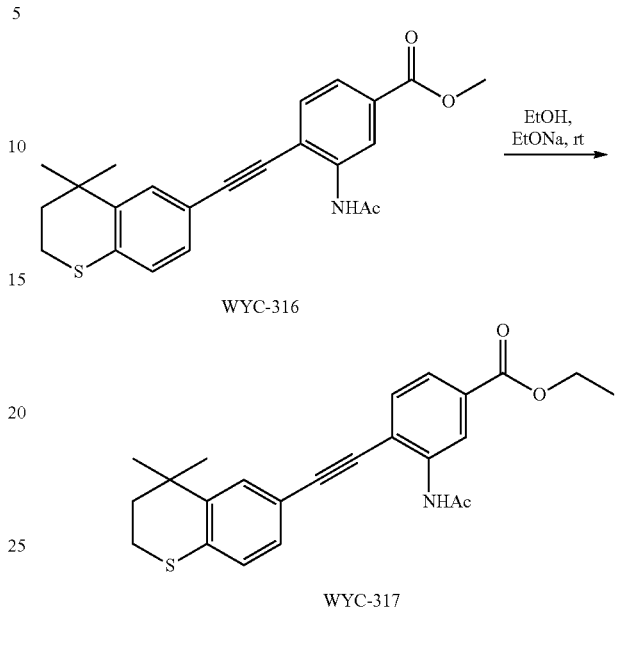

WYC-316 (56 mg, 0.142 mmol) was added to a flask, followed by addition of sodium ethoxide (29 mg, 0.426 mmol) and 2 mL ethanol. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EA=20:1) to give WYC-317 (48 mg, 83%). $^1$H NMR (500 MHz, CDCl$_3$) δ 9.00 (s, 1H), 7.97 (s, 1H), 7.75 (d, J=8.0 Hz, 1H), 7.53 (d, J=7.2 Hz, 2H), 7.18 (dd, J=8.1, 1.3 Hz, 1H), 7.10 (d, J=8.1 Hz, 1H), 4.38 (q, J=7.1 Hz, 2H), 3.09-3.02 (m, 2H), 2.26 (s, 3H), 1.98-1.94 (m, 2H), 1.39 (t, J=7.1 Hz, 3H), 1.35 (s, 6H). $^{13}$C NMR (126 MHz, CDCl$_3$) δ 168.22, 166.08, 142.53, 138.76, 135.00, 131.47, 131.21, 129.72, 128.91, 126.93, 124.64, 120.38, 117.07, 110.12, 99.54, 83.31, 61.39, 37.11, 33.12, 30.04, 25.03, 23.36, 14.44. ESI(+)-MS: 408.2 [M+1]$^+$.

Embodiment 61: ethyl 3-acetamido-4-((4,4-dimethyl-1-oxothiochroman-6-yl)ethynyl)benzoate

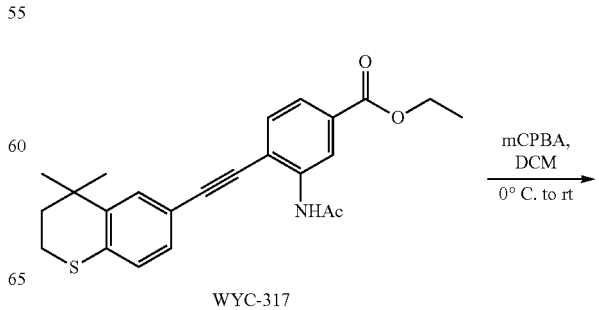

WYC-317

-continued

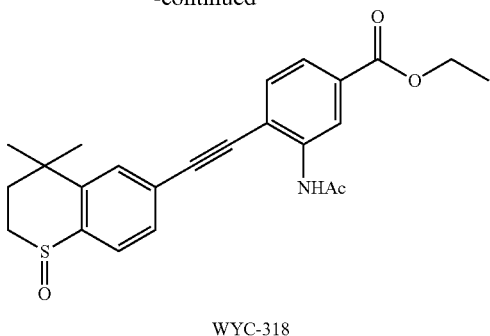

WYC-318

WYC-317 (86 mg, 0.211 mmol) was added to a flask, followed by addition of 2 mL dry dichloromethane. After the mixture was cooled to 0° C. under an ice bath, mCPBA (37 mg, 0.211 mmol) was added. Then the reaction was continued for 1 h under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:1) to give WYC-318 (80 mg, 98.6%). $^1$H NMR (500 MHz, CDCl$_{33}$) δ 8.98 (s, 1H), 7.93 (s, 1H), 7.78 (d, J=8.0 Hz, 2H), 7.61 (d, J=1.3 Hz, 1H), 7.57 (d, J=8.1 Hz, 1H), 7.50 (dd, J=8.0, 1.3 Hz, 1H), 4.38 (q, J=7.1 Hz, 2H), 3.24 (dd, J=17.2, 6.3 Hz, 1H), 3.17-3.09 (m, 1H), 2.45 (ddd, J=14.8, 10.3, 1.9 Hz, 1H), 2.27 (s, 3H), 1.91 (ddd, J=15.1, 8.9, 2.0 Hz, 1H), 1.48 (s, 3H), 1.39 (t, J=7.1 Hz, 3H), 1.35 (s, 3H). $^{13}$C NMR (126 MHz, CDCl$_3$) δ 168.29, 165.92, 145.31, 139.07, 131.97, 131.91, 131.19, 130.44, 129.98, 125.33, 124.80, 124.76, 120.86, 115.83, 97.48, 85.94, 61.51, 43.40, 34.66, 31.36, 31.27, 29.79, 14.43. ESI(+)-MS: 424.1 [M+1]$^+$.

Embodiment 62: 3-acetamido-4-((4,4-dimethylthiochroman-6-yl)ethynyl)benzoic Acid

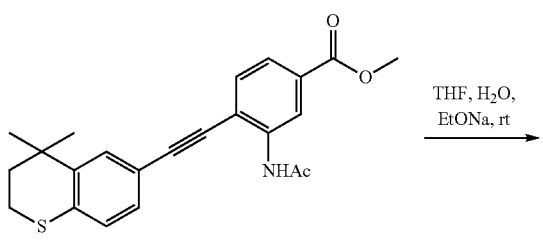

WYC-316

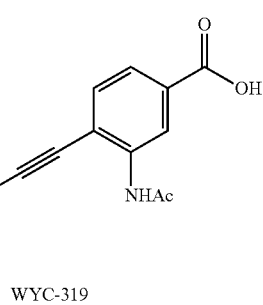

WYC-319

WYC-316 (63 mg, 0.16 mmol) was added to a flask, followed by addition of sodium ethoxide (14 mg, 0.2 mmol), 2 mL tetrahydrofuran and 0.2 mL water. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:4) to give WYC-319 (34 mg, 56%). ESI(+)-MS: 380.2 [M+1]$^+$.

Embodiment 63: ethyl 5-bromopyrazin-2-carboxylate

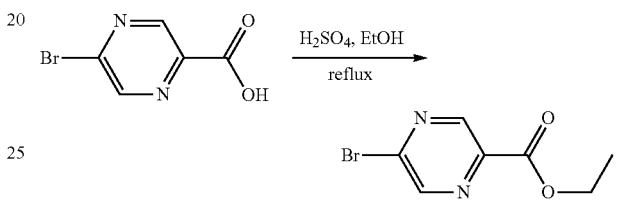

5-Bromopyrazin-2-carboxylic acid (1.0 g, 5 mmol) was added to a flask, followed by addition of 5 mL anhydrous ethanol under argon atmosphere. The mixture was cooled to 0° C. under an ice bath, then 0.3 mL concentrated sulfuric acid was added dropwise. After completion of the dropwise addition, the reaction solution was heated to reflux and stirred for 6 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=50:1) to give ethyl 5-bromopyrazin-2-carboxylate (0.42 g, 37%). $^1$H NMR (500 MHz, CDCl$_3$) δ 9.01 (d, J=1.3 Hz, 1H), 8.76 (d, J=1.3 Hz, 1H), 4.47 (q, J=7.1 Hz, 2H), 1.41 (t, J=7.1 Hz, 3H). $^{13}$C NMR (126 MHz, CDCl$_3$) δ 163.39, 147.30, 146.31, 144.65, 141.89, 62.67, 14.30. ESI(+)-MS: 231.2 [M+1]$^+$.

Embodiment 64: ethyl 2-((4,4-dimethyl-1,1-dioxothiochroman-6-yl)ethynyl)pyrimidin-5-carboxylate

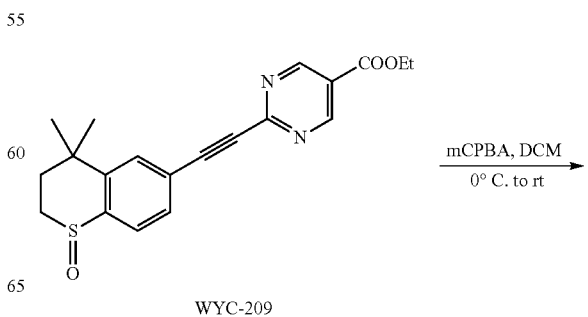

WYC-209

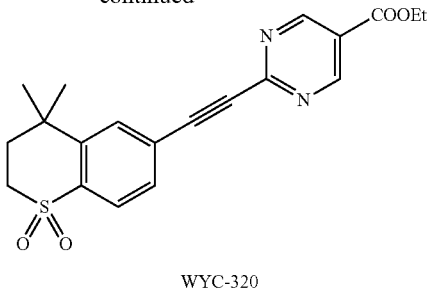

WYC-320

WYC-209 (1.1 g, 3 mmol) was added to a flask, followed by addition of 20 mL dry dichloromethane. After the mixture was cooled to 0° C. under an ice bath, mCPBA (0.663 g, 3.6 mmol) was added. Then the reaction was continued for 10 min under the ice bath and another 3 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:5) to give WYC-320 (0.99 g, 89%). $^1$H NMR (500 MHz, CDCl$_3$) δ 9.29 (s, 2H), 7.94 (d, J=8.2 Hz, 1H), 7.76 (d, J=1.3 Hz, 1H), 7.68 (dd, J=8.2, 1.5 Hz, 1H), 4.47 (q, J=7.1 Hz, 2H), 3.46-3.37 (m, 2H), 2.45-2.39 (m, 2H), 1.44 (s, 6H). $^{13}$C NMR (126 MHz, CDCl$_3$) δ 163.22, 158.51, 155.10, 145.17, 138.59, 132.27, 131.31, 125.41, 124.24, 122.74, 89.85, 88.71, 62.32, 47.06, 35.49, 34.47, 30.71, 14.35. ESI(+)–MS: 385.4 [M+1]$^+$.

Embodiment 65: methyl 3-acetamido-4-((4,4-dimethyl-1-oxothiochroman-6-yl)ethynyl)benzoate

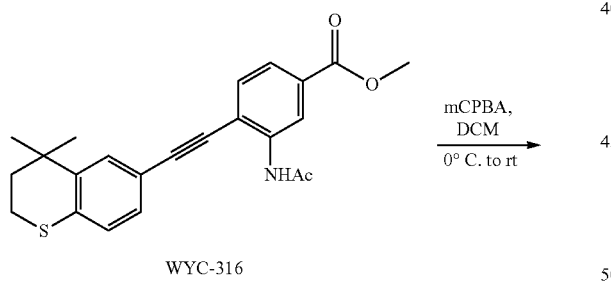

WYC-316

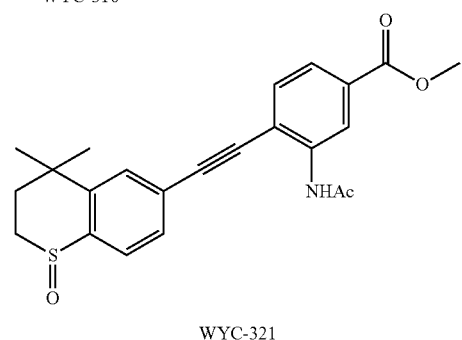

WYC-321

WYC-316 (107 mg, 0.272 mmol) was added to a flask, followed by addition of 3.5 mL dry dichloromethane. After the mixture was cooled to 0° C. under an ice bath, mCPBA (67.3 mg, 0.272 mmol) was added. Then the reaction was continued for 1 h under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:1) to give WYC-321 (84 mg, 78%). $^1$H NMR (500 MHz, CDCl$_3$) δ 8.97 (s, 1H), 7.96 (s, 1H), 7.80-7.72 (m, 2H), 7.60 (d, J=1.4 Hz, 1H), 7.56 (d, J=8.1 Hz, 1H), 7.49 (dd, J=8.0, 1.3 Hz, 1H), 3.90 (s, 3H), 3.14 (ddt, J=12.9, 8.9, 6.4 Hz, 2H), 2.45 (ddd, J=14.8, 10.3, 1.7 Hz, 1H), 2.26 (s, 3H), 1.90 (ddd, J=15.0, 8.9, 1.9 Hz, 1H), 1.47 (s, 3H), 1.34 (s, 3H). $^{13}$C NMR (126 MHz, CDCl$_3$) δ 168.28, 166.37, 145.28, 139.65, 139.09, 131.94, 131.52, 131.18, 130.41, 129.95, 125.29, 124.74, 120.91, 115.97, 97.52, 85.89, 52.49, 43.37, 34.63, 31.32, 31.25, 29.76, 24.99. ESI(+)–MS: 410.3 [M+1]$^+$.

Embodiment 66: ethyl 5-((4,4-dimethylthiochroman-6-yl)ethynyl)pyrazin-2-carboxylate

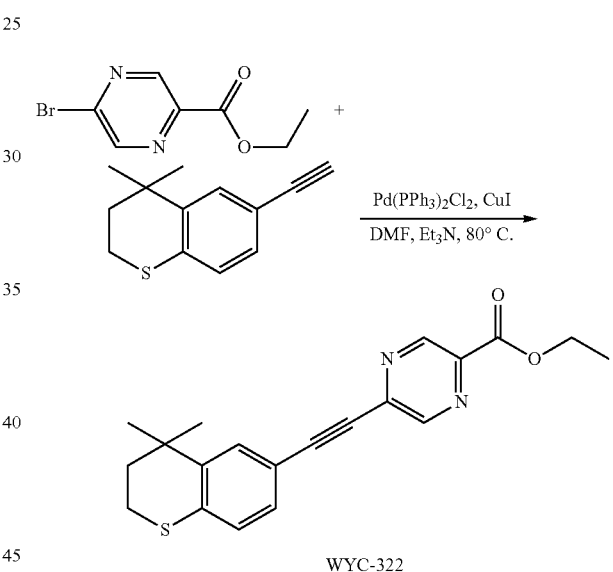

WYC-322

Ethyl 5-bromopyrazin-2-carboxylate (600 mg, 2.61 mmol) and 6-ethynyl-4,4-dimethylthiochroman (635 mg, 3.13 mmol) were added to a flask, followed by addition of Pd(PPh$_3$)$_2$Cl$_2$ (66 mg, 0.094 mmol) and CuI (36 mg, 0.188 mmol). After the flask was purged with argon for 3 times to remove oxygen, 6 mL dry DMF and 0.4 mL dry Et$_3$N were added via syringe. Then the reaction was continued at 80° C. for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=50:1) to give WYC-322 (656 mg, 71.5%). $^1$H NMR (500 MHz, CDCl$_3$) δ 9.20 (d, J=1.4 Hz, 1H), 8.76 (d, J=1.4 Hz, 1H), 7.58 (d, J=1.7 Hz, 1H), 7.23 (dd, J=8.2, 1.8 Hz, 1H), 7.04 (d, J=8.2 Hz, 1H), 4.46 (q, J=7.1 Hz, 2H), 3.02-2.97 (m, 2H), 1.92-1.87 (m, 2H), 1.41 (t, J=7.1 Hz, 3H), 1.29 (s, 6H). $^{13}$C NMR (126 MHz, CDCl$_3$) δ 163.65, 146.68, 145.70, 143.08, 142.31, 140.30, 136.14, 130.54, 129.51, 126.74, 116.00, 97.55, 85.68, 62.37, 36.91, 32.99, 29.89, 23.27, 14.31. ESI(+)-MS: 353.5 [M+1]+.

Embodiment 67: 5-((4,4-dimethylthiochroman-6-yl)ethynyl)pyrazin-2-carboxylic Acid

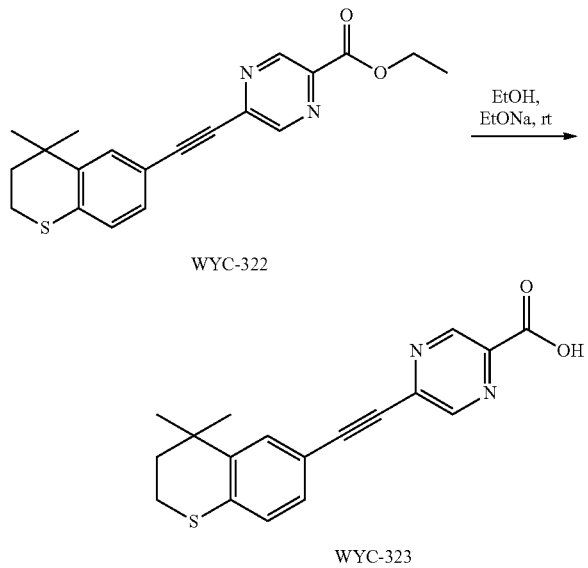

WYC-322 (50 mg, 0.14 mmol) was added to a flask, followed by addition of sodium ethoxide (29 mg, 0.426 mmol) and 2 mL ethanol. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (DCM:MeOH=15:1) to give WYC-323 (43 mg, 95%). $^1$H NMR (500 MHz, pyridine) δ 9.65 (s, 1H), 9.05 (s, 1H), 7.84 (d, J=1.4 Hz, 1H), 7.41 (dd, J=8.1, 1.4 Hz, 1H), 7.23 (d, J=8.1 Hz, 1H), 2.98-2.88 (m, 2H), 1.81-1.72 (m, 2H), 1.19 (s, 6H). $^{13}$C NMR (126 MHz, pyridine) δ 166.73, 147.26, 146.43, 143.36, 142.96, 142.56, 136.52, 130.88, 129.89, 127.24, 116.79, 96.42, 86.89, 36.94, 33.05, 29.59, 23.30. ESI(+)-MS: 325.2 [M+1]+.

Embodiment 68: ethyl 5-((4,4-dimethyl-1-oxothiochroman-6-yl)ethynyl)pyrazin-2-carboxylate

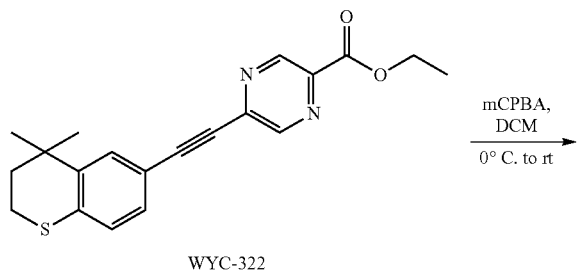

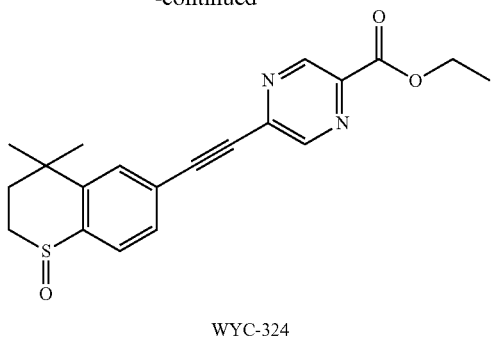

WYC-322 (100 mg, 0.284 mmol) was added to a flask, followed by addition of 3.5 mL dry dichloromethane. After the mixture was cooled to 0° C. under an ice bath, mCPBA (49 mg, 0.284 mmol) was added. Then the reaction was continued for 1 h under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:2) to give WYC-324 (78 mg, 75%). $^1$H NMR (500 MHz, CDCl$_{33}$) δ 9.29 (d, J=1.4 Hz, 1H), 8.87 (d, J=1.4 Hz, 1H), 7.80 (d, J=8.1 Hz, 1H), 7.71 (d, J=1.5 Hz, 1H), 7.61 (dd, J=8.1, 1.6 Hz, 1H), 4.52 (q, J=7.1 Hz, 2H), 3.29-3.06 (m, 2H), 2.43 (ddd, J=15.1, 10.2, 2.3 Hz, 1H), 1.91 (ddd, J=15.1, 9.2, 2.3 Hz, 1H), 1.47 (dd, J=8.8, 5.5 Hz, 6H), 1.34 (s, 3H). $^{13}$C NMR (126 MHz, CDCl$_3$) δ 163.62, 147.07, 145.93, 145.25, 142.41, 141.29, 140.60, 132.05, 130.63, 130.25, 124.32, 94.92, 87.36, 62.70, 43.44, 34.73, 31.35, 31.25, 29.91, 14.41. ESI(+)-MS: 396.2 [M+1]+.

Embodiment 69: ethyl 2-chloro-4-iodobenzoate

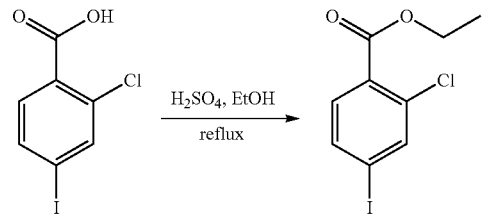

2-Chloro-4-iodobenzoic acid (1.0 g, 3.55 mmol) was added to a flask, followed by addition of 7 mL anhydrous ethanol under argon atmosphere. The mixture was cooled to 0° C. under an ice bath, then 0.4 mL concentrated sulfuric acid was added dropwise. After completion of the dropwise addition, the reaction solution was heated to reflux and stirred for 5 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=7:1) to give ethyl 2-chloro-4-iodobenzoate (0.98 g, 89%). $^1$H NMR (500 MHz, CDCl$_3$) δ 7.82 (d, J=1.6 Hz, 1H), 7.65 (dd, J=8.2, 1.6 Hz, 1H), 7.52 (d, J=8.2 Hz, 1H), 4.38 (q, J=7.1 Hz, 2H), 1.39 (t, J=7.2 Hz, 3H). $^{13}$C NMR (126 MHz, CDCl$_3$) δ 165.22, 139.57, 135.95, 134.63, 132.47, 129.91, 98.35, 61.87, 14.32. ESI(+)-MS: 311.3 [M+1]$^+$.

Embodiment 70: ethyl 2-chloro-4-((4,4-dimethylthiochroman-6-yl)ethynyl)benzoate

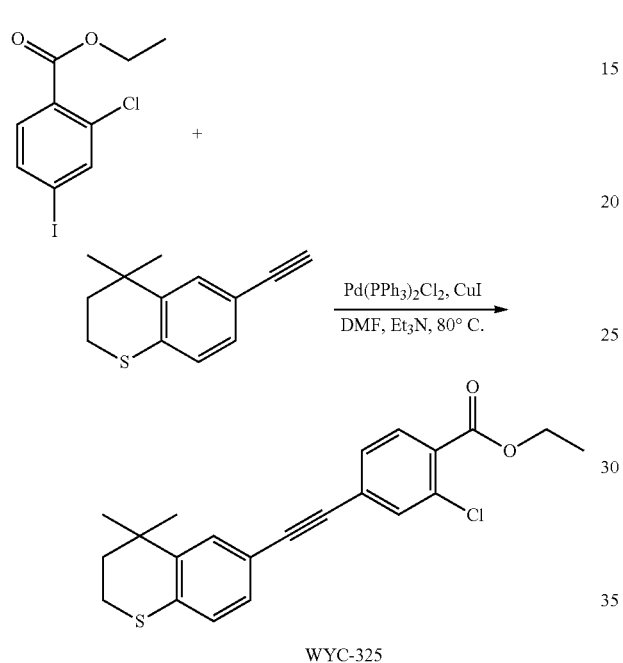

Ethyl 2-chloro-4-iodobenzoate (310 mg, 1 mmol) and 6-ethynyl-4,4-dimethylthiochroman (244 mg, 1.2 mmol) were added to a flask, followed by addition of Pd(PPh$_3$)$_2$Cl$_2$ (28 mg, 0.04 mmol) and CuI (11.4 mg, 0.06 mmol). After the flask was purged with argon for 3 times to remove oxygen, 3 mL dry DMF and 0.3 mL dry Et$_3$N were added via syringe. Then the reaction was continued at 80° C. for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=50:1) to give WYC-325 (365 mg, 95%). $^1$H NMR (500 MHz, CDCl$_3$) δ 7.81 (d, J=8.1 Hz, 1H), 7.59 (d, J=1.5 Hz, 1H), 7.52 (d, J=1.7 Hz, 1H), 7.42 (dd, J=8.1, 1.5 Hz, 1H), 7.18 (dd, J=8.2, 1.8 Hz, 1H), 7.07 (d, J=8.1 Hz, 1H), 4.40 (q, J=7.1 Hz, 2H), 3.06-3.02 (m, 2H), 1.97-1.93 (m, 2H), 1.40 (t, J=7.1 Hz, 3H), 1.34 (s, 6H). $^{13}$C NMR (126 MHz, CDCl$_3$) δ 165.27, 142.26, 134.37, 133.89, 133.65, 131.41, 129.92, 129.38, 129.30, 129.14, 128.27, 126.72, 117.56, 93.73, 86.76, 61.71, 37.21, 33.06, 30.04, 23.32, 14.33. ESI(+)-MS: 385.2 [M+1]$^+$.

Embodiment 71: ethyl 2-chloro-4-((4,4-dimethyl-1-oxothiochroman-6-yl)ethynyl)benzoate

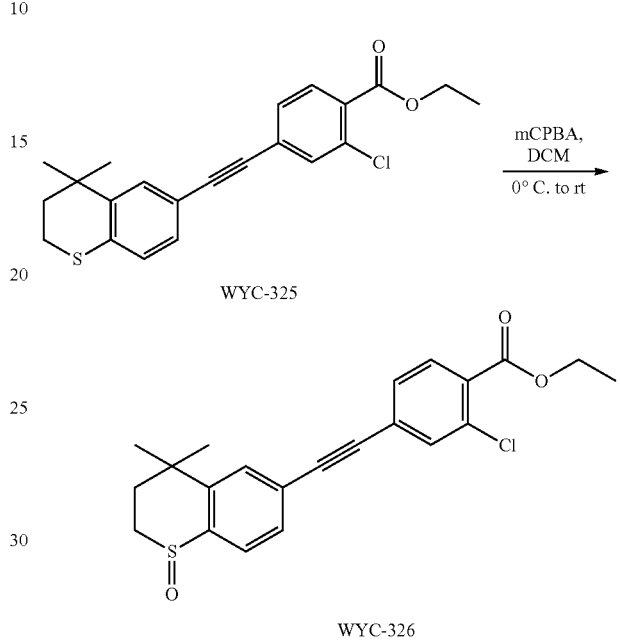

WYC-325 (100 mg, 0.26 mmol) was added to a flask, followed by addition of 3 mL dry dichloromethane. After the mixture was cooled to 0° C. under an ice bath, mCPBA (60 mg, 0.26 mmol) was added. Then the reaction was continued for 1 h under the ice bath and another 2 h at room temperature, meanwhile TLC was used to monitor the reaction. After completion of the reaction, the reaction was quenched with sodium thiosulfate solution, the mixture was diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=1:3) to give WYC-326 (86 mg, 83%). $^1$H NMR (500 MHz, CDCl$_3$) δ 7.79 (d, J=8.1 Hz, 1H), 7.71 (d, J=8.1 Hz, 1H), 7.59 (d, J=1.5 Hz, 1H), 7.57 (d, J=1.5 Hz, 1H), 7.46 (dd, J=8.0, 1.5 Hz, 1H), 7.42 (dd, J=8.1, 1.6 Hz, 1H), 4.36 (q, J=7.1 Hz, 2H), 3.17 (ddd, J=12.7, 10.5, 2.1 Hz, 1H), 3.06 (ddd, J=13.1, 8.8, 2.2 Hz, 1H), 2.41 (ddd, J=14.9, 10.4, 2.1 Hz, 1H), 1.85 (ddd, J=15.1, 8.8, 2.2 Hz, 1H), 1.43 (s, 3H), 1.36 (t, J=7.1 Hz, 3H), 1.30 (s, 3H). $^{13}$C NMR (126 MHz, CDCl$_3$) δ 165.05, 144.93, 138.96, 133.81, 133.81, 131.36, 131.23, 130.19, 130.08, 130.05, 129.58, 127.12, 125.66, 91.67, 89.03, 61.74, 43.16, 34.45, 31.20, 31.06, 29.59, 14.22. ESI(+)-MS: 401.2 [M+1]$^+$.

Embodiment 72: 2-chloro-4-((4,4-dimethylthiochroman-6-yl)ethynyl)benzoic Acid

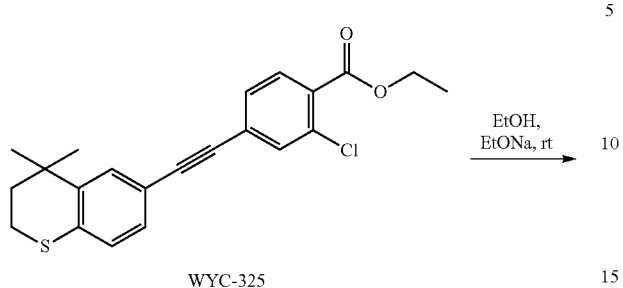

WYC-325 (100 mg, 0.26 mmol) was added to a flask, followed by addition of sodium ethoxide (29 mg, 0.426 mmol) and 2 mL ethanol. Then the reaction was continued at room temperature overnight and monitored by TLC. After completion of the reaction, the reaction solution was neutralized to neutral with acid resin and filtered, the filtrate was diluted with ethyl acetate, washed with saturated sodium bicarbonate solution and saturated sodium chloride solution. The organic phase was dried over anhydrous sodium sulfate, filtered, concentrated and purified by flash column chromatography (PE:EA=1:2) to give WYC-327 (89 mg, 94%). $^1$H NMR (500 MHz, CDCl$_3$) δ 7.98 (d, J=8.1 Hz, 1H), 7.61 (s, 1H), 7.52 (d, J=1.6 Hz, 1H), 7.44 (d, J=7.9 Hz, 1H), 7.18 (dd, J=8.2, 1.6 Hz, 1H), 7.07 (d, J=8.1 Hz, 1H), 3.07-3.04 (m, 2H), 1.98-1.94 (m, 2H), 1.35 (s, 6H). $^{13}$C NMR (126 MHz, CDCl$_3$) δ 170.29, 142.32, 134.90, 134.53, 134.00, 132.52, 130.02, 129.51, 129.36, 129.25, 127.76, 126.79, 117.54, 94.44, 86.79, 37.25, 33.12, 30.09, 23.39. ESI(+)–MS: 355.2 [M+1]$^+$.

Embodiment 73: 2-cyano-5-((5,5,8,8-tetramethyl-5,6,7,8-tetrahydronaphth-2-yl)ethynyl)pyrimidine

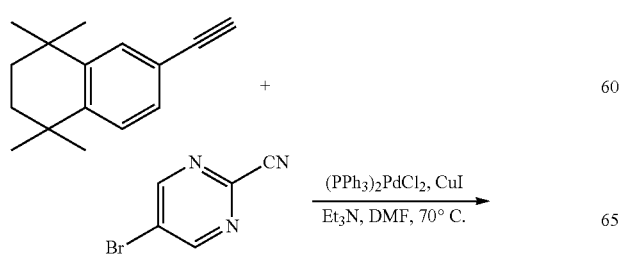

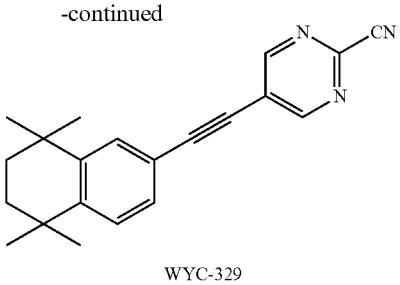

6-Ethynyl-1,1,4,4-tetramethyl-1,2,3,4-tetrahydronaphthalene (50 mg, 0.235 mmol) and 2-cyano-5-bromopyrimidine (49.9 mg, 0.271 mmol) were added to a flask, followed by addition of Pd(PPh$_3$)$_2$Cl$_2$ (14 mg, 0.02 mmol) and CuI (5.6 mg, 0.03 mmol). After the flask was purged with argon for 3 times to remove oxygen, 2 mL dry DMF and 0.14 mL dry Et$_3$N were added via syringe. Then the reaction was continued at 70° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=10:0 to 10:1) to give WYC-329 (75 mg, 77%). $^1$H NMR (400 MHz, CDCl$_3$) δ 8.90 (s, 2H), 7.52 (d, J=1.4 Hz, 1H), 7.38-7.29 (m, 2H), 1.70 (s, 4H), 1.31 (s, 6H), 1.29 (s, 6H). $^{13}$C NMR (101 MHz, CDCl3) δ 159.24, 147.92, 145.68, 141.75, 130.54, 129.00, 127.11, 122.82, 117.86, 115.58, 101.75, 80.64, 77.35, 77.04, 76.72, 34.78, 34.73, 34.59, 34.31, 31.77, 31.64. ESI(+)–MS: 338.4 [M+1]+.

Embodiment 74: 2-amino-4-((5,5,8,8-tetramethyl-5,6,7,8-tetrahydronaphth-2-yl)ethynyl)benzoic Acid

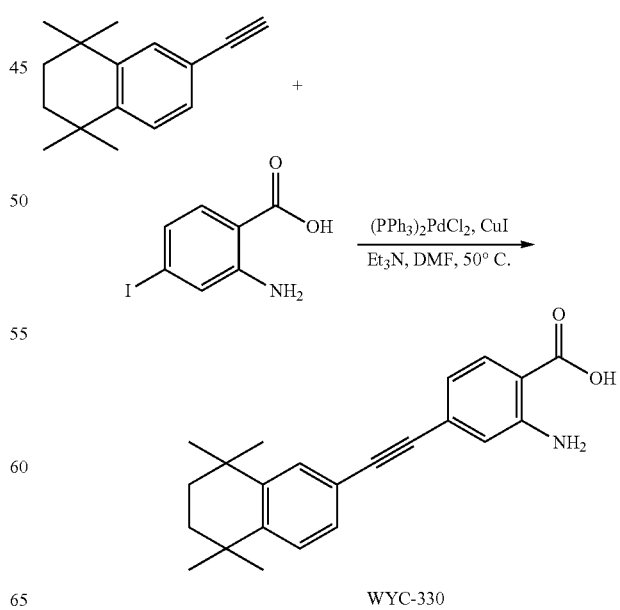

6-Ethynyl-1,1,4,4-tetramethyl-1,2,3,4-tetrahydronaphthalene (100 mg, 0.47 mmol) and 2-amino-4-iodobenzoic acid (141.8 mg, 0.54 mmol) were added to a flask, followed by addition of Pd(PPh$_3$)$_2$Cl$_2$ (28 mg, 0.04 mmol) and CuI (11.2 mg, 0.059 mmol). After the flask was purged with argon for 3 times to remove oxygen, 2 mL dry DMF and 0.28 mL dry Et$_3$N were added via syringe. Then the reaction was continued at 50° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=50:1 to 10:1) to give WYC-330 (97 mg, 60%). $^1$H NMR (400 MHz, MeOD) δ 7.81 (s, 1H), 7.46 (s, 1H), 7.33 (d, J=8.2 Hz, 1H), 7.24 (d, J=8.2 Hz, 1H), 6.88 (s, 1H), 6.68 (s, 1H), 1.72 (s, 4H), 1.30 (s, 6H), 1.29 (s, 6H). ESI(+)–MS: 348.3 [M+1]$^+$.

Embodiment 75: ethyl 2-((5,5,8,8-tetramethyl-5,6,7,8-tetrahydronaphth-2-yl)ethynyl)pyrimidin-5-carboxylate

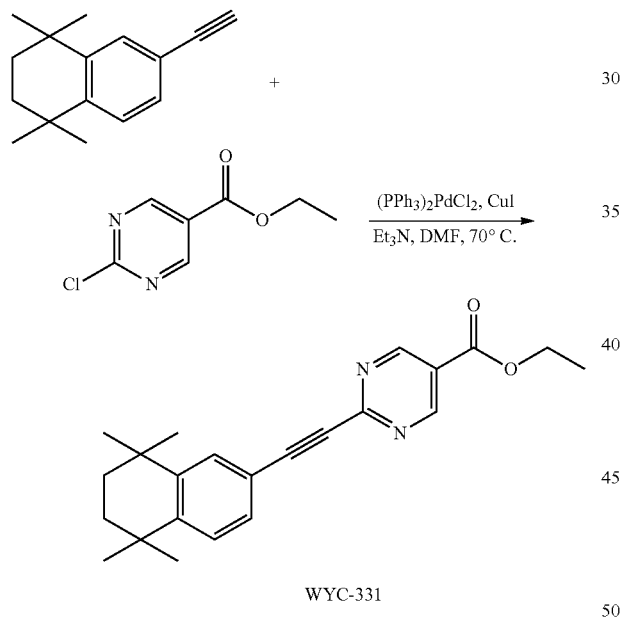

6-Ethynyl-1,1,4,4-tetramethyl-1,2,3,4-tetrahydronaphthalene (50 mg, 0.235 mmol) and ethyl 2-chloropyrimidin-4-carboxylate (50.3 mg, 0.27 mmol) were added to a flask, followed by addition of Pd(PPh$_3$)$_2$Cl$_2$ (14 mg, 0.02 mmol) and CuI (5.6 mg, 0.03 mmol). After the flask was purged with argon for 3 times to remove oxygen, 1 mL dry DMF and 0.14 mL dry Et$_3$N were added via syringe. Then the reaction was continued at 70° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=100:1 to 50:1) to give WYC-331 (67.2 mg, 79%). $^1$H NMR (500 MHz, CDCl$_3$) δ 9.26 (s, 2H), 7.67 (d, J=1.7 Hz, 1H), 7.45 (dd, J=8.2, 1.8 Hz, 1H), 7.33 (d, J=8.2 Hz, 1H), 4.46 (q, J=7.1 Hz, 2H), 1.69 (s, 4H), 1.44 (t, J=7.1 Hz, 3H), 1.29 (s, 6H), 1.28 (s, 6H). $^{13}$C NMR (101 MHz, CDCl$_3$) δ 163.42, 158.33, 155.80, 148.01, 145.46, 131.77, 129.86, 126.94, 121.83, 117.66, 92.54, 87.31, 62.02, 34.81, 34.77, 34.58, 34.31, 31.72, 31.60. ESI(+)–MS: 363.3 [M+1]$^+$.

Embodiment 76: methyl 3-hydroxy-4-((5,5,8,8-tetramethyl-5,6,7,8-tetrahydronaphth-2-yl)ethynyl)benzoate

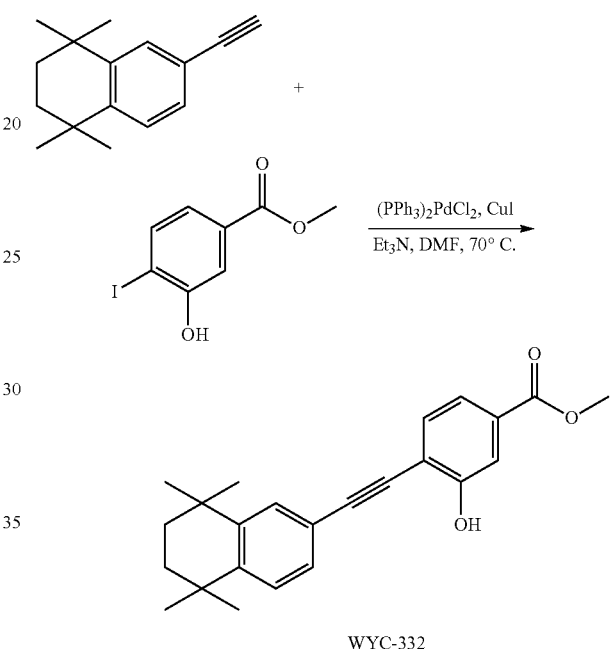

6-Ethynyl-1,1,4,4-tetramethyl-1,2,3,4-tetrahydronaphthalene (120 mg, 0.566 mmol) and methyl 3-hydroxy-4-iodobenzoate (180.7 mg, 0.65 mmol) were added to a flask, followed by addition of Pd(PPh$_3$)$_2$Cl$_2$ (33.7 mg, 0.048 mmol) and CuI (13.5 mg, 0.072 mmol). After the flask was purged with argon for 3 times to remove oxygen, 3 mL dry DMF and 0.338 mL dry Et$_3$N were added via syringe. Then the reaction was continued at 70° C. for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=50:1 to 10:1) to give WYC-332 (118 mg, 58%). $^1$H NMR (400 MHz, CDCl$_3$) δ 8.23 (s, 1H), 7.95 (dd, J=8.2, 1.4 Hz, 1H), 7.85 (d, J=1.9 Hz, 1H), 7.63 (dd, J=8.3, 1.9 Hz, 1H), 7.58 (d, J=8.1 Hz, 1H), 7.41 (d, J=8.3 Hz, 1H), 7.01 (d, J=0.8 Hz, 1H), 3.96 (s, 3H), 1.74 (s, 4H), 1.38 (s, 6H), 1.33 (d, J=4.9 Hz, 6H). $^{13}$C NMR (126 MHz, cdcl3) δ 167.34, 159.55, 154.18, 146.62, 145.60, 133.81, 127.20, 127.09, 125.67, 124.35, 123.49, 122.72, 120.13, 112.70, 100.54, 77.25, 76.99, 76.74, 52.10, 35.01, 34.90, 34.43, 34.42, 31.84, 31.72. ESI(+)–MS: 363.2 [M+1]$^+$.

Embodiment 77: 2-((5,5,8,8-tetramethyl-5,6,7,8-tetrahydronaphth-2-yl)ethynyl)-5-cyanopyridine

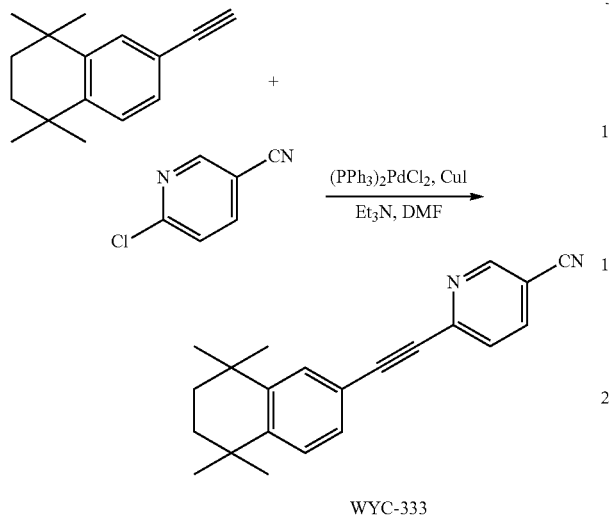

WYC-333

6-Ethynyl-1,1,4,4-tetramethyl-1,2,3,4-tetrahydronaphthalene (60 mg, 0.283 mmol) and 2-chloro-5-cyanopyridine (59.5 mg, 0.325 mmol) were added to a flask, followed by addition of Pd(PPh$_3$)$_2$Cl$_2$ (16.8 mg, 0.024 mmol) and CuI (6.8 mg, 0.036 mmol). After the flask was purged with argon for 3 times to remove oxygen, 2 mL dry DMF and 0.17 mL dry Et$_3$N were added via syringe. Then the reaction was continued at 70° C. for 8 h and monitored by TLC. After completion of the reaction, the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EtOAc=100:1 to 20:1) to give WYC-333 (59 mg, 67%). $^1$H NMR (500 MHz, CDCl$_3$) δ 8.86 (dd, J=2.1, 0.8 Hz, 1H), 7.93 (dd, J=8.2, 2.2 Hz, 1H), 7.60 (dd, J=8.2, 0.8 Hz, 1H), 7.58 (d, J=1.7 Hz, 1H), 7.36 (dd, J=8.2, 1.7 Hz, 1H), 7.32 (d, J=8.2 Hz, 1H), 1.69 (s, 4H), 1.29 (s, 6H), 1.29 (s, 6H). $^{13}$C NMR (126 MHz, CDCl$_3$) δ 152.56, 147.56, 147.09, 145.45, 139.13, 130.99, 129.26, 126.92, 126.59, 118.07, 116.52, 107.95, 95.22, 86.91, 77.25, 76.99, 76.74, 34.81, 34.76, 34.52, 34.28, 31.73, 31.61. ESI(+)–MS: 315.6 [M+1]$^+$.

Embodiment 78: ethyl 5-((5,5,8,8-tetramethyl-5,6,7,8-tetrahydronaphth-2-yl)ethynyl)pyrimidin-2-carboxylate

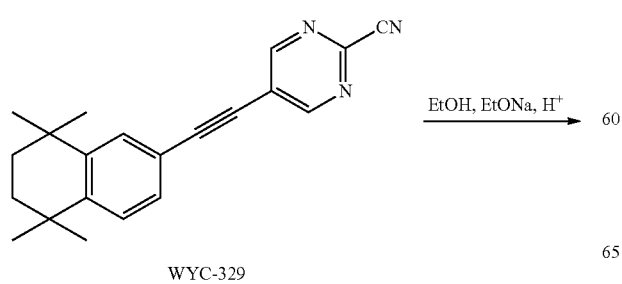

WYC-329

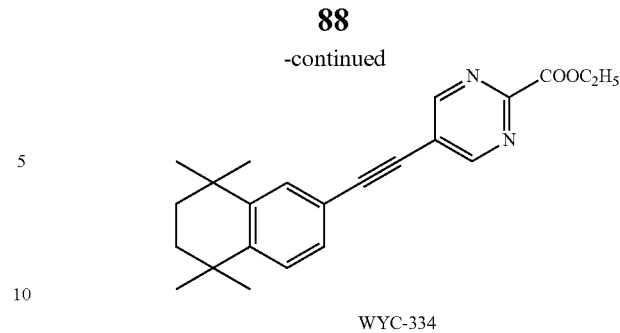

WYC-334

WYC-329 (15 mg, 0.0475 mmol) was dissolved in 2 mL ethanol, followed by addition of sodium ethoxide (9.7 mg, 0.143 mmol). The reaction was continued at room temperature overnight. After completion of the reaction, the reaction solution was neutralized to weak acidic with 1 mol/L HCl, diluted with ethyl acetate, washed with saturated sodium bicarbonate solution and saturated sodium chloride solution. The organic phase was dried over anhydrous sodium sulfate, filtered, concentrated and purified by flash column chromatography (PE:EA=1000:1 to 20:1) to give WYC-334 (15 mg, 88%). $^1$H NMR (400 MHz, CDCl$_3$) δ 8.63 (s, 2H), 7.47 (d, J=1.2 Hz, 1H), 7.33-7.24 (m, 2H), 4.45 (q, J=7.1 Hz, 2H), 1.69 (s, 4H), 1.45 (t, J=7.1 Hz, 3H), 1.30 (s, 6H), 1.28 (s, 6H). $^{13}$C NMR (101 MHz, CDCl$_3$) δ 163.53, 161.19, 146.22, 145.28, 129.93, 128.61, 126.82, 119.29, 113.07, 94.57, 81.42, 77.35, 77.04, 76.72, 63.94, 34.91, 34.85, 34.41, 34.25, 31.77, 31.68, 14.42. ESI(+)–MS: 362.3 [M+1]$^+$.

Embodiment 79: methyl 2-hydroxy-4-((5,5,8,8-tetramethyl-5,6,7,8-tetrahydronaphth-2-yl)ethynyl)benzoate

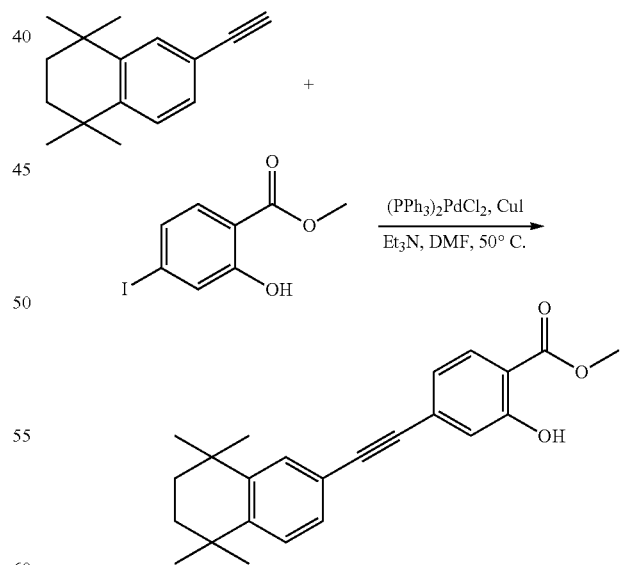

6-Ethynyl-1,1,4,4-tetramethyl-1,2,3,4-tetrahydronaphthalene (50 mg, 0.205 mmol) and Compound c (75.3 mg, 0.271 mmol) were added to a flask, followed by addition of Pd(PPh$_3$)$_2$Cl$_2$ (14 mg, 0.02 mmol) and CuI (5.6 mg, 0.03 mmol). After the flask was purged with argon for 3 times to remove oxygen, 2 mL dry DMF and 0.14 mL dry Et$_3$N were added via syringe. Then the reaction was continued at 70° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE) to give the product (45.2 mg, 61%). $^1$H NMR (400 MHz, CDCl$_3$) δ 10.76 (s, 1H), 7.80 (d, J=8.2 Hz, 1H), 7.48 (s, 1H), 7.29 (d, J=0.8 Hz, 2H), 7.13 (d, J=1.4 Hz, 1H), 7.03 (dd, J=8.2, 1.5 Hz, 1H), 3.96 (s, 3H), 1.69 (s, 4H), 1.30 (s, 6H), 1.28 (s, 6H). ESI(+)-MS: 363.3 [M+1]$^+$.

Embodiment 80: 2-hydroxy-4-((5,5,8,8-tetramethyl-5,6,7,8-tetrahydronaphth-2-yl)ethynyl)benzoic Acid

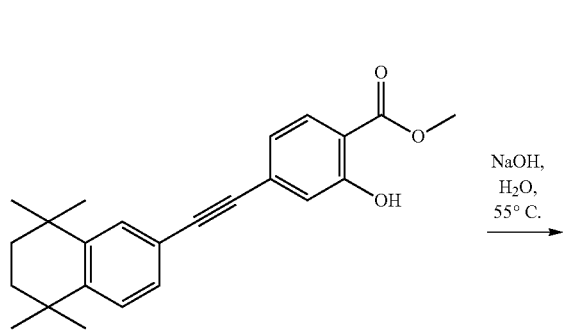

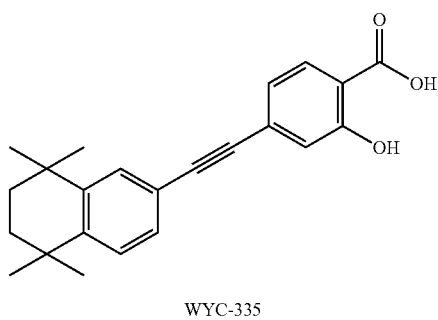

WYC-335

The product (30 mg, 0.082 mmol) obtained in the previous step was added to a flask, followed by addition of 2 mL 2.0 mol/L NaOH and 2 mL methanol. The reaction was continued at 55° C. overnight. After completion of the reaction, the reaction solution was neutralized to pH 5-6 with 1 mol/L HCl, diluted with ethyl acetate, extracted, washed with saturated sodium chloride solution. The organic phase was dried over anhydrous sodium sulfate, filtered, concentrated and purified by flash column chromatography (PE:EA=100:0 to 10:1) to give WYC-335 (26.3 mg, 93%). $^1$H NMR (400 MHz, DMSO) δ 7.80 (d, J=8.1 Hz, 1H), 7.53 (d, J=1.6 Hz, 1H), 7.39 (d, J=8.2 Hz, 1H), 7.31 (dd, J=8.2, 1.6 Hz, 1H), 7.12-7.04 (m, 2H), 1.65 (s, 4H), 1.26 (s, 6H), 1.25 (s, 6H). $^{13}$C NMR (101 MHz, DMSO) δ 171.27, 160.85, 146.07, 145.05, 130.58, 129.74, 129.16, 128.67, 126.98, 122.01, 119.29, 118.76, 92.56, 87.48, 40.12, 39.91, 39.70, 39.49, 39.29, 39.08, 38.87, 34.36, 34.25, 34.08, 33.89, 31.39, 31.32. ESI(-)-MS: 347.3 [M-1]$^-$.

Embodiment 81: 2-acetyl amino-4-((5,5,8,8-tetramethyl-5,6,7,8-tetrahydronaphth-2-yl)ethynyl)benzoic Acid

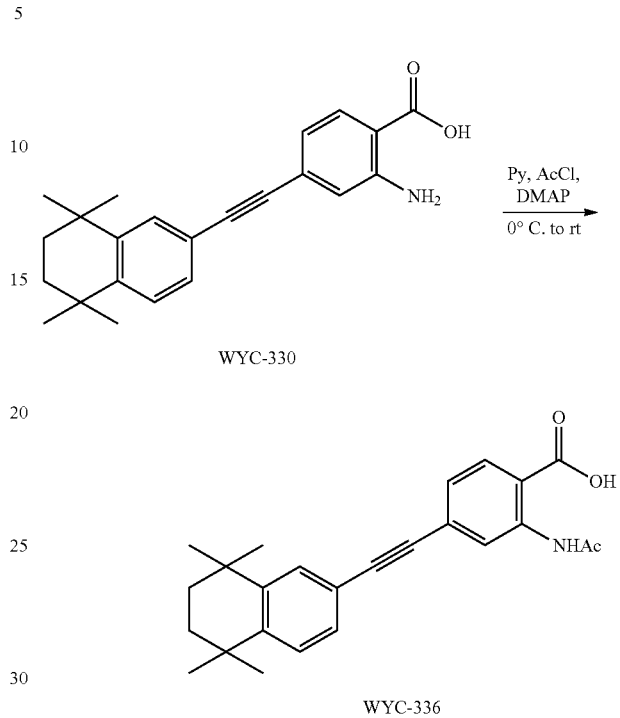

WYC-330 (52 mg, 0.15 mmol) was added to a flask, followed by addition of 1 mg DMAP, then 3 mL dry pyridine was added under argon atmosphere. After the mixture was cooled to 0° C. under an ice bath, 7.8 μL acetyl chloride was added dropwise, and the reaction was continued for 5 min under the ice bath and another 5 h at room temperature, meanwhile TLC was used to monitor the reaction. After completion of the reaction, the reaction was quenched with methanol. The mixture was diluted with ethyl acetate, washed with 1 mol/L hydrochloric acid to remove pyridine, then washed with saturated sodium bicarbonate solution and saturated sodium chloride solution. The organic phase was dried over anhydrous sodium sulfate, filtered, concentrated and purified by flash column chromatography (PE:EtOAc=20:1) to give WYC-336 (39.5 mg, 85%). $^1$H NMR (400 MHz, CDCl$_3$) δ 8.13 (d, J=8.1 Hz, 1H), 7.66 (d, J=1.2 Hz, 1H), 7.60 (dd, J=8.1, 1.5 Hz, 1H), 7.51 (s, 1H), 7.32 (d, J=1.0 Hz, 2H), 2.47 (s, 3H), 1.69 (d, J=5.7 Hz, 4H), 1.31 (s, 6H), 1.29 (s, 6H). ESI(-)-MS: 388.4 [M-1]$^-$.

Embodiment 82: methyl 5-((5,5,8,8-tetramethyl-5,6,7,8-tetrahydronaphth-2-yl)ethynyl)pyridin-2-carboxylate

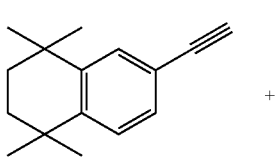 +

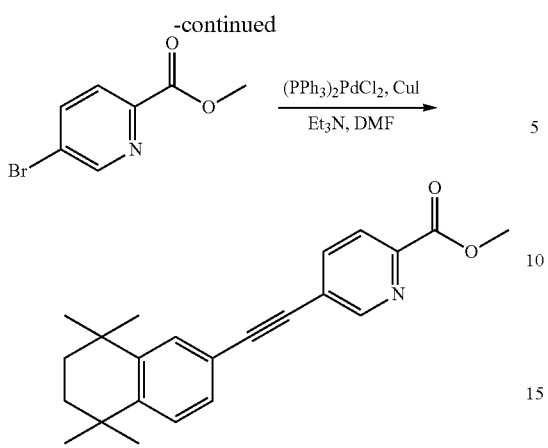

6-Ethynyl-1,1,4,4-tetramethyl-1,2,3,4-tetrahydronaphthalene (60 mg, 0.283 mmol) and methyl 5-bromo-pyridin-2-carboxylate (70 mg, 0.325 mmol) were added to a flask, followed by addition of Pd(PPh$_3$)$_2$Cl$_2$ (16.8 mg, 0.024 mmol) and CuI (6.8 mg, 0.036 mmol). After the flask was purged with argon for 3 times to remove oxygen, 2 mL dry DMF and 0.17 mL dry Et$_3$N were added via syringe. Then the reaction was continued at 70° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EA=100:1 to 20:1) to give the product (68.7 mg, 70%). $^1$H NMR (400 MHz, CDCl$_3$) δ 8.85 (dd, J=2.0, 0.7 Hz, 1H), 8.12 (dd, J=8.1, 0.7 Hz, 1H), 7.94 (dd, J=8.1, 2.1 Hz, 1H), 7.51 (s, 1H), 7.32 (d, J=1.0 Hz, 2H), 4.02 (d, J=4.5 Hz, 3H), 1.69 (d, J=5.5 Hz, 4H), 1.31 (s, 6H), 1.29 (s, 6H). ESI(+)–MS: 348.2 [M+1]$^+$.

Embodiment 83: 5-((5,5,8,8-tetramethyl-5,6,7,8-tetrahydronaphth-2-yl)ethynyl)pyridin-2-carboxylic Acid

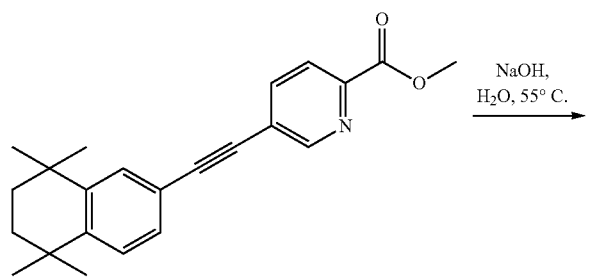

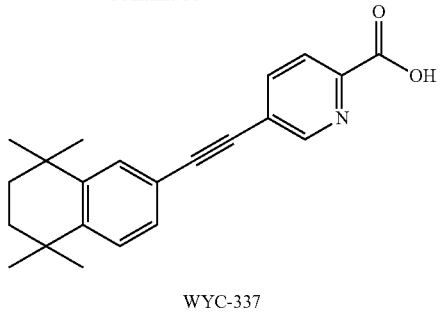

The product (50 mg, 0.143 mmol) obtained in the previous step was added to a flask, followed by addition of 2 mL 2.0 mol/L NaOH and 2 mL methanol. The reaction was continued at 55° C. overnight. After completion of the reaction, the reaction solution was neutralized to pH 5-6 with 1 mol/L HCl, diluted with ethyl acetate, extracted, washed with saturated sodium chloride solution. The organic phase was dried over anhydrous sodium sulfate, filtered, concentrated and purified by flash column chromatography (PE:EA=20:1 to 5:1) to give WYC-337 (42.2 mg, 88%). $^1$H NMR (400 MHz, MeOD) δ 8.67 (s, 1H), 8.00 (d, J=7.9 Hz, 1H), 7.94 (dd, J=8.1, 2.0 Hz, 1H), 7.52 (d, J=1.6 Hz, 1H), 7.36 (d, J=8.2 Hz, 1H), 7.30 (dd, J=8.2, 1.7 Hz, 1H), 1.73 (s, 4H), 1.31 (s, 6H), 1.29 (s, 6H). ESI(+)–MS: 334.4 [M+1]$^+$.

Embodiment 84: methyl 5-((5,5,8,8-tetramethyl-5,6,7,8-tetrahydronaphth-2-yl)ethynyl)pyrimidin-2-carboxylate

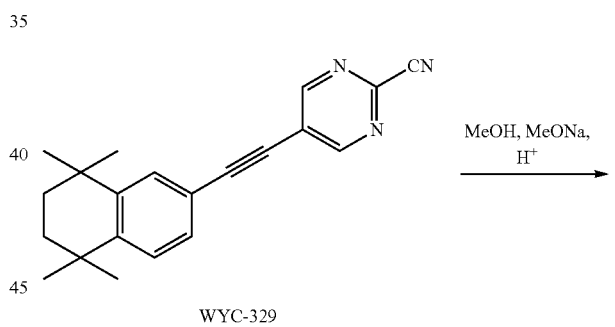

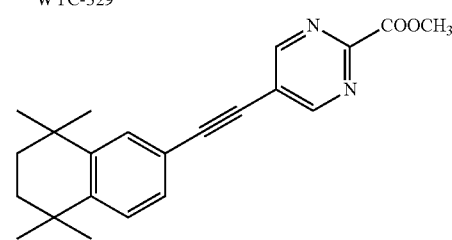

WYC-329 (15 mg, 0.0475 mmol) was dissolved in 2 mL methanol, followed by addition of sodium methoxide (7.7 mg, 0.143 mmol). The reaction solution was stirred at room temperature overnight. After completion of the reaction, the reaction solution was neutralized to weak acidic with 1 mol/L HCl, diluted with ethyl acetate, washed with saturated sodium bicarbonate solution and saturated sodium chloride solution. The organic phase was dried over anhydrous sodium sulfate, filtered, concentrated and purified by flash column chromatography (PE:EtOAc=100:1 to 20:1) to give WYC-338 (14.9 mg, 90%). ¹H NMR (500 MHz, CDCl₃) δ 8.64 (s, 2H), 7.47 (d, J=1.2 Hz, 1H), 7.34-7.27 (m, 2H), 4.05 (s, 3H), 1.69 (s, 4H), 1.30 (s, 6H), 1.28 (s, 6H). ESI(+)–MS: 348.4 [M+1]⁺.

Embodiment 85: ethyl 2-hydroxy-4-((5,5,8,8-tetramethyl-5,6,7,8-tetrahydronaphth-2-yl)ethynyl)benzoate

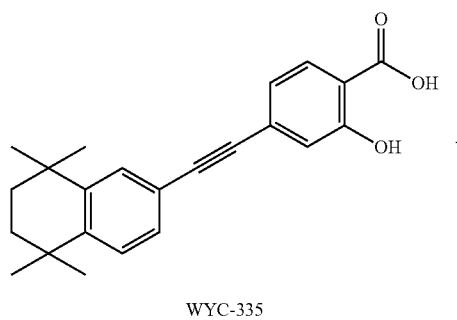

WYC-335

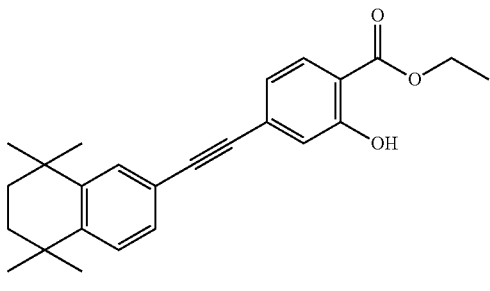

WYC-339

WYC-335 (15 mg, 0.043 mmol) was added to a flask, followed by addition of 0.8 mL anhydrous ethanol under argon atmosphere. The mixture was cooled to 0° C. under an ice bath, then 3 μL concentrated sulfuric acid was added dropwise. After completion of the dropwise addition, the reaction solution was heated to reflux and stirred for 4 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=100:1 to 10:1) to give WYC-339 (14 mg, 87%). ESI(+)–MS: 377.3 [M+1]⁺.

Embodiment 86: ethyl 3-hydroxy-4-((5,5,8,8-tetramethyl-5,6,7,8-tetrahydronaphth-2-yl)ethynyl)benzoate

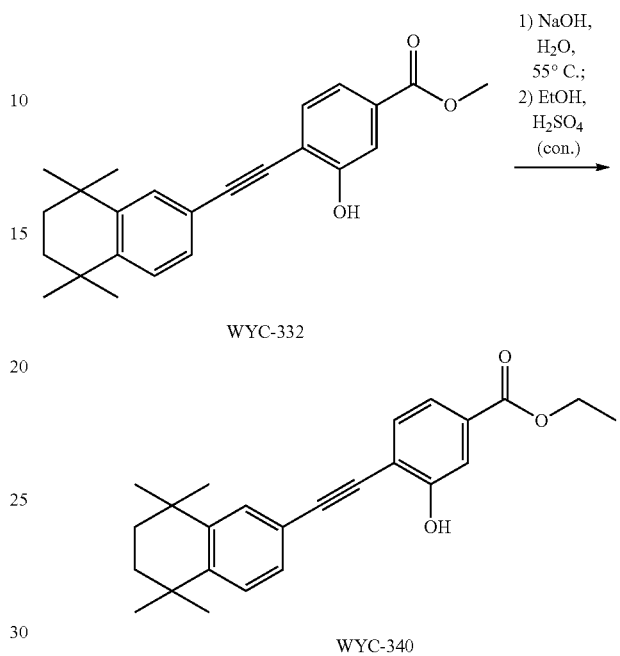

WYC-332 (50 mg, 0.143 mmol) was added to a flask, followed by addition of 2 mL 2.0 mol/L NaOH and 2 mL methanol. The reaction was continued at 55° C. overnight. After completion of the reaction, the reaction solution was neutralized to pH 5-6 with 1 mol/L HCl, diluted with ethyl acetate, extracted, washed with saturated sodium chloride solution. The organic phase was dried over anhydrous sodium sulfate, filtered, concentrated and purified by flash column chromatography (PE:EA=20:1 to 5:1) to give the corresponding carboxylic acid (47 mg, 87%). The corresponding carboxylic acid (25 mg, 0.072 mmol) was added to a flask, followed by addition of 1.5 mL anhydrous ethanol under argon atmosphere. After the mixture was cooled to 0° C. under an ice bath, 5 μL concentrated sulfuric acid was added dropwise. After completion of the dropwise addition, the reaction solution was heated to reflux and stirred for 4 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=50:1 to 10:1) to give WYC-340 (24 mg, 90%). ¹H NMR (400 MHz, CDCl₃) δ 8.24 (s, 1H), 7.95 (dd, J=8.2, 1.4 Hz, 1H), 7.84 (d, J=1.9 Hz, 1H), 7.63 (dd, J=8.3, 1.9 Hz, 1H), 7.58 (d, J=8.2 Hz, 1H), 7.41 (d, J=8.3 Hz, 1H), 7.01 (d, J=0.8 Hz, 1H), 4.42 (q, J=7.1 Hz, 2H), 1.73 (s, 4H), 1.43 (t, J=7.1 Hz, 3H), 1.37 (s, 6H), 1.32 (s, 6H); ¹³C NMR (101 MHz, CDCl₃) δ 166.91, 159.50, 154.23, 146.62, 145.62, 133.74, 127.23, 127.15, 126.07, 124.37, 123.49, 122.73, 120.12, 112.68, 100.57, 60.95, 35.03, 34.92, 34.44, 31.86, 31.74; ESI(+)–MS: 377.4 [M+1]⁺.

Embodiment 87: ethyl 5-((5,5,8,8-tetramethyl-5,6,7,8-tetrahydronaphth-2-yl)ethynyl)pyridin-2-carboxylate

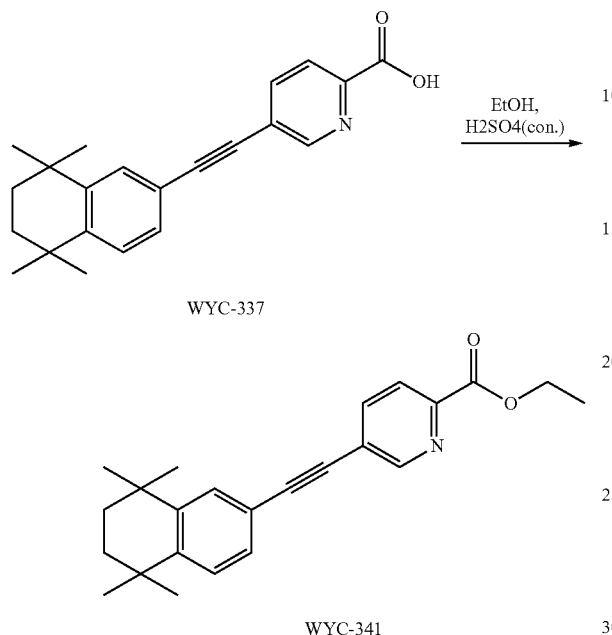

WYC-337 (25 mg, 0.075 mmol) was added to a flask, followed by addition of 1.5 mL anhydrous ethanol under argon atmosphere. After the mixture was cooled to 0° C. under an ice bath, 5 μL concentrated sulfuric acid was added dropwise. After completion of the dropwise addition, the reaction solution was heated to reflux and stirred for 4 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=50:1 to 10:1) to give WYC-341 (24 mg, 90%). $^1$H NMR (400 MHz, CDCl$_3$) δ 8.85 (dd, J=2.0, 0.6 Hz, 1H), 8.11 (dd, J=8.1, 0.7 Hz, 1H), 7.92 (dd, J=8.1, 2.1 Hz, 1H), 7.50 (t, J=1.2, 1H), 7.34 (d, J=2.5 Hz, 1H), 7.26 (dd, J=8.4, 2.1 Hz, 3H), 4.49 (q, J=7.2 Hz, 2H), 1.69 (s, 4H), 1.45 (t, J=6.8 Hz, 3H), 1.30 (s, 6H), 1.28 (s, 6H). ESI(+)–MS: 362.7 [M+1]$^+$.

Embodiment 88: methyl 5-((5,5,8,8-tetramethyl-5,6,78-tetrahydronaphth-2-yl)ethynyl)pyrazin-2-carboxylate

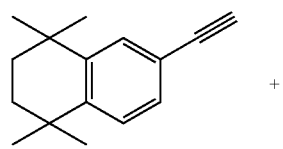 +

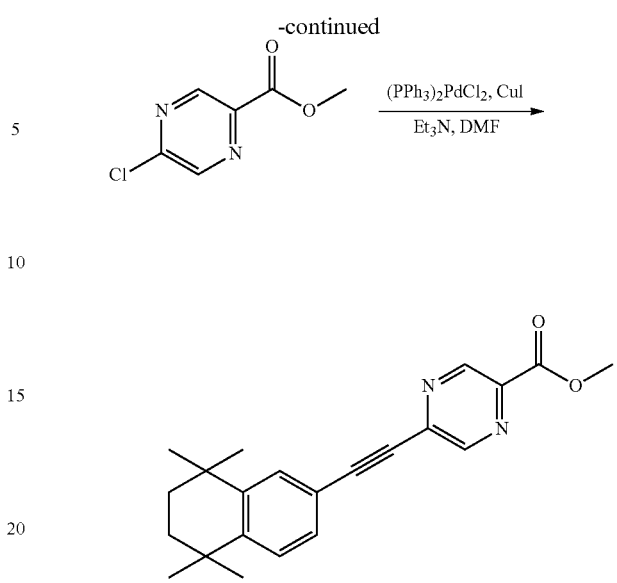

6-Ethynyl-1,1,4,4-tetramethyl-1,2,3,4-tetrahydronaphthalene (60 mg, 0.283 mmol) and methyl 2-chloropyrazin-4-carboxylate (56 mg, 0.325 mmol) were added to a flask, followed by addition of Pd(PPh$_3$)$_2$Cl$_2$ (16.8 mg, 0.024 mmol) and CuI (6.8 mg, 0.036 mmol). After the flask was purged with argon for 3 times to remove oxygen, 2 mL dry DMF and 0.17 mL dry Et$_3$N were added via syringe. Then the reaction was continued at 70° C. for 8 h and monitored by TLC. After completion of the reaction, the reaction solution was cooled to room temperature and the reaction was quenched with saturated ammonium chloride solution. The mixture was diluted with ethyl acetate, washed with saturated ammonium chloride solution and saturated sodium chloride solution. The organic phase was dried over anhydrous sodium sulfate, filtered, concentrated and purified by flash column chromatography (PE:EA=100:1 to 20:1) to give the product (55 mg, 56%). $^1$H NMR (400 MHz, CDCl$_3$) δ 9.28 (d, J=1.4 Hz, 1H), 8.83 (d, J=1.4 Hz, 1H), 7.61 (d, J=1.7 Hz, 1H), 7.40 (dd, J=8.2, 1.7 Hz, 1H), 7.34 (d, J=8.2 Hz, 1H), 4.06 (s, 3H), 1.70 (s, 4H), 1.30 (s, 6H), 1.29 (s, 6H). $^{13}$C NMR (101 MHz, CDCl$_3$) δ 164.18, 147.91, 146.83, 145.74, 145.57, 143.39, 140.07, 131.12, 129.38, 127.01, 117.83, 97.82, 85.11, 77.34, 77.23, 77.02, 76.70, 53.19, 34.80, 34.76, 34.58, 34.31, 31.75, 31.62. ESI(+)–MS: 349.2 [M+1]$^+$.

Embodiment 89: ethyl 5-((5,5,8,8-tetramethyl-5,6,7,8-tetrahydronaphth-2-yl)ethynyl)pyrazin-2-carboxylate

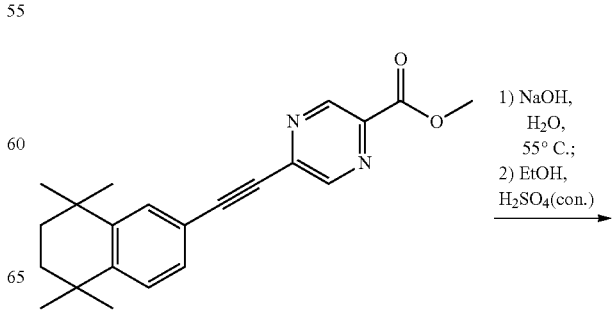

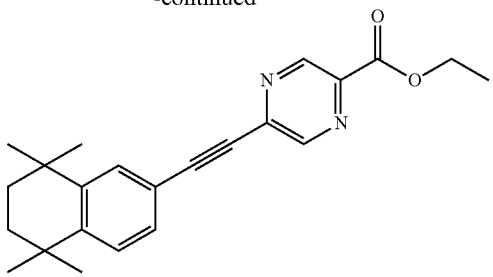

The product (35 mg, 0.1 mmol) obtained in the previous step was added to a flask, followed by addition of 1.5 mL 2.0 mol/L NaOH and 1.5 mL methanol. The reaction was continued at 55° C. overnight. After completion of the reaction, the reaction solution was neutralized to pH 5-6 with 1 mol/L HCl, diluted with ethyl acetate, extracted, washed with saturated sodium chloride solution. The organic phase was dried over anhydrous sodium sulfate, filtered, concentrated and purified by flash column chromatography (PE:EA=20:1 to 5:1) to give the corresponding carboxylic acid (28.3 mg, 85%). The corresponding carboxylic acid (25 mg, 0.075 mmol) was added to a flask, followed by addition of 1.5 mL anhydrous ethanol under argon atmosphere. After the mixture was cooled to 0° C. under an ice bath, 5 μL concentrated sulfuric acid was added dropwise. After completion of the dropwise addition, the reaction solution was heated to reflux and stirred for 4 h, meanwhile TLC was used to monitor the reaction. After completion of the reaction, the reaction solution was cooled to room temperature, treated with 1 mol/L sodium hydroxide to neutralize sulfuric acid to make a neutral solution, then washed with saturated sodium bicarbonate solution and saturated sodium chloride solution. The organic phase was dried over anhydrous sodium sulfate, filtered, dried, and purified by flash column chromatography (PE:EtOAc=50: 1 to 10:1) to give WYC-342 (20 mg, 75%). $^1$H NMR (400 MHz, CDCl$_3$) δ 9.26 (d, J=1.4 Hz, 1H), 8.82 (d, J=1.4 Hz, 1H), 7.60 (d, J=1.6 Hz, 1H), 7.38 (dd, J=8.2, 1.7 Hz, 1H), 7.32 (d, J=8.2 Hz, 1H), 4.51 (q, J=7.1 Hz, 2H), 1.68 (s, 4H), 1.45 (t, J=7.1 Hz, 3H), 1.29 (s, 6H), 1.27 (s, 6H). $^{13}$C NMR (101 MHz, CDCl$_3$) δ 163.72, 147.84, 146.83, 145.72, 145.53, 143.21, 140.41, 131.09, 129.37, 127.00, 117.87, 97.61, 85.15, 77.38, 77.07, 76.75, 62.42, 34.81, 34.76, 34.56, 34.30, 31.75, 31.62. ESI(+)–MS: 363.6 [M+1]$^+$.

Effect Embodiment 1: In Vitro Inhibitory Activity on the Proliferation of Tumor-Repopulating Cells (TRCs)

B16-F1 Melanoma cells were incubated with 3D fibrin gel medium (90-Pa) for 5 days, and the desired tumor-repopulating cells of melanoma were screened (*Nat. Mater.* 2012, 11, 734). Subsequently, the culture medium was respectively treated with collagenase and neutral protease II, and the tumor-repopulating cells of B16-F1 melanoma were released, then the obtained repopulating cells were transferred to a freshly prepared medium to be resuspended and maintained at single-cell state. The tumor-repopulating cells of B16-F1 melanoma were inoculated in 3D fibrin gel medium (90-Pa) for 5 days, with 0.1% DMSO as the negative control group, Tazarotene and Bexarotene as the positive control drugs respectively, the drug was added at a concentration of 10 μM and the cells were incubated for 5 days. The colony tumor size was measured and calculated, and the inhibition rate of each drug on the tumor-repopulating cells of B16-F1 melanoma was calculated. The results of inhibitory activity of the compound of the present invention on the proliferation of tumor-repopulating cells of B16-F1 melanoma were shown in Table 2 below.

TABLE 2

Inhibitory activity on the proliferation of tumor-repopulating cells (TRCs) of B16-F1 melanoma

| Compound number | Inhibition rate on TRCs of B16-F1 melanoma at a concentration of 10 μM (%) |
| --- | --- |
| WYC-101 | 76.0 |
| WYC-102 | 59.1 |
| WYC-103 | 86.8 |
| WYC-105 | 64.1 |
| WYC-106 | 72.4 |
| WYC-107 | 75.0 |
| WYC-202 | 85.3 |
| WYC-203 | 90.5 |
| WYC-204 | 25.6 |
| WYC-205 | 91.5 |
| WYC-206 | 77.2 |
| WYC-207 | 92.5 |
| WYC-208 | 27.7 |
| WYC-209 | 98.8 |
| WYC-209A | 98.9 |
| WYC-209B | 98.7 |
| WYC-210 | 18.1 |
| WYC-212 | 93.2 |
| WYC-213 | 71.1 |
| WYC-214 | 51.6 |
| WYC-215 | 80.2 |
| WYC-216 | 84.0 |
| WYC-217 | 90.3 |
| WYC-218 | 90.4 |
| WYC-219 | 64.8 |
| WYC-220 | 65.5 |
| WYC-301 | 34.4 |
| WYC-302 | 21.9 |
| WYC-303 | 71.1 |
| WYC-304 | 75.8 |
| WYC-305 | 26.0 |
| WYC-306 | 15.2 |
| WYC-307 | 70.3 |
| WYC-308 | 71.9 |
| WYC-309 | 56.8 |
| WYC-310 | 76.8 |
| WYC-311 | 80.2 |
| WYC-312 | 71.0 |
| WYC-313 | 62.2 |
| WYC-314 | 70.1 |
| WYC-315 | 70.1 |
| WYC-316 | 76.2 |
| WYC-317 | 86.4 |
| WYC-318 | 60.0 |
| WYC-319 | 65.8 |
| WYC-320 | 92.6 |
| WYC-321 | 78.2 |
| WYC-322 | 78.8 |
| WYC-323 | 76.0 |
| WYC-324 | 85.1 |
| WYC-325 | 74.2 |
| WYC-326 | 73.4 |
| WYC-327 | 75.7 |
| WYC-329 | 94.5 |
| WYC-330 | 79.0 |
| WYC-331 | 96.0 |
| WYC-332 | 55.9 |
| WYC-333 | 69.1 |
| WYC-334 | 80.6 |
| WYC-335 | 86.9 |
| WYC-336 | 86.7 |
| WYC-337 | 87.5 |
| WYC-338 | 69.0 |
| WYC-341 | 87.0 |
| WYC-342 | 77.6 |

TABLE 2-continued

Inhibitory activity on the proliferation of tumor-repopulating cells (TRCs) of B16-F1 melanoma

| Compound number | Inhibition rate on TRCs of B16-F1 melanoma at a concentration of 10 μM (%) |
|---|---|
| Tazarotene | 67.6 |
| Bexarotene | 63.3 |

The test result of inhibition rate on tumor-repopulating cells of B16-F1 melanoma showed that most compounds showed significant inhibitory activity on tumor growth at a concentration of 10 μM, such as compound WYC-103 (86.8%), WYC-207 (92.5%), WYC-209 (98.8%), WYC-209A (98.9%), WYC-209B (98.7%), WYC-212 (93.2%), WYC-217 (90.3%), WYC-218 (90.4%), WYC-329 (94.5%), WYC-331 (96.0%) etc., the corresponding colony tumor basically did not grow or grew very slowly. The results were not only in sharp contrast to the negative control group, but also reached or exceeded the inhibitory activity of the positive drugs of Tazarotene (67.6%) and Bexarotene (63.3%) on colony tumor growth.

A dose-response curve study of the inhibition on tumor growth was then performed on the compounds which exhibited significant inhibitory activity on tumor growth in the primary screening test. The colony tumor which was administered at an equivalent gradient was fixed, the nuclear was stained with DAPI, the volume was measured, the inhibition rate was calculated and regression of the dose-response curve was performed, it had been confirmed that the compounds with better activity included WYC-103, WYC-209, WYC-320, WYC-329, WYC-331, the $IC_{50}$ values of which were shown in Table 3 below.

TABLE 3

$IC_{50}$ of the compound against tumor-repopulating cells of B16-F1 melanoma

| Compound number | Inhibition rate on TRCs of B16-F1 melanoma at a concentration of 10 μM/% | $IC_{50}$ of inhibition on TRCs of B16-F1 melanoma/μM |
|---|---|---|
| WYC-103 | 86.8 | 1.50 |
| WYC-107 | 75.0 | 2.12 |
| WYC-207 | 92.5 | 3.3 |
| WYC-209 | 98.8 | 0.19 |
| WYC-209A | 98.9 | 0.15 |
| WYC-209B | 98.7 | 0.22 |
| WYC-212 | 93.2 | 2.28 |
| WYC-320 | 92.6 | 1.65 |
| WYC-329 | 94.5 | 0.5 |
| WYC-331 | 96.0 | 0.017 |

Figure 2:
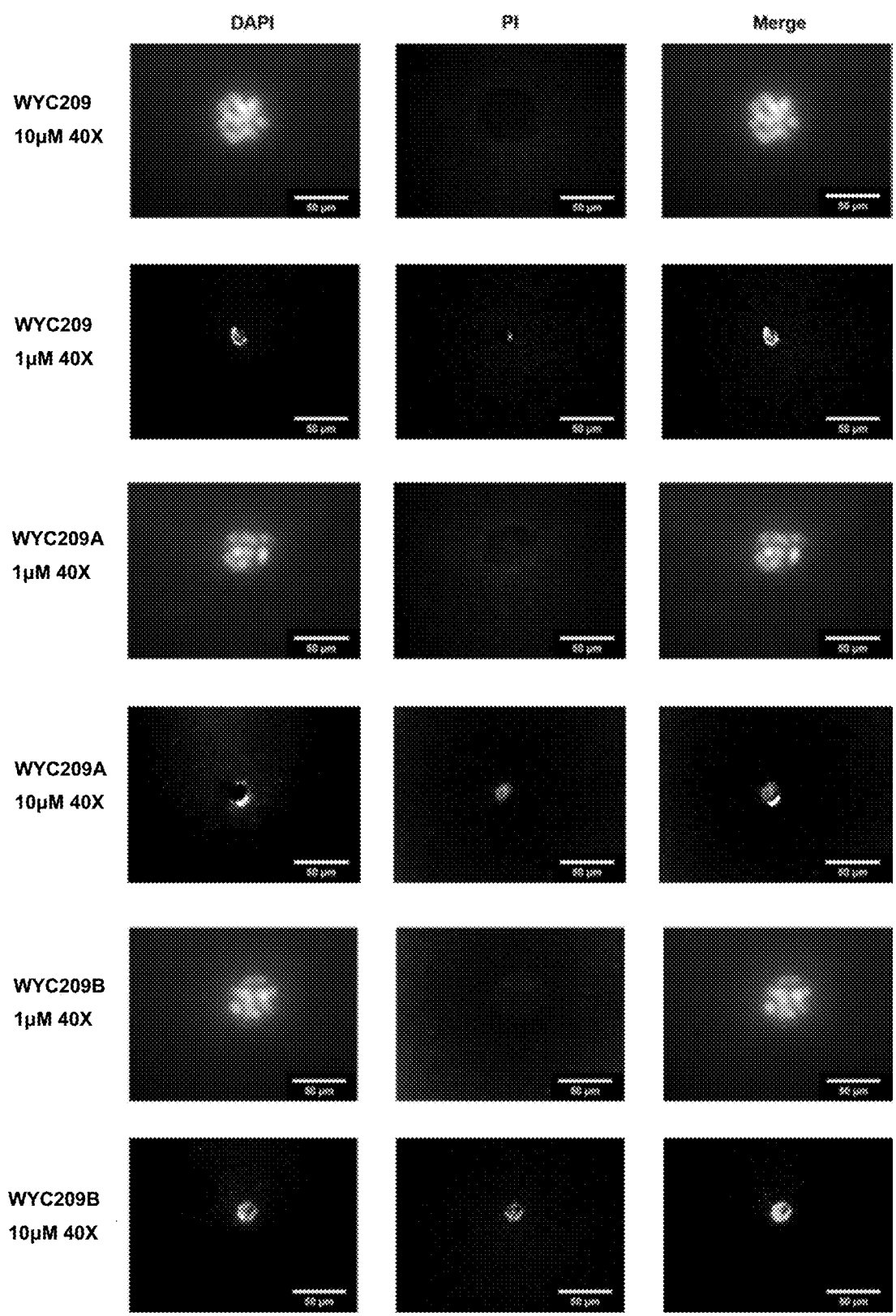
FIG. 2 shows the study of the effect of WYC-209 on the apoptosis of tumor-repopulating cells of B16-F1 melanoma.
Figure 3:
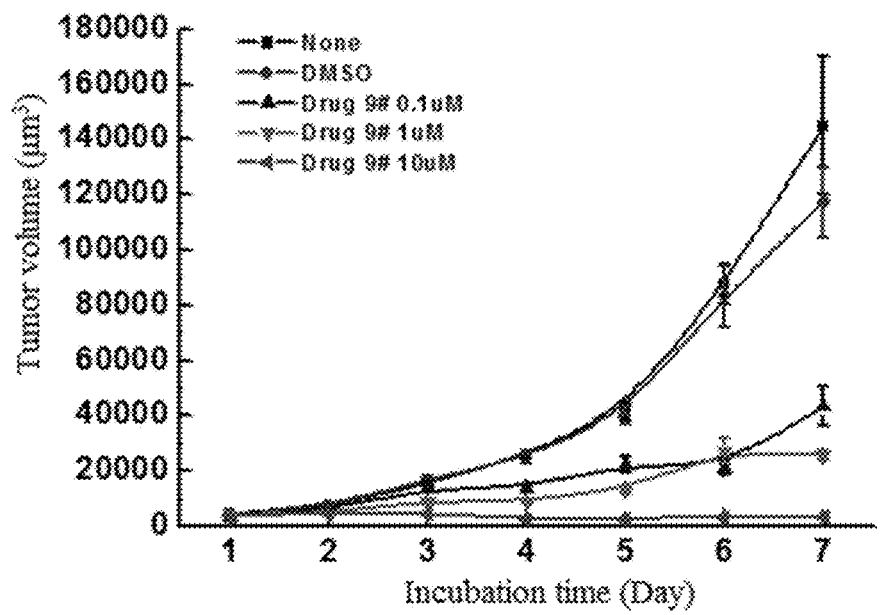
Figure 3:
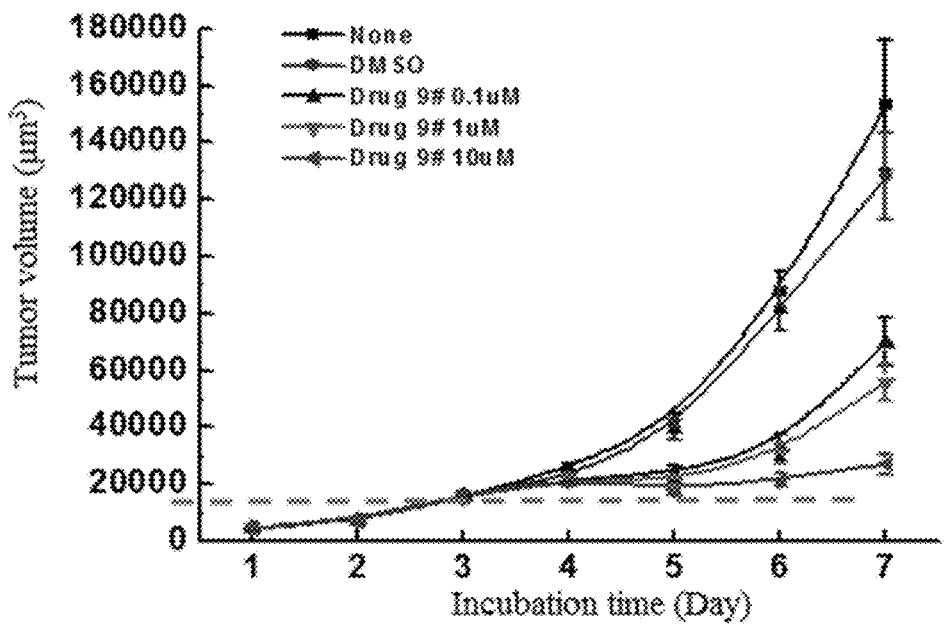
Figure 4:
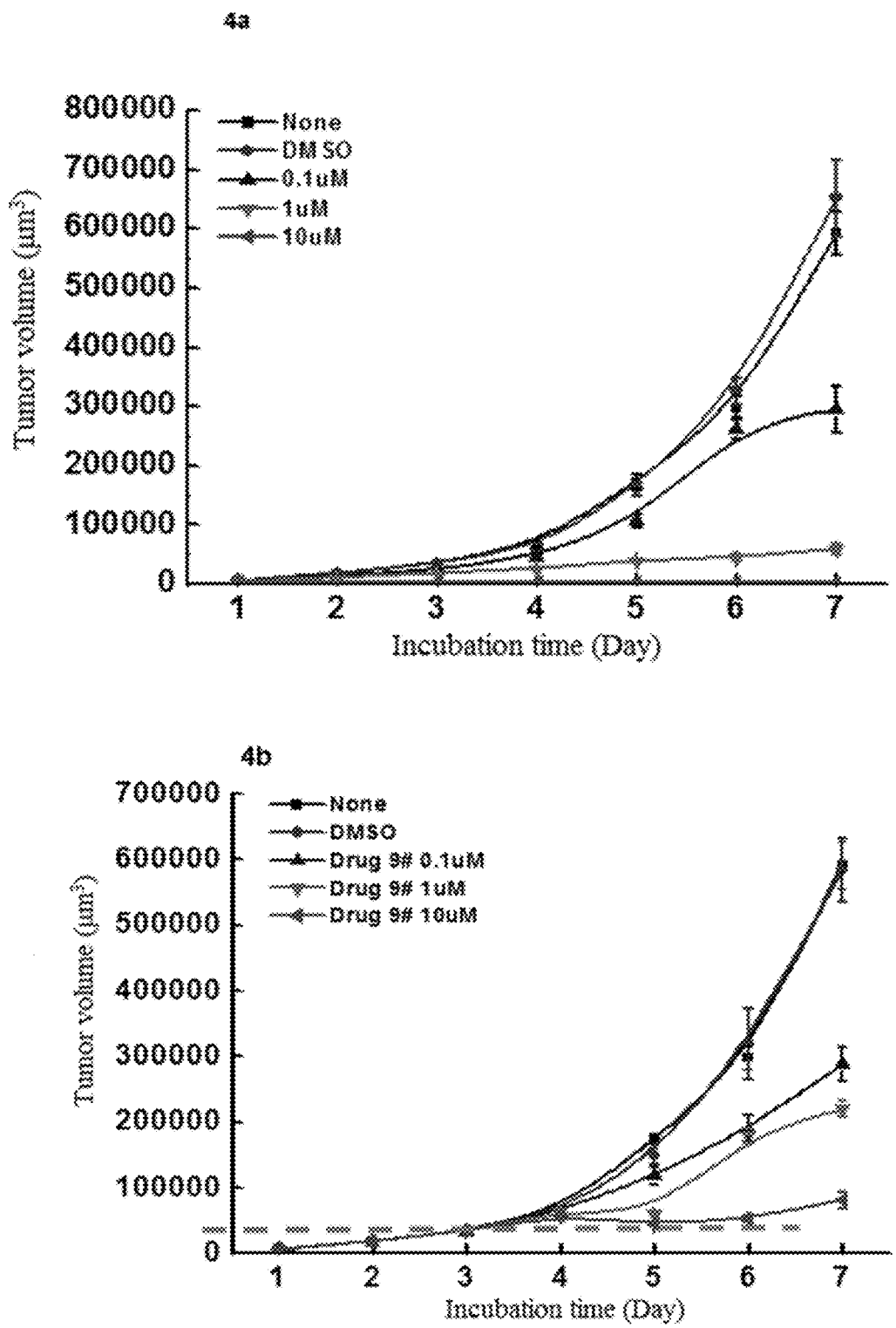
Figure 5:
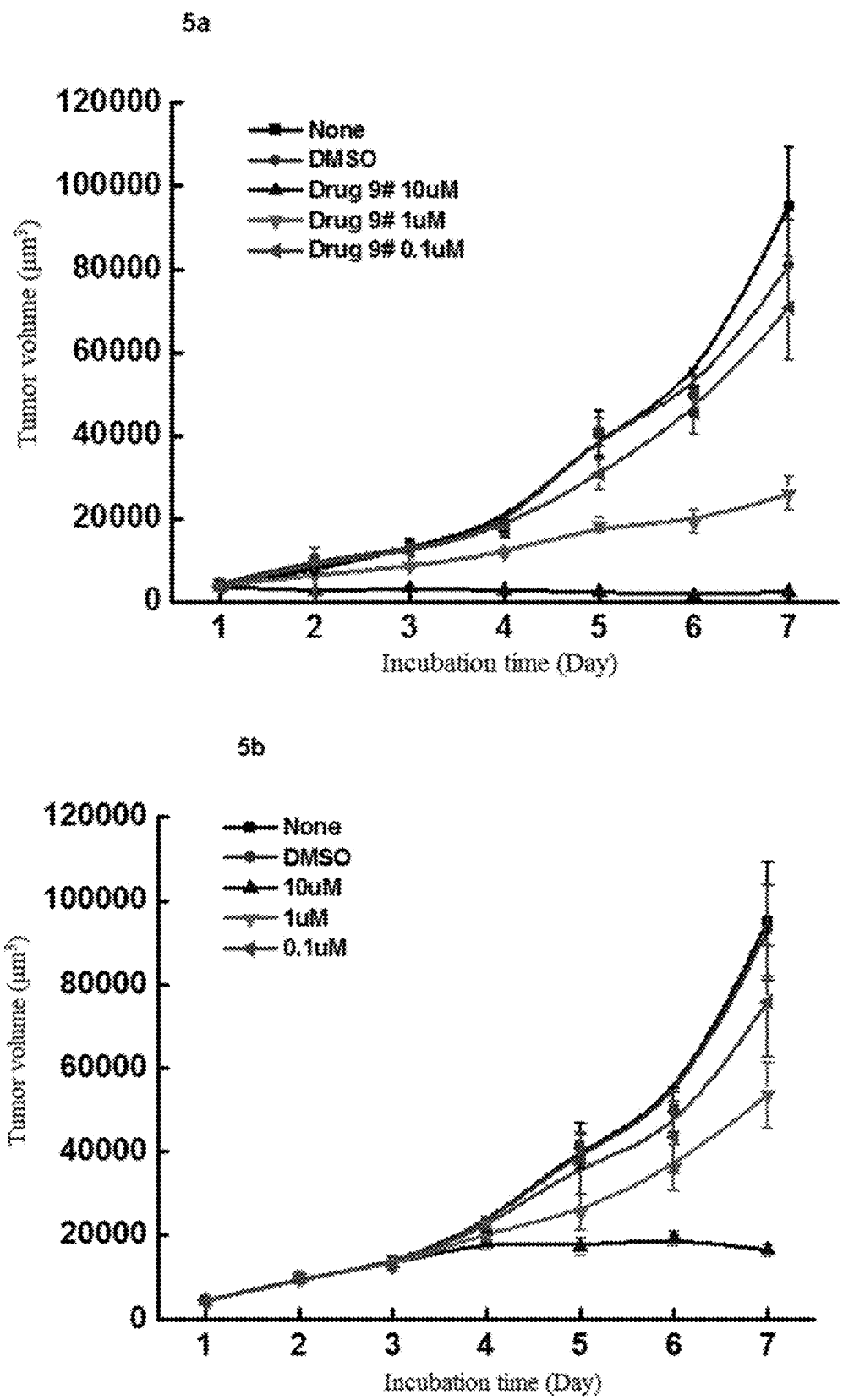
Figure 6:
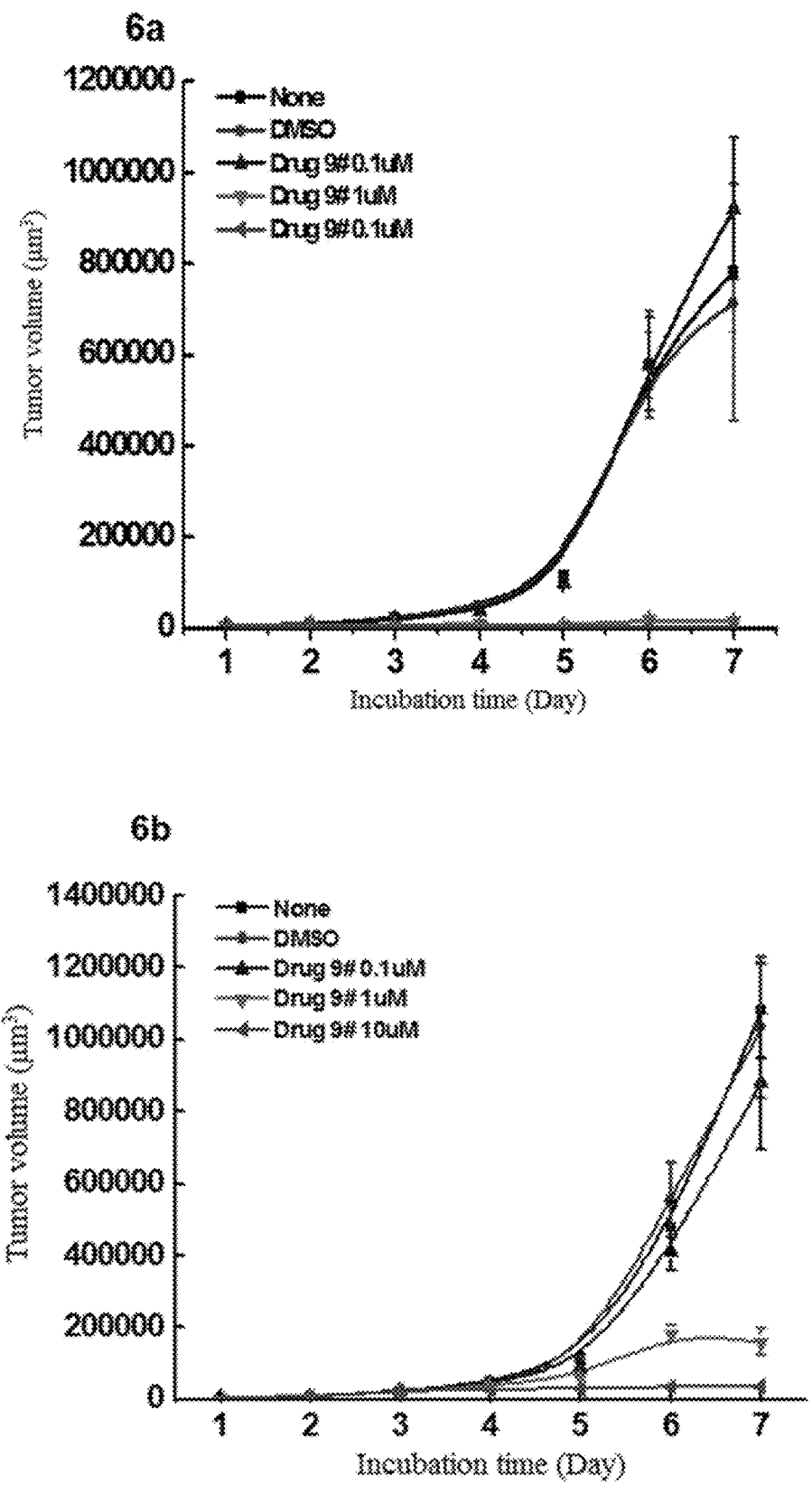
Figure 7:
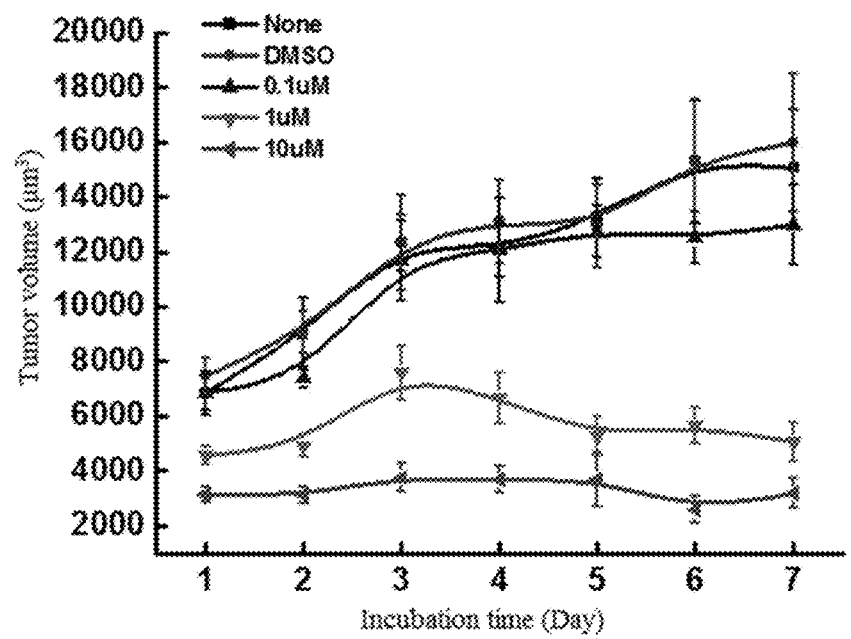
Figure 7:
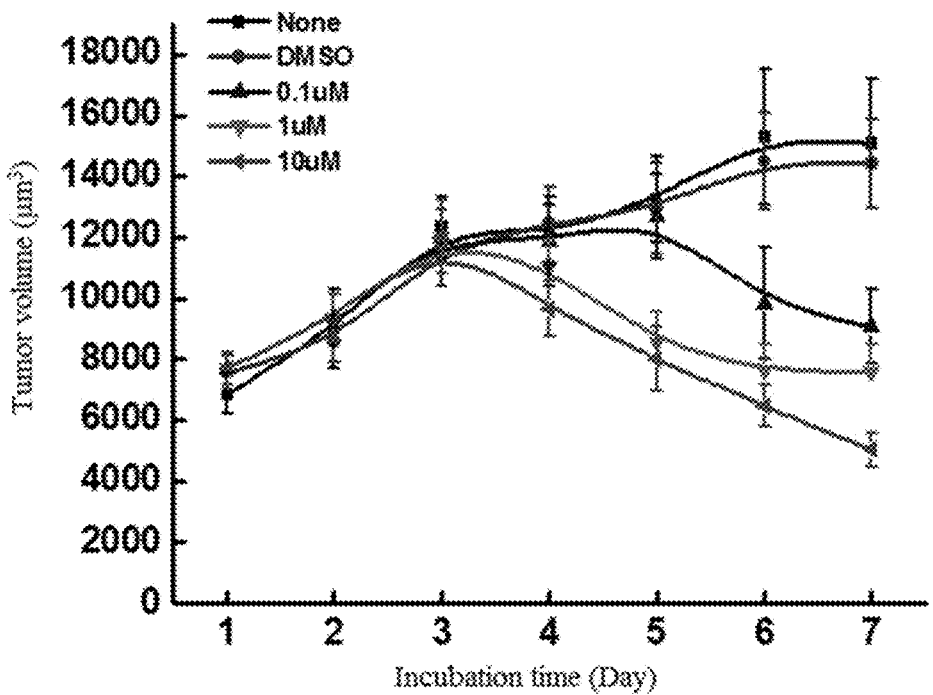
Figure 8:
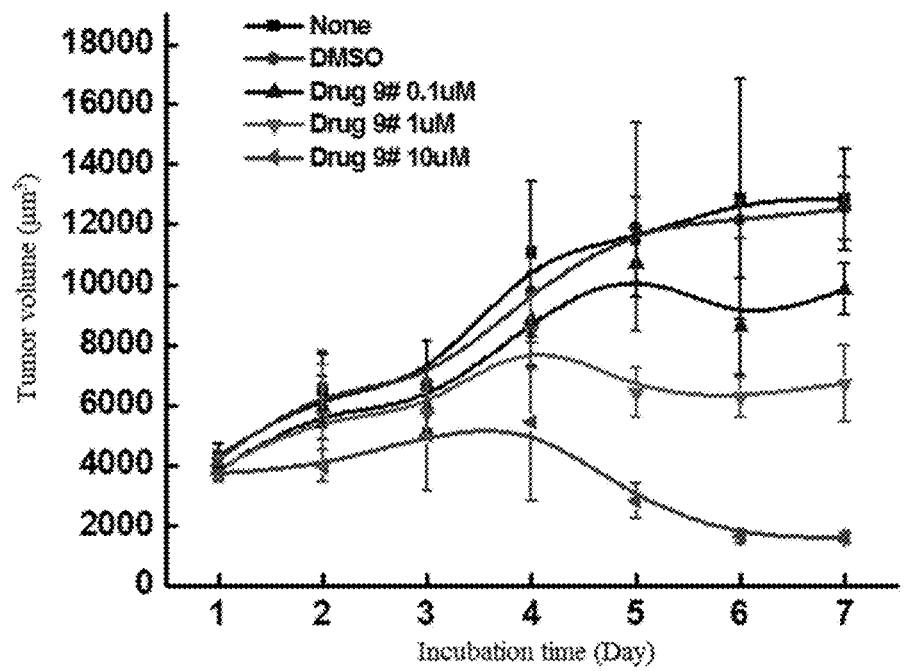
Figure 8:
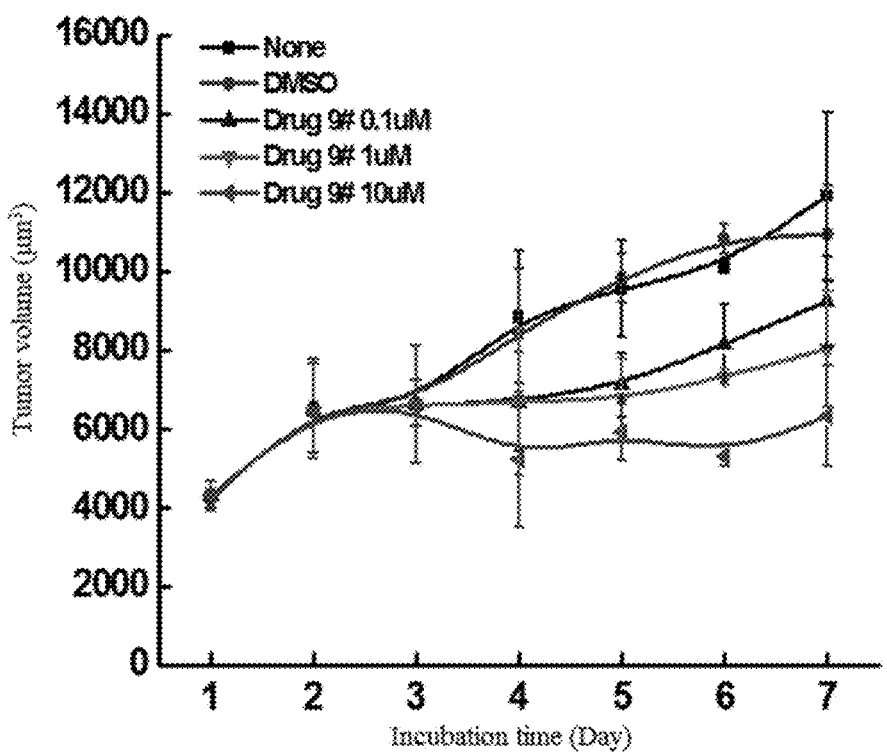

Wherein, the inhibition and differentiation of WYC-103 and WYC-209 on tumor-repopulating cells of B16-F1 melanoma were shown in the electron micrograph (FIG. 1, FIG. 2), In FIG. 1 and FIG. 2, cell survival was shown by DAPI staining, apoptosis was shown by PI staining, and merge showed superposition of DAPI and PI staining images.

2, Inhibitory Activity of WYC-209 on the Proliferation of Various Tumor-Repopulating Cells Many of the above compounds exhibited excellent inhibitory activity on the proliferation of tumor-repopulating cells of B16-F1 melanoma, wherein the activity WYC-209 was particularly excellent. Therefore, we further studied the inhibitory activity of this compound against tumor-repopulating cells of six other kinds of human tumor, including A549 lung cancer cell, MCF-7 breast cancer cell, MDA-MB-435S melanoma cell, A2780 ovarian cancer cell, Hs-746T gastric cancer cell, MDA-MB-231 breast cancer cell.

The above cancer cells were incubated with 3D fibrin gel medium (90-Pa) for 5 days, and the desired tumor-repopulating cells were screened. Subsequently, the culture medium was respectively treated with collagenase and neutral protease II, and the tumor-repopulating cells of B16-F1 melanoma were released, then the obtained repopulating cells were transferred to a freshly prepared medium to be resuspended and maintained at single-cell state. The tumor-repopulating cells of individual tumor were inoculated in 3D fibrin gel medium (90-Pa) for 5 days, with 0.1% DMSO as the negative control group (represented by DMSO group in FIGS. 3-8), the drug-free group as vehicle control group (represented by None group in FIGS. 3-8), and the study was performed by beginning administrating on the day 0 and the 3rd day respectively, and the colony tumor volume was measured and calculated.

The results showed that WYC-209 could effectively inhibit the proliferation of various tumor-repopulating cells at a concentration of 1.0 μM compared with None group, which greatly blocked the growth of colony tumor volume, the volume of tumor colony treated with WYC-209 was only 25-30% of None group (FIGS. 3-8, drug9# in FIGS. 3-8 refers to WYC-209). When the concentration of WYC-209 was increased to 10 μM, the proliferation of the above six kinds of tumor-repopulating cells was inhibited at a higher level, and the volume of colony tumor was even less than 10% of the volume of None group. Especially for Hs-746T, WYC-209 could even reverse the growth trend of colony tumor.

3, Inhibitory Activity of WYC-331 on the Proliferation of Various Tumor-Repopulating Cells WYC-331 exhibited excellent inhibitory activity on the proliferation of tumor-repopulating cells of B16-F1 melanoma. Next, we studied the inhibitory activity of this compound against tumor-repopulating cells of A2780 ovarian cancer and MDA-MB-231 breast cancer.

The above human tumor cells were incubated with 3D fibrin gel medium (90-Pa) for 5 days, and the desired tumor-repopulating cells were screened. Subsequently, the culture medium was respectively treated with collagenase and neutral protease II, and the tumor-repopulating cells of B16-F1 melanoma were released, then the obtained repopulating cells were transferred to a freshly prepared medium to be resuspended and maintained at single-cell state. The tumor-repopulating cells of B16-F1 melanoma were inoculated in 3D fibrin gel medium (90-Pa) for 5 days, with 0.1% DMSO as the negative control group (represented by DMSO group in FIG. 9), the drug-free group as vehicle control group (represented by None group in FIGS. 3-8), and the study was performed by beginning administrating on the day 0 and the 3rd day respectively, and the colony tumor volume was measured and calculated, beginning administrating from the 3rd day at a concentration of 0.1 μM, 1.0 μM, and 10 μM respectively, the colony tumor volume was measured and calculated.

Figure 9:
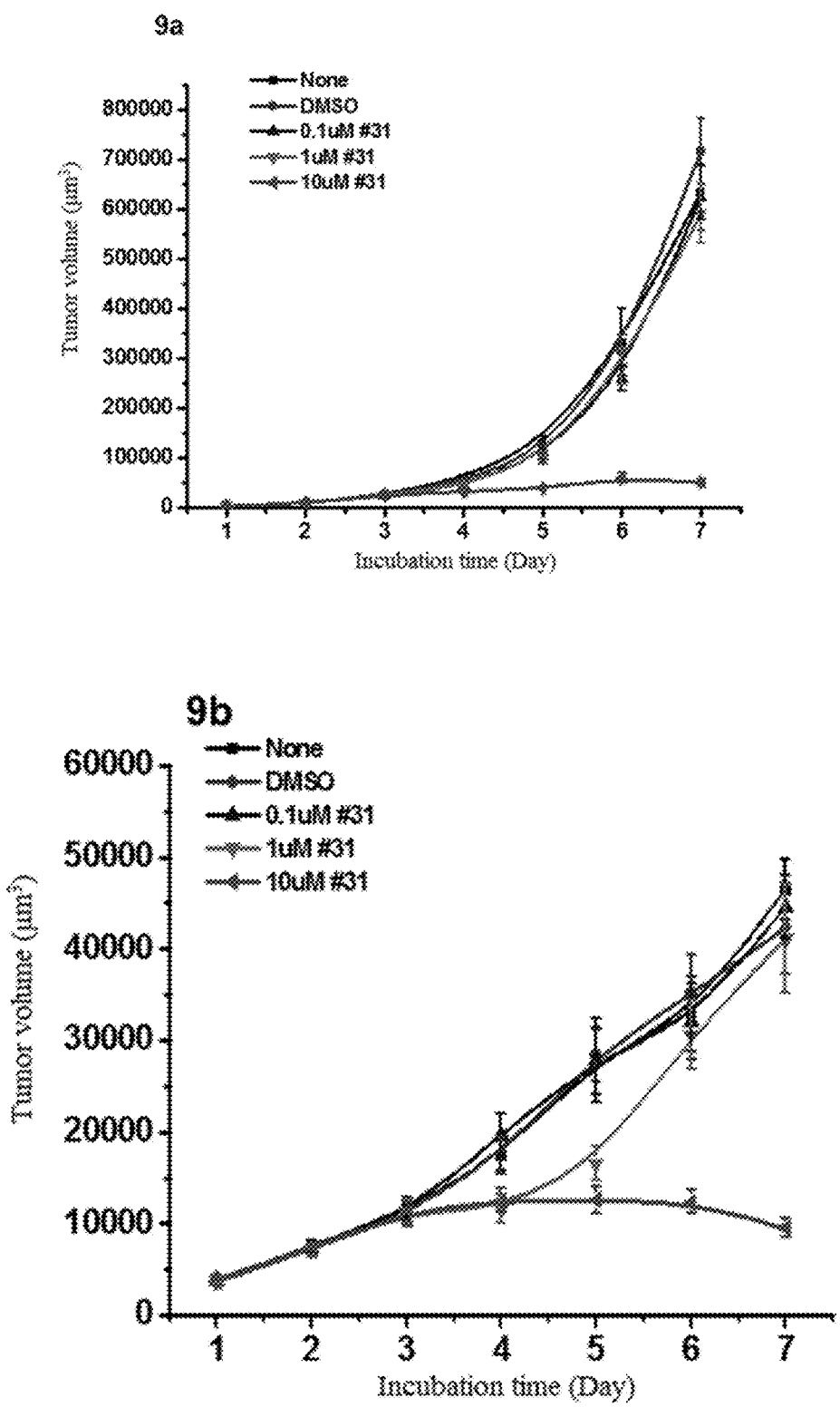

The results showed that WYC-331 could completely inhibit the proliferation of tumor-repopulating cells of A2780 ovarian cancer and MDA-MB-231 breast cancer at a concentration of 10 μM, which greatly blocked the growth of colony tumor volume, the volume of colony tumor of WYC-331 was only 10-15% of None group. As for tumor-repopulating cells of MDA-MB-231 breast cancer, WYC-331 could even reverse the growth trend of colony tumor (FIG. 9, wherein #31 refers to WYC-331). Meanwhile, it had been found from cell staining study that colony tumor cells inhibited by WYC-331 remained survival, and cell apoptosis appeared among only a few cells.

4, Toxicity of WYC-209 and WYC-331

Figure 10:
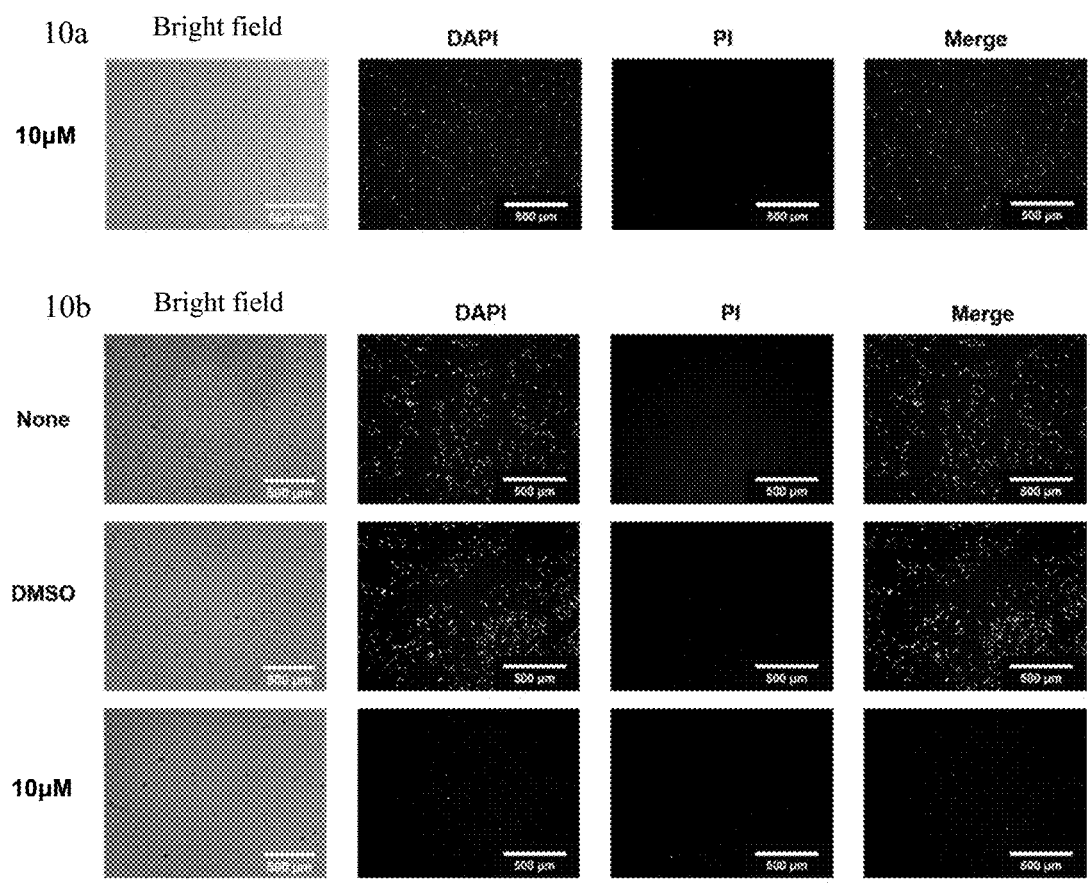

The 3T3 mouse embryonic fibroblast cells and B16-F1 melanoma cells were used as the model to study in vitro toxicity of WYC-209 and WYC-331 respectively. The effect of compound WYC-209 and WYC-331 on the proliferation of 3T3 mouse embryonic fibroblast cells and B16-F1 melanoma cells were studied at a concentration of 10 µM. The results showed that WYC-209 did not affect the proliferation of 3T3 mouse embryonic fibroblast cells, and did not induce apoptosis of these cells; meanwhile, WYC-209 could significantly block the growth of colony tumor cells of melanoma, and significant cell apoptosis appeared within 6-48 hours. The results showed that WYC-209 had a certain specificity for tumor-repopulating cells of melanoma, a weak effect on normal cells and less cytotoxicity (FIG. 10).

Figure 11:
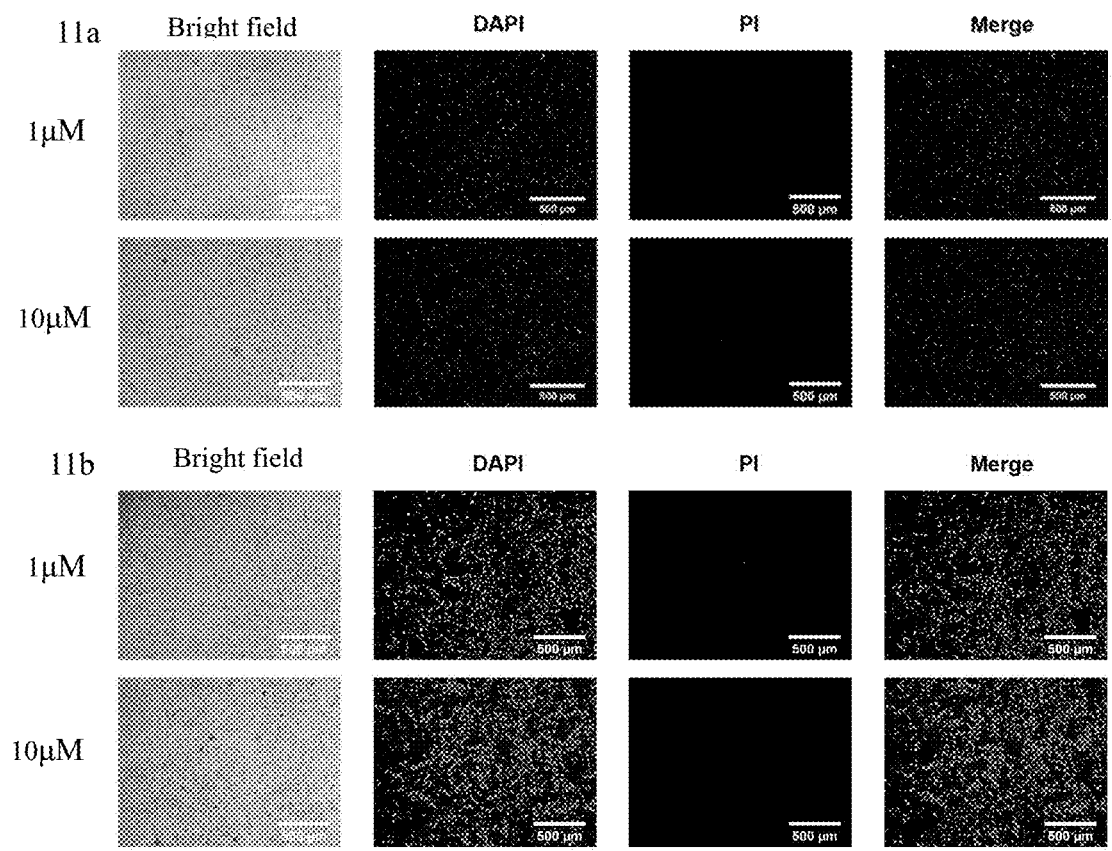

Under the same condition, WYC-331 strongly inhibited the proliferation of B16-F1 melanoma cells, but did not exhibit significant apoptosis-inducing effect on 3T3 mouse embryonic fibroblasts cells and B16-F1 melanoma cells. The results showed that WYC-331 also had a certain specificity for tumor-repopulating cells of melanoma, and obvious cytotoxicity had not been observed, but the mechanism of action thereof might be different from WYC-209 (FIG. 11).

5, Inhibitory Activity of WYC-103 on Subcutaneous Transplantation Tumor of Melanoma A subcutaneous implantation model of B16-F1 melanoma in immunocompetent mice (C57BL/6, female, 6-8 weeks) was established to study the inhibitory activity of compound WYC-103 on the tumor in situ. Firstly, B16-F1 cells were incubated within 3D fibrin gel (90-Pa in gel stiffness) that was immersed in culture medium for 5 days, and the desired tumor-repopulating cells were screened. Subsequently, the culture medium was respectively treated with collagenase and neutral protease II, and the tumor-repopulating cells of B16-F1 melanoma were released, then the obtained repopulating cells were transferred to a freshly prepared medium to be re-suspended and maintained at single-cell state.

Figure 12:
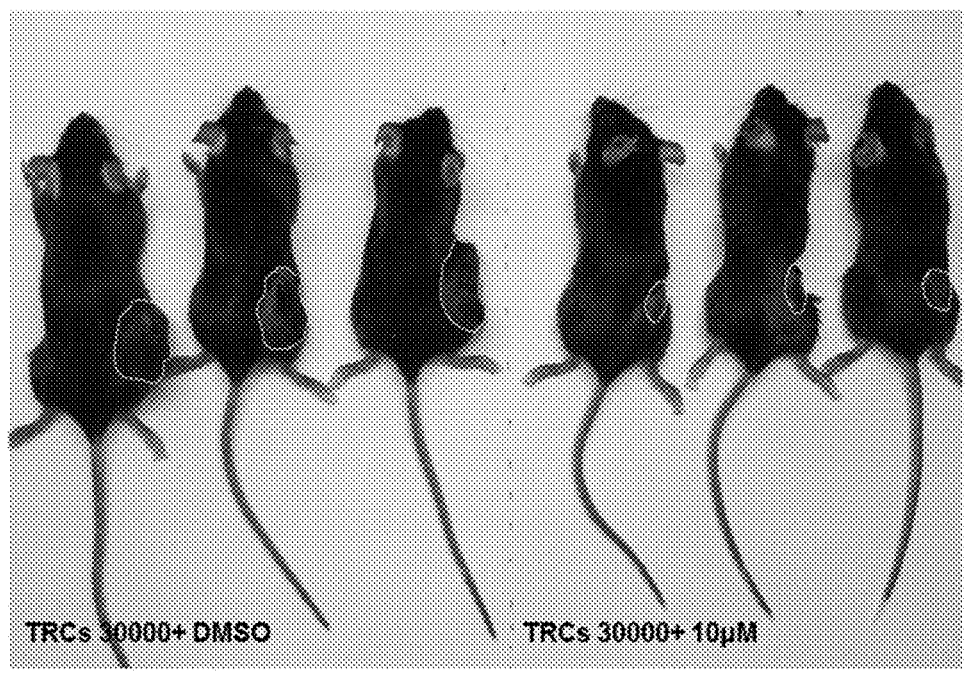
FIG. 12 shows the tumor volume on the 19th day of the experiment in the study of the inhibitory activity of WYC-103 on subcutaneous melanoma.

Six immunocompetent mice were randomly divided into two groups which were respectively the treatment group and the DMSO negative control group. Mice were subcutaneously injected with 30,000 tumor-repopulating cells of melanoma to establish a subcutaneous implantation model of melanoma. Subsequently, Mice were administered via tail vein injection based on the body weight and the blood volume of the mice. From day 0, mice in the treatment group were administrated with WYC-103 once every 2 days at a blood concentration of 10 µM and fed normally, observing the survival of the mice. The results were shown below. After 19 days experiment, the volume of the subcutaneous melanoma in the treatment group was significantly smaller than that of the DMSO control group. According to the statistical analysis, the tumor volume in the treatment group was only 50% of the control group (FIG. 12).

This experiment was repeated in order to further confirm the inhibitory activity of WYC-103 on subcutaneous implantation tumor of B16-F1 melanoma. In the present experiment, 18 immunocompetent mice (C57BL/6, female, 6-8 weeks) were randomly divided into three groups which were respectively the treatment group, the positive control group (BMS-453 was used as the positive drug) and the DMSO negative control group. Subsequently, Mice were administered via tail vein injection based on the body weight and the blood volume of the mice. From day 0, mice in the treatment group were administrated with WYC-103 once every 2 days at a blood concentration of 10 µM; mice in the positive control group were administered with BMS-453 (WYC-114) as the positive drug in the same route of administration; mice in the negative control group was administered with 0.1% DMSO in a same route of administration.

Figure 13:
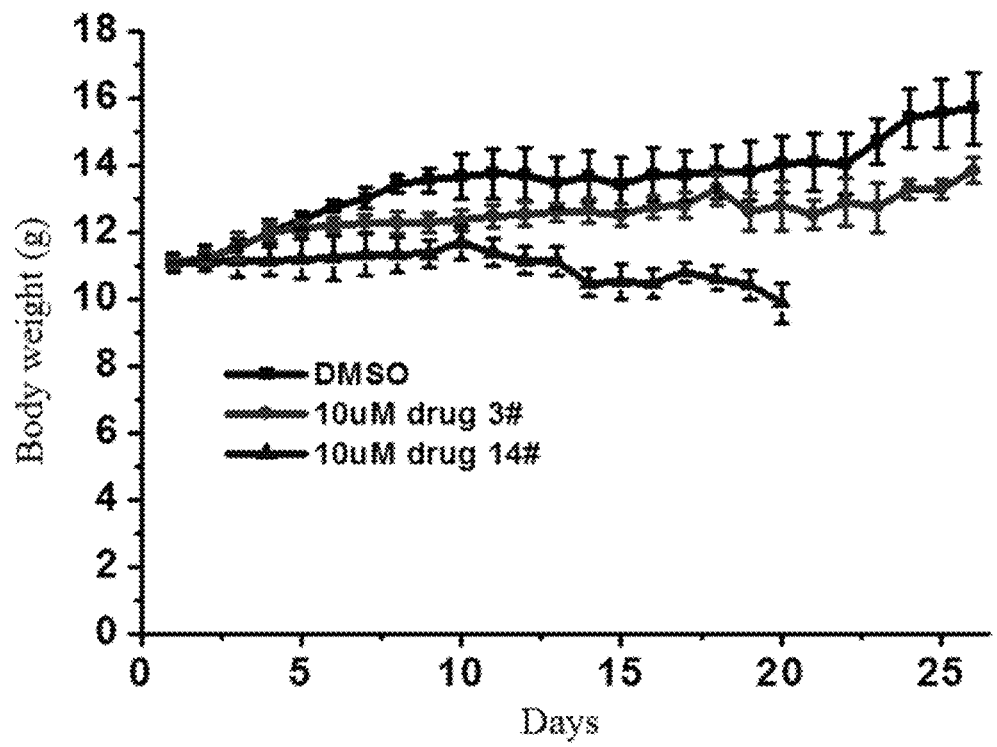
FIG. 13 shows the study of the body weight of mice and in vivo toxicity of WYC-103 on subcutaneous melanoma.
Figure 14:
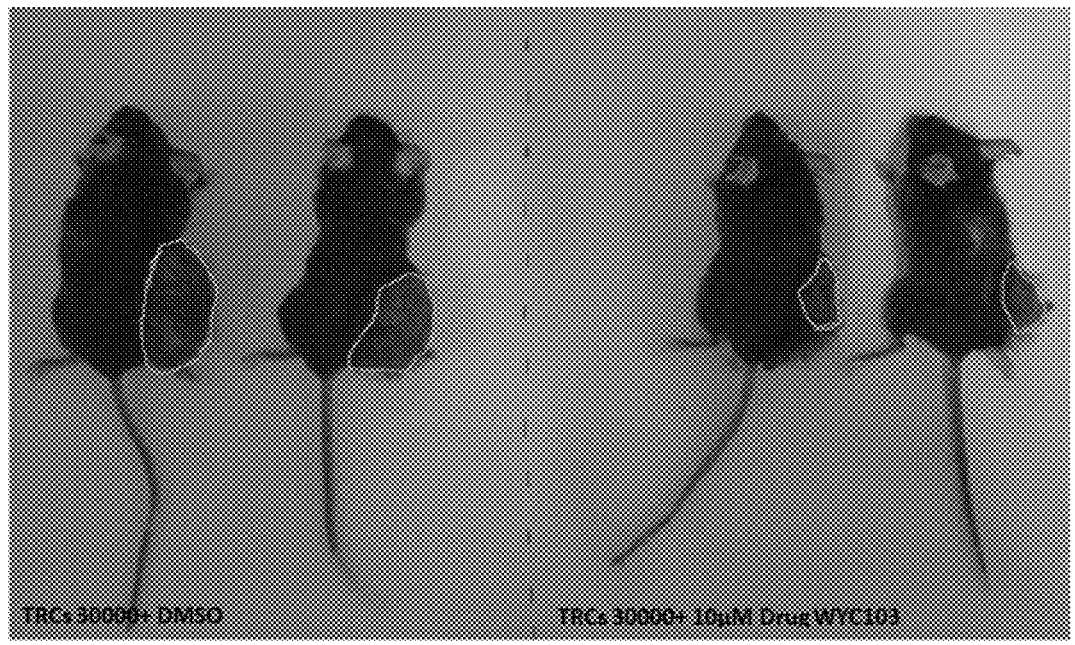
FIG. 14 shows the tumor volume on the 26th day of the experiment in the study of the inhibitory activity of WYC-103 on subcutaneous melanoma.

On the 20th day from the beginning of the experiment, all the mice in the positive control group died. On the 26th day from the beginning of the experiment, 50% of the mice in the treatment group and the negative control group died. According to the statistical analysis, the tumor volume of the mice in the treatment group was only 50% of the negative control group, and the growth of the subcutaneous implantation tumor of the mice in the treatment group was significantly inhibited. The study of the body weight of the mice showed that the body weight of the mice in the treatment group was stable and balanced, and there was no obvious toxic side effects (FIG. 13, wherein drug3# refers to WYC-103, drug14# refers to BMS-453). The body weight of the mice in the positive control group was significantly reduced, which indicated that there was a greater toxic side effect in the individual; while the body weight of the mice in the negative control group had a significant increase due to large tumor volume (FIG. 14). Further dissection experiment of the mice in each group showed that a large number of abnormal foamy structure appeared in the peritoneal cavity of the dead mice in the positive control group, which might be the cause of death in this group. No abnormalities were found in the abdominal cavity of the mice in the treatment group and the negative control group. This experiment showed that WYC-103 was much better than BMS-453 in terms of the efficacy and overall toxic side effects of the inhibition on the melanoma in situ.

6, Inhibitory Activity of WYC-103 on Metastatic Melanoma in the Lung

A metastatic melanoma model in the mouse was established to study whether WYC-103 could inhibit metastatic melanoma in the lung thus prevent secondary tumorigenesis. Firstly, 12 normally immunocompetent mice (C57BL/6, female, 6-8 weeks) were randomly selected and injected via the tail vein with 3000 tumor-repopulating cells of melanoma to establish a metastatic melanoma model in the mouse. The model mice were randomly divided into two groups which were respectively the treatment group and the negative control group. The mice were administered with WYC-103 (the treatment group) and DMSO (the negative control group) via tail vein injection once every 2 days at a blood concentration of 10 µM based on the body weight and the blood volume of the mice.

On the 29th day of the experiment, the first dead mouse in the negative control group appeared. For the convenience of comparison, killing one mouse in the treatment group, the dissection showed that obvious tissue of metastatic melanoma in the lung appeared in the dead mouse in the negative control group, while the lung tissue of the mouse in the treatment was normal. On the 35th day of the experiment, the second dead mouse in the negative control group appeared, and a large number of tissue of metastatic melanoma in the lung appeared in the mouse in the negative control group, while the lung tissues of the corresponding mouse in the treatment group was normal. On the 37th day of the experiment, 3 more mice died in the negative control group, and only 1 mouse remained alive in the negative control group; then all the mice in both groups were killed and dissected. According to the dissection results, metastatic melanoma appeared in the tissues of the lungs in 3 mice in the negative control group, while the lung tissues of all the mice in the treatment group was normal.

Figure 15:
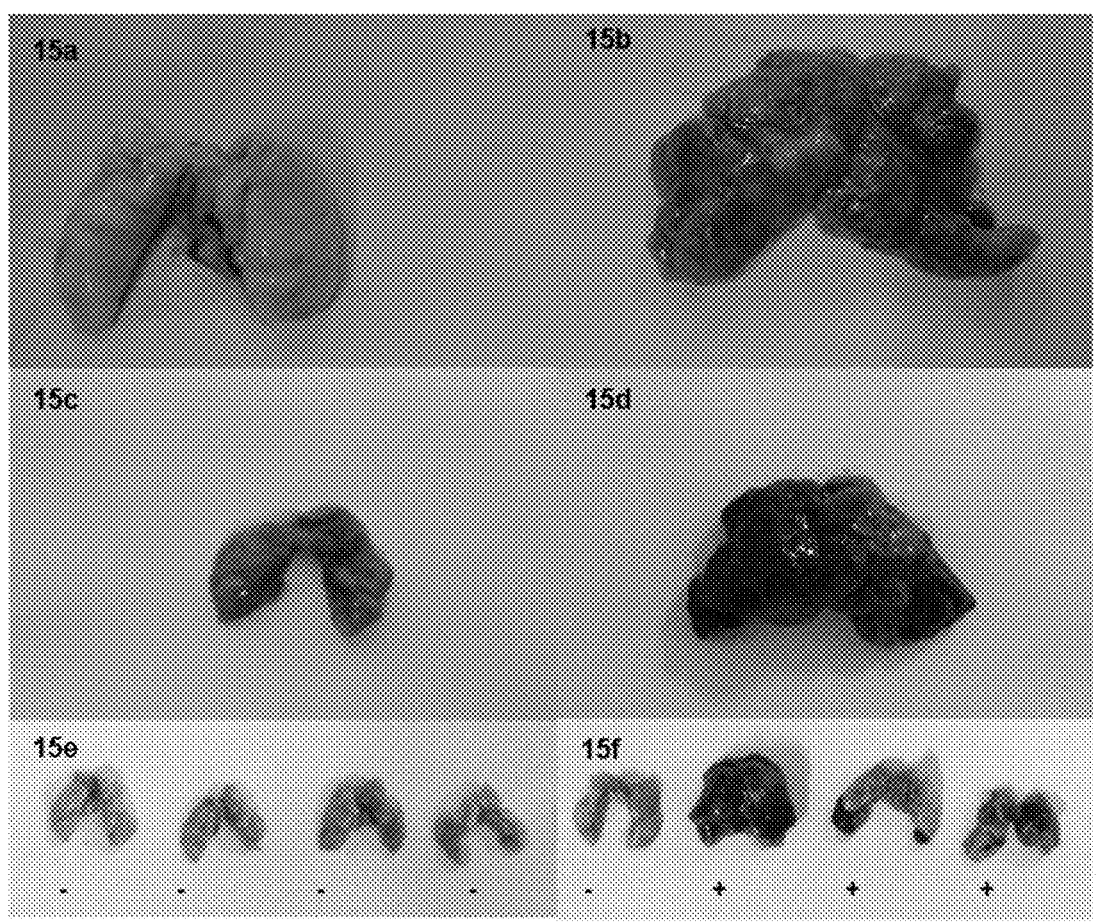

According to the statistical analysis, metastatic melanoma appeared in the tissues of the lungs in 5 mice among the 6 mice in the negative control group, which were all dead, only one mouse remained alive and healthy; while the lung tissues of all the 6 mice in the treatment group was healthy and intact and there were no signs of metastatic melanoma, indicating preventing the occurrence of metastatic melanoma with 100% efficiency. Meanwhile, according to statistical analysis, the average lung weight of the mice in the treatment group was only ⅓ of the negative control group (FIG. 15, "+" in FIGS. 15e and 15f refers to metastasis, and "−" refers to no metastasis).

This experiment showed that WYC-103 could effectively prevent repopulating cells of melanoma from metastasizing to the lung to form secondary lung tumor at a blood concentration of 10 μM, and there was no obvious toxic side effects accompanied with WYC-103 during the whole experiment. So WYC-103 was expected to be further used for the prevention and treatment of human metastatic cancer.

7, Inhibitory Activity of WYC-209 on Metastatic Melanoma in the Lung

This experiment was performed to study whether WYC-209 could inhibit the metastasis of melanoma to the lung thus prevent secondary tumorigenesis. The B16-F1 cells were incubated with 3D fibrin gel medium (90-Pa) for 5 days, and the desired tumor-repopulating cells were screened. Subsequently, the culture medium was respectively treated with collagenase and neutral protease II, and the tumor-repopulating cells were released, then the obtained repopulating cells were transferred to a freshly prepared medium to be re-suspended and maintained at single-cell state. Then 24 immunocompetent mice (C57BL/6, female, 6-8 weeks) were randomly selected and divided into three groups which were respectively low-dose group (1.0 μM), high-dose group (10 μM) and DMSO negative control group, with 8 mice per group. Subsequently, the mice were injected via the tail vein with 30,000 tumor-repopulating cells of melanoma to establish a B16-F1 metastatic melanoma model in the mouse. Subsequently, Mice were administered via tail vein injection based on the body weight and the blood volume of the mice. From the 5th day on, mice in the treatment group were administrated with WYC-209 once every 2 days at a blood concentration of 1.0 μM and 10 μM; mice in the DMSO group was administered with 0.1% DMSO in a same route of administration as negative control. At this time, there was no significant difference in the body weight between the groups, the mice were fed normally, observing the survival of the mice.

Figure 16:
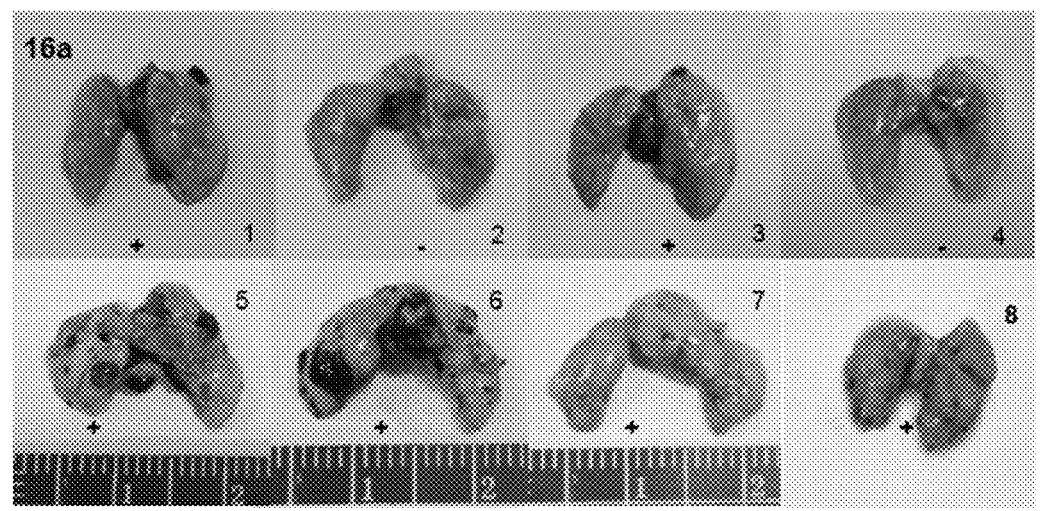
Figure 16:
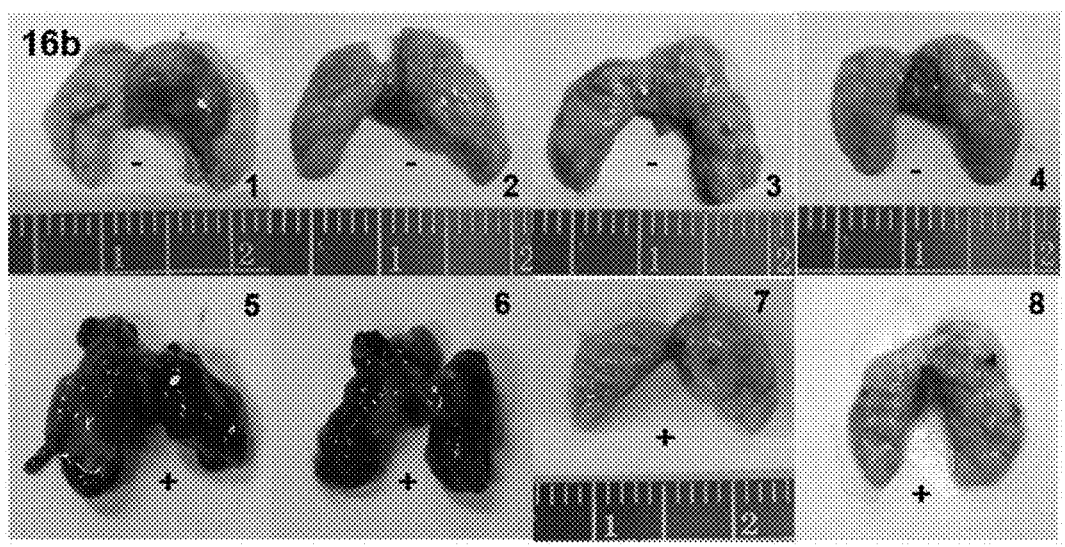
Figure 16:
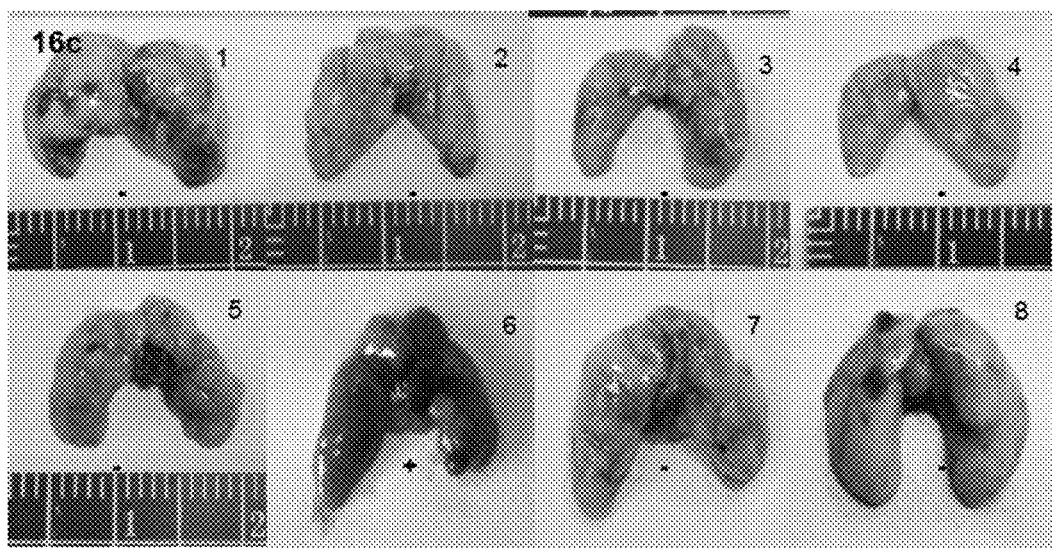

On the 23th day of the experiment, the first dead mouse (the lung tissue thereof was shown in FIG. 16a, No. 8) in the DMSO group appeared. On the 30th day, all the remaining mice were killed. Obvious tissue of metastatic melanoma appeared in the lungs of 6 mice among the 8 mice in the DMSO group, and there was no abnormalities found in the liver and stomach (referring to FIG. 16a, No. 1-7). During the same period (the night of the 29th day), one mouse died in the 1.0 μM treatment group (the lung tissue refers to FIG. 16b, No. 8); the metastatic melanoma appeared in the tissues of lungs of 4 mice among the 8 mice in the 1.0 μM treatment group, and there was no abnormalities found in the liver and stomach (FIG. 16b, No. 1-7 showed the lung tissue on the 30th day). During the same period, the metastatic melanoma appeared in the tissues of the lungs of only one mouse among the 8 mice in the 10 μM treatment group, and there was no abnormalities found in the liver and stomach. On the 30th day, 6 mice (75%) in the DMSO group suffered pulmonary metastatic melanoma, 4 mice (50%) in the 1.0 μM treatment group suffered pulmonary metastatic melanoma, and 1 mouse (12.5%) suffered pulmonary metastatic melanoma in the 10 μM treatment group only (referring to FIG. 16c, wherein No. 1-5 showed the lung tissue on the 30th day, and No. 6-8 showed the lung tissue on the 29th, 24th, 20th day respectively). There was a statistically significant difference among the lung tissue weight of the mice in each group, the DMSO group >1.0 μM treatment group >10 μM treatment group ("+" refers to metastasis, "−" refers to no metastasis in FIG. 16).

This experiment showed that WYC-209 could prevent repopulating cells of melanoma from metastasizing to the lung to form secondary lung tumor with 50% efficiency at a blood concentration of 1.0 μM, and with 87.5% efficiency at a blood concentration of 10.0 μM. The DMSO group showed 75% mortality rate of metastatic melanoma in the lung. WYC-209 exhibited an excellent activity of inhibiting and even healing secondary tumorigenesis in the immunocompetent mice in vivo. Meanwhile, there was no obvious toxic side effects accompanied with WYC-209 during the whole experiment, so WYC-209 was expected to be further used for the prevention and treatment of various primary or metastatic cancers.

In summary, the above in vitro activity experiments showed that WYC-103, WYC-209 and WYC-331 had strong inhibitory activity against tumor-repopulating cells of melanoma, the $IC_{50}$ reached 0.45 μM, 0.25 μM and 0.017 μM respectively. WYC-209 had strong inhibitory activity against A549 lung cancer cells, MCF-7 breast cancer cells, MDA-MB-435S melanoma cells, A2780 ovarian cancer cells, Hs-746T gastric cancer cells, MDA-MB-231 breast cancer cell.

In vivo activity experiments showed that WYC-103 had a strong inhibitory activity on subcutaneous transplantation tumor of melanoma in mice, the tumor volume was only 50% of the control group at a concentration of 10 μM. WYC-103 and WYC-209 inhibited the metastasis of repopulating cells of melanoma to the lung with 100% and 87% efficiency at a concentration of 10 μM respectively, which could bring new treatment for prevention and treatment of metastasis of human tumor.

It had been confirmed from In vitro experiment that WYC-209 and WYC-331 had no effect on the growth of 3T3 cell clones and could not induce apoptosis of 3T3 cells. Meanwhile, WYC-103 and WYC-209 exhibited highly safety in the in vitro and in vivo experiments. From the above biological study embodiments, the compounds of the present invention provided new possibilities for the prevention and treatment of leukemia, lymphoma, primary solid tumors and metastatic tumors.

It is to be understood that the foregoing description of two preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A compound represented by formula I, an enantiomer, a diastereomer or a pharmaceutically acceptable salt thereof,

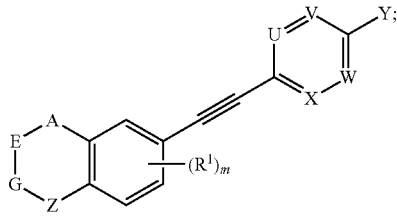

wherein:

(i) U is N, V is $CR^{9b}$, X is N, W is $CR^{9d}$, and the compound is represented by:

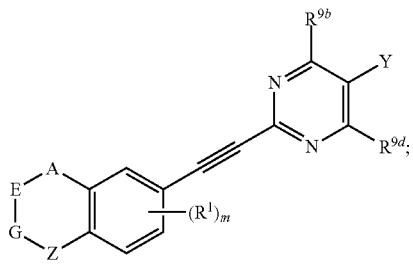

(ii) U is $CR^{9a}$, V is N, X is $CR^{9c}$, W is N, and the compound is represented by:

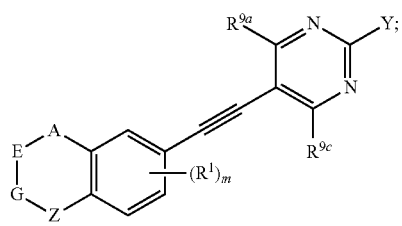

(iii) U is N, V is $CR^{9b}$, X is $CR^{9c}$, W is N, and the compound is represented by:

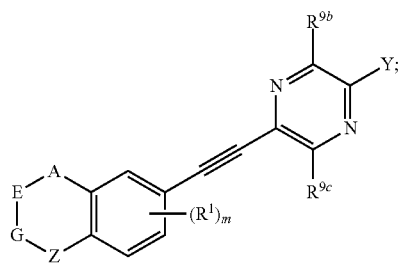

(iv) U is $CR^{9a}$, V is $CR^{9b}$, X is $CR^{9c}$, W is N, and the compound is represented by:

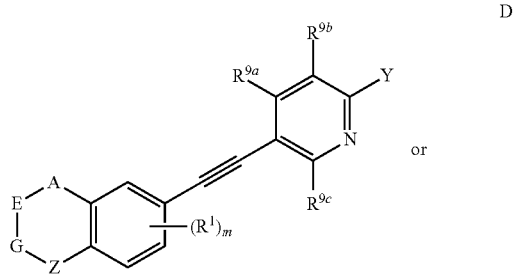

(v) U is $CR^{9a}$, V is $CR^{9b}$, X is $CR^{9c}$, W is $CR^{9d}$, and the compound is represented by:

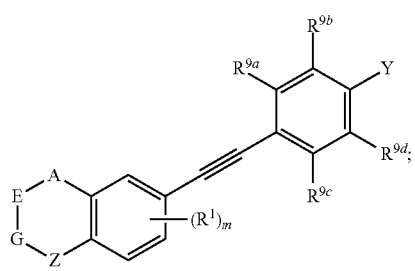

in the definition of compound F, one, two, three, or four of $R^{9a}$, $R^{9b}$, $R^{9c}$ and $R^{9d}$ is not hydrogen;

in the definition of U, V, X and W, each of $R^{9a}$, $R^{9b}$, $R^{9c}$ and $R^{9d}$ is independently hydrogen, hydroxy, nitro, cyano, halogen, $C_1$-$C_6$ alkyl, $C_1$-$C_6$ alkyl substituted with halogen, $C_1$-$C_6$ alkoxy, —$NR^{10}R^{11}$,

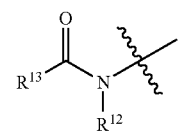

or —$COOR^{14}$;

each of $R^{10}$, $R^{11}$, $R^{12}$, $R^{13}$ and $R^{14}$ is independently hydrogen or $C_1$-$C_6$ alkyl;

the bond connecting AE, EG or GZ is independently a single bond;

Z is —O—, —S—, —S(=O)— or —$SO_2$—;

E is —$CH_2$—;

G is —$CH_2$—;

A is —($CR^2R^3$)—;

each of $R^2$ and $R^3$ is independently hydrogen, hydroxy, halogen, $C_1$-$C_6$ alkyl, $C_2$-$C_6$ alkenyl, $C_1$-$C_6$ alkyl substituted with halogen, $C_1$-$C_6$ alkoxy, $C_1$-$C_6$ acyl, $C_6$-$C_{10}$ aryl or "$C_3$-$C_6$ heteroaryl having 1 to 2 heteroatoms selected from the group consisting of oxygen, sulfur and nitrogen";

m is 0, 1, 2 or 3;

when there are more than one substituents of $R^1$, the substituents are identical or different; $R^1$ is hydrogen, hydroxy, nitro, cyano, halogen, $C_1$-$C_6$ alkyl, $C_1$-$C_6$ alkyl substituted with halogen, $C_1$-$C_6$ alkoxy, —$NR^6R^7$ or —$COOR^8$;

each of $R^6$, $R^7$ and $R^8$ is independently hydrogen or $C_1$-$C_6$ alkyl;

Y is —CN, —COOR$^{15}$ or —CO$_2$NHR$^{16}$;
each of R$^{15}$ and R$^{16}$ is independently hydrogen, C$_1$-C$_6$ alkyl, C$_2$-C$_6$ alkenyl or C$_1$-C$_6$ alkylacyl;
with a proviso that the compound represented by formula I is not

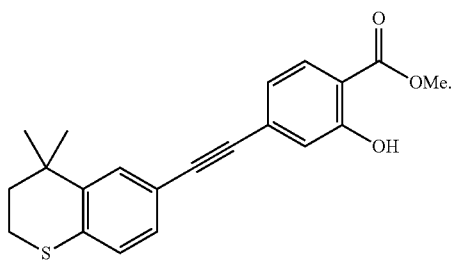 [SMILES: COC(=O)c1ccc(C#Cc2ccc3c(c2)C(C)(C)CCS3)cc1O]

2. The compound represented by formula I as defined in claim 1, wherein,
when each of R$^2$ and R$^3$ is independently halogen, the "halogen" is fluorine, chlorine, bromine or iodine;
when each of R$^2$ and R$^3$ is independently "C$_1$-C$_6$ alkyl", the "C$_1$-C$_6$ alkyl" is methyl, ethyl, n-propyl, isopropyl, n-butyl, isobutyl, tert-butyl, pentyl or hexyl;
when each of R$^2$ and R$^3$ is independently "C$_2$-C$_6$ alkenyl", the "C$_2$-C$_6$ alkenyl" is vinyl or propenyl;
when each of R$^2$ and R$^3$ is independently "C$_1$-C$_6$ alkyl substituted with halogen", the "C$_1$-C$_6$ alkyl substituted with halogen" is trifluoromethyl;
when each of R$^2$ and R$^3$ is independently "C$_1$-C$_6$ alkoxy", the "C$_1$-C$_6$ alkoxy" is methoxy, ethoxy, n-propoxy, isopropoxy, n-butoxy, isobutoxy, tert-butoxy, pentoxy or hexoxy;
when each of R$^2$ and R$^3$ is independently "C$_1$-C$_6$ acyl", the "C$_1$-C$_6$ acyl" is acetyl or formyl;
when each of R$^2$ and R$^3$ is independently "C$_6$-C$_{10}$ aryl", the "C$_6$-C$_{10}$ aryl" is phenyl;
when each of R$^2$ and R$^3$ is independently "C$_3$-C$_6$ heteroaryl having 1 to 2 heteroatoms selected from the group consisting of oxygen, sulfur and nitrogen", the "C$_3$-C$_6$ heteroaryl having 1 to 2 heteroatoms selected from the group consisting of oxygen, sulfur and nitrogen" is pyridinyl or pyrimidinyl;
when R$^1$ is "halogen", the "halogen" is fluorine, chlorine, bromine or iodine;
when R$^1$ is "C$_1$-C$_6$ alkyl", the "C$_1$-C$_6$ alkyl" is methyl, ethyl, n-propyl, isopropyl, n-butyl, isobutyl, tert-butyl, pentyl or hexyl;
when R$^1$ is "C$_1$-C$_6$ alkyl substituted with halogen", the "C$_1$-C$_6$ alkyl substituted with halogen" is trifluoromethyl;
when R$^1$ is "C$_1$-C$_6$ alkoxy", the "C$_1$-C$_6$ alkoxy" is methoxy, ethoxy, n-propoxy, isopropoxy, n-butoxy, isobutoxy, tert-butoxy, pentoxy or hexoxy;
when each of R$^6$, R$^7$ and R$^8$ is independently "C$_1$-C$_6$ alkyl", the "C$_1$-C$_6$ alkyl" is methyl, ethyl, n-propyl, isopropyl, n-butyl, isobutyl, tert-butyl, pentyl or hexyl;
when each of R$^{9a}$, R$^{9b}$, R$^{9c}$ and R$^{9d}$ is independently "halogen", the "halogen" is fluorine, chlorine, bromine or iodine;
when each of R$^{9a}$, R$^{9b}$, R$^{9c}$ and R$^{9d}$ is independently "C$_1$-C$_6$ alkyl", the "C$_1$-C$_6$ alkyl" is methyl, ethyl, n-propyl, isopropyl, n-butyl, isobutyl, tert-butyl, pentyl or hexyl;
when each of R$^{9a}$, R$^{9b}$, R$^{9c}$ and R$^{9d}$ is independently "C$_1$-C$_6$ alkyl substituted with halogen", the "C$_1$-C$_6$ alkyl substituted with halogen" is trifluoromethyl;
when each of R$^{9a}$, R$^{9b}$, R$^{9c}$ and R$^{9d}$ is independently "C$_1$-C$_6$ alkoxy", the "C$_1$-C$_6$ alkoxy" is methoxy, ethoxy, n-propoxy, isopropoxy, n-butoxy, isobutoxy, tert-butoxy, pentoxy or hexoxy;
when each of R$^{10}$, R$^1$, R$^{12}$, R$^{13}$ and R$^{14}$ is independently "C$_1$-C$_6$ alkyl", the "C$_1$-C$_6$ alkyl" is methyl, ethyl, n-propyl, isopropyl, n-butyl, isobutyl, tert-butyl, pentyl or hexyl;
when each of R$^{15}$ and R$^{16}$ is independently "C$_1$-C$_6$ alkyl", the "C$_1$-C$_6$ alkyl" is methyl, ethyl, n-propyl, isopropyl, n-butyl, isobutyl, tert-butyl, pentyl or hexyl;
when each of R$^{15}$ and R$^{16}$ is independently "C$_2$-C$_6$ alkenyl", the "C$_2$-C$_6$ alkenyl" is vinyl or propenyl;
when each of R$^{15}$ and R$^{16}$ is independently "C$_1$-C$_6$ acyl", the "C$_1$-C$_6$ acyl" is formyl or acetyl.

3. The compound represented by formula I as defined in claim 1, wherein,
A, E, G together with Z form the ring selected from the group consisting of

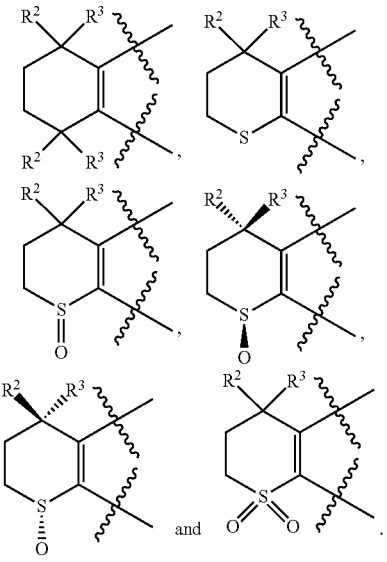

4. The compound represented by formula I as defined in claim 3, wherein,
in compound A, when Y is —COOR$^{15}$, R$^{15}$ is hydrogen or ethyl;
and/or, in compound A, Z is —S—, —S(=O)— or —SO$_2$—;
and/or, in compound B, when Y is —COOR$^{15}$, R$^{15}$ is methyl or ethyl;
and/or, in compound B, Z is —S— or —S(=O)—;
and/or, in compound C, when Y is —COOR$^{15}$, R$^{15}$ is hydrogen or ethyl;
and/or, in compound C, Z is —S— or —S(=O)—;
and/or, in compound D, when Y is —COOR$^{15}$, R$^{15}$ is hydrogen or ethyl;
and/or, in compound F, when Y is —COOR$^{15}$, R$^{15}$ is hydrogen, methyl or ethyl;
and/or, in compound F, Z is —S—, —S(=O)— or —SO$_2$—.

5. The compound represented by formula I as defined in claim 4, wherein, in compound A, when Y is COOH, Z is —S—;

and/or, in compound A, when Y is COOEt, Z is —S(=O)— or —SO$_2$—;

and/or, in compound B, when Y is COOEt, Z is —S—;

and/or, in compound B, when Y is CNOEt, Z is —S— or —S—;

and/or, in compound B, when Y is CN, Z is —S— or;

and/or, in compound C, when Y is COOEtH, Z is —S—;

and/or, in compound C, when Y is COOEt, Z is —S— or —S(=O)—.

6. The compound represented by formula I as defined in claim 1, wherein, the compound represented by formula I is selected from the group consisting of

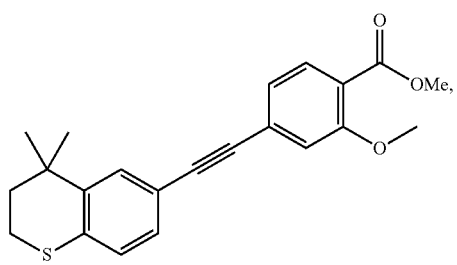

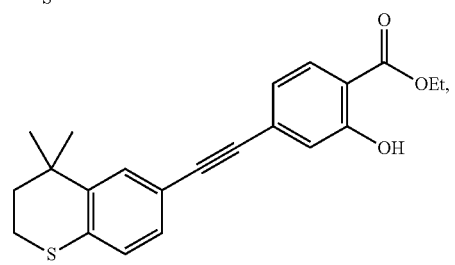

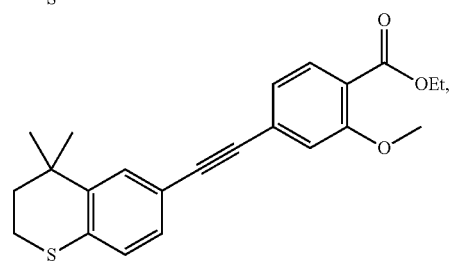

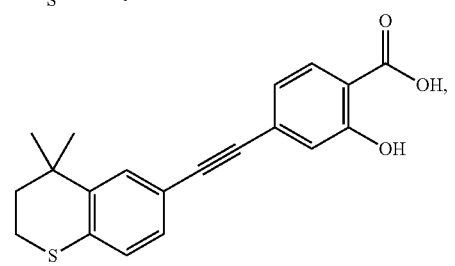

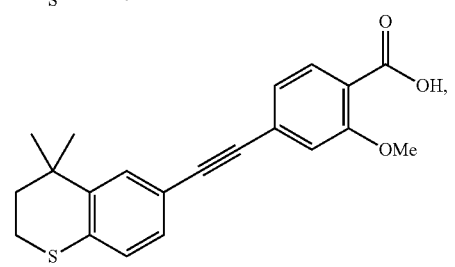

-continued

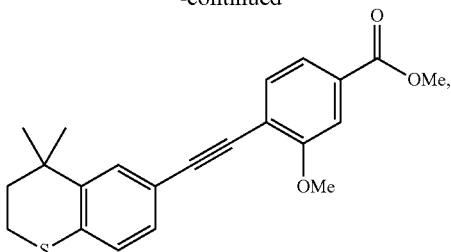

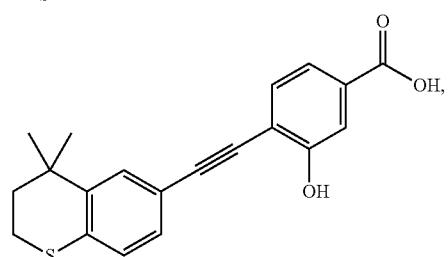

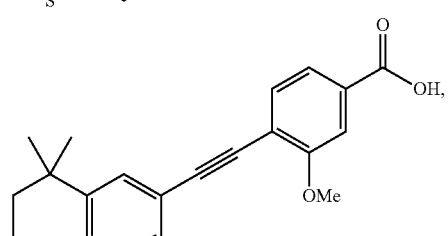

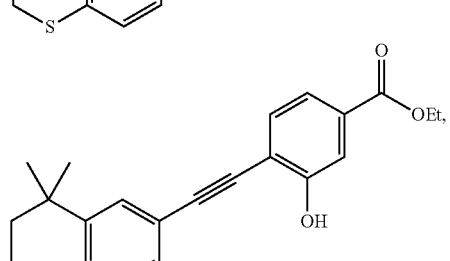

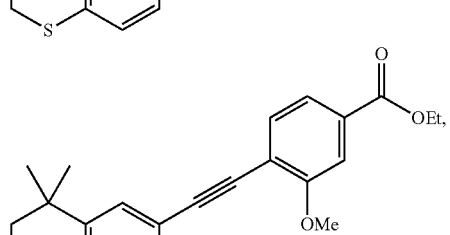

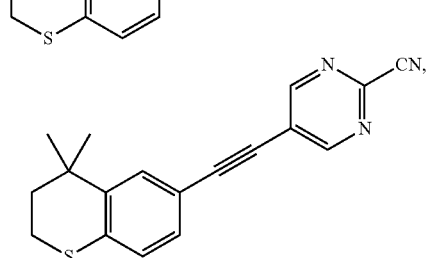

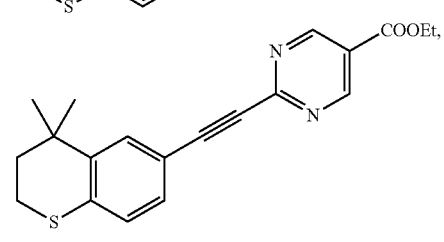

111
-continued
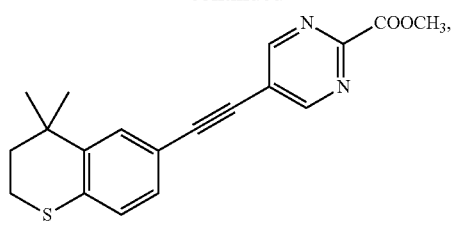
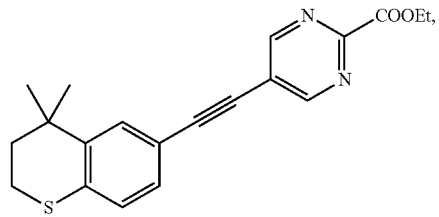
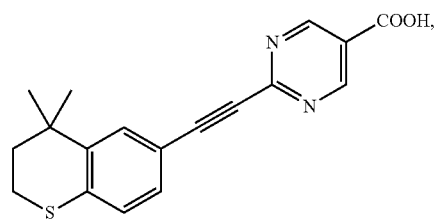
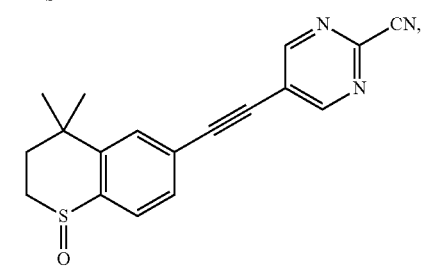
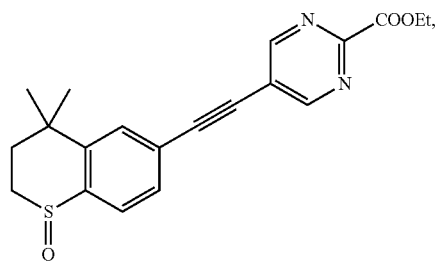
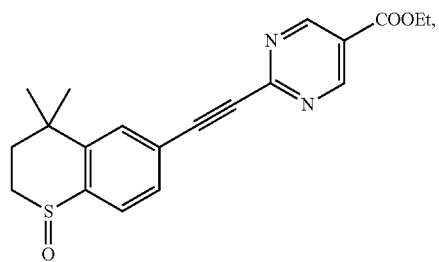
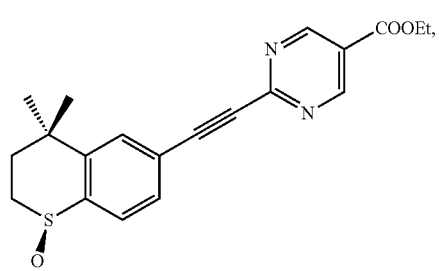
112
-continued
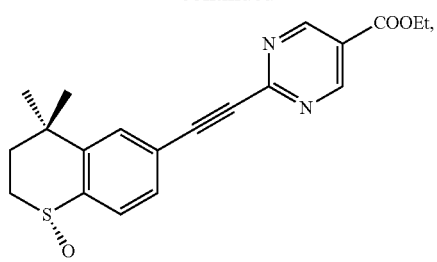
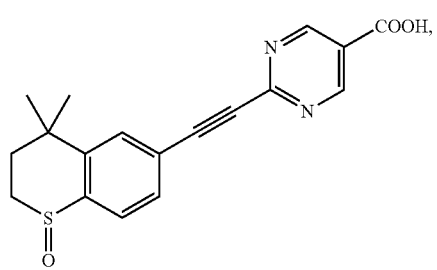
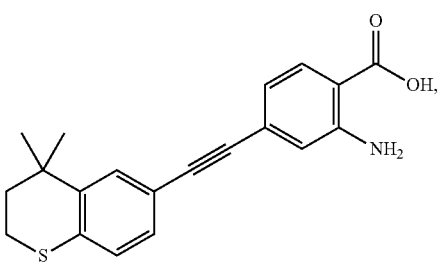
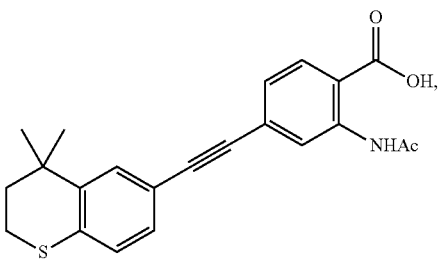
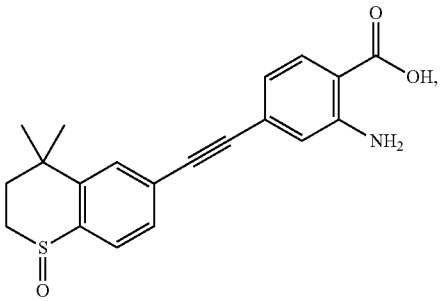
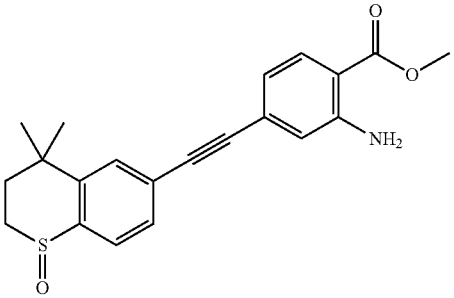

113
-continued
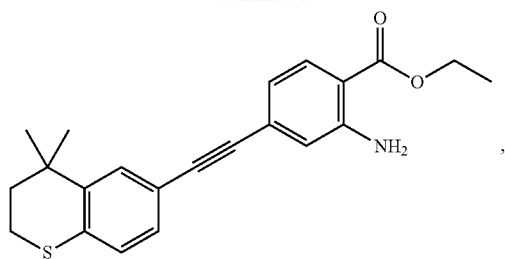
,
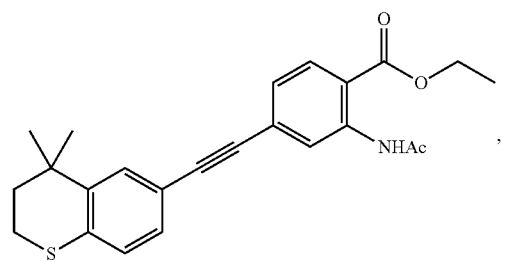
,
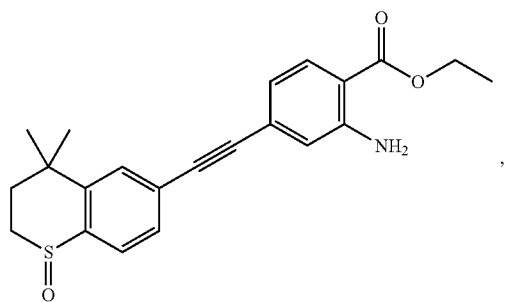
,
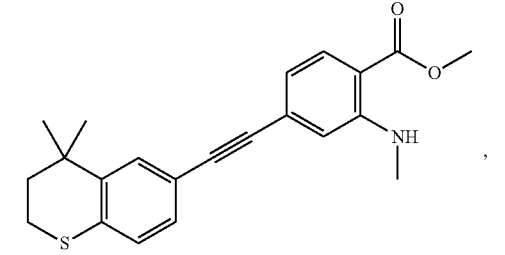
,
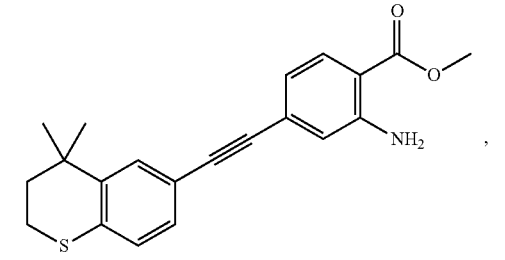
,
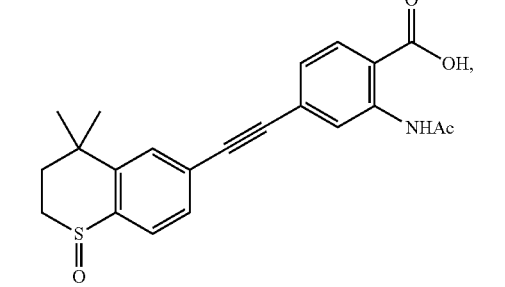
,
114
-continued
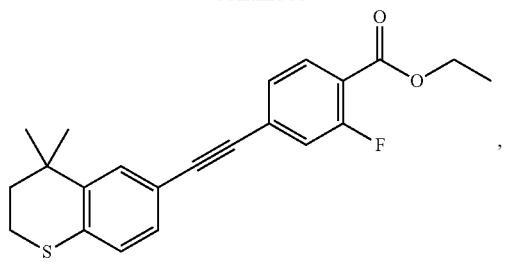
,
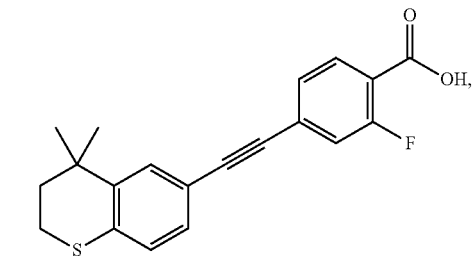
,
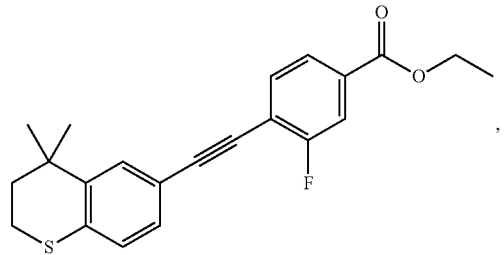
,
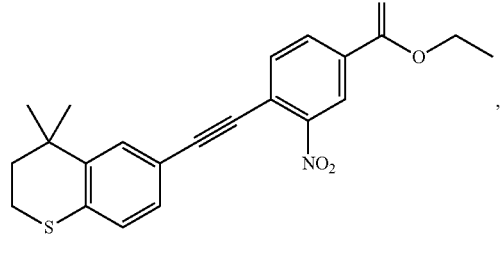
,
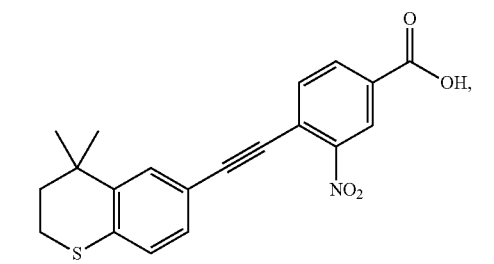
,
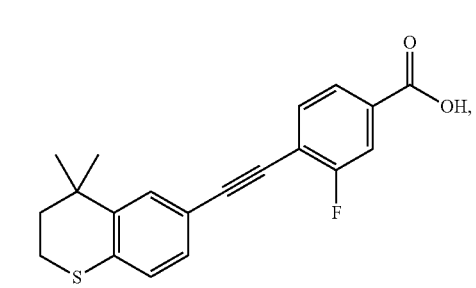
,

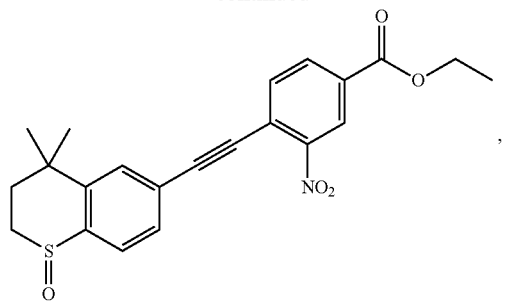
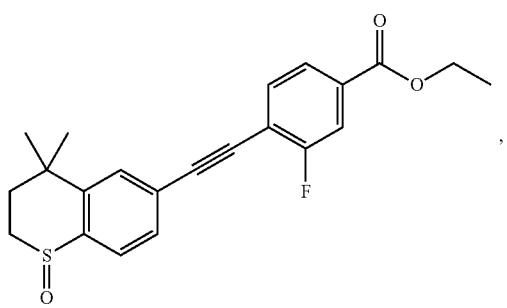
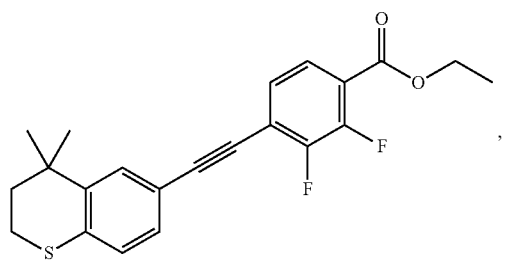
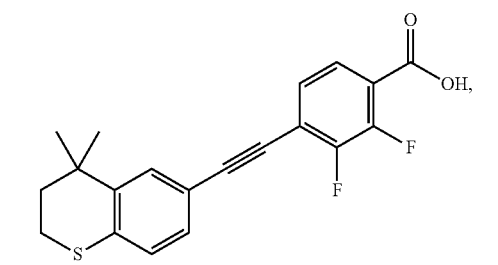
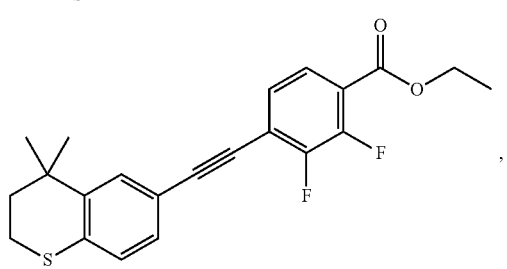
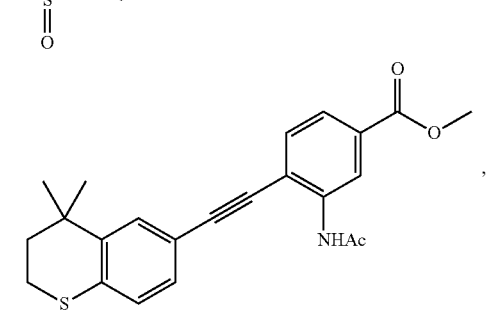
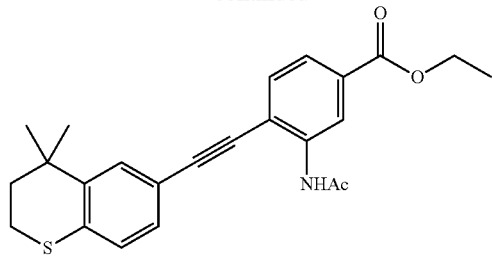
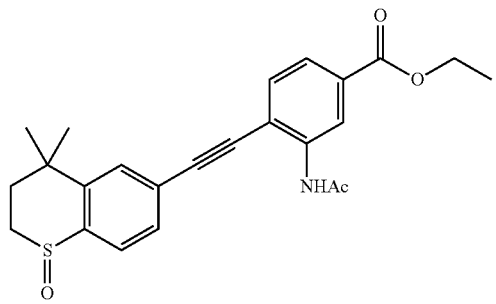
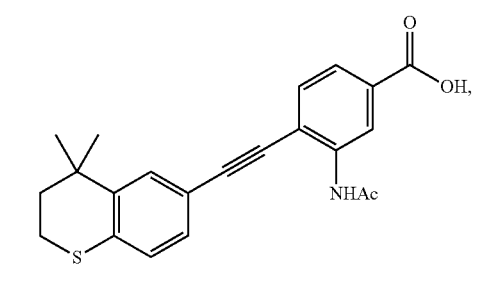
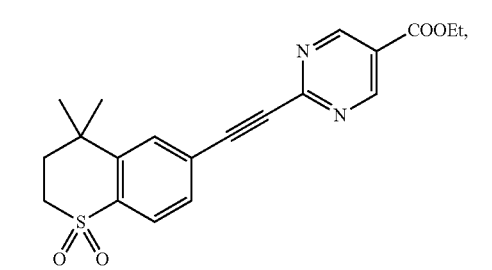
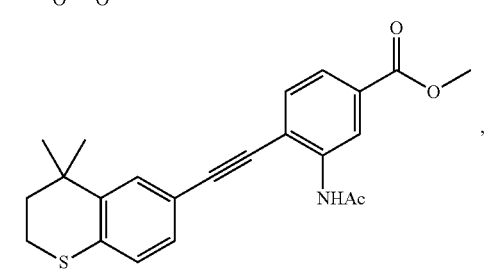
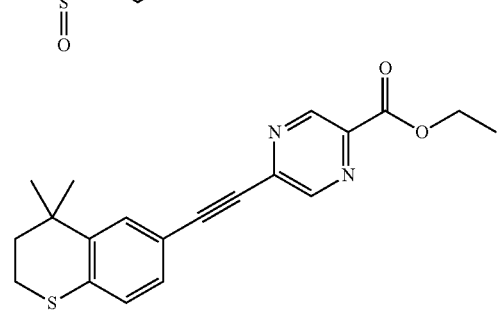

117
-continued

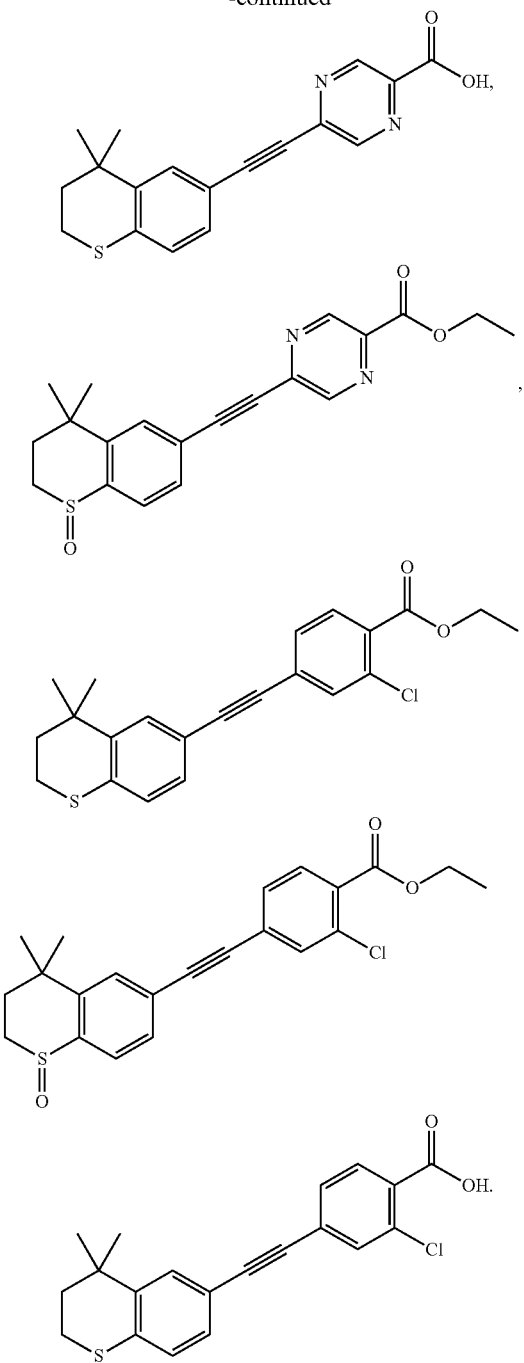

7. A preparation method for the compound represented by formula I as defined in claim 1, which comprises conducting a coupling reaction with compound II and III to give compound I;

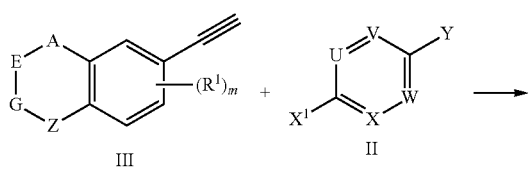

118
-continued

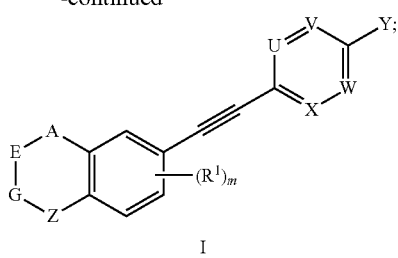

wherein, $X^1$ is halogen.

8. A pharmaceutical composition, which comprises the compound represented by formula I, the enantiomer, the diastereomer or the pharmaceutically acceptable salt thereof as defined in claim 1, and a pharmaceutically acceptable carrier.

9. The compound represented by formula I as defined in claim/wherein, in compound A, A, E, G together with Z form the ring selected from the group consisting of

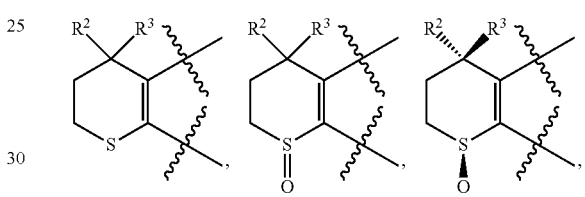

and

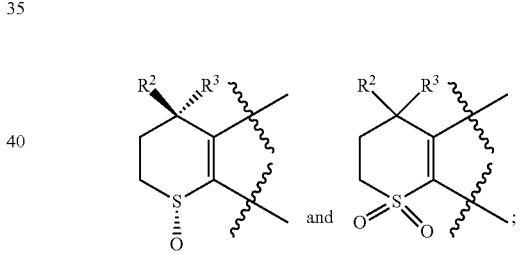

and/or, in compound B, A, E, G together with Z form the ring selected from the group consisting of

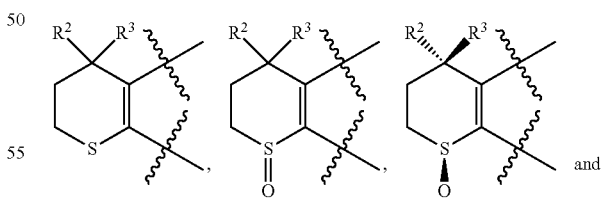

and/or, in compound C, A, E, G together with Z form the ring selected from the group consisting of

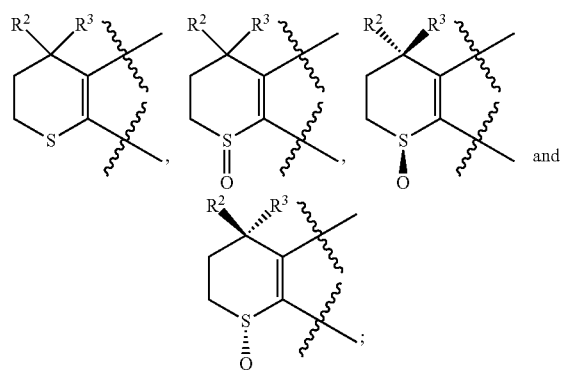
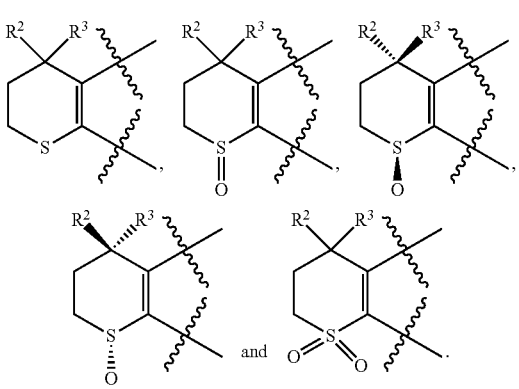
and/or, in compound F, A, E, G together with Z form the ring selected from the group consisting of
* * * * *